US011857598B2

(12) United States Patent
Totary-Jain

(10) Patent No.: US 11,857,598 B2
(45) Date of Patent: *Jan. 2, 2024

(54) SELF-REPLICATING CELL SELECTIVE GENE DELIVERY COMPOSITIONS, METHODS, AND USES THEREOF

(71) Applicant: University of South Florida, Tampa, FL (US)

(72) Inventor: Hana Totary-Jain, Wesley Chapel, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 125 days.

This patent is subject to a terminal disclaimer.

(21) Appl. No.: 17/400,984

(22) Filed: Aug. 12, 2021

(65) Prior Publication Data

US 2021/0369810 A1 Dec. 2, 2021

Related U.S. Application Data

(60) Continuation of application No. 16/902,198, filed on Jun. 15, 2020, now abandoned, which is a division of application No. 16/247,022, filed on Jan. 14, 2019, now Pat. No. 10,709,759, which is a continuation of application No. 15/333,074, filed on Oct. 24, 2016, now Pat. No. 10,188,750.

(60) Provisional application No. 62/264,609, filed on Dec. 8, 2015, provisional application No. 62/245,457, filed on Oct. 23, 2015.

(51) Int. Cl.
*C07H 21/04* (2006.01)
*A61K 38/17* (2006.01)
*A61K 31/7115* (2006.01)
*A61K 31/7088* (2006.01)

(52) U.S. Cl.
CPC ...... *A61K 38/1709* (2013.01); *A61K 31/7088* (2013.01); *A61K 31/7115* (2013.01); *C12Y 207/07048* (2013.01); *C12N 2310/113* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 4,921,475 | A | 5/1990 | Sibalis |
| 5,008,110 | A | 4/1991 | Benecke et al. |
| 5,087,240 | A | 2/1992 | Sibalis |
| 5,088,977 | A | 2/1992 | Sibalis |
| 5,139,941 | A | 8/1992 | Muzyczka et al. |
| 5,163,899 | A | 11/1992 | Sibalis |
| 5,164,189 | A | 11/1992 | Farhadieh et al. |
| 5,252,479 | A | 10/1993 | Srivastava |
| 5,254,346 | A | 10/1993 | Tucker et al. |
| 5,290,561 | A | 3/1994 | Farhadieh et al. |
| 5,328,470 | A | 7/1994 | Nabel et al. |
| 5,332,213 | A | 7/1994 | Klose |
| 5,336,168 | A | 8/1994 | Sibalis |
| 5,352,456 | A | 10/1994 | Fallon et al. |
| 5,407,713 | A | 4/1995 | Wilfong et al. |
| 5,614,670 | A | 6/1997 | Treco et al. |
| 5,747,469 | A | 5/1998 | Roth et al. |
| 6,017,524 | A | 1/2000 | Roth et al. |
| 6,143,290 | A | 11/2000 | Zhang et al. |
| 6,410,010 | B1 | 6/2002 | Zhang et al. |
| 6,511,847 | B1 | 1/2003 | Zhang et al. |
| 7,232,806 | B2 | 6/2007 | Tuschl et al. |
| 8,398,968 | B2 | 3/2013 | Mayall |
| 8,404,653 | B2 | 3/2013 | Zsebo |
| 2004/0057937 | A1 | 3/2004 | Jahoda et al. |
| 2006/0105360 | A1 | 5/2006 | Croce et al. |
| 2009/0131354 | A1 | 5/2009 | Bader et al. |
| 2010/0041737 | A1 | 2/2010 | Naldini et al. |
| 2011/0218234 | A1 | 9/2011 | Annoni et al. |
| 2012/0128643 | A1 | 5/2012 | Biffi et al. |
| 2013/0202532 | A1 | 8/2013 | Benenson et al. |
| 2015/0167003 | A1 | 6/2015 | Naldini et al. |
| 2015/0190532 | A1 | 7/2015 | Totary-Jain et al. |
| 2016/0089453 | A1 | 3/2016 | Zamore et al. |

FOREIGN PATENT DOCUMENTS

| | | | |
|---|---|---|---|
| WO | 1994013788 | A1 | 6/1994 |
| WO | 2001032840 | A2 | 5/2001 |
| WO | 2007100870 | A2 | 9/2007 |
| WO | 2013152230 | A1 | 10/2013 |

OTHER PUBLICATIONS

Altaras et al., 2005. Adv Biochem Eng Bintechnol.; 99:193-260.
Anderson et al., 1992. Proc. Science 256:808-813.
Bandyopadhyay & Temin, 1984. Mol Cell Biol. 4(4):749-54.
Bartel, 2009. Micro RNAs: Target Recognition and Regulatory Functions. Cell, 136(2), 215-233.
Berkner, 1988. Biotechniques, 6(7):616-29.
Berkner, 1992. Curr Top Microbiol Immunol. 158:39-66.
Bleuyard et al., 2006. DNA Repair 5: 1-12.
Breakefield & Geller, 1987. Mol Neurobiol. 1(4):339-71.
Brower, 1998. Nature Biotechnology, 16:1304-1305.
Brown et al., 2006. Nat Med 12, 585-591.
Brown & Naldini, 2009. Exploiting and antagonizing microRNA regulation for therapeutic and experimental applications. Nature Reviews. Genetics, 10(8), 578-585.
Brummelkamp et al., 2002. Science 296:550-553.
Buchschacher & Panganiban, 1992. J Virol. 66(5)2731-9.
Calin et al., 2002. Proc. Natl. Acad. Sci. USA 99:15524-29.
Carillo & Lipman, 1988. SIAM J. Applied Math, 48: 1073.
Carr & Church, 2009. Nature Biotechnol. 27: 1151-1162.

(Continued)

*Primary Examiner* — Kimberly Chong
(74) *Attorney, Agent, or Firm* — Quarles & Brady LLP

(57) ABSTRACT

Described herein are cell-selective mRNA constructs that can contain a RNA of interest and one or more miRNA targets. The cell-selective mRNA constructs described herein can be used to express an RNA of interest to a cell in a cell-selective manner.

15 Claims, 34 Drawing Sheets

Specification includes a Sequence Listing.

(56) References Cited

OTHER PUBLICATIONS

Cassese & Kastrati, 2012. JAMA 308, 814-815.
Chen et al., 1994. Proc. Natl. Acad. Sci. USA 91:3054-3057.
Ciccarelli et al., 2008. Endothelial alpha 1-adrenoceptors regulate neoangiogenesis. Br J Pharmacol 153, 936-946.
Cleveland et al., 1993. J Immunol Methods, 56(2): 221-234.
Dzau et al., 1993. Trends in Biotechnology J 1:205-2W.
Eglitis, 1988. Biotechniques 6:608-614.
Eliyahu et al., 2005. Molecules, Jan. 31; 10(1):34-64.
Fiers et al., 1973. Nature 273: 113-120.
Fink et al., 1992. Hum Gene Ther. 3(1):11-9.
Finn et al., 2007. Vascular responses to drug eluting stents: importance of delayed healing. Arteriscler Thromb Vasc Biol 27(7), 1500-1510.
Fischer et al., 1996. J. Virol. 70:520-532.
Freese et al., 1990. Biochem Pharmacol. 40(10):2189-99.
Friedmann, 1989. Science, 244:1275-1281.
Garg & Serruys, 2010. Coronary stents: looking forward. J Am Coll of Cardiol 56(10 Suppl), S43-78.
Garg & Serruys, 2010. Journal of the American College of Cariology 56, S1-42.
Geall, et al., Nonviral delivery of self-amplifying RNA vaccines, PNAS U.S.A. 2012, 109(36): 14604-14609.
Gorziglia & Kapikian, 1992. J Virol. 66(7):4407-12.
Hager et al., 2002. Curr Opin Genet Dev, 12(2): 137-41.
Hammond, 2006. Curr Opin Genet Dev. 16(1):4-9.
Hayashi et al., 2009. The American journal of pathology 175, 2226-2234.
Helseth et al., 1990. J Virol. 64(12):6314-8.
Heron et al., 2009. Deaths: final data for 2006. Natl Vital Stat Rep 57(14), 1-134.
Herweijer et al., 2007. Gene Ther. Jan.; 14(2):99-107.
Hoffman, 2001. Ann NY Acad Sci 944:62-73.
Hoffman, 2002. Adv Drug Deliv Rev. 43:3-12.
Horowitz et al., "Bax protein-immunoreactivity in midbrain neurons of Parkinson's disease patients." Brain research bulletin 62. 1 (2003): 55-61.
Hwang & Mendell, 2006. Br J Cancer 94(6):776-80.
Iaccarino et al., 1999. Targeting Gbeta gamma signaling in arterial vascular smooth muscle proliferation: a novel strategy to limit restenosis. Proc Natl Acad Sci USA 96, 3945-3950.
Iaccarino et al., 2004. AKT participates in endothelial dysfunction in bypertension. Circulation 109, 2587-2593.
Iakovou et al., 2005. JAMA 293, 2126-2130.
Isaka et al., 2007. Expert Opin Drug Deliv. Sep; 4(5):561-71.
Ishida et al., 2013. Author's Manuscript 1-14. Published as: miRNA-Based Therapeutic Strategies, Curr Anesthesiol Rep., 1(1):63-70.
Janssen et al., 2013. Treatment of HCV infection by targeting microRNA. The New England Journal of Medicine, 368, 1685-94.
Jensen et al., 2007. Ann Med.; 39(2): 108-15.
Shimada et al., 1991. J Clin Invest. 88(3):1043-7.
Shivdasani, 2006. Blood 108(12):3646-53.
Siebert & Puchta, 2002. Plant Cell 14:1121-1131.
Sorge et al., 1984. Mol Cell Biol. 4(9):1730-7.
Stratford-Perricaudet et al., 1990. Hum Gene Ther. 1(3):241-56.
Totary-Jain et al., 2012. Author's Manuscript, pp. 1-14. Published as: Rapamycin resistance is linked to defective regulation of Skp2. Cancer Res 72, 1836-1843.
Tuschl, 2002. Nat. Biotechnol, 20:446-448.
Van Rooij & Olson, 2012. Nat Rev Drug Discov 11, 860-872.
Verma, 1990. Scientific American: 68-84.
Vestweber, 2008. VE-cadherin: the major endothelial adhesion molecule controlling cellular junctions and blood vessel formation. Arterioscler Thromb Vasc Biol 28, 223-232.
Waehler et al., 2007. Nat Rev Genet. Aug.; 8(8):573-87.
Wang et al., 2008. Dev Cell 15, 261-271.
Wenaweser et al., 2008. Journal of the American College of Cardiology 52, 1134-1140.
Wijns, 2009. Late stent thrombosis after drug-eluting stent: seeing is understanding. Circulation 120(5), 364-365.
Wilkinson et al., 1992. Nucleic Acids Res. 20(9):2233-9.
Xia et al., 2002. Nat Biotech. 20:1006-1010.
Yamaguchi et al., 2011. Local persistent hypercoagulability after sirolimuseluting stent implantation in patients with stable angina. Int J Cardio/153, 272-276.
Yeung et al., 2005. siRNA, miRNA and HIV: promises and challenges. Cell Research, 15(11-12), 935-946.
Yoshioka, et al., Efficient Generation of Human iPSCs by a Synthetic Self-Replicative RNA, Cell Stem Cell 2013, 13(2):246-254.
Zhang et al., 2007. Dev Biol. 302(1):1-12.
Zeng et al., 2002. Molecular Cell 9:1327-1333.
Zuker & Stiegler, 1981. Nucleic Acids Res. 9, 133-148.
Johnson et al., 1992. Brain Res Mol Brain Res. 12(1-3):95-102.
Joner et al., 2006. Pathology of drug-eluting stents in humans: delayed healing and late thrombotic risk. J Am Coll Cardiol 48(1), 193-202.
Jukema et al., 2011. Restenosis after PCI. Part 1: pathophysiology and risk factors. Nat. Rev. Cardiol. Advance Online Publication, 1-10.
Kalos et al., 2011. Sci. Transl. Med. 201 3(95): 1-11.
Karikö et al., 2008. Incorporation of pseudouridine into mRNA yields superior nonimmunogenic vector with increased translational capacity and biological stability. Molecular Therapy: The Journal of the American Society of Gene Therapy, 16(11), 1833-1840.
Kikuchi et al., 2008. J Dermatol Sci. May; 50(2):87-98.
Kirik et al., 2000. EMBO J. 19: 5562-5566.
Konermann et al., 2015. Author Manuscript, 1-37. Published as: Genome-scale transcriptional activation by an engineered crispr-cas9 complex. Nature. 517:583-588.
Kotani et al., 2006. Journal of the American College of Cardiology 47, 2108-2111.
Krek et al., 2005. Combinatorial microRNA target predictions. Nature Genetics, 37(5), 495-500.
Landgraf et al., 2007. Cell 129:1401-1414.
Laursen et al., 2010. Utilization of unlocked mucleic acid (UNA) to enhance siRNA performance in viro and in vivo. Molecular bioSystems, 6(5), 862-870.
Lee et al., 2002. Nat. Biotechnol. 20:500-505.
Lee et al., 2004. Biomaterials 25:2461-2466.
Lieber, 2010. Author's Manuscript, 1-24. Published in: Annu. Rev. Biochem. 79: 181-211.
Liu et al., 2008. Tex Heart Inst J 37, 194-2010.
Madzak et al., 1992. J Gen Virol. 73(pt 6): 1533-6.
Malek et al., 2001. A mouse knock-in model exposes sequential proteolytic pathways that regulate p27Kipl in G1 and S phase, Nature, 413, 323-327.
Mann & Baltimore, 1985. J Virol. 54(2):401-7.
Margolskee, 1992. Curr Top Microbiol Immunol. 158:67-95.
Marks, 2003. Sirolimus for the prevention of in-stent restenosis in a coronary artery. N Engl J Med 349(14), 1307-1309.
Marx et al., 2011. Author Manuscript pp. 1-16. Published as: Vascular smooth muscle cell proliferation in restenosis. Circ Cardiovasc Interv 4(1), 104-111.
Mendell, 2005. Cell Cycle 4(9):1179-84.
Miller et al., 1985. J Virol. 55(3):521-6.
Miller et al., 1988. J Virol. 62(11):4337-45.
Miller, 1990. Hum. Gene Therap. 1:5-14.
Miller et al., 1992. Mol Cell Biol. 12(7):3262-72.
Miyagishi et al., 2002. Nat. Biotechnol. 20:497-500.
Montgomery et al., 2011. Therapeutic inhibition of miR-208a improves cardiac function and survival during heart failure. Circulation, 124, 1-12 and S1-S19.
Moss, 1992. Curr Opin Biotechnol. 3(5):518-22.
Muzyczka, 1992. Curr Top Microbiol Immunol. 158:97-129.
Needelman & Wunsch, 1970. J. Mol. Biol., 48: 443-453.
Ohi et al., 1990. Gene. 89(2):279-82.
Osada & Takahashi, 2007. Carcinogenesis 28(1):2-12.
Pacher et al., 2007. Genetics 175: 21-29.
Paddison et al., 2002. Genes Dev. 16:948-958.
Page et al., 1990. J Virol. 64(11):5270-6.
Paul et al., 2002. Nat. Biotechnol. 20:505-508.
Peppas et al., 2006. Adv Mater. 18:1345-60.
Petropoulos et al., 1992. J Virol. 66(6):3391-7.

(56) References Cited

OTHER PUBLICATIONS

Porter et al., 2011. NEJM 365:725-733.
Quantin et al., 1992. Proc Natl Acad Sci USA. 89(7):2581-4.
Rabinowitz et al., 2002. J Virol 76:791-801.
Rosenfeld et al., 1992. Cell. 68(1):143-55.
Samulski et al., 1987. J. Virol. 61:3096-3101.
Samulski et al., 1989. J. Virol. 63:3822-3826.
Santulli et al., 2009. In vivo properties of the proangiogenic peptide QK. J Transl Med 7:41, 1-10.
Santulli et al., 2011. Evaluation of the anti-angiogenic properties of the new selective alphaVbeta3 integrin antagonist RGDechiHCit. J Tranl Med 9, 7.
Santulli et al., 2012. CaMK4 Gene Deletion Induces Hypertension. J Am Heart Assoc 1, e001081.
Santulli et al., 2014. A selective microRNA-based strategy inhibits restenosis while preserving endothelial function. Journal of Clinical Investigation, 124(9), 4102-4114.

| Nucleotide | Catalog Number |
|---|---|
| Pseudouridine | N-1019 |
| N-1-methylpseudouridine | N-1081 |
| 5-methoxyuridine | N-1093 |
| 5-hydroxymethylcytidine | N-1087 |
| Immune Stimulation Reduction Transcription Nucleotide Set | K-1018 |
| ARCA Cap | N-7003 |
| Unmodified dNTP Set | N-2505 |

FIG. 30

SELF-REPLICATING CELL SELECTIVE GENE DELIVERY COMPOSITIONS, METHODS, AND USES THEREOF

CROSS-REFERENCE TO RELATED APPLICATIONS

This application is a continuation of U.S. patent application Ser. No. 16/902,198, filed Jun. 15, 2020, which is a divisional of U.S. patent application Ser. No. 16/247,022, filed Jan. 14, 2019, now U.S. Pat. No. 10,709,759, issued Jul. 14, 2020, which is a continuation of U.S. patent application Ser. No. 15/333,074, filed on Oct. 24, 2016, now U.S. Pat. No. 10,188,750, issued Jan. 29, 2019, which claims the benefit of U.S. Provisional Patent Application No. 62/245,457, filed on Oct. 23, 2015, and U.S. Provisional Patent Application No. 62/264,609, filed on Dec. 8, 2015. The entire content of each application is incorporated by reference herein in its entirety.

STATEMENT REGARDING FEDERALY SPONSORED RESEARCH OR DEVELOPMENT

This invention was made with government support under Grant Number HL109133 awarded by National Institutes of Health. The government has certain rights to the invention.

SEQUENCE LISTING

The application includes an electronically submitted Sequence Listing in .txt format. The .txt file contains a sequence listing entitled "2021-08-12_173738-02385_Sequence_Listing_15B161CON.txt" and was created on Aug. 12, 2021, and is 145,882 bytes in size. The Sequence Listing contained in this .txt file is part of the specification and is hereby incorporated herein in its entirety.

BACKGROUND

Despite the remarkable advance in therapeutic strategies over the past decades, the lack of cell selective therapies remains a major hurdle in clinical medicine. As such, there exists a need for improved cell selective therapies.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 30 shows a table listing modified nucleotides that can be used in the cell-selective RNA molecule.

DETAILED DESCRIPTION

Figure 1:
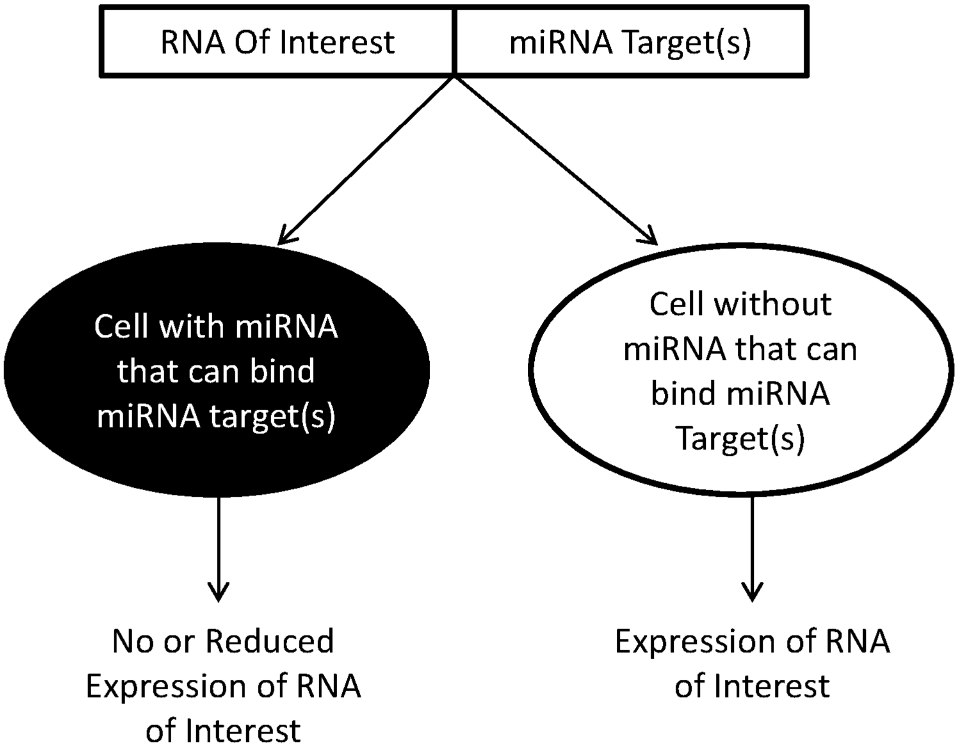
FIG. 1 shows embodiments of a cell-selective RNA molecule and its operation.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "control" is an alternative subject or sample used in an experiment for comparison purpose and included to minimize or distinguish the effect of variables other than an independent variable.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "biodegradable" refers to the ability of a material or compound to be decomposed by bacteria or other living organisms or organic processes.

As used herein, "about," "approximately," and the like, when used in connection with a numerical variable, generally refers to the value of the variable and to all values of the variable that are within the experimental error (e.g., within the 95% confidence interval for the mean) or within±10% of the indicated value, whichever is greater.

As used herein, "effective amount" is an amount sufficient to effect beneficial or desired results. An effective amount can be administered in one or more administrations, applications, or dosages.

As used herein, "administering" can refer to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "preventative" refers to hindering or stopping a disease or condition before it occurs or while the disease or condition is still in the sub-clinical phase.

As used herein, "therapeutic" can refer to treating or curing a disease or condition.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, the terms "cancer," "cancer cells," "neoplastic cells," "neoplasia," "tumor," and "tumor cells" (used interchangeably) refer to cells which exhibit relatively autonomous growth so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wlms tumor. In some embodiments, the cancer is prostate cancer.

The terms "guide polynucleotide," "guide sequence," or "guide RNA" as used herein refers to any polynucleotide sequence having sufficient complementarity with a target polynucleotide sequence to hybridize with the target sequence and direct sequence-specific binding of a CRISPR complex to the target sequence. The degree of complementarity between a guide polynucleotide and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). A guide polynucleotide (also referred to herein as a guide sequence and includes single guide sequences (sgRNA)) can be about or more than about 5, 10, 11, 12, 13, 14, 15, 16, 17, 18, 19, 20, 21, 22, 23, 24, 25, 26, 27, 28, 29, 30, 35, 40, 45, 50, 75, 90, 100, 110, 112, 115, 120, 130, 140, or more nucleotides in length. The guide polynucleotide can include a nucleotide sequence that is complementary to a target DNA sequence. This portion of the guide sequence can be referred to as the complementary region of the guide RNA. In some contexts, the two are distinguished from one another by calling one the complementary region or target region and the rest of the polynucleotide the guide sequence or trans-activating crRNAln (tracrRNA). The guide sequence can also include one or more miRNA target sequences coupled to the 3' end of the guide sequence. The guide sequence can include one or more MS2 RNA aptamers incorporated within the portion of the guide strand that is not the complementary portion. As used herein the term guide sequence can include any specially modified guide sequences, including but not limited to those configured for use in synergistic activation mediator (SAM) implemented CRISPR (*Nature* 517, 583-588 (29 Jan. 2015). A guide polynucleotide can be less than about 150, 125, 75, 50, 45, 40, 35, 30, 25, 20, 15, 12, or fewer nucleotides in length. In some ebodiments, a guide polynucleotide can be 150 nucleotides or more, including, but not limited to 175, 200, 250, 300, 450, 500 or more. It will also be appreciated that the exact number of nucleotides may be any integer bweteen any of the specific numbers given, for example 1, 4, 123, 36, etc. and are all within the spirit and scope of this disclosure. The ability of a guide polynucleotide to direct sequence-specific binding of a CRISPR complex to a target sequence may be assessed by any suitable assay. For example, the components of a CRISPR system sufficient to form a CRISPR complex, including the guide polynucleotide to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide polynucleotide to be tested and a control guide polynucleotide different from the test guide polynucleotide, and comparing binding or rate of cleavage at the target sequence between the test and control guide polynucleotide reactions. Other assays are possible, and will occur to those skilled in the art.

A complementary region of the gRNA can be configured to target any DNA region of interest. The complementary region of the gRNA and the gRNA can be designed using a suitable gRNA design tool. Suitable tools are known in the art and are available to the skilled artisan. As such, the constructs described herein are enabled for any desired target DNA so long as it is CRISPR compatible according to the known requirements for CRISPR activation.

A guide polynucleotide can be selected to reduce the degree of secondary structure within the guide polynucleotide. Secondary structure may be determined by any suitable polynucleotide folding algorithm. Some programs are based on calculating the minimal Gibbs free energy. An example of one such algorithm is mFold, as described by Zuker & Stiegler ((1981) *Nucleic Acids Res.* 9, 133-148). Another example folding algorithm is the online webserver RNAfold, developed at Institute for Theoretical Chemistry at the University of Vienna, using the centroid structure prediction algorithm (see e.g. Gruber et al., (2008) *Cell* 106: 23-24; and Carr & Church (2009) *Nature Biotechnol.* 27: 1151-1162).

Homology-directed repair (HDR) refers to a mechanism in cells to repair double-stranded and single stranded DNA breaks. Homology-directed repair includes homologous recombination (HR) and single-strand annealing (SSA) (Lieber. (2010) *Annu. Rev. Biochem.* 79: 181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks.

Error-prone DNA repair refers to mechanisms that can produce mutations at double-strand break sites. The Non-Homologous-End-Joining (NHEJ) pathways are the most common repair mechanism to bring the broken ends together (Bleuyard et al., (2006) *DNA Repair* 5: 1-12). The structural integrity of chromosomes is typically preserved by the repair, but deletions, insertions, or other rearrangements are possible. The two ends of one double-strand break are the most prevalent substrates of NHEJ (Kirik et al., (2000) *EMBO J.* 19: 5562-5566), however if two different double-strand breaks occur, the free ends from different breaks can be ligated and result in chromosomal deletions (Siebert & Puchta, (2002) *Plant Cell* 14:1121-1131), or chromosomal translocations between different chromosomes (Pacher et al., (2007) *Genetics* 175: 21-29).

It will also be appreciated that CRISPR can also be used to activate specific genes through CRISPR/synergistic activation mediator procedures. These procedures can utilize a guide polynucleotide that incorporates 2 MS2 RNA aptamers at the tetraloop and the stem-loop of the guide RNA such as that described in, but not limited to (*Nature* 517, 583-588 (29 Jan. 2015).

The term "operatively linked" as used herein can refer to the association of nucleic acid sequences on a single nucleic acid fragment so that the function of one is regulated by the other. For example, a promoter is operatively linked with a coding sequence when it is capable of regulating the expression of that coding sequence (i.e., the coding sequence is under the transcriptional control of the promoter). Coding sequences can be operatively linked to regulatory sequences in a sense or antisense orientation. In one example, the complementary RNA regions can be operatively linked, either directly or indirectly, 5' to the target mRNA, or 3' to the target mRNA, or within the target mRNA, or a first complementary region is 5' and its complement is 3' to the target mRNA. The term "operatively linked" as used herein can also refer to the direct or indirect linkage of any two nucleic acid sequences on a singly nucleic acid fragment such that they are indirectly or directly physically connected on the same nucleic acid fragment. The term "operatively linked" as used herein can also refer to the insertion of a nucleic acid within the 5' and 3' end of another nucleic or the direct coupling of a nucleic acid to the 5' or 3' end of another nucleic acid.

As used herein, "specific binding" can refer to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. As another non-limiting example, a miRNA can specifically bind preferably to a miRNA target and not to a non-specific nucleic acid sequence or if binding to a non-specific nucleic acid sequence occurs that no change in the expression or function of the non-specific nucleic acid can be observed or detected.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" can refer to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic RNA molecule including but not limited to tRNA, siRNA, piRNA, miRNA, long-non-coding RNA and shRNA.

As used herein, "deoxyribonucleic acid (DNA)" and "ribonucleic acid (RNA)" generally refer to any polyribonucleotide or polydeoxribonucleotide, which can be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers or coding mRNA (messenger RNA).

As used herein, "nucleic acid sequence" and "oligonucleotide" also encompasses a nucleic acid and polynucleotide as defined elsewhere herein.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide.

"Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "microRNA" can refer to a small non-coding RNA molecule containing about 21 to about 23 nucleotides found in organisms, which functions in transcriptional and post-transcriptional regulation of transcription and translation of RNA. "MicroRNA" can exist as part of a larger nucleic acid molecule such as a stem-loop structure that can be processed by a cell and yield a microRNA of about 21-23 nucleotides.

As used herein, "pharmaceutically acceptable carrier, diluent, binders, lubricants, glidant, preservative, flavoring agent, coloring agent, and excipient" refers to a carrier, diluent, binder, lubricant, glidant, preservative, flavoring agent, coloring agent, or excipient that is useful in preparing a pharmaceutical formulation that is generally safe, non-toxic, and is neither biologically or otherwise undesirable, and includes a carrier or excipient that is acceptable for veterinary use as well as human pharmaceutical use.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "overexpressed" or "overexpression" refers to an increased expression level of an RNA (coding or non-coding RNA) or protein product encoded by a gene as compared to the level of expression of the RNA or protein product in a normal or control cell.

As used herein, "underexpressed" or "underexpression" refers to decreased expression level of an RNA (coding or non-coding RNA) or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein "gene editing", "genome editing," "genome modification" can refer to the non-natural manipulation of genomic DNA such that the genomic DNA contains one or more additional nucleotides or has one or more nucleotides removed from the genomic sequence. Such genome editing can be achieved by techniques such as viral integration of a transgene, homologous recombination insertion of a transgene, and CRISPR related methods and techniques, including but not limited to, the self-replicating RNA and self-replicating cell-selective CRISPR methods described herein. "Gene editing" and "genome editing" or "genome modification" can refer to the deletion and/or addition of nucleotides into the genomic DNA.

As used herein with reference to the relationship between DNA, cDNA, cRNA, RNA, and protein/peptides, "corresponding to" can refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "promoter" can refer to all nucleotide sequences capable of driving or initiating transcription of a coding or a non-coding DNA sequence. The term "promoter" as used herein can refer to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, "selectable marker" can refer to a gene whose expression allows one to identify cells that have been transformed or transfected with a vector containing the marker gene. For instance, a recombinant nucleic acid may include a selectable marker operatively linked to a gene of interest and a promoter, such that expression of the selectable marker indicates the successful transformation of the cell with the gene of interest.

As used herein, "constitutive promoter" can refer to a promoter that allows for continual or ubiquitous transcription of its associated gene or polynucleotide. Constitutive promoters are generally are unregulated by cell or tissue type, time, or environment.

As used herein, "inducible promoter" can refer to a promoter that allows transcription of its associated gene or polynucleotide in response to a substance or compound (e.g. an antibiotic, or metal), an environmental condition (e.g.temperature), developmental stage, or tissue type.

As used herein, "electroporation" is a transformation method in which a high concentration of plasmid DNA (containing exogenous DNA) or RNA is added to a suspension of host cell protoplasts, and the mixture shocked with an electrical field of about 200 to 600 V/cm.

As used herein, "plasmid" can refer to a non-chromosomal double-stranded DNA sequence including an intact "replicon" such that the plasmid is replicated in a host cell.

As used herein, the term "vector" can refer to a vehicle used to introduce an exogenous nucleic acid sequence into a cell. A vector can include a DNA molecule, linear or circular (e.g. plasmids), which includes a segment encoding a polypeptide of interest operatively linked to additional segments that provide for its transcription and translation upon introduction into a host cell or host cell organelles. Such additional segments can include promoter and terminator sequences, internal ribosome entry site, and may also include one or more origins of replication, one or more selectable markers, an enhancer, a polyadenylation signal, microRNA target sequences etc. Expression vectors are generally derived from yeast or bacterial genomic or plasmid DNA, or viral DNA, or can contain elements of both. The term "vector" can also include RNA or circular RNA vectors linked to additional segments that provide for its translation upon introduction into a host cell or host cell organelles. Such additional segments can include 5'Cap, one or more selectable markers, an enhancer, a polyadenylation signal, polyA tail, microRNA target sequences etc.

As used herein, "identity," can refer to a relationship between two or more polypeptide or polynucleotide sequences, as determined by comparing the sequences. In the art, "identity" also refers to the degree of sequence relatedness between polypeptides or polynucleotides as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Neede/man and Wunsch, (J. Mol. Biol., 1970, 48: 443-453,) algorithm (e.g., NBLAST, and XBLAST). The default parameters are used to determine the identity for the polypeptides of the present disclosure.

As used herein, the term "transfection" can refer to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA (unmodified or modified), it may be associated with various proteins or regulatory elements (e.g., a promoter and/or signal element, miRNA target sequences as described herein), or the nucleic acid may be incorporated into a vector or a chromosome.

As used herein, "transformation" or "transformed" can refer to the introduction of a nucleic acid (e.g., DNA or RNA) into cells in such a way as to allow expression of the coding or non-coding portions of the introduced nucleic acid.

As used herein a "transformed cell" can refer to a cell transfected with a nucleic acid sequence.

As used herein, a "transgene" can refer to an artificial gene which is used to transform a cell of an organism, such as a bacterium or a plant.

As used herein, "transgenic" can refer to a cell, tissue, or organism that contains a transgene.

As used herein, the term "recombinant" generally refers to a non-naturally occurring nucleic acid, nucleic acid construct, or polypeptide. Such non-naturally occurring nucleic acids can include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g, a nucleic acid and a constitutive promoter etc.). Recombinant also refers to the polypeptide encoded by the recombinant nucleic acid. Non-naturally occurring nucleic acids or polypeptides include nucleic acids and polypeptides modified by man, including but not limited to miRNA target sequences described herein.

As used herein, the term "exogenous DNA" or "exogenous RNA" or exogenous nucleic acid sequence" or "exogenous polynucleotide" can refer to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

As used herein "miRNA target" or "miRNA target sequence" can refer to the nucleic acid sequence, typically RNA, that a miRNA specifically binds to. The miRNA target can be or include a sequence that is complementary to the miRNA. As an example, microRNA 126 (miR-126) can specifically bind a miR-126 target. Binding of a miRNA to a miRNA target can result in transcription and/or translation inhibition of the nucleic acid sequence, such as through degradation of the nucleic acid sequence (typically mRNA or other type of RNA), that the miRNA target is part of). A microRNA does not have to have perfect complementarity to a miRNA target for specific binding or transcription inhibition to occur.

As used herein "seed sequence" or "seed region" can refer to the conserved heptametrical sequence of a microRNA that has perfect complementarity to the miRNA target. The seed sequence can be at about positions 2-7 from the miRNA 5'-end.

As used herein, "nonstructural viral protein" and similar phrases can refer to proteins encoded by a virus, but are not incorporated into the viron particle.

As used herein "differentially expressed", "differential expression," and the like can refer to the difference in spatial, temporal, and/or amount of expression of a gene, transcript, and/or protein that can be observed between the same or different genes, transcripts, and/or proteins.

Discussion

Despite the remarkable advance in therapeutic strategies over the past decades, the lack of cell selective therapies remains a major hurdle in clinical medicine. Side effects and reduced efficacy due to poor or no selectivity remains the Achilles' heel in the treatment of many diseases and contributes to the significant morbidity and mortality rates associated with many diseases.

Gene therapy holds significant promise to treat, if not cure, many diseases for which there currently is no effective treatment or cure. However, the benefits of gene therapy still remain illusive. Traditional gene therapy approaches rely on pseudo-viral packaging and delivery of the gene to cells. Off-target effects due to ubiquitous overexpression and oncogenesis due to insertional mutagenesis as a result of poor cell selectivity and insertion control remain issues with virus-based gene therapy. Further, size limitations of currently viral-based systems prevent the use of many viral-based systems for the delivery of many genes of interest.

With that said, described herein are cell-selective RNA molecules that can include a gene of interest or guide sequence RNA (gRNA) operatively coupled to one or more miRNA target sites. The cell-selective RNA molecules can be linear or circular, self-replicating, and/or contain one or more chemical modifications that can reduce immunogenecity of the cell-selective RNA molecules. The compositions described herein can be used for the treatment of diseases or symptoms thereof and/or cell selective gene editing. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Cell Selective RNA Molecules

Figure 2:
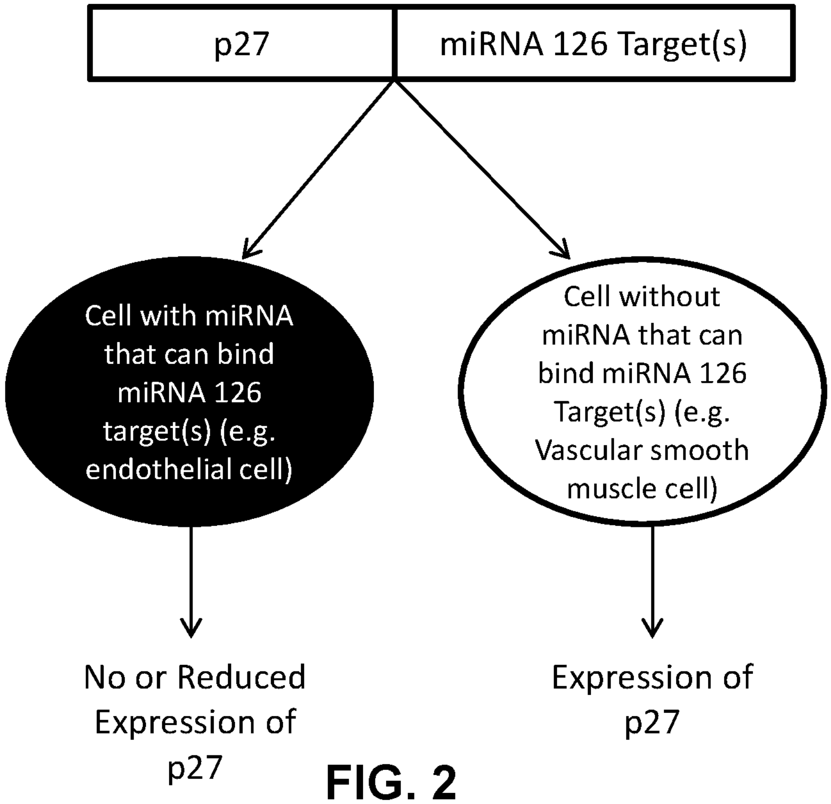
FIG. 2 shows an embodiment of a cell-selective RNA molecule and its operation.
Figure 3:
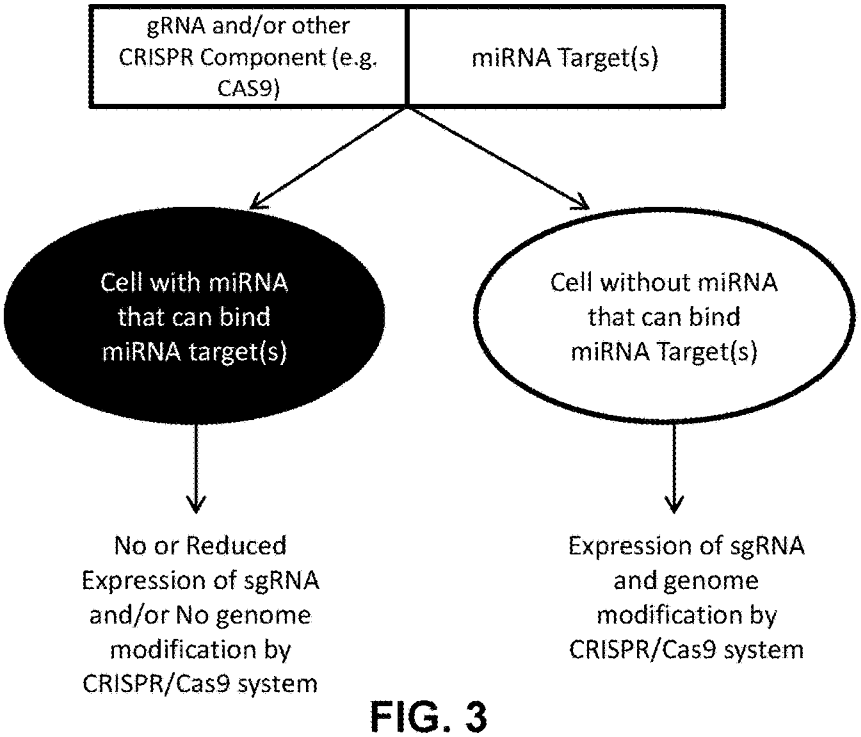
FIG. 3 shows an embodiment of a cell-selective RNA molecule and its operation.

As shown in FIG. 1, the cell-selective RNA molecules can contain one or more RNA molecules of interest. The RNA molecule(s) can be operatively coupled to one or more miRNA target sequences. When introduced to cells that have miRNA that can specifically bind to the miRNA target(s), the miRNA can specifically bind the miRNA target(s) of the cell-selective RNA molecules. This can result in degradation and/or prevent translation of the cell-selective RNA molecules through endogenous pathways (e.g. RISC complex-mediated degradation). Thus, there is no observable expression of the RNA of interest. When introduced into cells that do not express miRNA that can specifically bind to the miRNA target(s) of the cell-selective RNA molecule, the cell-selective RNA molecule can be translated by the cell. It will be appreciated that the same outcome can be realized if a cell expresses the miRNA that can specifically bind the miRNA target(s) at such a low level that binding to the cell-selective RNA does not reduce translation (through degradation or otherwise) of enough cell-selective RNA molecules to inhibit or ablate effective expression of the RNA of interest. In this way expression and/or translation of the RNA of interest can be selective to only cells that do not express miRNA that can bind to the miRNA target(s) in the cell-selective RNA molecule. By way of non-limiting example, FIGS. 2-3 show cell-selective expression of p27, Cas9, and/or gRNA that can be used as part of a CRISPR/Cas9 genome modification system.

In some embodiments, the cell-selective RNA molecule can be a RNA molecule. In other embodiments, the cell-selective molecule can be a DNA molecule that corresponds to (or encodes) cell-selective RNA molecule. The cell-selective RNA molecule or its corresponding DNA molecule can exist as naked RNA or DNA molecule (i.e. not contained in a vector) or contained within a vector.

RNA Molecules of Interest

The cell-selective RNA molecules can contain one or more RNA molecules of interest (ROI). The RNA molecule can correspond to a gene of interest. The ROI can correspond to an untranslated RNA molecule. The ROI can be any RNA molecule, linear or circular. The ROI can contain one or more ROI separated by a self-cleaving 2a peptide sequence. The ROI can contain a sequence corresponding to B18R to mitigate the innate immune response. The B18R can have a sequence that can be 90-100% identical to a sequence that corresponds to SEQ ID NO. 1. ROI can correspond to p27 that can be 90-100% identical to a sequence that corresponds to SEQ ID NO. 2, or any other tumor suppressor gene or suicide gene.

The ROI can be a RNA corresponding to a Cas9 protein. The Casp can have a polypeptide sequence that is identical to or that corresponds to SEQ NO. 3, Cas9n (D10A nickase version of the Cas9 enzyme generates a single-strand DNA break) that correspond to SEQ NO. 4, dCas9 (A catalytically inactive Cas9 or dCas9-repressor peptide fusion can be used to knock-down gene expression by interfering with transcription of the gene) that correspond to SEQ NO. 5 or dCAS9-VP64 activator that corresponds to SEQ NO. 6. The ROI can have or include a sequence 100% identical to any one of SEQ ID NOs: 2-6. The ROI can have or include a sequence that is 90-100% identical to a sequence corresponding to any one of SEQ ID NOs: 2-6. The ROI can be a guide RNA (gRNA).

The ROI can have or include a sequence that is 90-100% identical to SEQ ID NOs: 7. The ROI can be gRNA incorporating two MS2 RNA aptamers gRNA(MS2) cloning backbone include a sequence that is 90-100% identical to SEQ ID NO: 8. The ROI can encode MS2-P65-HSF1 activation helper proteins separated by 2a peptide sequence that have or include a sequence that is 90-100% identical to SEQ ID NO: 9 that can be used as part of a CRISPR/Cas9 genome modification system. The ROI can be self-replicating cell-selective RNA molecules (described below).

miRNA Targets

The cell-selective RNA molecules can contain one or more miRNA targets. In some embodiments, the number of miRNA targets can range from 1 to 20 or more. For example, in some embodiments, the cell-selective RNA molecules can contain 1, 2, 3, 4, or 5 miRNA targets. The miRNA target(s) can be operatively linked to the 5' and/or 3' end of the ROI. The miRNA target(s) can be operatively linked to a 5' untranslated region (UTR) of the ROI and/or a 3' UTR of the ROI. In embodiments having one or more miRNA targets, the miRNA targets can be the same miRNA target, they can each be a different miRNA target. In some embodiments at least two of the miRNA targets are the same. In some embodiments, at least two of the miRNA targets are different. The miRNA targets can be operatively linked to each other and/or the ROI of interest. The miRNA target(s) are nucleotide sequences that can specifically bind one or more miRNAs. The miRNA(s) can have differential spatial and temporal expression. As such, effective expression of the ROI can be controlled both spatially and temporally depending on the miRNA target(s) included in the cell-selective RNA molecule as previously described. Some exemplary constructs incorporating various ROIs are demonstrated in FIGS. 4, 5, 17, 18, 19, 20, 22, and 31-42.

Suitable miRNA targets include, but are not limited to, targets for miR-126, miR-145, miR-296, miR-21, miR-22, miR-15a, miR-16, miR-19b, miR-92, miR-93, miR-96, miR-130, miR-130b, miR-128, miR-9, miR-125b, miR-131, miR-178, miR-124a, miR-266, miR-103, miR-9*, miR-125a, miR-132, miR-137, miR-139, miR-7, miR-124b, miR-135, miR-153, miR-149, miR-183, miR-190, miR-219, miR-18, miR-19a, miR-24, miR-32, miR-213, miR-20, miR-141, miR-193, miR-200b, miR99a, miR127, miR142-a, miR-142-s, miR-151, miR-189b, miR-223, miR-142, miR-122a, miR-152, miR-194, miR-199, miR-215, miR-1b, miR-1d, miR-133, miR-206, miR-208, miR-143, miR-30b, miR-30c, miR-26a, miR-27a, let-7a, and miR-7b.

In some embodiments, an miRNA target can have a sequence or include a sequence that is about 20-100% identical to the complement of any one of SEQ ID NOs: 10-135. In some embodiments, an miRNA target can have a sequence or include a sequence that is about 30-100% identical to the complement of a portion of any one of SEQ ID NOs: 10-135, where the portion is at least 5 consecutive nucleotides that corresponds to the seed sequence. The miRNAs that can specifically bind to the miRNA target(s) included in the cell-selective RNA molecule can have or include a sequence or portion thereof that is about 20-100% identical to any of SEQ ID NOs: 10-135, where a portion is at least 6 consecutive nucleotides that corresponds to the seed sequence. Where a stem-loop sequence is provided, those of skill in the art will appreciate, which portions correspond to the mature miRNA sequences that can be produced from the stem-loop sequences.

Self-Replicating Cell-Selective RNA Molecules

The cell-selective RNA molecules can be configured such that they are self-replicating. In other words, the cell-selective RNA molecules can be RNA replicons. The cell-selective RNA molecules can also include one or more viral RNA sequences that confer self-replication functionality once the cell-selective RNA molecule is introduced to a cell. The viral RNA sequence(s) can be alphavirus RNA sequences. The viral RNA sequence(s) can be Venezuelan Equine Encephalitis, Sindbis, and/or Semliki Forest virus sequence(s). Such sequences will be appreciated and determined by those of skill in the art. The sequences can encode one or more nonstrucutrual proteins and/or an RNA replicase. The viral sequences can be operatively linked to the ROI and/or miRNA target(s). Noninfectious self-replicating viral RNA that lacks the genes encoding the viral structural proteins that encodes four nonstructural replication complex proteins (NSPs) as a single open reading frame (ORF) in addition to the ROI. In some embodiments, the cell-selective RNA molecules do not include an RNA replicase. Replicases are generally known in the art. Non-limiting examples include, but are not limited to, those set forth in Geall et al., (2012) PNAS 109(36) 14604-14609 and Yoshioka et al. (2013) Stem Cell. 13(2):246-254, which are incorporated by reference as if expressed in their entirety.

Promoter Sequences and Other Transcription Elements

The cell-selective RNA molecules can contain one or more promoters. The promoter(s) can be operatively linked to the 5' end of the cell selective RNA molecule. The promoter(s) can be operatively linked at any position between the 5' and 3' end of the cell-selective RNA molecules. The promoter(s) can be operatively linked to the 5' end of an ROI. The promoter(s) can be operatively linked to the 5' end of a miRNA target. The promoter(s) can drive in vitro and/or in vivo transcription of the cell-selective RNA molecule or corresponding DNA molecule.

The promoter can be a eukaryotic promoter. The promoter can be a prokaryotic promoter. The promoter can be a Pol I promoter. The promoter can be a Pol II promoter. The promoter can be a Pol III promoter. The promoter can be a T7, Sp6 or T3 polymerase promoter. Example promoters include, but are not limited to 26S subgenomic promoter, CMV, CAG, SV40, EF1a, PGK1, Unc, beta actin promoter, TRE, UAS, Ac5, Polyhedrin, CaMKlla, GAL1, GAL10, TEF1, GDS, GAPDH promoter, ADH1, cAMV355, Ubi, H1, 7SK, U6, T7, SP6, T7lac. araBAD, trp, lac, Ptac, and pL. The sequences and variants thereof of these promoters as well as other promoters that would be suitable to one of ordinary skill in the art in view of this description are generally known in the art. See also Yoshioka et al. (2013) Stem Cell. 13(2):246-254 and Addgene Plasmid No.: 58976, which are incorporated by reference as if expressed in their entirety.

Markers

The cell-selective RNA molecule can include one or more markers or reporter molecules. Example markers and reporter molecules include, but are not limited to, Examples of selectable markers include, but are not limited to, DNA and/or RNA segments that contain restriction enzyme sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; epitope tags (e.g. FLAG- and His-tags), and, the inclusion of a DNA sequences required for a specific modification (e.g., methylation) that allows its identification. Other suitable markers will be appreciated by those of skill in the art.

The terms "plasmid", "vector" and "cassette" as used herein can refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell.

Vectors

Also provided herein are nucleic acid vectors containing a nucleic acid molecule corresponding to a cell-selective RNA molecule described herein. All or part of the vectors can be capable of being transcribed in vitro without a host cell or in a host cell. The vectors can be capable of being replicated by a host cell. All or part of the vector or a RNA molecule produced from the vector template can be capable of being integrated directly or indirectly into a host cell genome. The vectors can be viral vectors, i.e. vectors that are virus based or incorporate viral proteins or nucleic acids corresponding to a viral protein. Suitable viral vectors can include adenoviral, lentiviral, retroviral, and alpha viral vectors.

Synthesis of the Cell-Selective RNA Molecules

The cell-selective RNA molecules can be synthesized using de novo chemical synthesis. The cell-selective RNA molecules can be synthesized using in vitro transcription from a DNA molecule template. In vitro transcription can occur within a host cell or without a host cell. The cell-selective RNA molecules can also be transcribed in vivo after delivery to a subject. The DNA molecule template can be a DNA molecule or DNA vector containing a DNA sequence corresponding to the cell-selective RNA molecules. These DNA molecules and vectors are described elsewhere herein. The cell-selective RNA molecules can be polyadenylated at the 3' end. The cell-selective RNA molecules can be 5' capped in vitro. The cell-selective RNA molecules can be synthesized with an ARCA Cap at the 5' end. The RNA molecule can be expressed in a bacterial, viral, yeast, plant, insect, or mammalian expression system. Suitable systems will be appreciated by those skilled in the art. The RNA molecule produced from transcription can be purified from a solution and/or other cellular components. Methods of RNA purification will be appreciated by those of skill in the art.

In some embodiments, the cell-selective RNA molecules are modified. The modification can occur during or after synthesis (transcription of the RNA molecule). The modification can be a nucleotide modification. As such, the cell-selective RNA molecules can be synthesized with one or more modified nucleotides. Suitable nucleotide modifications include, but are not limited to, pseudouridine (ΨU), N-1-methylpseudouridine, 5-methoxyuridine, and 5-hydroxymethylcytidine. In some embodiments 0-100% of the nucleotides are substituted. The modifications can reduce immunogenicity of the cell-selective RNA molecules. The modifications can increase transcription and/or translation of the cell-selective RNA molecules.

Delivery of the Cell-Selective RNA Molecules

The cell-selective RNA molecules, corresponding DNA molecule, vectors, virons, or pseudoviral particles described herein can be delivered to a subject as part of a pharmaceutical formulation as described herein. As described elsewhere herein, the cell-selective RNA molecules can be delivered to a cell by transfection, transduction, or by other suitable method. In other embodiments, a DNA based vector or polynucleotide that encodes a cell-selective RNA molecule as described herein can be configured to be delivered to a cell as being incorporated in a virus, pseudovirus, or virus particle. In these embodiments, the cells can be transduced or infected with a virus, pseudovirus, or other virus particle that can deliver the corresponding DNA molecule to the cell. In other embodiments, the cell-selective RNA molecules and/or corresponding DNA molecule can be delivered to a cell via chemical transfection of a cell. Chemical transfection methods include encapsulating the cell-selective RNA molecules and/or corresponding DNA molecules in a liposome or micelle (e.g. cationic liposome), which can then be taken in by the cell via endocytosis. Suitable transfection reagents will be appreciated by those of skill in the art. In further embodiments, the cell-selective RNA molecules and/or corresponding DNA molecules can be incorporated with mesoporous silica nanoparticles that can include a polycation adjunct or large pore mesoporous silica nanoparticles. The mesoporous silica nanoparticles that include the cell-selective RNA molecules and/or corresponding DNA molecules can be taken up by the cell via endocytosis. In other embodiments, the cell-selective RNA molecules and/or corresponding DNA molecules can couple to organic/inorganic silica hybrid nanoparticleswhich can be taken up by a cell via endocytosis. Other delivery methods include electroporation or chitosan polymers. Other delivery methods will be appreciated by those of ordinary skill in the art.

Pharmaceutical Formulations

Also provided herein are pharmaceutical formulations containing an amount of a cell-selective RNA molecule, corresponding DNA molecule (including vectors), and/or viron particle as described herein. The amount can be an effective amount. Pharmaceutical formulations can be formulated for delivery via a variety of routes and can contain a pharmaceutically acceptable carrier. Techniques and formulations generally can be found in *Remmington's Pharmaceutical Sciences*, Meade Publishing Co., Easton, Pa. (20th Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

The pharmaceutical formulations can be administered to a subject in need thereof. The subject in need thereof can have a disease, disorder, or a symptom thereof. Example disease or disorder can include, but are not limited to, a cardiovascular disease, a pulmonary disease, a brain disease, a renal disease, a liver disease, a blood disease, a nervous system disease, an intestinal disease, an ocular disease, and cancer. The pharmaceutical formulations can be disposed on or otherwise coupled to or integrated with a medical device, such as, but not limited to, catheters or stents, such that the pharmaceutical formulation is eluted from the medical device over a time period. The pharmaceutical formulation can therefore be delivered to a subject in need thereof during and/or after a procedure such as an angioplasty, vein draft or organ transplant. Other procedures where such a medical device would be useful will be appreciated by those of skill in the art.

A pharmaceutical formulation can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The construct, biologic molecules and pharmaceutical formulations thereof described herein can be disposed on or otherwise integrated with or coupled to a medical device such as, but not limited to, a catheter or stent, such that the construct, biological molecule can be released to the surrounding local area or systemically over a period of time after insertion or implantation into a subject in need thereof. These can also be referred to as drug eluting medical devices.

Pharmaceutical formulations suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating any of the cell-selective RNA molecules, corresponding DNA molecules, or viron particles as described herein in an amount in an appropriate solvent with one or a combination of ingredients enumerated herein, as required, followed by filtered sterilization. Generally, dispersions can be prepared by incorporating the nucleic acid vectors into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents, bile salts, and fluidic acid derivatives. Transmucosal administration can be accomplished through the use of nasal sprays or suppositories. For transdermal administration, the cell-selective RNA molecules, corresponding DNA molecules, and/or viron particles can be formulated into ointments, salves, gels, or creams as generally known in the art. In some embodiments, the cell-selective RNA molecules, corresponding DNA molecules, and/or viron particles can be applied via transdermal delivery systems, which can slowly release the cell-selective RNA, corresponding DNA molecule, and/or viron particles for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Administration of the cell-selective RNA molecules, corresponding DNA molecules, and/or viron particles is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The pharmaceutical formulations can be administered to a subject by any suitable method that allows the agent to exert its effect on the subject in vivo. For example, the formulations or other compositions described herein can be administered to the subject by known procedures including, but not limited to, by oral administration, sublingual or buccal administration, parenteral administration, transdermal administration, via inhalation, via nasal delivery, vaginally, rectally, and intramuscularly. The formulations or other compositions described herein can be administered parenterally, by epifascial, intracapsular, intracutaneous, subcutaneous, intradermal, intrathecal, intramuscular, intraperitoneal, intrasternal, intravascular, intravenous, parenchymatous, and/or sublingual delivery. Delivery can be by injection, infusion, catheter delivery, or some other means, such as by tablet or spray. In some embodiments, the nucleic acid vectors of the invention are administered to the subject by way of delivery directly to the heart tissue, such as by way of a catheter inserted into, or in the proximity of the subject's heart, or by using delivery vehicles capable of targeting the drug to the heart. For example, the cell-selective RNA molecules, corresponding DNA molecules, and/or viron particles described herein can be conjugated to or administered in conjunction with an agent that is targeted to the heart, such as an aptamer, antibody or antibody fragment. The cell-selective RNA molecules, corresponding DNA molecules, and/or viron particles can be administered to the subject by way of delivery directly to the tissue of interest, such as by way of a catheter inserted into, or in the proximity of the subject's tissue of interest, or by using delivery vehicles capable of targeting the nucleic acid vectors to the muscle, such as an antibody or antibody fragment.

For oral administration, a formulation as described herein can be presented as capsules, tablets, powders, granules, or as a suspension or solution. The formulation can contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the formulations described herein can be combined with a sterile aqueous solution that is isotonic with the blood of the subject. Such a formulation can be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulation described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

Dosage Forms

The pharmaceutical formulations or compositions described herein can be provided in unit dose form such as a tablet, capsule or single-dose injection or infusion vial. Where appropriate, the dosage forms described herein can be microencapsulated. The dosage form can also be prepared to prolong or sustain the release of any ingredient. In some embodiments, the complexed active agent can be the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

In some embodiments, such as for treatments of plants, the topical formulation of a composition or pharmaceutical formulation described herein can be further formulated as a spray and can include a suitable surfactant, wetting agent, adjuvants/surfactant (stickers, extender, plant penetrant, compatibility agents, buffers, drift control additives, and defoaming agents), or any combination thereof so as to formulated as a spray. The compounds, any optional auxiliary active ingredient, suitable surfactant, wetting agent, adjuvants, or any combination thereof can be formulated as a solution, suspension, or emulsion. The spray dosage from can be administered through a spraying device. In some embodiments, the spraying device can be configured to generate the sprayable formulation as a liquid solution is contacted with the complexed active agent compound or formulation thereof. In other embodiments, the sprayable dosage form is pre-made prior to spraying. As such, the spraying device can act solely as an applicator for these embodiments.

In further embodiments, such as for treatments of plants (e.g. such as a herbicide), the dosage form of composition or pharmaceutical formulation described herein thereof can be further formulated as a dust and can include a suitable dry inert carrier (e.g. talc chalk, clay, nut hull, volcanic ash, or any combination thereof so as to be formulated as a dust. The dust can contain dust particles of varying sizes. In some embodiments, the particle size can be substantially homogenous. In other embodiments, the particle size can be heterogeneous. Dosage forms adapted as a dust can contain one or more adjuvants/surfactants (stickers, extender, plant penetrant, compatibility agents, buffers, drift control additives, and defoaming agents).

In some embodiments, the dosage form can be formulated as a bait. In these embodiments, the complexed active agent compound or other formulation thereof can be further formulated to include a food or other attractive substance that can attract one or more insect or other pest. The bait dosage form can be formulated as a dust, paste, gel, or granule. Dosage forms adapted as baits can contain one or more adjuvants/surfactants (stickers, extender, plant penetrant, compatibility agents, buffers, drift control additives, and defoaming agents).

In additional embodiments, the dosage form can be formulated as granules or pellets that can be applied to the environment. These dosage formulations are similar to dust formulations, but the particles are larger and heavier. The granules can be applied to soil or other environmental area. Dosage forms adapted as granules or pellets can contain one or more adjuvants/surfactants (stickers, extender, plant penetrant, compatibility agents, buffers, drift control additives, and defoaming agents).

The dusts, granules, and pellets described herein can be formulated as wetable dusts, granules, and pellets, soluble dusts granules, and pellets, and/or water-dispersible granules, and/or dry flowables.

The dosage form can be adapted for impregnating (saturating) an object or device, which then can be carried by, worn, or otherwise coupled to an organism in need thereof. In some embodiments, the dosage form can be impregnated onto a collar, bracelet, patch, adhesive tape, livestock ear tags, clothing, blankets, plastics, nets, and paints. The composition or pharmaceutical formulation thereof can be formulated and impregnated in the object or device such that the composition or pharmaceutical formulation evaporates over time, which releases the composition and/or pharmaceutical formulation into the air and/or environment surrounding the organism and/or onto the organism.

The dosage form can be adapted as a fumigant, which is a formulation that forms a gas when utilized or applied. In some embodiments, the composition and/or pharmaceutical formulation thereof can be supplied as a liquid when packaged under pressure and change to a gas when they are released. In other embodiments, the composition and/or pharmaceutical formulation thereof can be supplied as a volatile liquid when enclosed in a container (not under pressure). Others can be formulated as solids that release gases when applied under conditions of high humidity or in the presence of high water vapor. Dosage forms adapted as fumigants can contain one or more adjuvants/surfactants (stickers, extender, plant penetrant, compatibility agents, buffers, drift control additives, and defoaming agents).

Effective Amounts

The pharmaceutical formulations can contain an effective amount of a composition described herein and/or an effective amount of an auxiliary agent. In some embodiments, the effective amount ranges from about 0.001 pg to about 1,000 g or more of the composition described herein. In some embodiments, the effective amount of the composition described herein can range from about 0.001 mg/kg body weight to about 1,000 mg/kg body weight. In yet other embodiments, the effective amount of the composition can range from about 1% w/w to about 99% or more w/w, w/v, or v/v of the total pharmaceutical formulation.

Combination Therapy

The pharmaceutical formulations or other compositions described herein can be administered to a subject either as a single agent, or in combination with one or more other agents. Additional agents include but are not limited to DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Multiple cell-selective ROI can be administered simultaneously in a combination treatment.

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/ tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Devices Containing the Cell Selective RNA Molecules

Also described herein are medical devices that can contain a composition or pharmaceutical formulation as described herein. In some embodiments, the composition or pharmaceutical formulation described herein can be encapsulated in one or more polymers. In some embodiments, the polymers are biocompatible polymers. The polymers can be FDA approved polymers. Suitable polymers can include, but are not limited to phosphorylcholine-based polymers, poly lactic-co-glycolic acid (PLGA), polyethylene glycol (PEG), chitosan, cationic nanoemulsion, cationic electrodeposition coating or lipid nanoparticles. The composition or pharmaceutical formulations can be encapsulated in the polymer and the polymer can be applied to the medical device. In use, the compositions and/or pharmaceutical formulations described herein can be released from the polymer into the surrounding environment and be utilized by cells in the surrounding environment.

Suitable medical devices include, but are not limited to, stents, spinal plates, pins, screws, replacement joints and components thereof, catheters, coated balloons, cannulas, bone plates, spacers, replacement discs, stabilization rods, and surgical mesh.

Uses of the Cell Selective RNA Molecules and Devices

The compositions and formulations described herein can be used to selectively deliver a translated RNA (e.g. a gene) or untranslated RNA (gRNA) to a cell. In this way, the compositions and formulations described herein can be used to treat and/or prevent a disease, disorder, or symptom thereof by delivering the ROI to a cell. Selective expression of the ROI can increase treatment or preventive efficacy by decreasing side effects.

When the ROI includes a gRNA or sgRNA(MS2), dCas9, dCas9-VP64 fusion or MS2-P65-HSF1 the compositions can be also used for genome editing using the CRISPR/Cas9 system, which includes the addition or deletion of one or more nucleotides to the genome or exon skipping. This can result in gene knock down, knock out, gene repair, gene suppression or gene activation. Thus, in this way genome editing can be cell-selective because the gRNA and/or sgRNA(MS2), Cas9, dCas9, dCas9-VP64 fusion or MS2-P65-HSF1 will only be present in cells lacking the miRNA that can bind the target(s) in the cell-selective RNA molecule.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Despite the remarkable advances in therapeutic strategies over the past decades the lack of cell selective therapies remain a major overarching problem in clinical medicine. One clear example for this challenge is the deadly consequences of the non-selective agent used on the drug-eluting stents (DES) that were developed to inhibit neointimal overgrowth of vascular smooth muscle cells (VSMCs) following percutaneous intervention.

While DES significantly reduced the occurrence of restenosis compared with a bare-metal stent (BMS), they do not completely eliminate this challenging problem. Moreover, stent thrombosis (ST), reinfarction, and neoatherosclerosis within stent segments have emerged as major safety concerns with DES, all predominantly attributed to the lack of reendothelialization of diseased vessel walls with competent endothelial cells (ECs). DES deployment inevitably traumatizes the normal competent endothelium structure. Compounding this insult, the drugs eluted from the stents, while not delivered systemically, are still universally deleterious to all cell types exposed to the eluted drug, proving toxic to ECs and drastically reducing the quality of regenerating endothelium. This incompetent endothelium, with poorly formed cell-to-cell junctions reduced expression of anti-thrombotic molecules and endothelial nitric oxide synthase (eNOS), can no longer function normally to maintain vascular tone and fluid-tissue homeostasis. Thus, this requires patients to comply with at least 12 months of dual anti-platelet therapy.

Newer generations of DES, with more sophisticated platforms, thinner struts, and biocompatible polymers have been developed to combat DES-associated risks. Yet, they still deploy the same non-selective drugs (paclitaxel, sirolimus or its analogs, everolimus, zotarolimus and biolimus, with improved pharmacokinetics). Current DES devices with low rates of restenosis and ST translate into a significant number of patients that will suffer from myocardial infarction and death due to the large number of percutaneous coronary intervention (PCI) procedures performed worldwide every year. In fact, percutaneous interventions are among the most performed procedures in Medicine. In the US alone, nearly 1 million patients undergo PCI for symptomatic coronary artery disease (CAD) every year, and non-selective DES are deployed in at least 75% of these cases. In 2010, the DES segment contributed 55%-60% of the global coronary stent market and is expected to reach USD 5.3 billion in 2016 due to the growing aging population and lifestyle changes leading to obesity. The market for DES is growing at 9.0% in the United States, 3.1% in Europe, 10% in Asia-Pacific and 3.1% in the rest of the world. These numbers will potentially expand as DES deployment is used in percutaneous interventions to treat peripheral artery disease (PAD) that affects more than 10 million people in the US, with symptomatic lower-extremity PAD, renal artery stenosis and carotid artery disease.

Although percutaneous transluminal angioplasty (PTA) and stenting achieve a greater lumen diameter, vessel remodeling and restenosis remain its Achilles' heel contributing to significant morbidity and mortality rates in these patients. To date, cell-selective drugs that can discriminate between proliferating VSMCs, inflammatory cells and ECs are not available. Since vascular ECs provide crucial protection against thrombosis, lipid uptake and inflammation, there is a need to develop a cell-selective therapy that can inhibit VSMC proliferation and inhibit infiltration of inflammatory cells, yet spare ECs to carry on their vital functions.

A viral vector approach has been previously developed that contained an EC specific miRNA target sequence (target for miR-126). In that work an adenoviral vector (Ad-p27-126TS) containing target sequences complementary to the mature miR-126-3p strand at the 3'-end of the cyclin-dependent kinase inhibitor p27Kip1 (p27). This approach allowed for exogenous p27 to be selectively overexpressed in VSMCs and infiltrate inflammatory cells, yet preserving the ECs. This therapy achieved results in an established rat model of balloon angioplasty, selectively inhibiting neointimal hyperplasia and inflammation while simultaneously promoting vessel reendothelialization, reducing hypercoagulability and restoring the endothelium-dependent vasodilatory response to levels indistinguishable from uninjured controls. (FIGS. 21-29).

Due to complications with viral gene delivery, this Example describes a messenger RNA based, cell-selective nanotherapy utilizing the mRNA or self-replicating RNA that can be based on an alphavirus genome. This strategy can match the potency of viral vectors yet avoid the serious safety concerns associated with recombinant virus-based therapeutics. This approach can reduce the need for repeated revascularization, reduce the need for prolonged dual anti-platelet drug regimens, and ultimately reduce the morbidity and mortality of CAD and PAD patients. This mRNA based cell-selective nanotherapy could not only replace the use of stents, but potentially treat lesions where DES cannot be deployed or DES is contraindicated, such as in stent restenosis, bifurcations, torturous vessels, small vessels or long calcifications. In addition to its potential benefit in CAD and PAD, this approach can be applied to benefit multiple other stenotic conditions, including transplant vasculopathy, arteriovenous fistulae, and vein graft failure, which all result from VSMC hyperplasia and EC dysfunction. Over 200,000 cardiovascular surgical procedures utilizing venous grafts fail each year in the US, primarily due to restenosis caused by VSMC hyperplasia. This mRNA based cell-selective approach may also inhibit vascular remodeling in deadly diseases such as pulmonary hypertension and pulmonary fibrosis, which still has no cure. The versatile concept of mRNA based, cell-selective nanotherapy can be broadly applied across disciplines and for treating any disease, including but not limited to, liver cirhosis and cancer. This tailored mRNA-based, cell-selective nanotherapy represents an exciting translational and potentially transformative approach in modern clinical medicine.

mRNA-based therapeutics represent a game-changing technology and hold great promise for the treatment of human diseases including genetic disorders, infections, degenerative diseases and cancer. Many are the advantages of these versatile mRNA-based therapies. They can be produced very quickly, cost effectively and in a cell-free system at good manufacturing practice quality. Furthermore, any nucleotide sequence needed can be synthetically produced and stored at room temperature. Importantly, chemically modified mRNA that does not change the amino acid sequence of the corresponding protein not only decreases activation of the innate immune pathway but also improves the stability and enhances the translation levels. mRNA is non-replicative and therefore considered a very safe biomolecule that allows transient protein expression of every protein in virtually all cell types including non-dividing cells. Moreover, no nuclear localization, promoter elements or transcription is required and unlike recombinant virus-vectors the probability of genomic integration is nearly nonexistent. Lastly, chemically modified mRNAs that elude the body's innate immune response make therapeutic gene products and protein replacement therapies possible. However, there still exists the challenge of cell- or tissue-specific delivery that hinders virtually any type of therapeutic agent.

To overcome the deficiencies stated above the miRNA-based cell selective approach can be utilized in a chemically modified self-replicating RNA platform to achieve long lasting cell-selective targeting that can inhibit proliferating VSMCs and infiltration of inflammatory cells while allowing ECs to reendothelialize vessel walls and maintain their crucial function. miR-126 is enriched in ECs and is a pivotal regulator of vascular integrity and angiogenesis. Moreover, miR-126 was observed to be up-regulated following arterial injury and in atherosclerotic plaques. The approach described herein utilizes EC-specific expression of miR-126 to drive cell-specific expression of therapeutic genes of interest.

Figure 22:
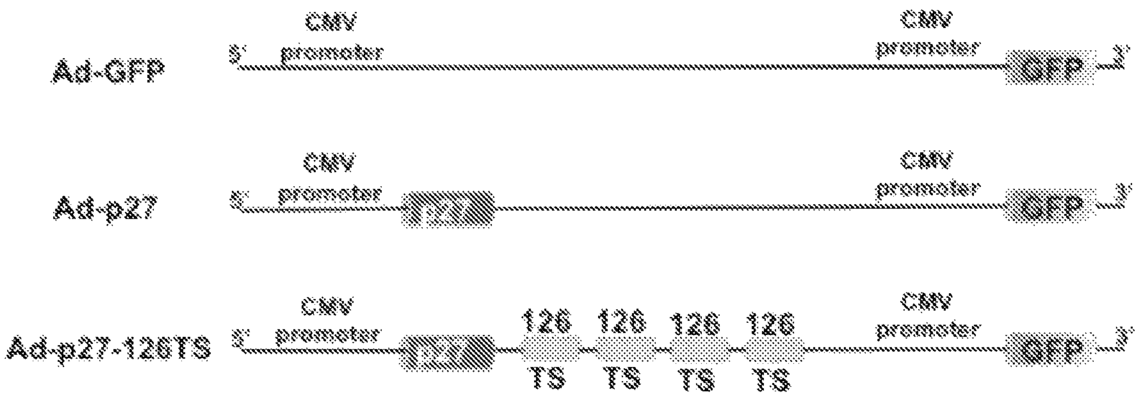
FIG. 22 shows embodiments of adenoviral vector constructs for cell-selective gene delivery.
Figure 23:
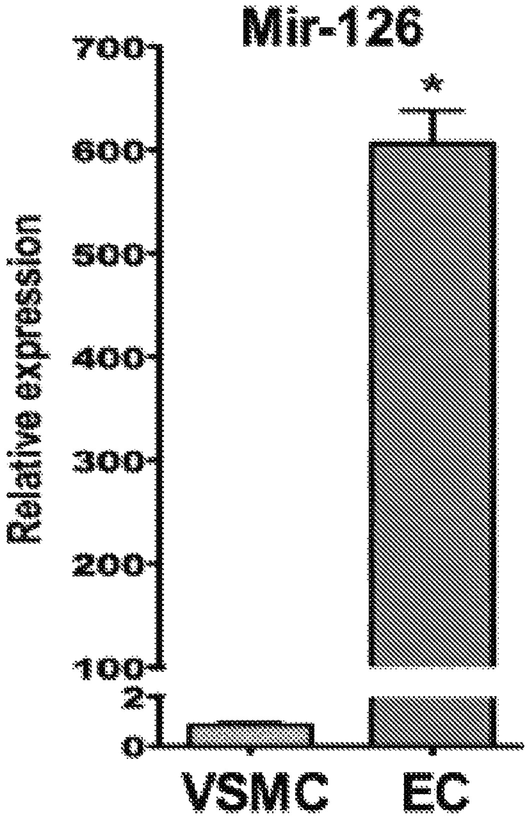
FIG. 23 shows a graph demonstrating high levels of expression of endogenous miR-126-3p in human ECs as determined by RT-qPCR.
Figure 24:
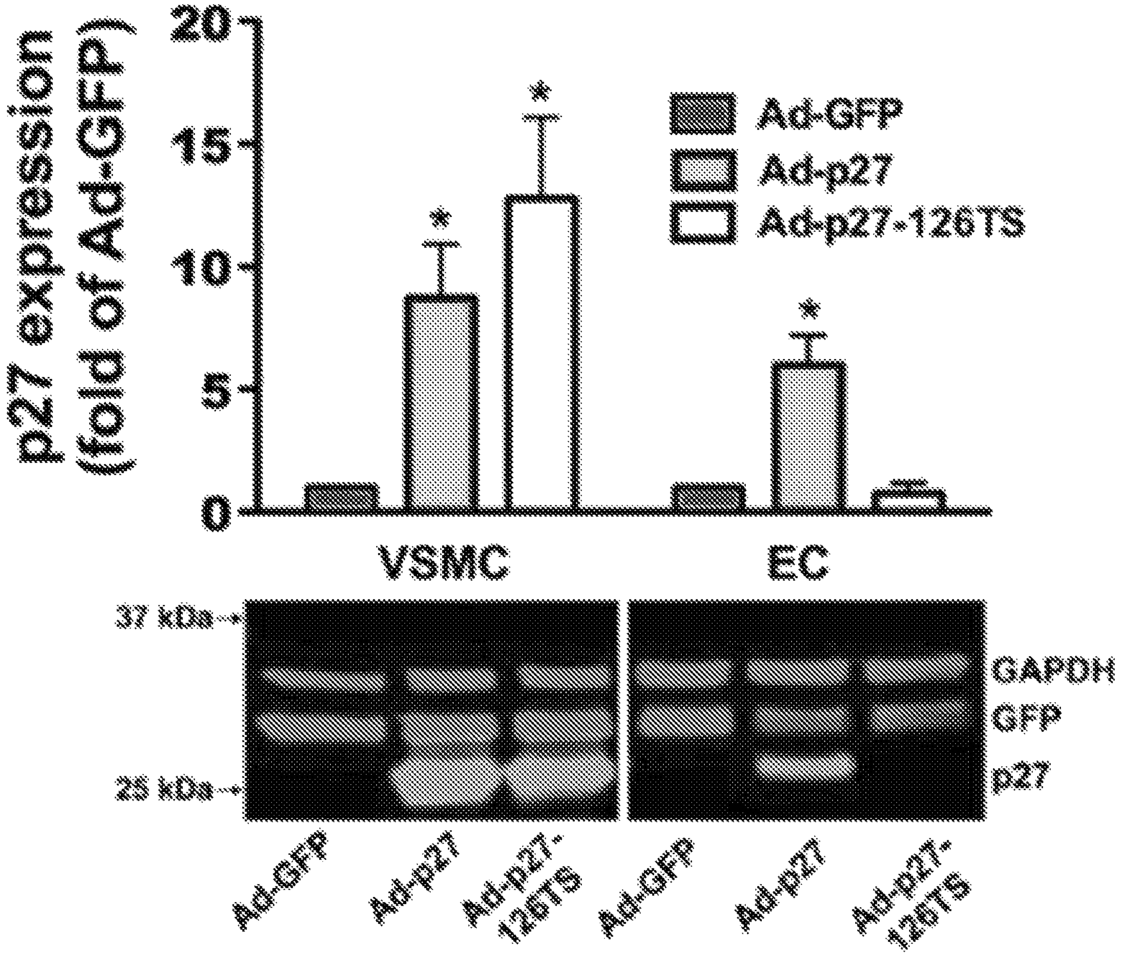
FIG. 24 shows representative immunoblots of p27 expression and corresponding graphs demonstrating densitometric quantification (n=3). Data represent the mean±SEM. Data comparisons were made using 1-way ANOVA with Tukey-Kramer's post hoc test. *P<0.01 versus Ad-GFP.
Figure 25:
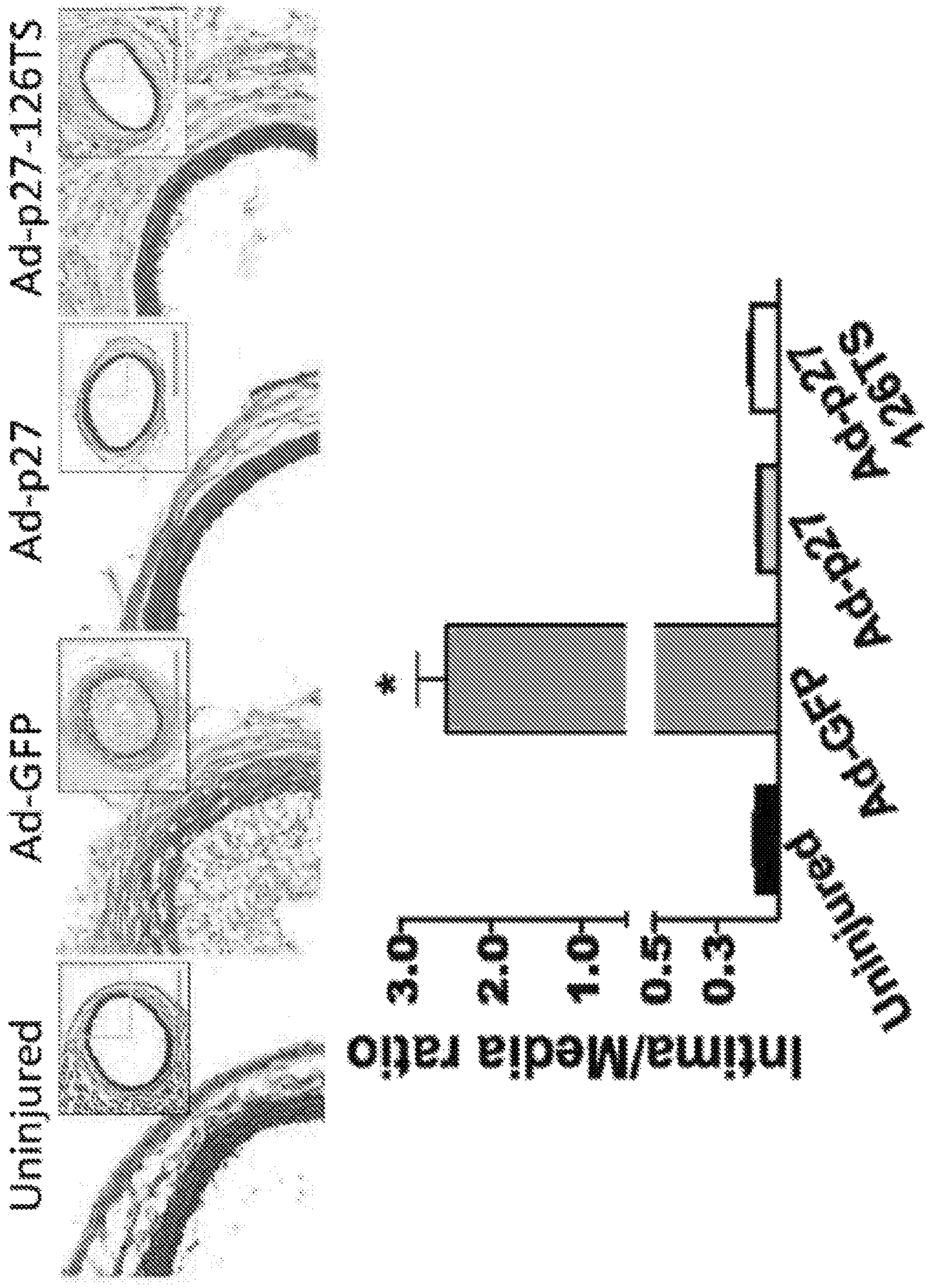
FIG. 25 shows images and corresponding graph demonstrating that treatment with Ad-p27-126TS inhibits neointimal hyperplasia. Representative H&E-stained sections 2 weeks after balloon injury. Scale bars: 500 μm; original magnification, ×10 (insets show the whole arterial section at ×5 original magnification). Intima/media ratios were calculated from at least 6 rats/group. Data represent the mean±SEM and were compared using 1-way repeated measures ANOVA followed by Tukey-Kramer's post hoc test. *P<0.01 versus uninjured arteries.
Figure 26:
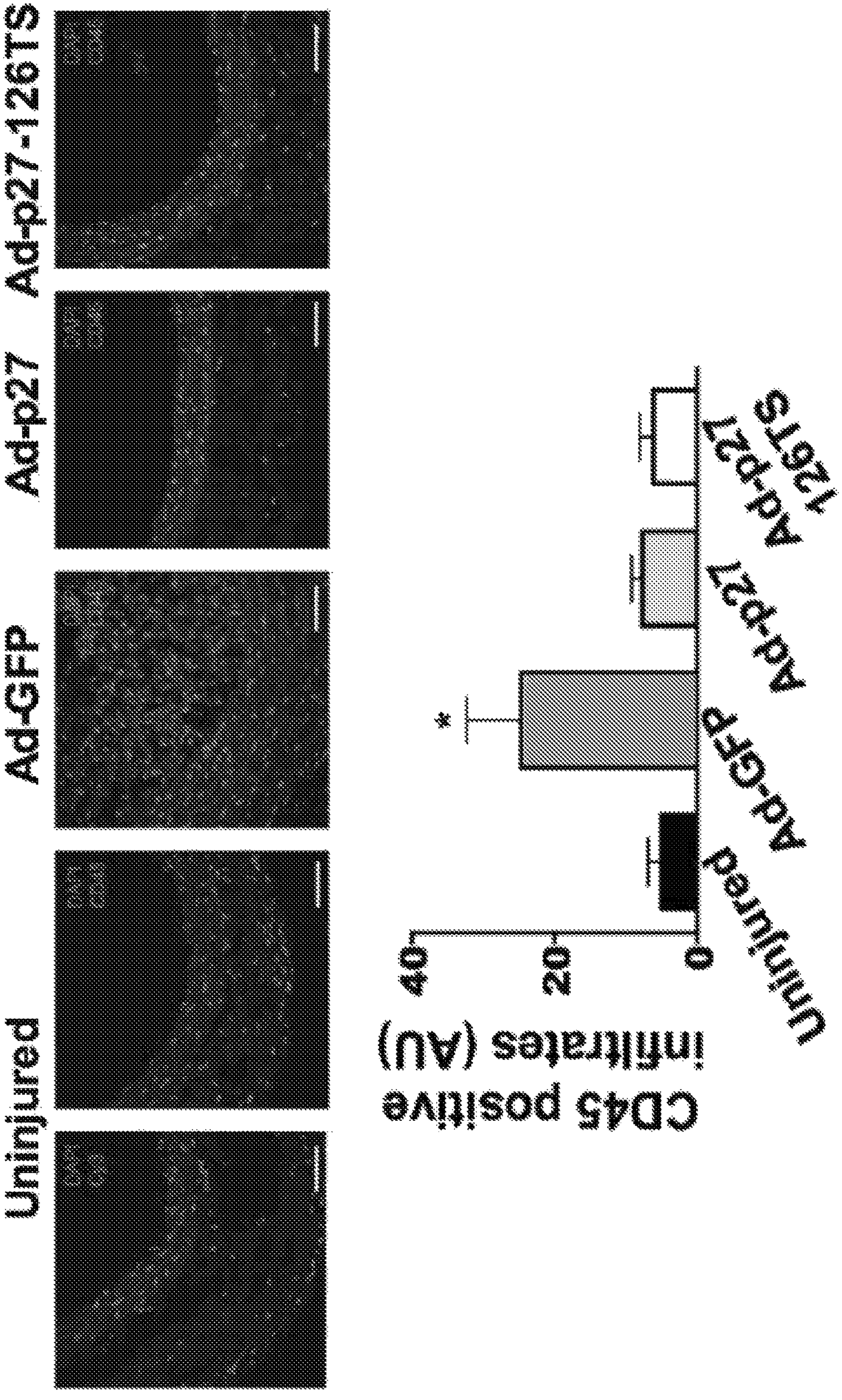
FIG. 26 shows images and corresponding graph demonstrating that treatment with Ad-p27 or Ad-p27-126TS inhibited infiltration of inflammatory cells to the balloon injured vessel. Representative cross-sections of rat carotid arteries immunostained for CD45, 2 weeks after balloon injury. Nuclei were counterstained with DAPI. No positive staining was observed in the negative control sections (Cy3 alone). White scale bars: 100 μm (magnification ×40). CD45 positive cells were quantified by counting the number of CD45 positive cells in the intimal and medial areas from at least 3 sections/group. Data represent the mean±SEM and were compared using 1-way repeated measures ANOVA followed by Tukey-Kramer's post hoc test. *P<0.01 versus uninjured arteries.
Figure 27A:
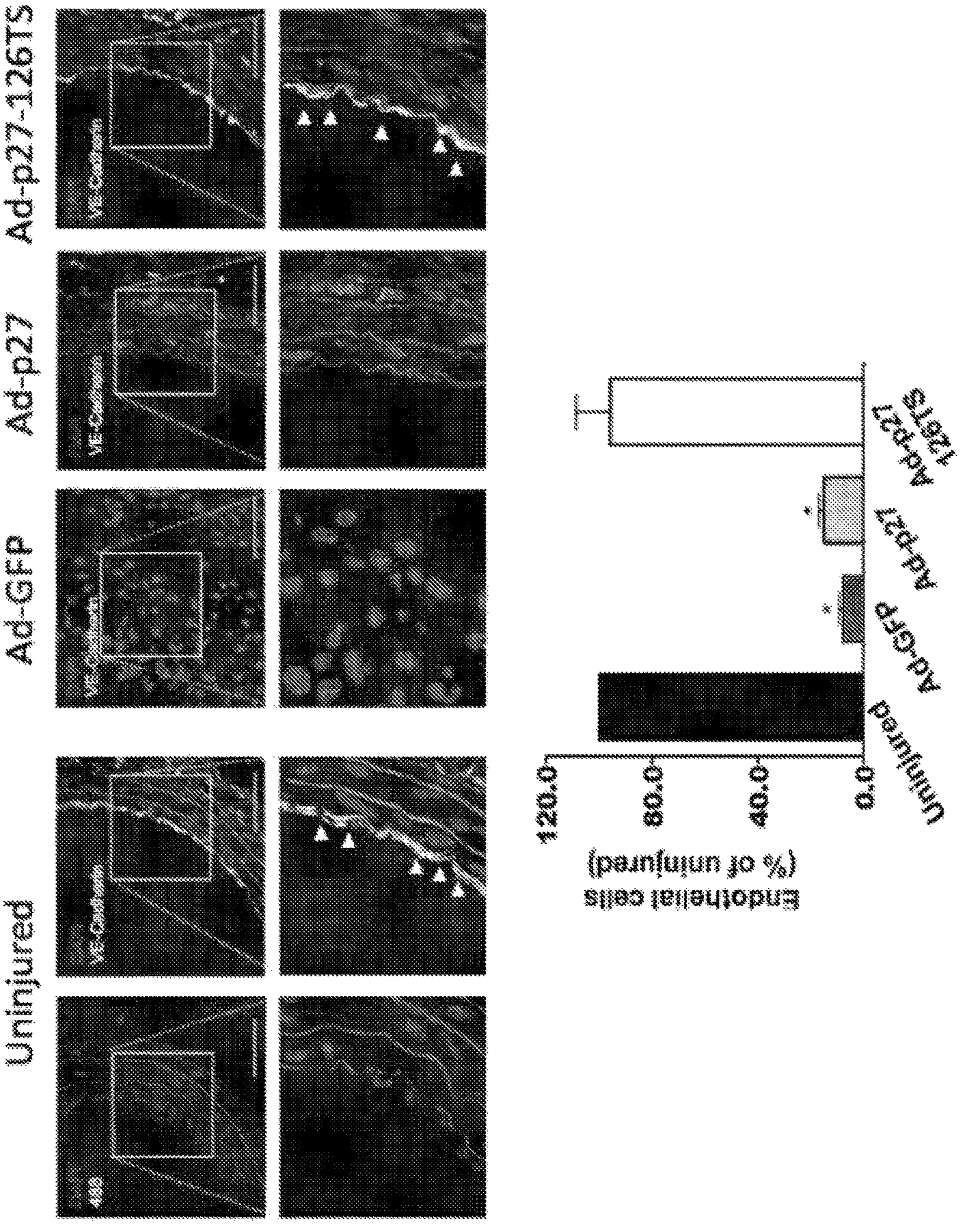
FIGS. 27A-27B show images and graphs demonstrating that treatment with Ad-p27-126TS can allow for rapid and extensive reendothelialization of injured arteries within 2 weeks. Representative confocal images of cross-sections (FIG. 27A) and tridimensional en-face longitudinal arterial preparations (FIG. 27B) of rat carotid arteries immunostained for VE cadherin 2 weeks after injury. Nuclei were counterstained with DAPI. Scale bars: 100 μm; original magnification, ×60 and ×120 (insets). Arrowheads indicate ECs beyond the inner autofluorescent elastic laminae. Endothelial coverage was quantified by counting the number of VEcadherin-positive cells in the circumference of the lumens from at least 6 rats/group. Data represent the mean±SEM and were compared using 1-way repeated measures ANOVA followed by Tukey-Kramer's post hoc test. *P<0.01 versus uninjured arteries.
Figure 27B:
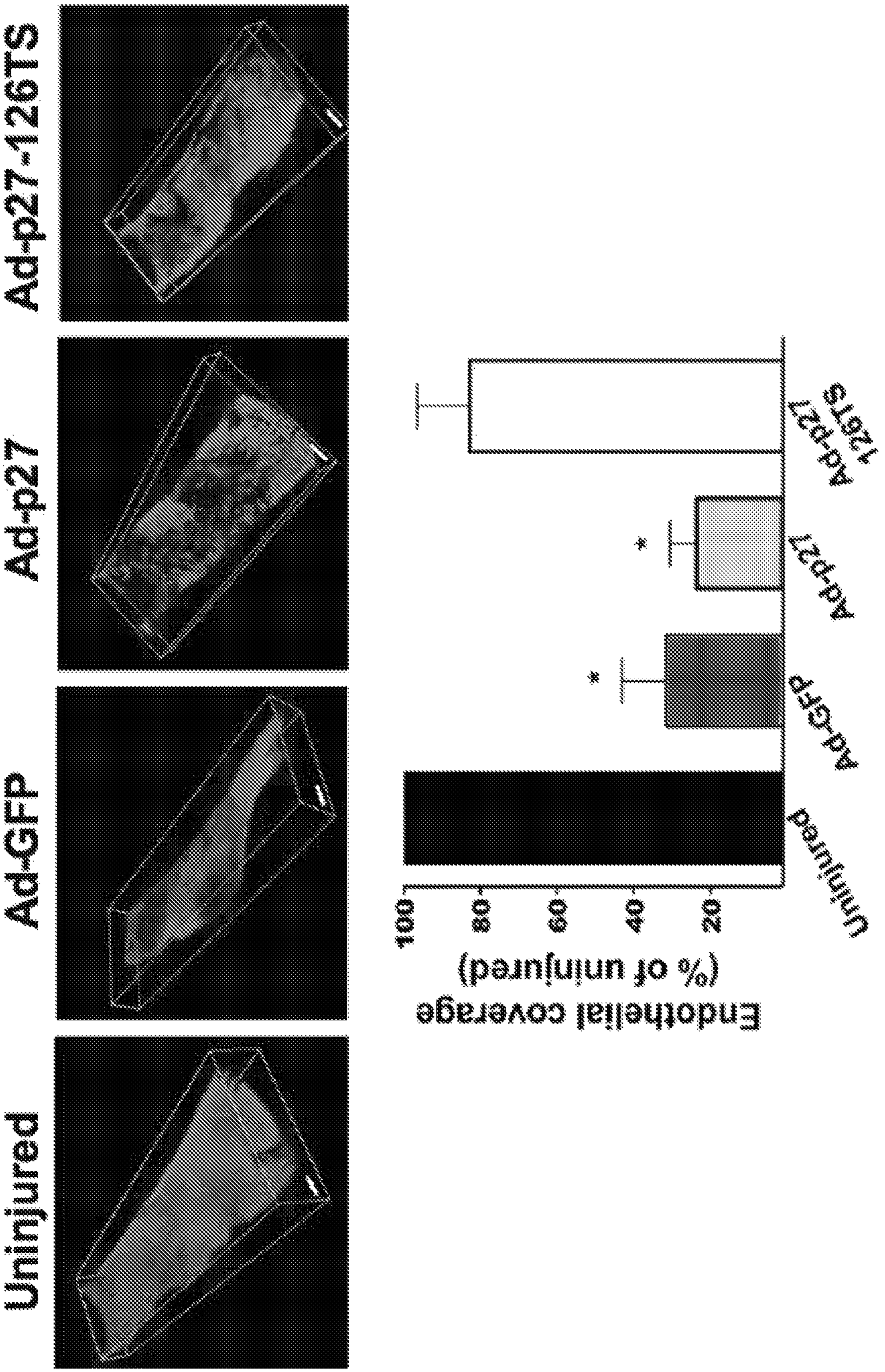
Figure 28:
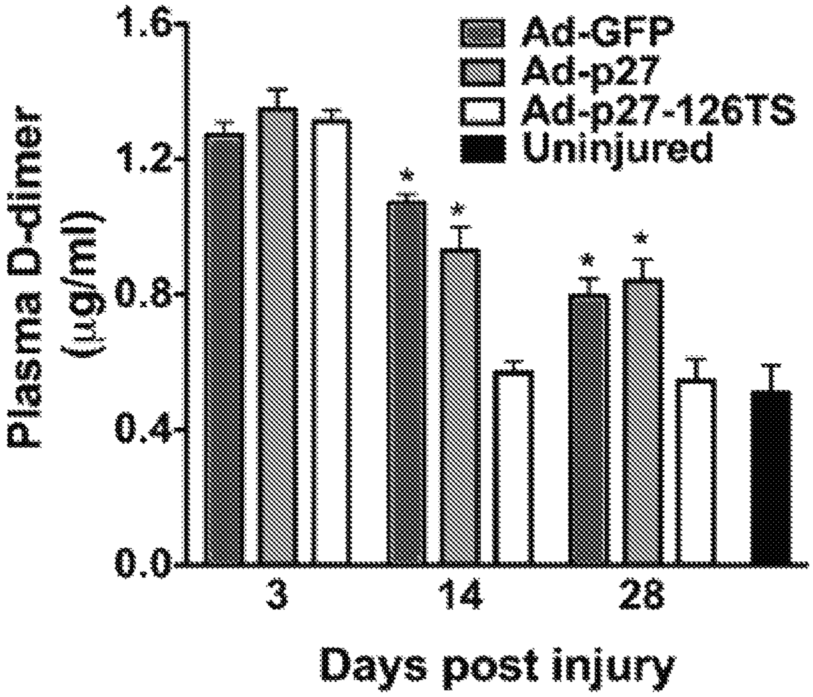
FIG. 28 shows a graph demonstrating that treatment with Ad-p27-126TS can reduce plasma D-Dimer levels of injured arteries. Immunoassay of plasma D-dimer levels before (uninjured) and 3, 14, and 28 days after balloon injury. n=5 rats/group. Data represent the mean±SEM and were compared using 1-way repeated measures ANOVA followed by Tukey-Kramer's post hoc test. *P<0.01 versus uninjured arteries.

As proof of principle, an adenoviral vector (Ad-p27-126TS) containing target sequences complementary to the mature miR-126-3p strand at the 3'-end of the p27 to selectively avoid p27 overexpression in ECs, but not in VSMCs was designed FIG. 22-23. Employing this single comprehensive nanotherapy in a rat carotid balloon injury model we were able to inhibit neointimal hyperplasia, inhibit infiltration of inflammatory cells to the injury site, and at the same time complete reendothelialization of the vessels was achieved as soon as 2 weeks post injury restoring the endothelium-dependent vasodilatory response to levels indistinguishable from uninjured controls and reducing the plasma D-Dimer levels of injured vessels to levels observed in uninjured controls FIG. 25-29.

Incomplete and incompetent endothelial coverage in the vessel when deployed with current DES in PCI procedures greatly increased the risk of potentially catastrophic events such as late ST, primarily caused by the lack of drug specificity. Therefore, a therapy that would selectively inhibit VSMC proliferation, migration and inflammatory cell infiltration without affecting reendothelialization and EC function in the treated vessels would be advantageous. To establish proof of principle for cell-selective inhibition we chose to overexpress p27 in a cells selective manner due to the proven role it plays in the pathophysiology of vascular remodeling. As one of the most potent members of the Cip/Kip family of cyclin-dependent kinase (CDK) inhibitors, p27 binds and modulates cyclin D-, E- and A-dependent kinases, resulting in G1/S transition failure and cell cycle arrest. In healthy arteries, p27 is constitutively expressed in quiescent VSMCs. Upon vascular injury, however, multiple response mechanisms are initiated to conclude with a rapid downregulation of p27, activating and enabling VSMCs to resume cell division. This reentry into the cell cycle triggers intimal hyperplasia, leading to vascular restenosis. p27 knockout mice display a significant increase in VSMC proliferation and develop extensive arterial lesions. In contrast, overexpression of exogenous p27 in VSMCs instigates G1 phase arrest, resulting in VSMC growth inhibition and a significant reduction of neointimal lesion formation in both a porcine femoral arterial injury model as well as a rat carotid model of balloon angioplasty. Moreover, p27 has been shown to play a key role in atherosclerosis. Indeed, p27 deficiency leads to increased atherosclerotic plaque formation in Apoe-/-mice. Lastly, previous reports show that p27 directly regulates the proliferation and migration of bone marrow-derived cells (hematopoietic and non-hematopoeitic) to the damaged vessels to reconstitute vascular lesions. Therefore, p27 is a particularly ideal candidate for cell-selective regulation. This approach also takes advantage of the established fact that miR-126 is robustly enriched in EC and is a pivotal regulator of vascular integrity and angiogenesis. Moreover, miR-126 was shown to be up-regulated following arterial injury and in atherosclerotic plaques.

Figure 29:
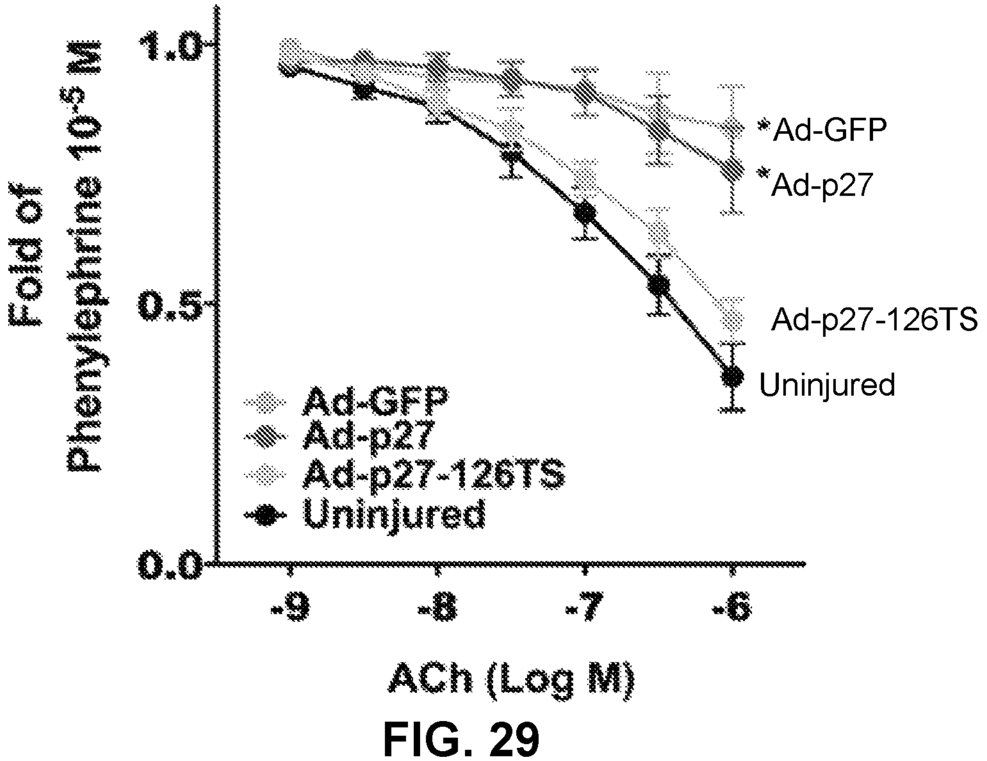
FIG. 29 shows a graph demonstrating that treatment with Ad-p27-126TS can restore the endothelium-dependent vasodilatory response of injured arteries to levels of uninjured controls. Vascular reactivity analysis on carotid rings 2 weeks after balloon injury Ad-p27-126TS treated vessels show vasodilatory in response to acetylcholine (ACh). n=5-6 rats/group. Data represent the mean±SEM and were compared using 2-way repeated measures ANOVA followed by Tukey-Kramer's post hoc test. *P<0.01 versus uninjured arteries.
Figure 31:
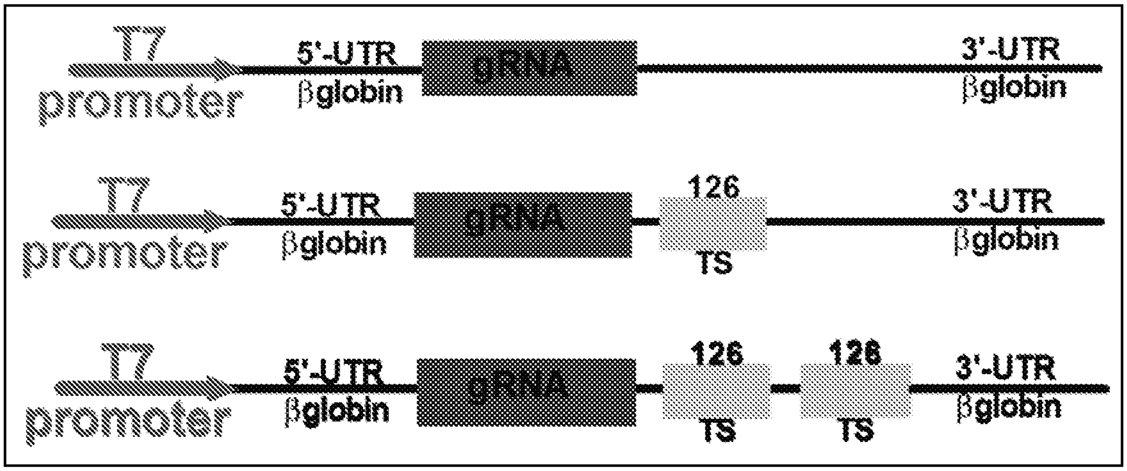
FIG. 31 shows embodiments of a cell-selective gRNA construct.
Figure 32:
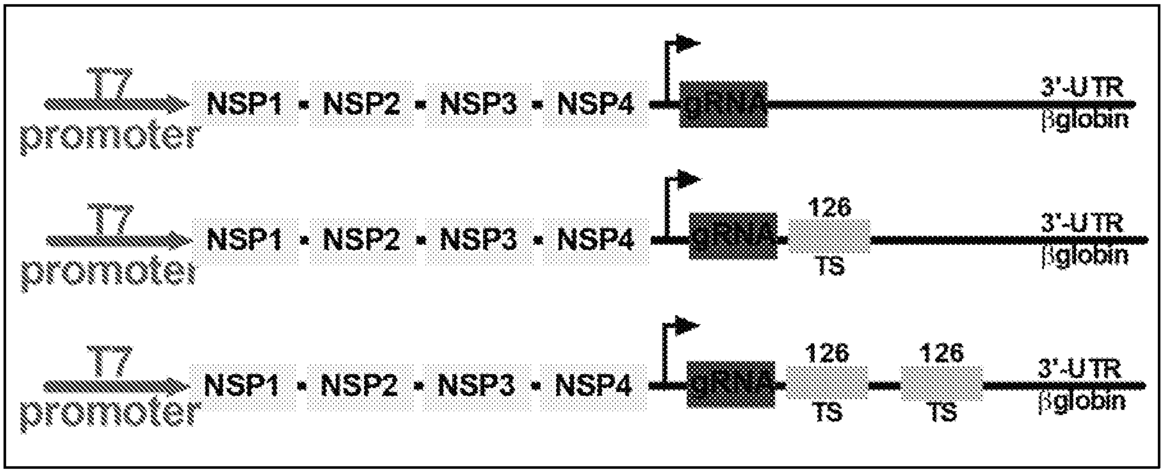
FIG. 32 shows embodiments of a self-replicating, cell-selective gRNA construct.
Figure 33:
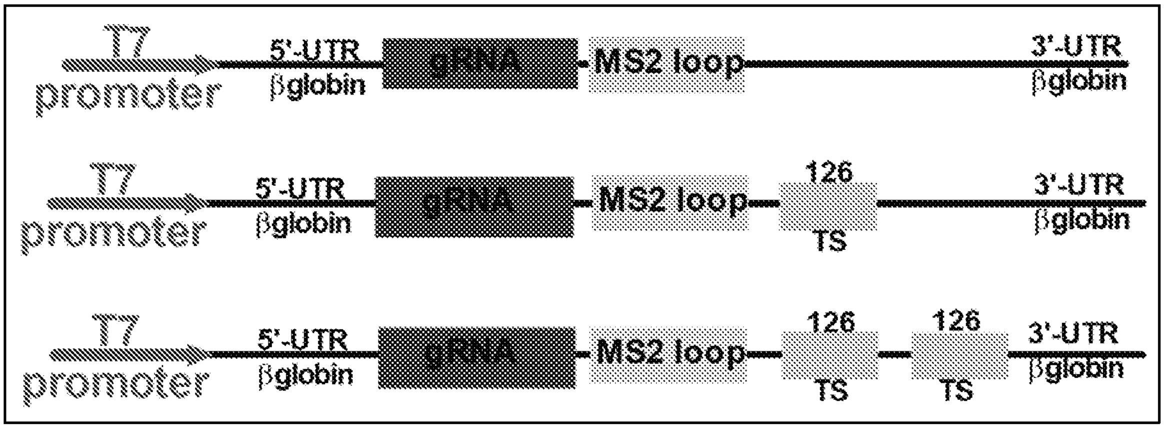
FIG. 33 shows embodiments of a cell-selective gRNA 2.0 construct for CRISPR/Cas9 Synergistic Activation Mediator (SAM) genome editing. *Nature* 517, 583-588 (29 Jan. 2015).
Figure 34:
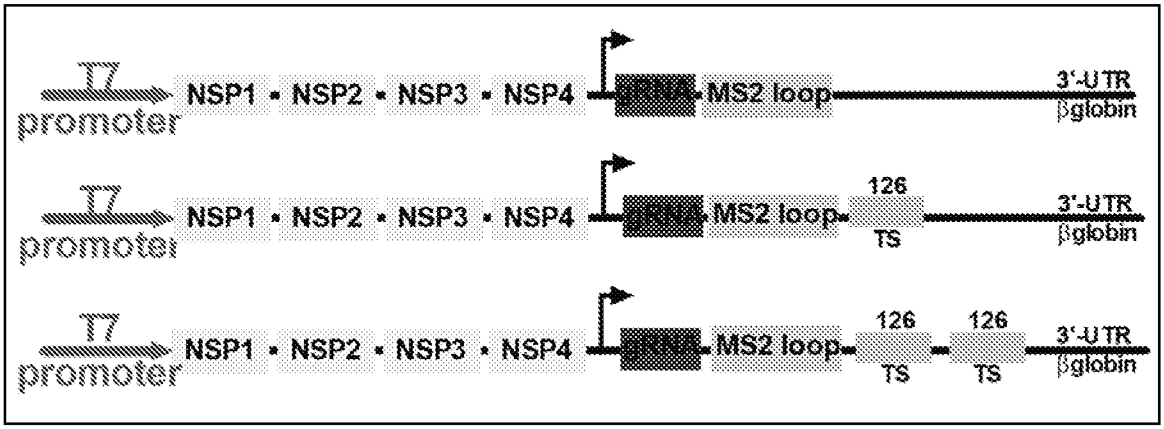
FIG. 34 shows embodiments of a self-replicating, cell-selective gRNA 2.0 construct for CRISPR/Cas9 Synergistic Activation Mediator (SAM) genome editing (Nature 517, 583-588 (29 Jan. 2015).
Figure 35:
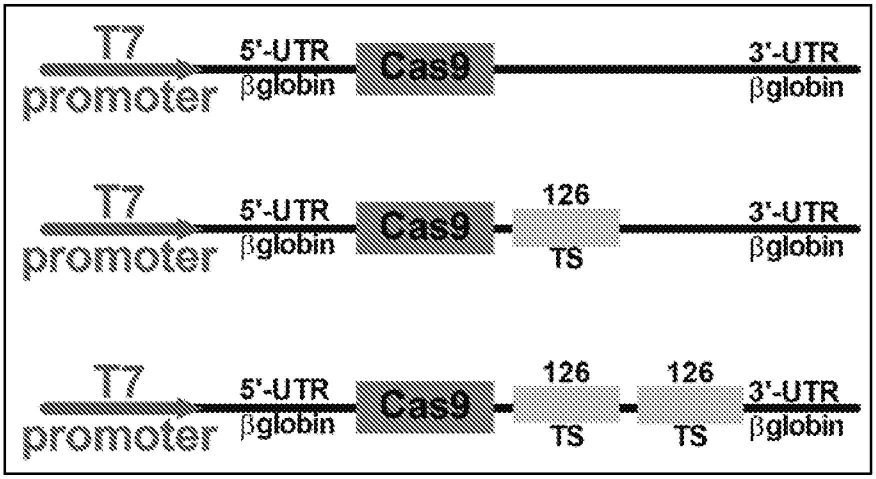
FIG. 35 shows embodiments of a cell-selective Cas9 or dCas9 construct that can be used in CRISPR/Cas9 Synergistic Activation Mediator (SAM) genome editing Nature 517, 583-588 (29 Jan. 2015).
Figure 36:
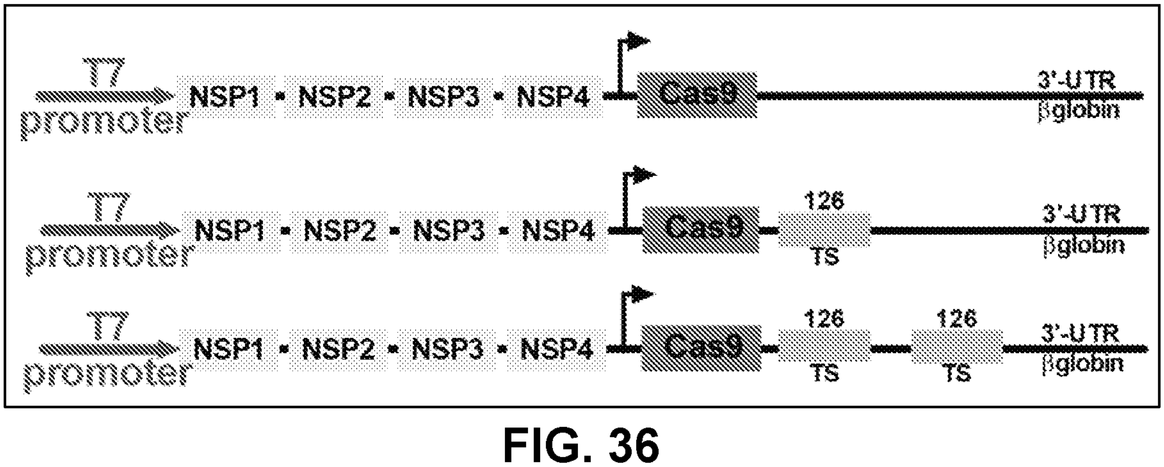
FIG. 36 shows embodiments of a self-replicating, cell-selective Cas9 or dCas9 construct that can be used in CRISPR/Cas9 Synergistic Activation Mediator (SAM) genome editing *Nature* 517, 583-588 (29 Jan. 2015).
Figure 37:
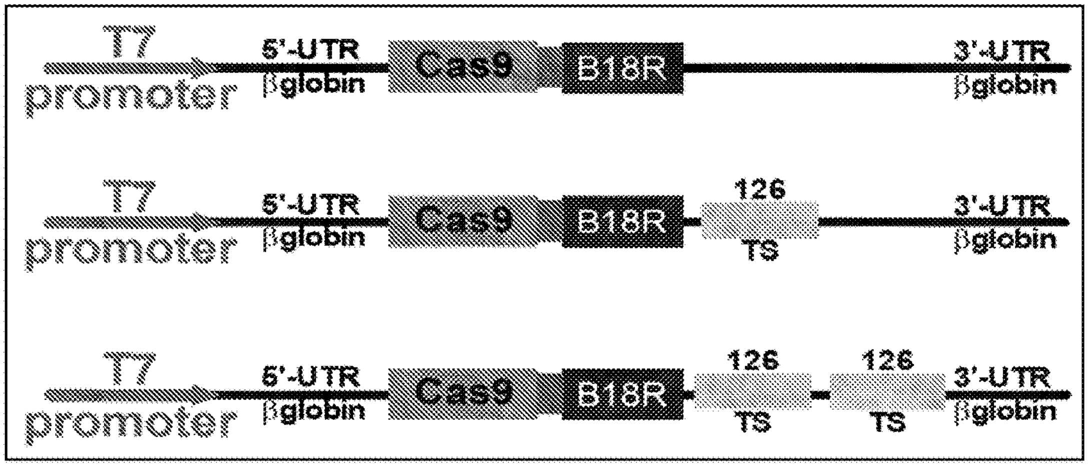
FIG. 37 shows embodiments of a cell selective Cas9 or dCas9 construct that can be used in CRISPR/Cas9 Synergistic Activation Mediator (SAM) genome editing. Embodiments can also include a B18R, separated from the Cas9 or dCas9 by a 2A polypeptide.
Figure 38:
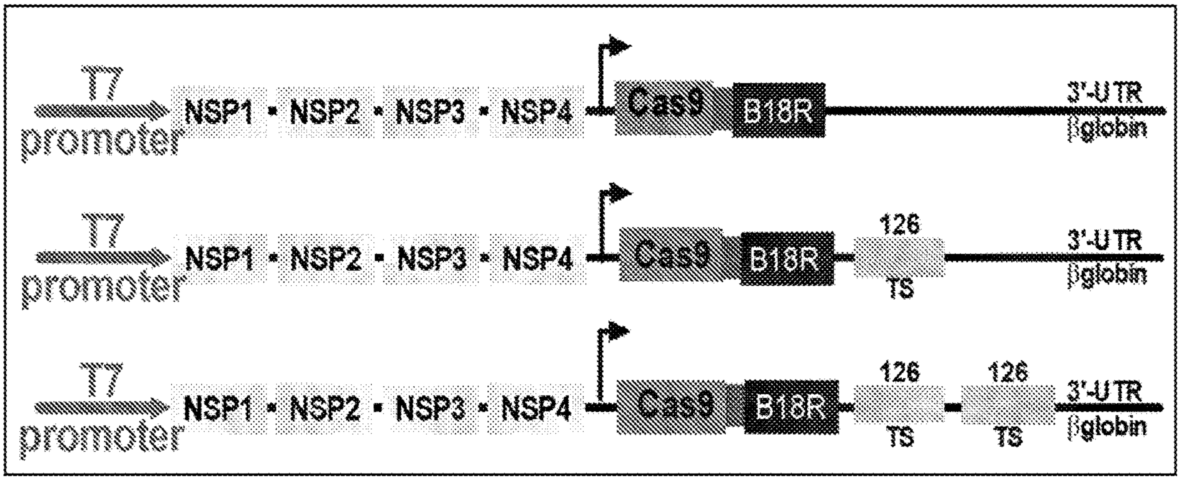
FIG. 38 shows embodiments of a self-replicating, cell-selective Cas9 or dCas9 construct that can be used in CRISPR/Cas9 Synergistic ActivationM (SAM) genome editing. Embodiments can also include a B18R, separated from the Cas9 or dCas9 by a 2A polypeptide.
Figure 39:
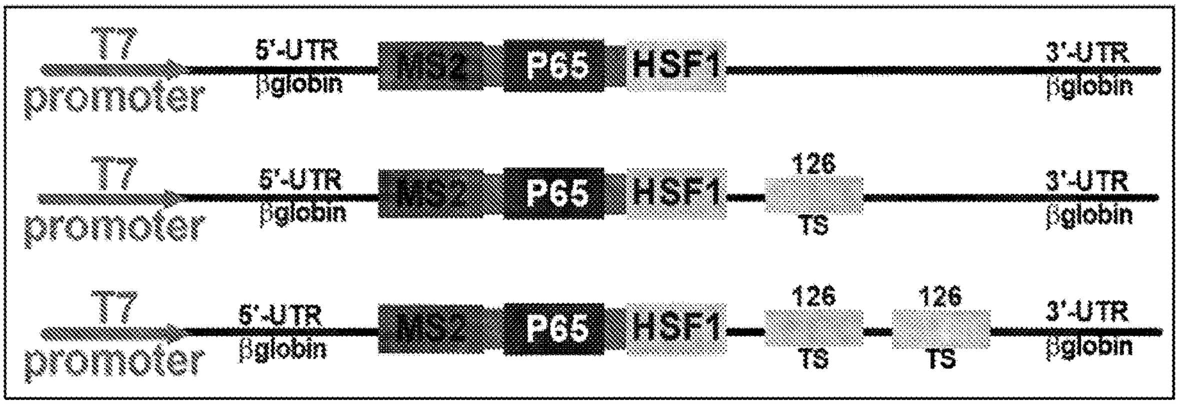
FIG. 39 shows embodiments of a cell-selective construct that can be used in CRISPR/Cas9 Synergistic Activation Mediator (SAM) genome editing. The construct can include a MS2-p65-HSF1 fusion polypeptide.
Figure 40:
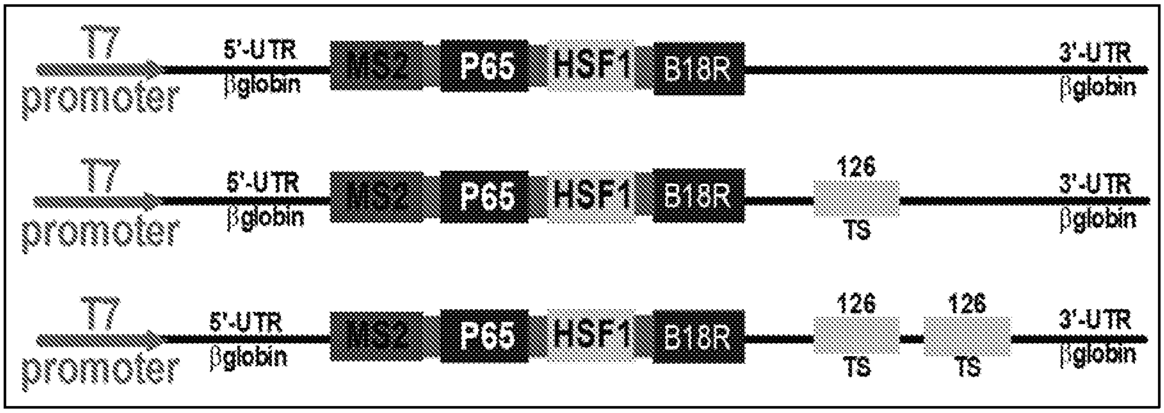
FIG. 40 shows embodiments of a cell-selective construct that can be used in CRISPR/Cas9 Synergistic Activation Mediator (SAM) genome editing. The construct can include a MS2-p65-HSF1 and B18R polypeptide separated by a 2A polypeptide.
Figure 41:
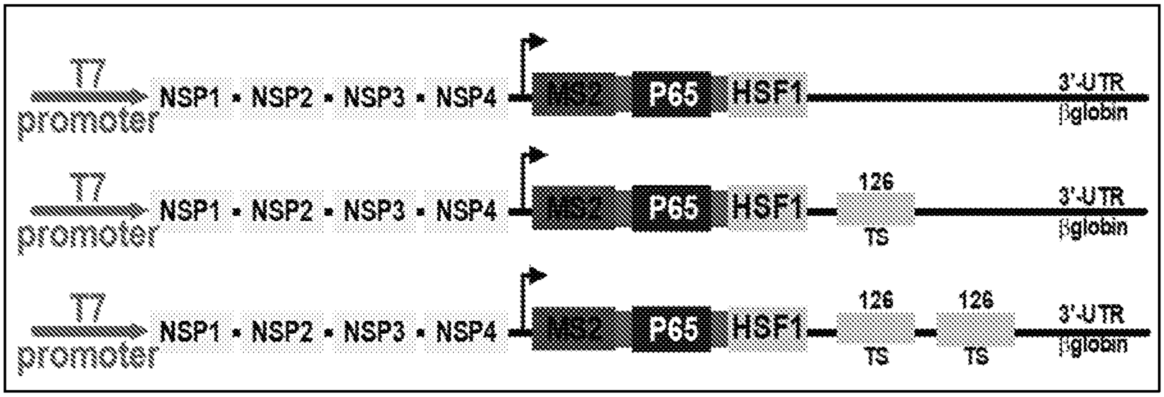
FIG. 41 shows embodiments of a self-replicating, cell-selective construct that can be used in CRISPR/Cas9 Synergistic Activation Mediator (SAM) genome editing. The construct can include a MS2-p65-HSF1 fusion polypeptide.
Figure 42:
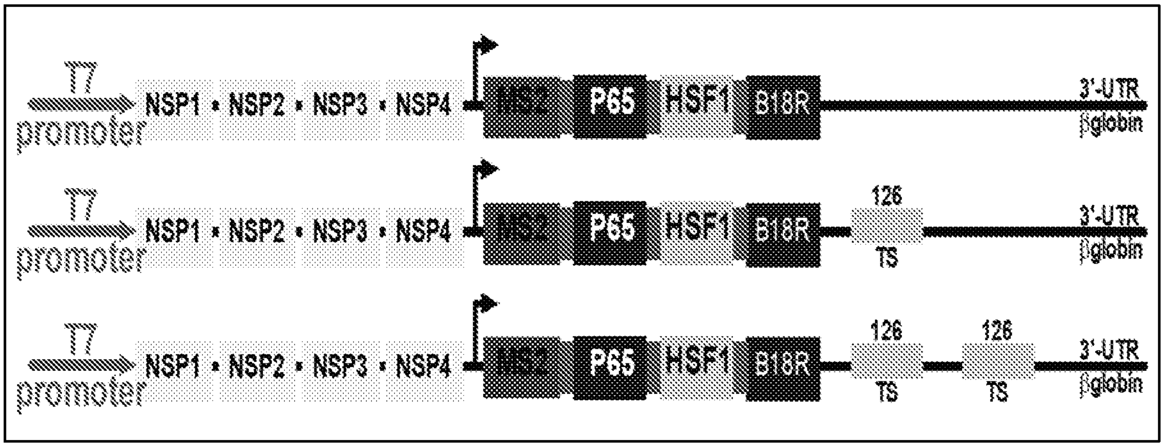
FIG. 42 shows embodiments of a self-replicating, cell-selective construct that can be used in CRISPR/Cas9 Synergistic Activation Mediator (SAM) genome editing. The construct can include a MS2-p65-HSF1 and B18R polypeptide separated by a 2A polypeptide.

An adenoviral (Ad) vector encoding p27 a known cell-cycle inhibitor, and incorporating 4 complementary target sequences for the mature miR-126-3p strand at its 3' end (Ad-p27-126TS) FIGS. 22-23. Our aim was to overexpress exogenous p27, yet effectively regulate its overexpression in a cell-specific manner with the incorporated EC-specific miR-126-3p target sequences FIG. 24. Employing this single comprehensive nanotherapy (Ad-p27-126TS) in a rat carotid balloon injury model the following was achieved: 1) inhibition of neointimal hyperplasia (FIG. 25); 2) inhibition of infiltration of inflammatory cells to the injury site (FIG. 26); 3) reendothelialize vessels rapidly and extensively (FIGS. 27A-B) 4) reduce the plasma D-Dimer levels of injured vessels to levels observed in uninjured controls (FIG. 28); and 5) restore the endothelium-dependent vasodilatory response to levels indistinguishable from uninjured controls (FIG. 29).

These data demonstrate that the simple incorporation of miR-126 target sequences within the Ad-p27-126TS vector provided robust EC protection and at the same time achieved significant inhibition of the neointimal hyperplasia and infiltration of inflammatory cells to the injury site. Although viral delivery systems are very efficient for in vivo transduction and delivery of nucleic acids, they suffer major drawbacks including their possible toxicity, immunogenicity, insertional mutagenicity and oncogenicity. Additionally, viral vectors are difficult and expensive to produce in large quantities. As such the design and engineering of alternative nonviral systems for delivery of therapeutic agents is needed. Presented here are mRNA-based, cell-selective nanotherapies that can self-replicate and can consistently express high levels of exogenous p27 and at the same time retain its cell-selective degradation in a miRNA-controlled fashion, in some cases over multiple cellular divisions.

Figure 4:
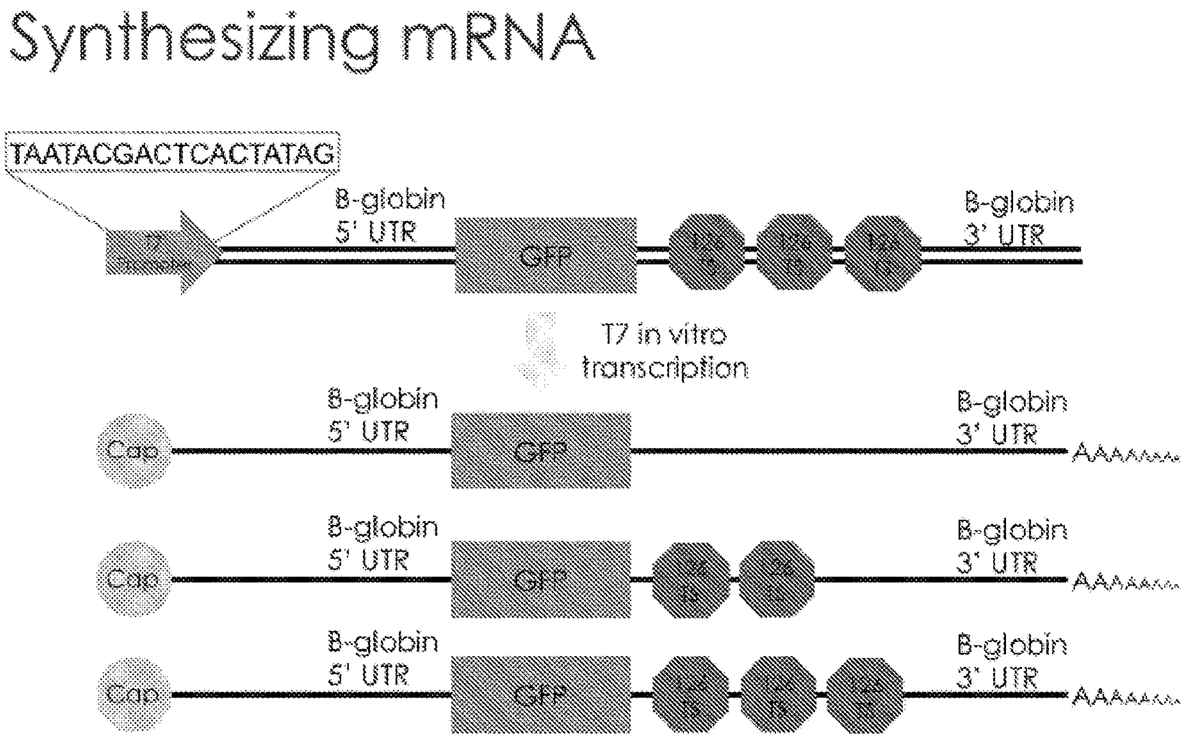
FIG. 4 shows several embodiments of constructs for synthesizing cell-selective mRNA molecules with 0, 2 or 3 microRNA target sites.

To provide proof of concept and to show the feasibility of our cell-selective mRNA approach we constructed the following GFP-encoding plasmids: A) GFP coding sequence placed under the control of the bacteriophage T7 RNA polymerase promoter. To increase the stability of the mRNA we flanked GFP coding sequence with β-globin 5'- and 3'-UTR (FIG. 4); B) GFP-2x126TS, a GFP-coding sequence placed under the control of the bacteriophage T7 RNA polymerase promoter, flanked with β-globin 5'- and 3'-UTR containing 2 or 3 tandem copies of a 22-bp target sequence perfectly complementary to the mature miR-126-3p strand at its 3' end (FIG. 4).

In vitro transcription reaction from the linear plasmid templates described in FIG. 4 was performed using T7 RNA polymerase to produce unmodified (regular nucleotides, NTPs) or modified RNA in which we substituted 100% of the uridine with pseudouridine. After removal of free NTPs, 5' capping and poly(A) tail addition was performed resulting in a high-yield RNA transcript. HEK cells were transfected with miR-126, miR-143 or control mimic and after 24 hr cells were transfected with either unmodified or modified GFP, GFP-2x126TS or GFP-3x126TS mRNAs. The effect of over-expression miR-126, miR-143 or control on GFP protein levels was assessed after 24 hr (FIGS. 6-14). First, a significant increase in GFP expression was observed when uridine was 100% substituted with pseudouridine (FIGS. 7 and 13. In cells transfected with the control unmodified or modified GFP mRNA neither over-expression of miR-126-3p or miR-143 had an effect on GFP expression (FIGS. 6-10 and 13-14). HEK cells transfected with GFP-2xmiR-126TS or GFP-3x126TS mRNA, over-expression of miR-126 dramatically inhibited GFP expression of the unmodified or the modified mRNA (FIGS. 6-8 and 11-14). These data demonstrate that pseudouridine modified GFP-2x126TS mRNA is susceptible to argonaute-dependent gene silencing by miR-126. This effect was miR-126 specific since over-expression of miR-143 had no effect on GFP expression in cells transfected with either unmodified or modified GFP-2xmiR-126TS or GFP-3x126TS (FIGS. 6-8 and 11-14). The data show that pseudouridine modified mRNA is susceptible to the endogenous miRNA machinery. Adding target sites in the 3'UTR of chemically modified mRNA can affect its expression only when this specific miRNA is expressed.

Example 2

A Flag tagged p27 encoding plasmids can be engineered to facilitate in vitro transcription of p27 encoding mRNA (FIG. 17): A) Flag-tagged p27); B) Flag-tagged p27 followed by two 2 fully complementary target sequences for the mature miR-126-3p strand at its 3'-UTR (p27-2x126TS). A Flag-tag can be incorporated to distinguish between endogenous and exogenous p27 expression.

Figure 17:
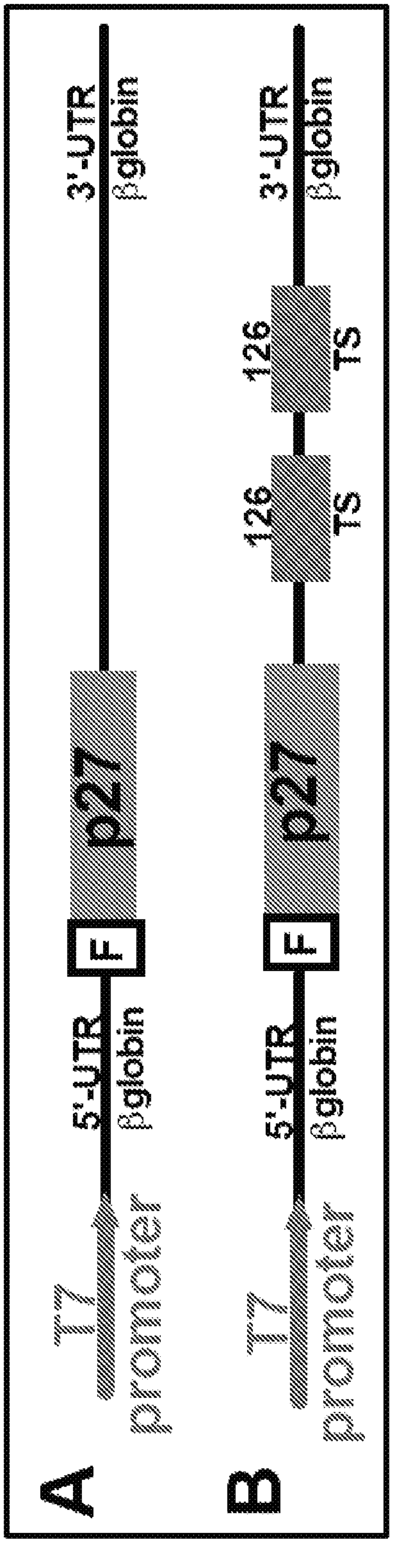
FIG. 17 shows schematics of (A) p27 coding sequence flanked with the 5'- and 3'-UTR of β-globin and placed under the control of the bacteriophage T7 RNA polymerase promoter (p27) and (B) p27 coding sequence flanked with the 5'- and 3'-UTR of β-globin and placed under the control of T7 RNA polymerase promoter, containing 2 fully complementary target sequences for the mature miR-126-3p strand at its 3'-UTR (p27-2x126TS). F, Flag-tag.

To reduce innate immune responses and toxicity and at the same time maximize the efficiency and duration of expression of the mRNA encoding p27 described in FIG. 17, the following modified nucleotide substitutions or combinations thereof can be used: 1) Pseudouridine; 2) N-1-methylpseudouridine; 3) 5-methoxy-U; 4) 5-hydroxymethyl-C; 5) 5-methyl-C and 6) combination of Pseudouridine and 5-methyl-C. mRNAs can be in vitro transcribed using T7 RNA polymerase followed by 5' capping and poly(A) tail addition using a Vaccinia Capping Enzyme and *E. coli* Poly(A)Polymerase (New England BioLabs Inc.), respectively.

Example 3

Example 1 demonstrates that substitution of uridine with pseudouridine and addition of miR-126 target sequences at the 3'-UTR of GFP mRNA increased the translational efficiently in a cell-selective manner. However, to increase its therapeutic potential, it is desirable that sustained cell selective inhibition matches the potency and the durability of the drugs eluted from the DES. To develop a long-lasting cell-selective mRNA-based therapy, we focused our efforts on an approach that (1) utilizes a single RNA species capable of self-replicating for a limited number of cell divisions; (2) is capable of encoding our gene of interest; (3) consistently expresses the protein at high threshold levels over multiple cellular divisions; and/or (4) can be susceptible to endogenous miRNA degradation in a cell-selective fashion. In this Example, an approach utilizing a noninfectious, self-replicating Venezuelan equine encephalitis (VEE) virus (lacks the genes encoding the viral structural proteins) and mimics cellular mRNA with a 5'-cap and poly(A) tail and does not utilize a DNA intermediate is described. This approach lacks the potential for genomic integration. VEE virus is a positive-stranded RNA that encodes four nonstructural replication complex proteins (NSPs) as a single open reading frame (ORF).

Design of self-replicating, cell-selective mRNA vectors: To ectopically express p27 in a cell-selective manner, a p27-coding sequence can be placed at the 5' end of VEE-structural protein genes. The following VEE10 GFP or Flag tagged p27 encoding plasmids will be engineered: A) VEE-p27, 3'-ORF replaced with flag-tag p27 coding sequence followed by β-globin 3'-UTR (FIG. 19); (B) VEE-p27-2x126TS, 3'-ORF replaced with flag-tag p27-coding sequence followed by two tandem copies of a 22-bp target sequence perfectly complementary to the mature miR-126-3p at its 3' end (FIG. 19). A Flag-tag can be included to distinguish between endogenous and exogenous p27 expression. More than two miR-126 targets can be incorporated (FIG. 18).

Figure 18:
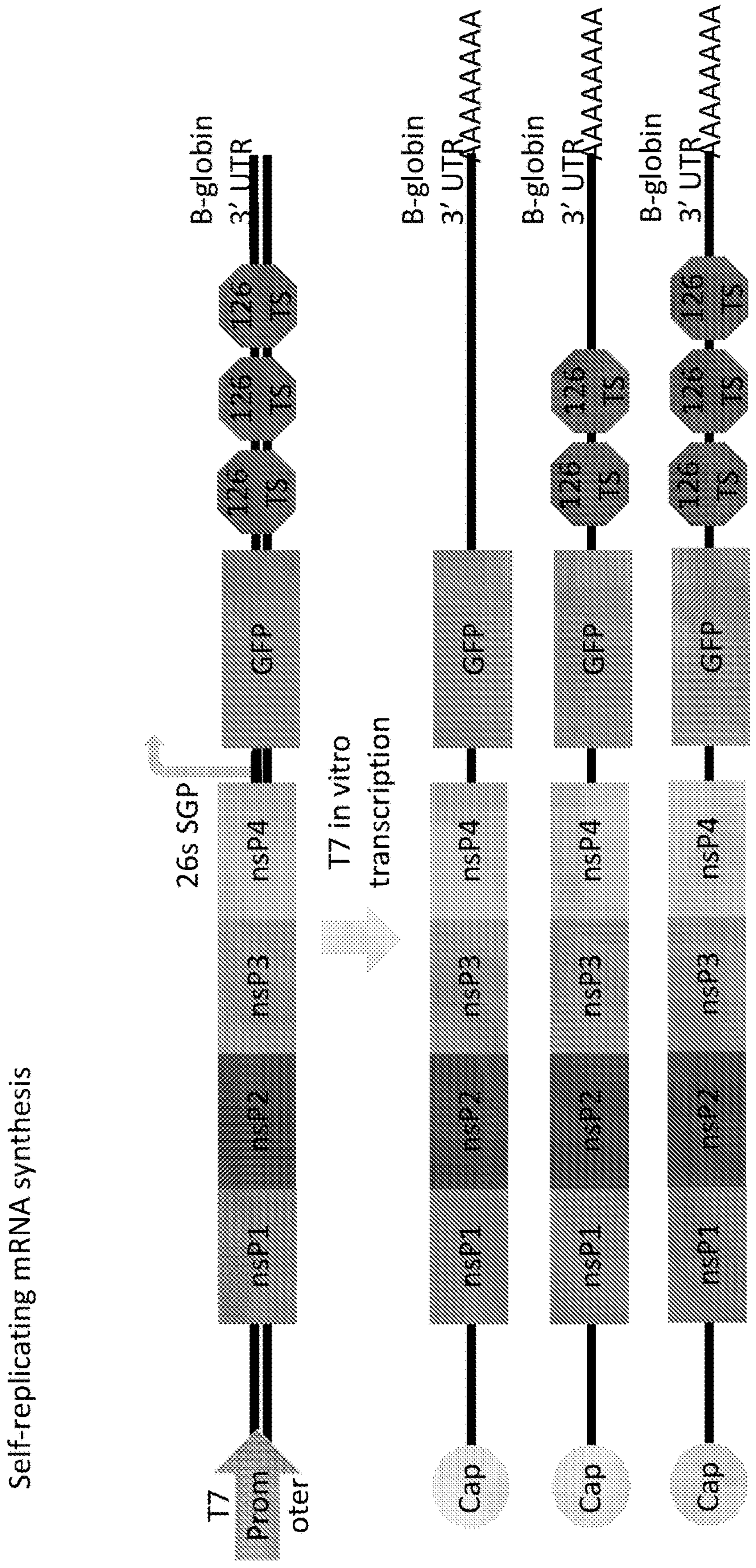
FIG. 18 shows schematics of embodiments of self-replicating VEE based cell-selective mRNA constructs.
Figure 19:
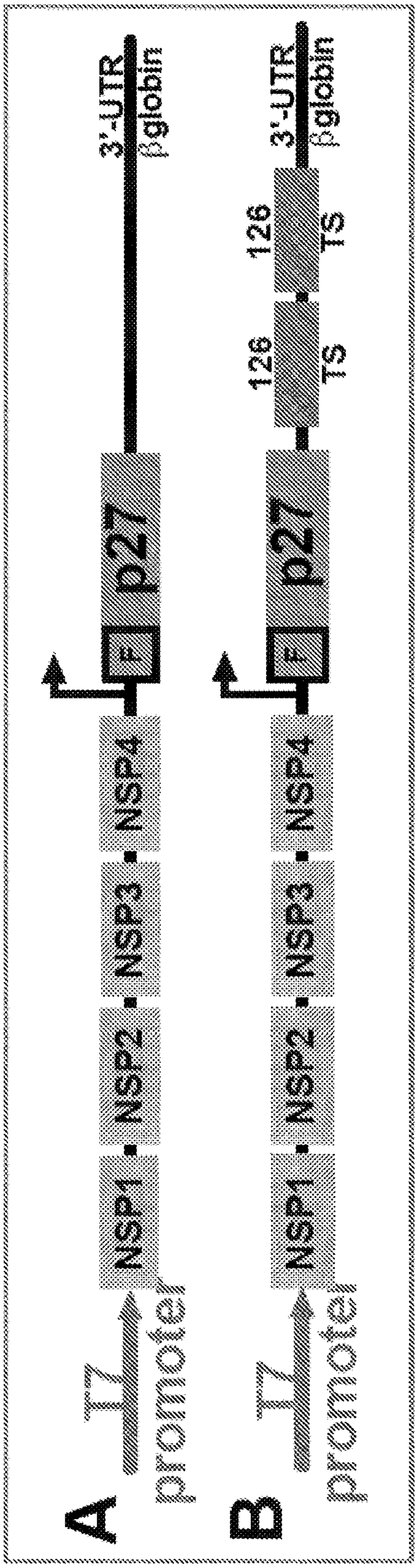
FIG. 19 shows embodiments of a self-replicating mRNA based, cell-selective construct for in vitro transcription. (A) Shows a schematic illustration of a self-replicating RNA derived from an alphavirus contains a 5' T7 RNA polymerase, nonstructural genes (NSP1-4), 26S subgenomic promoter (black arrow), p27 coding sequence followed by β-globin 3'-UTR (VEE-p27); (B) same as in A, p27 coding sequence with 2 fully complementary target sequences for the mature miR-126-3p strand at its 3'-UTR (p27-2x126TS). F, Flag-tag.

Self-replicating mRNA depicted in FIGS. 18-19 can be in vitro transcribed using T7 RNA polymerase in the presence of the unmodified and modified nucleotides (Pseudouridine, N-1-methylpseudouridine, 5-methoxy-U, 5-hydroxymethyl-C, 5-methyl-C or combination of Pseudouridine and 5-methyl-C). mRNAs can be in vitro transcribed using T7 RNA polymerase followed by 5' capping and poly(A) tailing.

Figure 20:
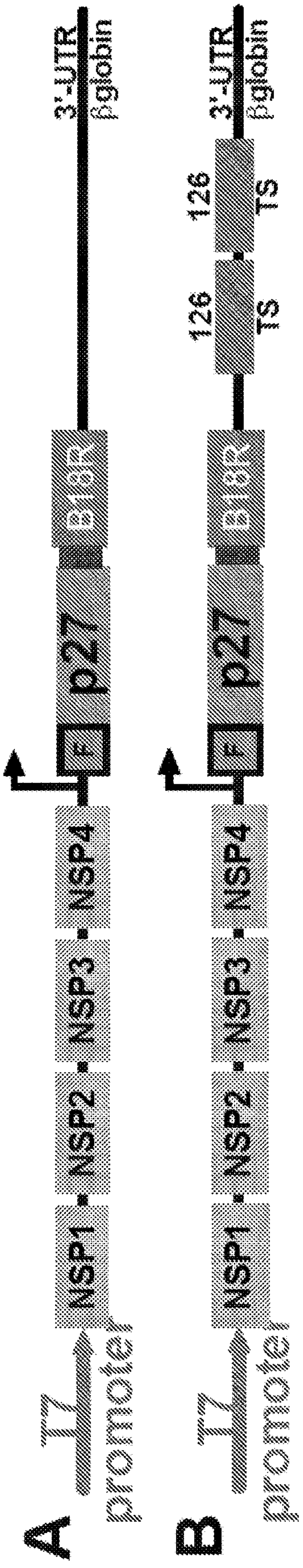
FIG. 20 shows embodiments of a VEE polyprotein constructs. (A) and (B) show constructs that contain a 5' T7 RNA polymerase, nonstructural genes (NSP1-4), 26S subgenomic promoter (black arrow), p27 and B18R polyprotein separated by 2A peptide (in green); 26S subgenomic promoter (black arrow) without (A) or with 2 fully complementary target sequences for the mature miR-126-3p strand at its 3'-UTR (p27-2x126TS) (B).
Figure 21:
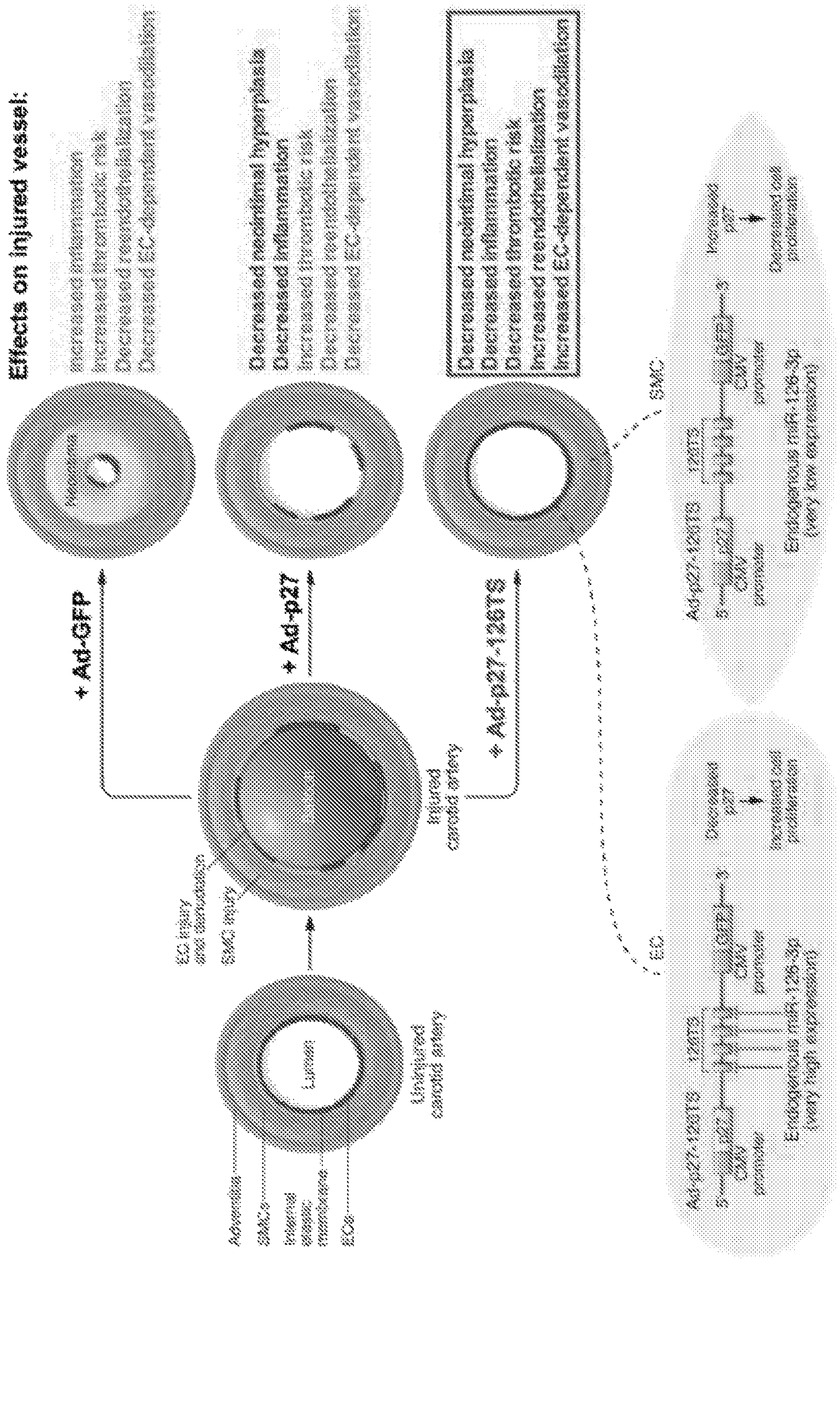
FIG. 21 shows an adenoviral based cell-selective construct for overexpression of exogenous p27 in VSMCs to reduce neointimal hyperplasia while sparing ECs to improve reedothelialization. This figure is a modification from J Clin Invest. 2014 September; 124(9):3694-7. PMID: 25133421, PMCID: PMC4151224.

The self-replicating mRNA can also be designed to include RNA encoding the B18R protein. This can reduce immunogenic reactions (FIG. 20).

The self-replicating mRNA can also incorporate RNA encoding a marker protein such as GFP. FIG. 18.

Example 4

Cell-selective alternatives to the current DES used in percutaneous interventions are needed to inhibit restenosis while promoting reendothelialization. The advantage of such a treatment is the local non-invasive administration of drug in conjunction with balloon angioplasty limiting systemic toxicity. In this Example, an approach using FDA approved polymers to encapsulate the cell-selective mRNA or cell-selective self-replicating mRNA transcripts to facilitate efficient gene delivery in vivo is presented. The cell-selective RNA molecules can be encapsulated with a polymer to form RNA polymer nanoparticles. The RNA polymer nanoparticles can be attached to the stent or other medical device using a suitable method such as surface by dip- or by spray-coating. The following FDA approved polymers can be used: Phosphorylcholine-based polymers, Poly lactic-co-glycolic acid (PLGA), chitosan, cationic nanoemulsion, cationic electrodeposition coating or lipid nanoparticles.

Example 5

Manipulation of gene expression via the RNAi system is a powerful new tool for the treatment of many diseases, including Hepatitis C and heart failure. The current trend in miRNA therapies focuses on the use of antagomirs, short RNA fragments that block the activity of a specific miRNA. RNAs with numerous target sites for miRNAs, referred to as miRNA sponges, are also able to effectively restore the repressed targeted mRNAs by sequestering the endogenous miRNA. Cell-specific miRNAs can be used to confer cell-protectivity to a gene therapy by incorporating miRNA target sites into the 3' UTR. This strategy prevents expression of the inserted gene in a specific cell type based on the miRNA target sequences.

Figure 15:
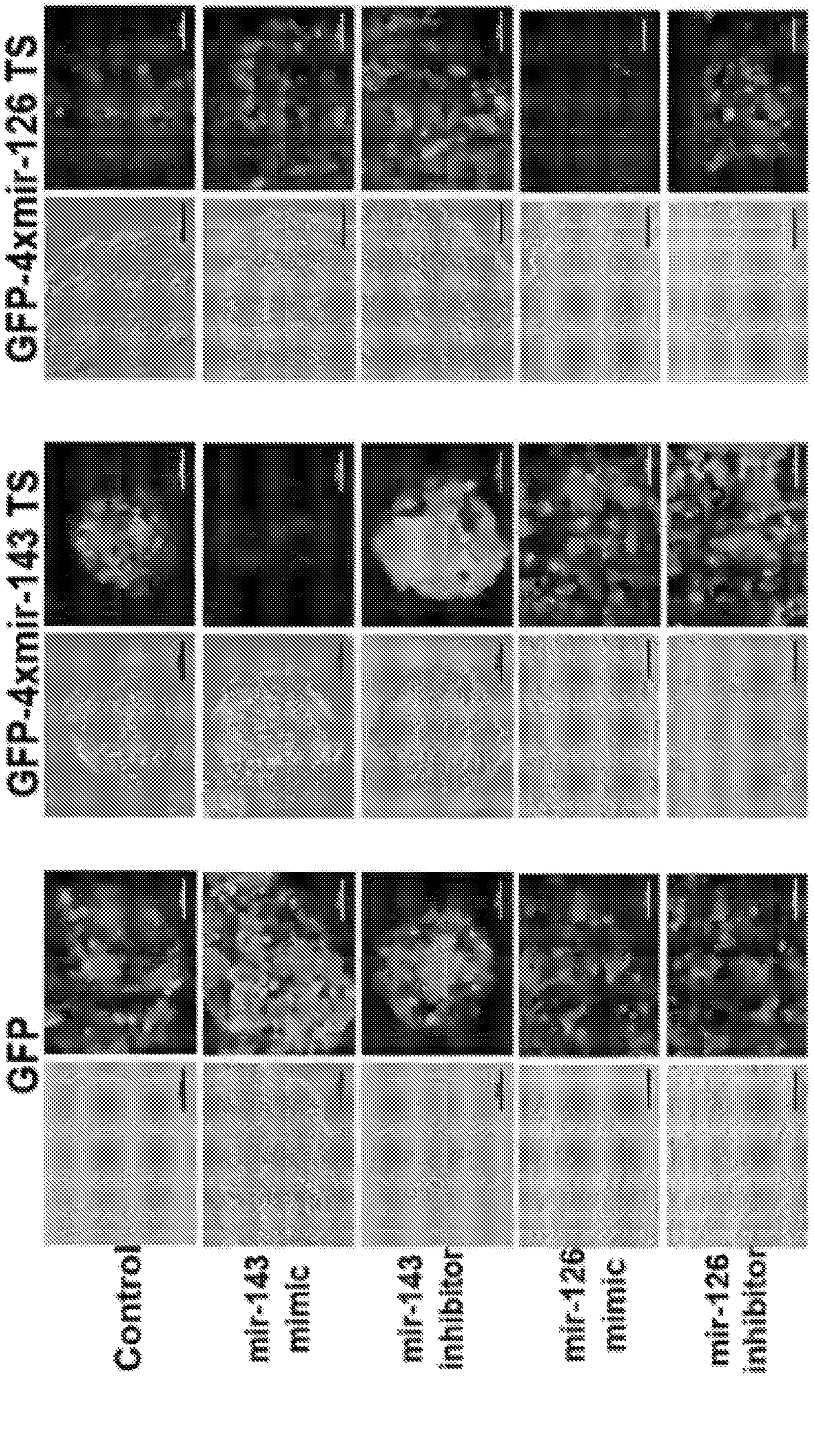
FIG. 15 shows images of HEK cells infected with lentivirus vectors encoding GFP, GFP-4xmiR-143TS or GFP-4xmiR-126TS ($10^9$ transducing units TU/ml). After 24 h incubation, cells were transfected with 200 nM of the indicated miR-mimic, inhibitor or control and fluorescent images were taken after 72 hrs.

To demonstrate that miRNA can be used to specifically regulate gene of interest a GFP-expressing lentiviral vector was used in which four target sequences for miR-126 were inserted, a vascular endothelial cell (VEC)-specific miRNA, in the GFP 3'UTR (GFP-4xmiR-126TS). To control for miRNA specificity, four target sequences for miR-143 (GFP- 4xmiR-143TS) were inserted, which is vascular smooth muscle cell (VSMC)-specific, or four scramble sequences (GFP) in the GFP-3'UTR region HEK cells were transduced with the different GFP expressing lentiviruses, and the effect of over-expression or inhibition of miR-143, miR-126 or control on GFP expression was assessed. In cells transduced with the control GFP virus, neither over-expression nor inhibition of miR-143 or miR-126 had an effect on GFP expression (FIG. 15, left). However, in HEK cells transduced with GFP-4xmiR-143TS virus, only over-expression of miR-143 dramatically inhibited GFP expression (FIG. 15, middle). Similarly, over-expression of miR-143 had no effect on GFP expression in cells transduced with GFP-4xmiR-126TS, while over-expression of miR-126 did inhibit GFP expression in these cells (FIG. 15, right).

Figure 16:
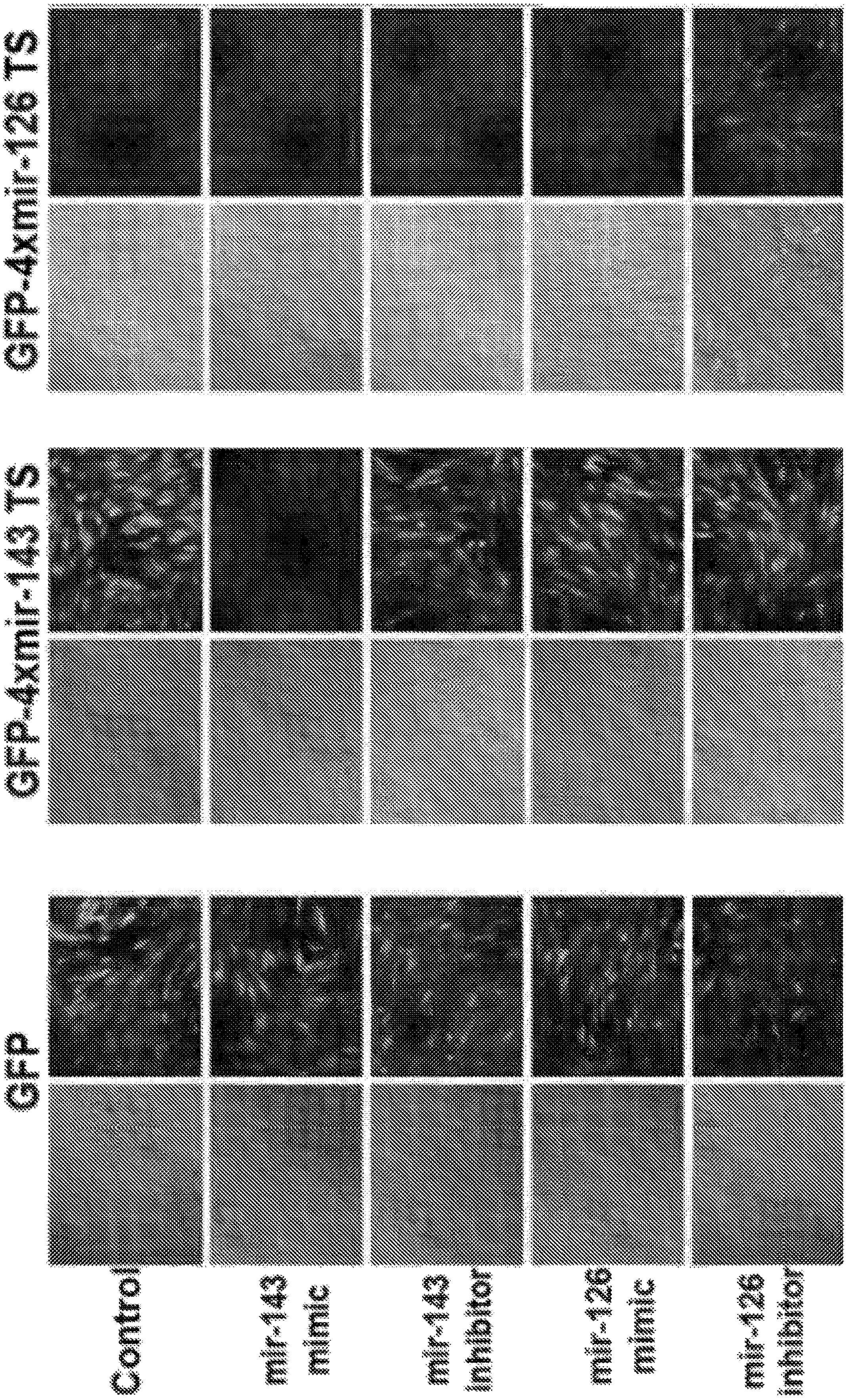
FIG. 16 shows images of VECs infected with lentivirus vectors encoding GFP, GFP-4xmiR-143TS or GFP-4xmiR-126TS ($10^9$ transducing units TU/ml). After 24 h incubation, cells were transfected with 200 nM of the indicated miR-mimic, inhibitor or control and photographed after 72 hours.

This strategy was used in VEC to ensure that the endogenous miR-126 targets the viral constructs as expected. VEC were transduced with the same lentiviruses. In control GFP virus transduced cells, neither over-expression nor inhibition of miR-143 or miR-126 had an effect on GFP expression (FIG. 16, left). Similarly, over-expression of miR-143 inhibited GFP expression only in GFP-4xmiR-143TS transduced cells, while over-expression of miR-126 had no effect (FIG. 16, middle). Interestingly, because miR-126 is highly expressed in VEC, it abolished the expression of GFP in the GFP-4xmir-126TS infected cells. Only inhibition of the endogenous miR-126 with a miR-126 antagomir rescued the expression of GFP (FIG. 16, right).

These results demonstrate the sensitivity and specificity of endogenous miRNA for target sites in the 3' UTR of unmodified mRNAs. Predictable patterns of expression can be observed when using cell-specific miRNA target to regulate expression of the inserted gene.

Example 6

Modified nucleotides can increase the translational efficiency and reduce cellular toxicity caused by the immunogenic response to exogenous mRNA. Here, 4 different representative modified nucleotide compositions (FIG. 30) can be included in the cell-selective mRNA. Each of the modified nucleotides can be used as a complete substitute for the unmodified nucleotides to achieve the maximum effect. Modified and unmodified mRNA can be synthesized with a 5' cap using an ARCA cap analog (TriLink) and PolyA tail using reagents to increase the stability of the mRNAs (TriLink).

Figure 5:
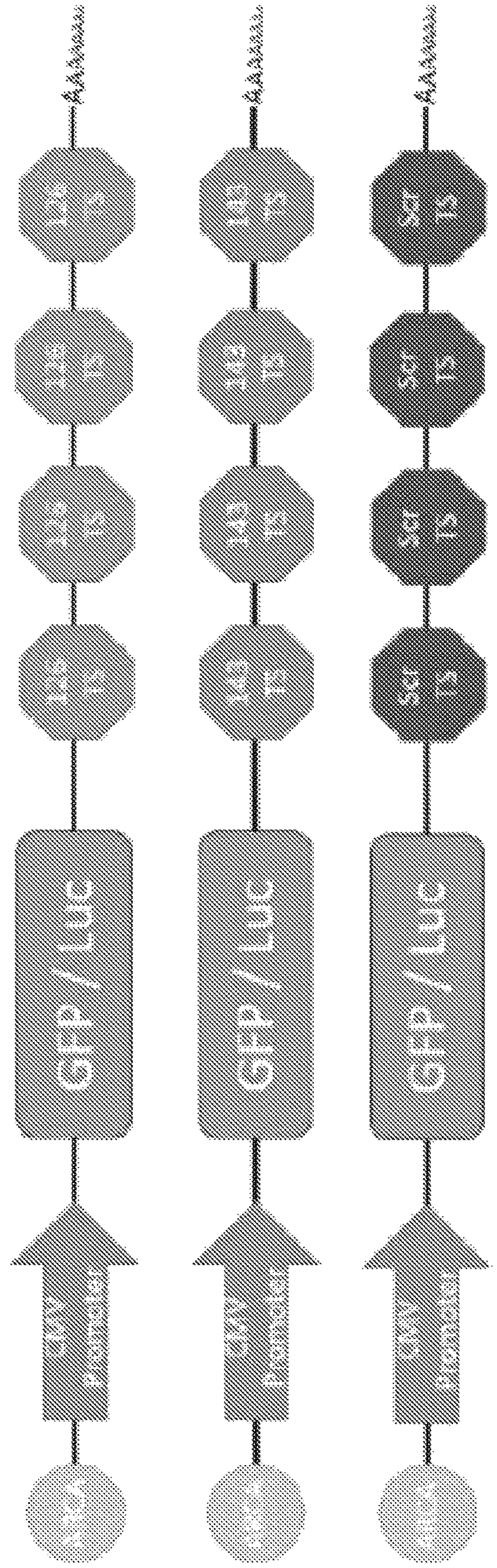
FIG. 5 shows embodiments of in vitro transcription of GFP, Luc or any gene of interest mRNA constructs. All mRNA constructs can be placed under the CMV promoter, capped and polyadenylated. The 3' UTR of each construct can have 4 target sites for miR-126, miR-143 or a scrambled control. The constructs can be used for in vitro transcription of mRNAs that incorporate the selected modified nucleotides.
Figure 6:
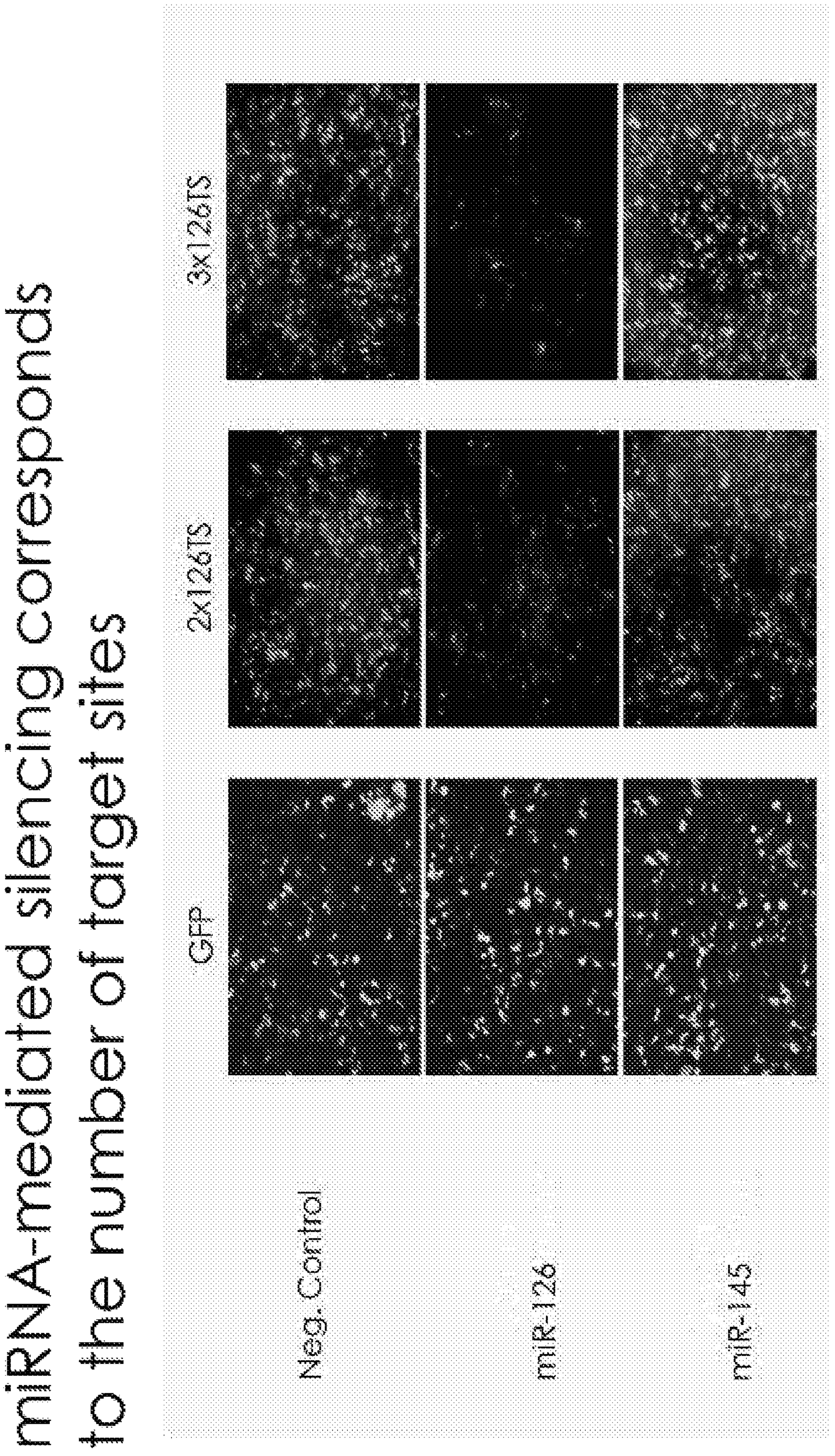
FIG. 6 shows images demonstrating the effect of the number of miR-126 target sites of unmodified mRNA molecule on GFP silencing in HEK cells transfected with miR-126 mimics but not in HEK cells transfected with miR-145 or control mimic.
Figure 7:
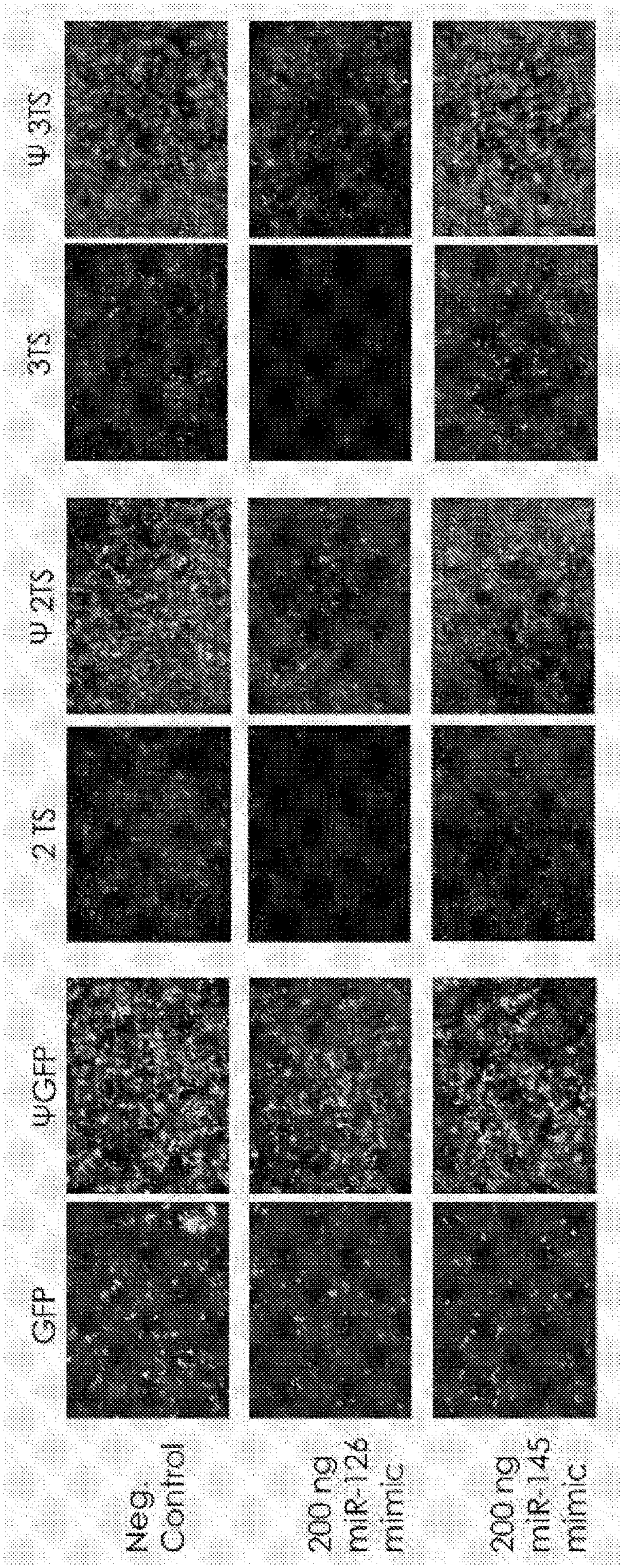
FIG. 7 shows images demonstrating GFP silencing by miR-126 mimics in HEK cells transfected with unmodified or pseudouridine modified mRNA molecule that includes 2 or 3 miR-126 target sites.
Figure 8:
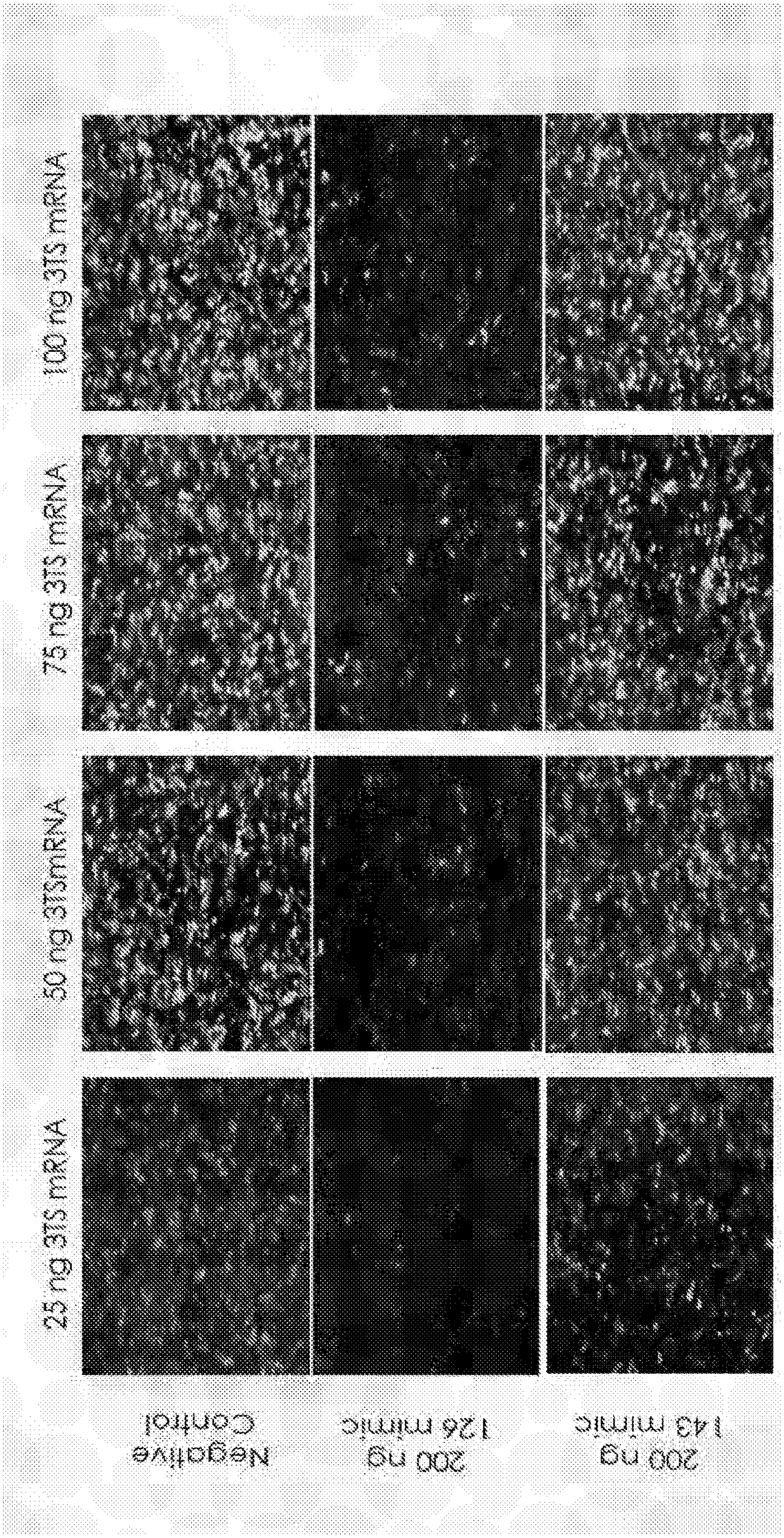
FIG. 8 demonstrates the dose dependency of GFP mRNA silencing of pseudouridine modified cell-selective mRNA by miR-126 mimics but not by miR-143 mimics.
Figure 9:
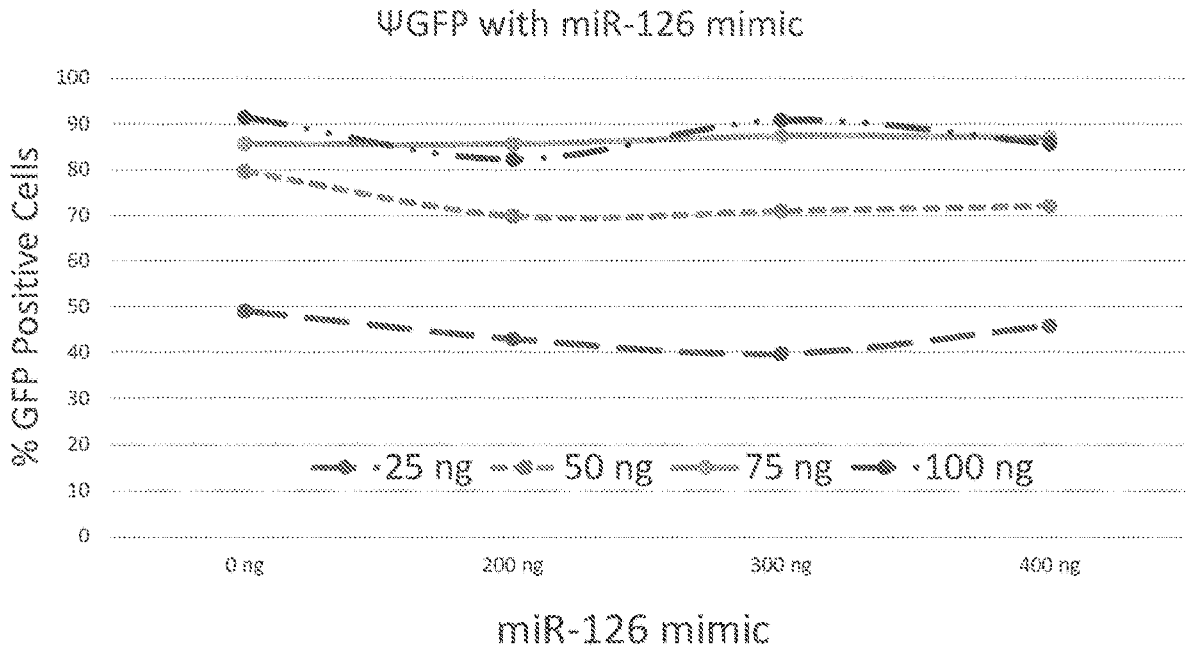
FIG. 9 shows a graph demonstrating flow cytometry analysis of pseudouridune modified GFP expressing mRNA construct with no miR-126 target sites exposed to a miR-126 mimic at varying amounts.
Figure 10:
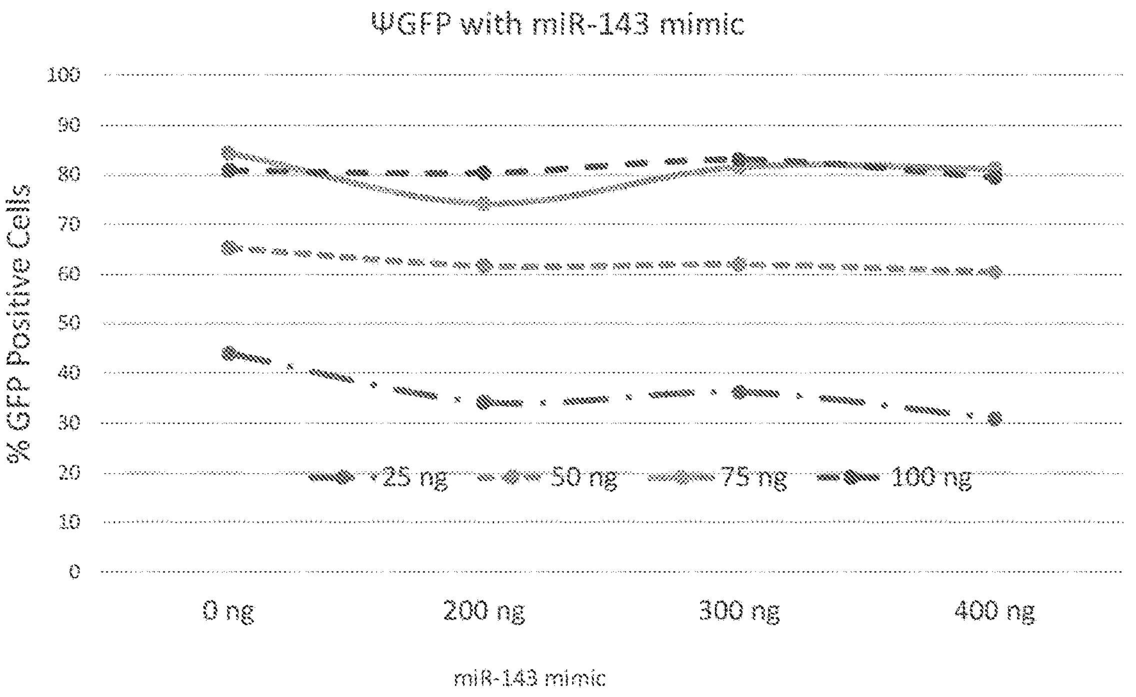
FIG. 10 shows a graph demonstrating flow cytometry analysis of pseudouridine modified GFP expressing mRNA construct with no miR-126 target sites exposed to a miR-143 mimic at varying amounts.
Figure 11:
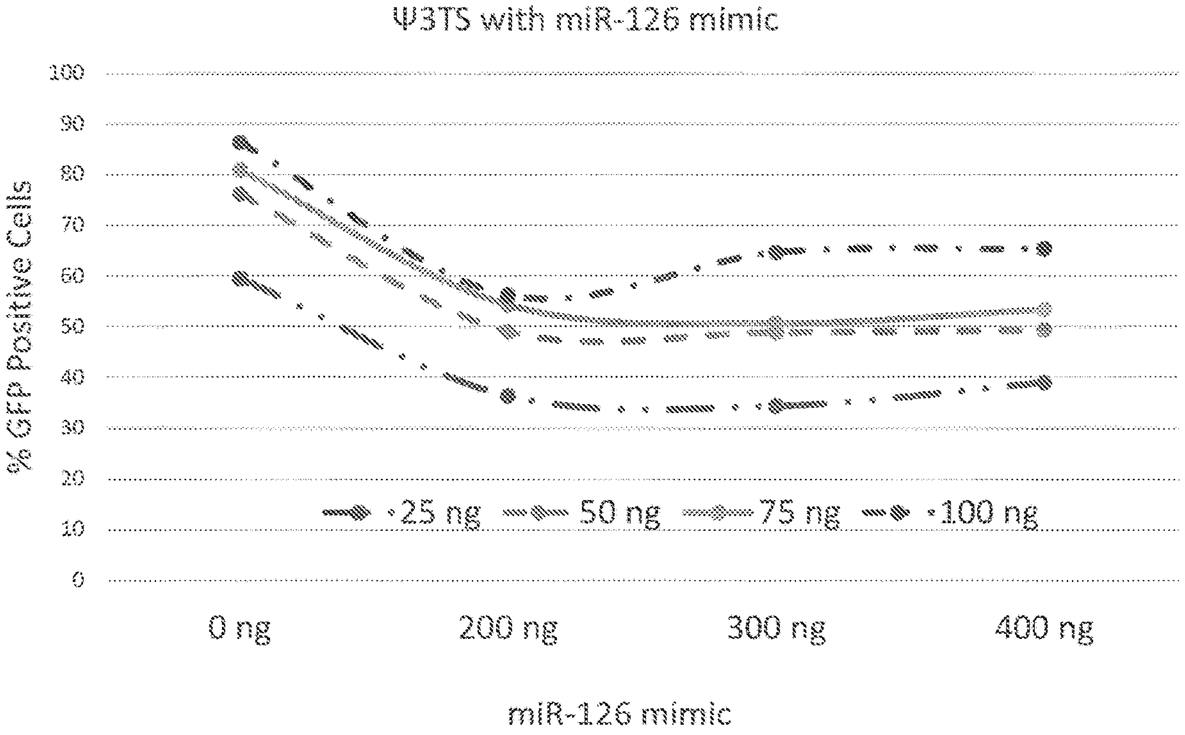
FIG. 11 shows a graph demonstrating flow cytometry analysis of pseudouridine modified GFP expressing mRNA containing 3 miR-126 target sites at its 3'UTR silencing when exposed to miR-126 mimic at varying amounts.
Figure 12:
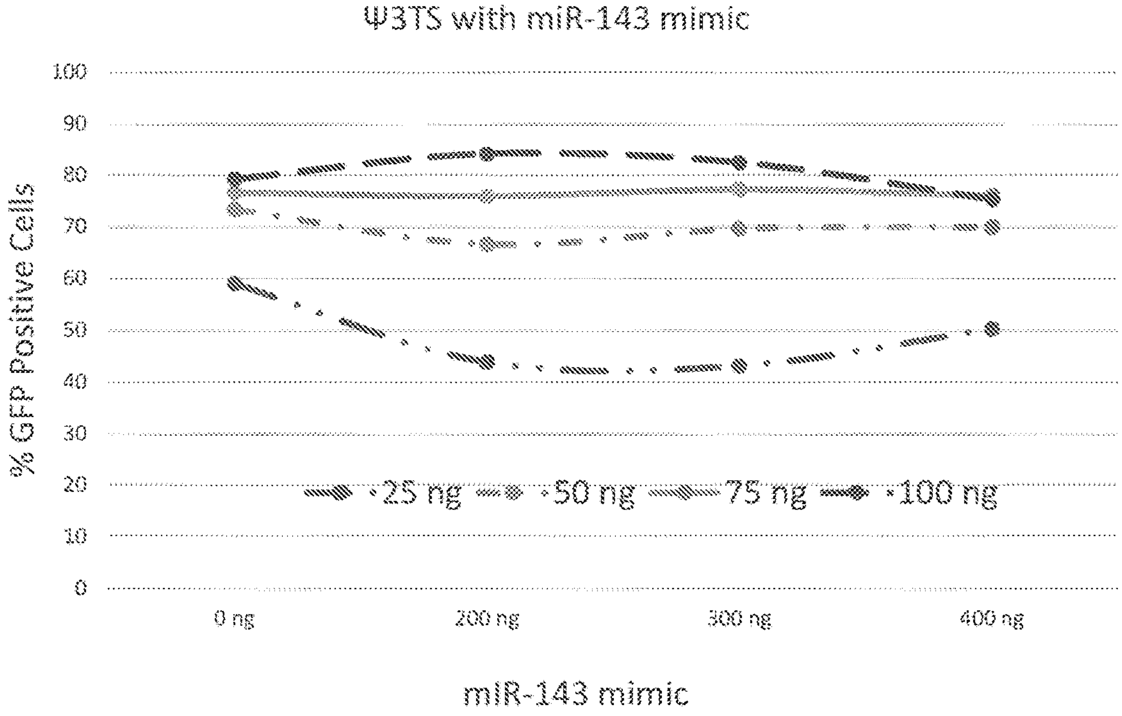
FIG. 12 shows a graph demonstrating flow cytometry analysis of pseudouridune modified GFP expressing mRNA construct containing 3 miR-126 target sites at its 3'UTR exposed to miR-143 mimic at varying amounts.
Figure 13:
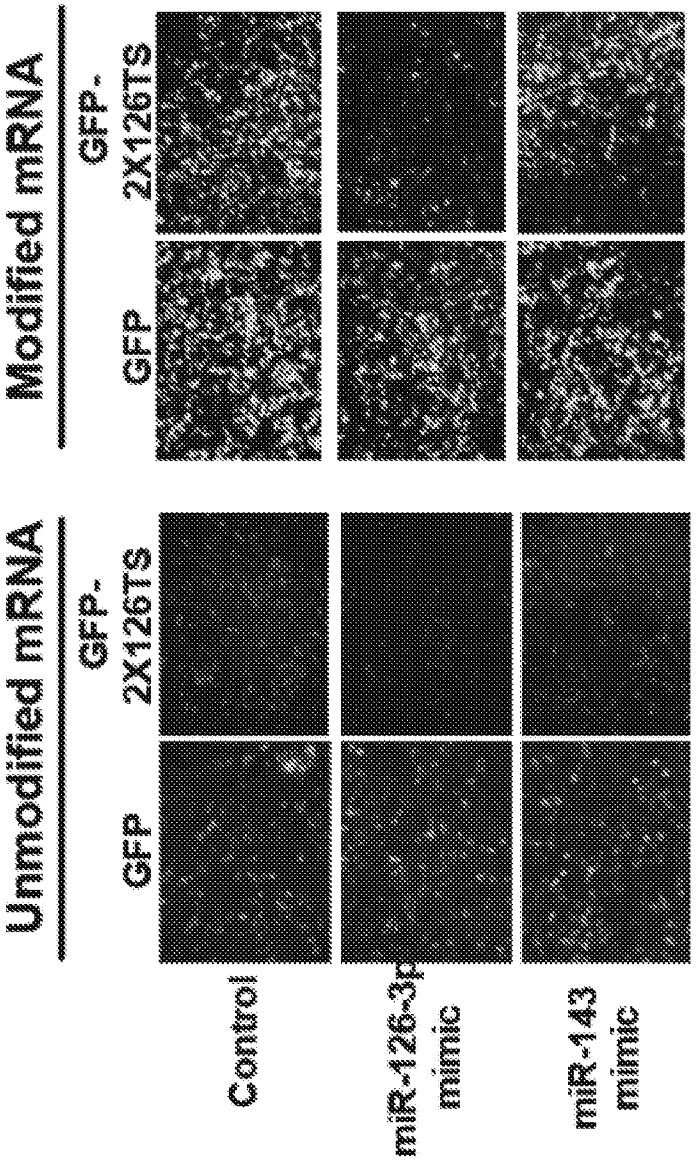
FIG. 13 shows fluorescent images demonstrating GFP expression in HEK cells transfected with 200 nM of the indicated miR-mimic or control. After 24 hr cells were transfection with 100 nM unmodified or pseudouridine modified GFP or GFP-2xmiR-126TS and the fluorescent images were taken 24 hr after the second transfection.
Figure 14:
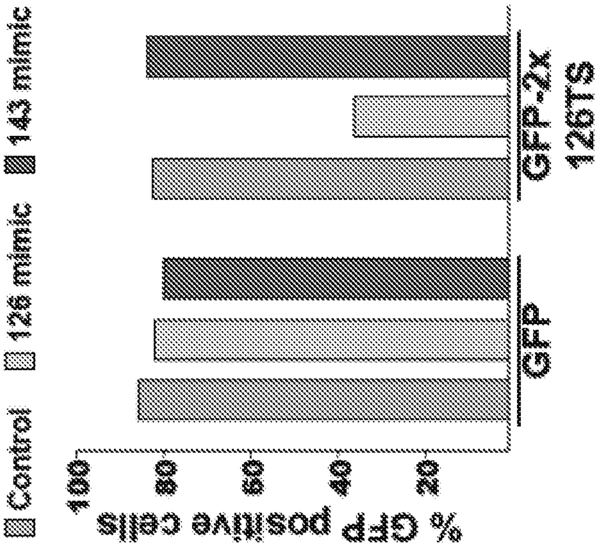
FIG. 14 shows a graph demonstrating the percent GFP positive cells transfected with pseudouridine modified mRNAs of FIG. 13 as determined by Flow Cytometry. The total number of cells analyzed was 10,000.

To determine if modified nucleic acids affect target site recognition, modified and unmodified mRNA encoding green fluorescent protein (GFP) or luciferase (Luc) followed by 4 target sequences (TS) for miR-126, miR-143 or control scrambled sequences will be transcribed in vitro by T7 RNA polymerase (FIG. 5).

Example 7

The number of miRNA silencing can be dependent on the number of miRNA target sites present in the construct. As demonstrated in FIGS. 6 and 7, an increase from 0 (GFP) to 2 (2X126TS) to 3 (3x126TS) miRNA target sites within the construct can result in a positively correlated increase in silencing. The data of FIGS. 6 and 7 further demonstrates the specificity of the miRNA target sequences.

Example 8

Figure 43A:
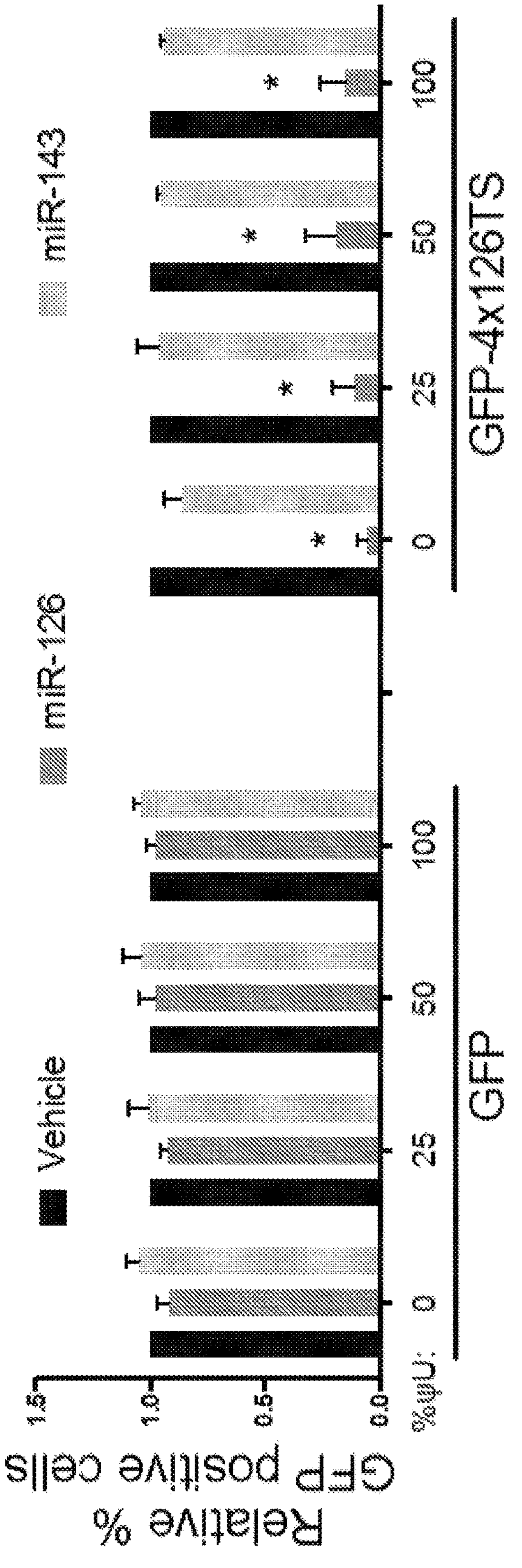
FIGS. 43A-43C show graphs demonstrating and an image of an immunoblot for GFP demonstrating the relative percent of GFP positive cells (FIG. 43A), relative median GFP intensity (FIG. 43B), and relative GFP expression (FIG. 43C) post transfection of HEK cells with GFP or GFP 4x126TS unmodified or with substitutions of uridine with pseudouridine (0%, 25%, 50% or 100%) when exposed to miR-126 or miR-143 mimics.
Figure 43B:
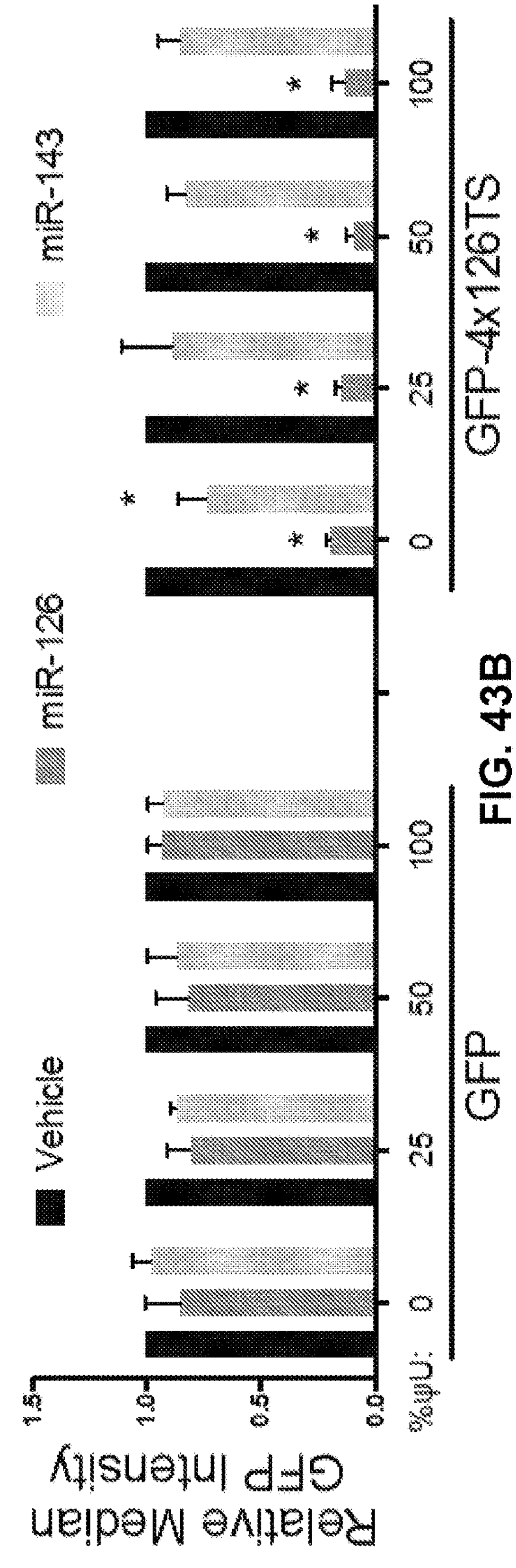
Figure 43C:
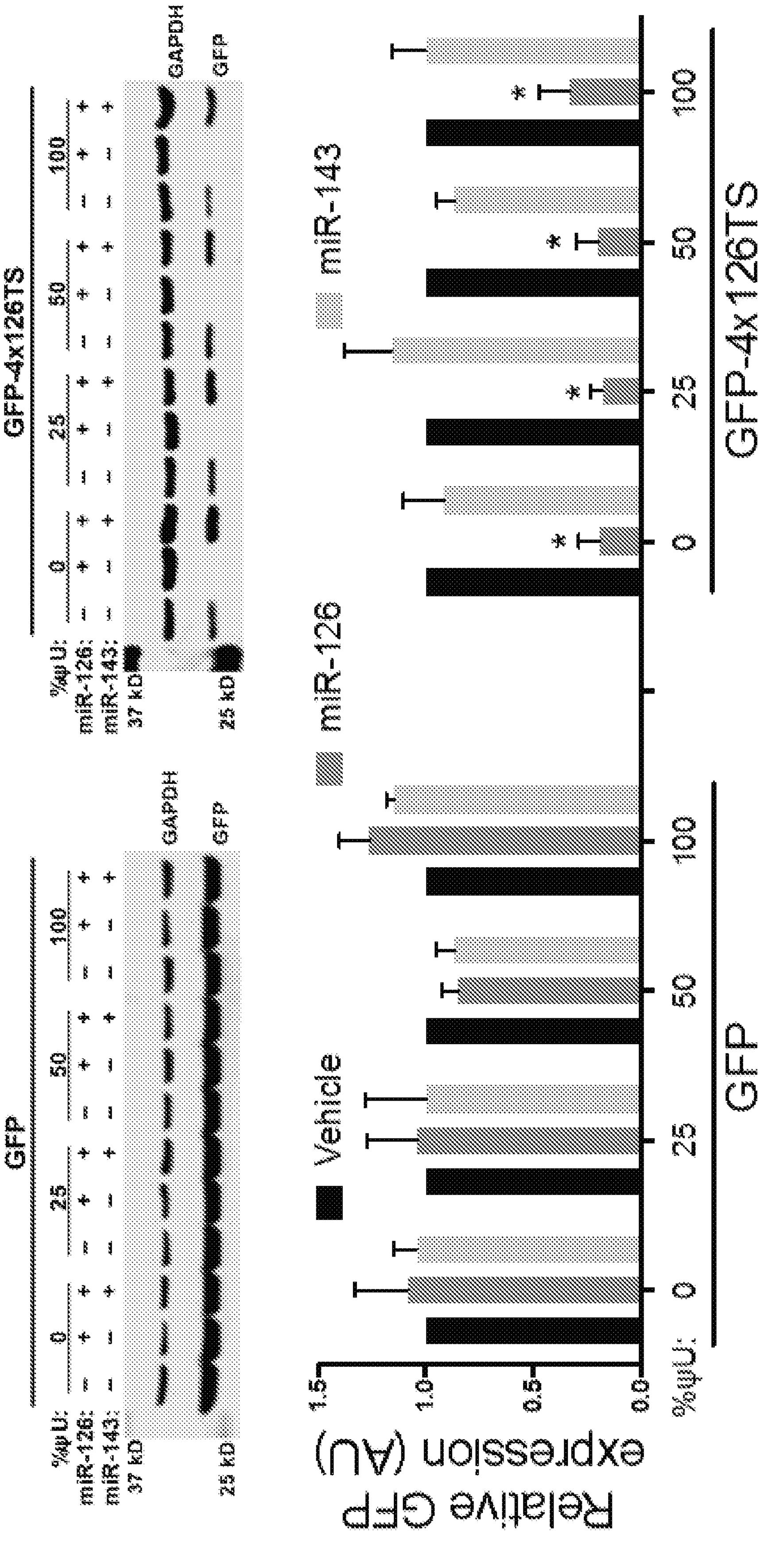

To test whether modified nucleic acids affect the efficiency of miRNA-target site recognition and miRNA-dependent gene silencing, GFP or GFP4x126TS mRNA was in vitro transcribed with substitutions of uridine with pseudouridine (0%, 25%, 50% or 100%). Since ad-HEK293 cells do not express miR-126 or miR-143, we transfected with miR-126 mimic or miR-143 mimic 24 hr prior to transfection with GFP or GFP4x126TS mRNAs to ensure for miRNA/RISC assembly and GFP expression levels were assessed after 24 hr. In the control, unmodified (0% Pseudouridine) GFP transfected cells, the over-expression of miR-126-3p or miR-143 did not have any effect on GFP expression (FIGS. 43A-43C). This was also observed in cells transfected with GFP-mRNA containing increasing percentage of Pseudouridine (FIGS. 43A-43C). However, in cells transfected with GFP4x126TS mRNA, the over-expression of miR-126 and not miR-143 dramatically reduced the percentage of GFP positive cells and inhibited GFP expression. The miR-126-specific inhibition was not affected by increasing the percentage of pseudouridine substitution (FIGS. 43A-43C).

Example 9

Figure 44A:
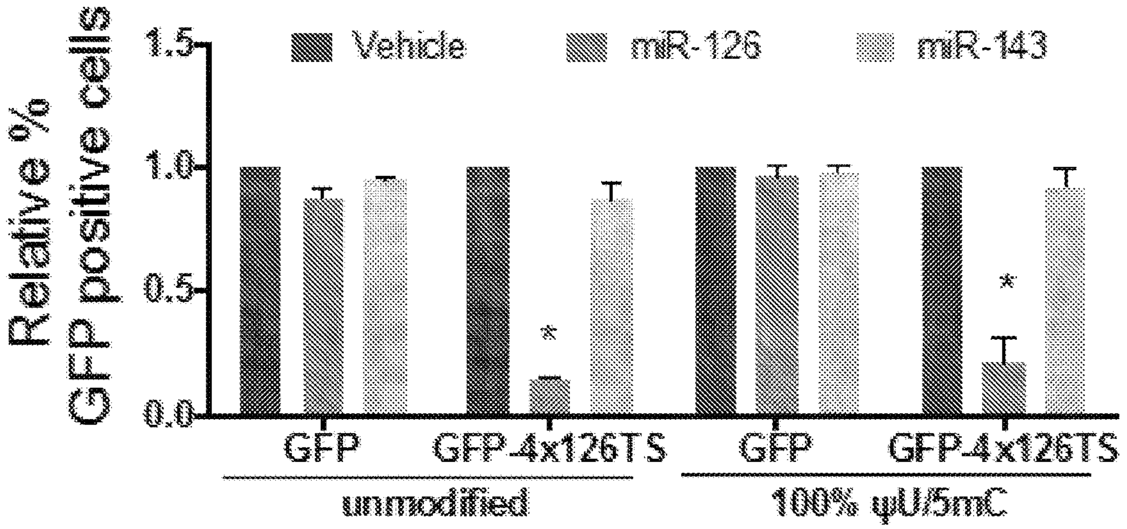
FIGS. 44A-44C show graphs and an image of an immunoblot for GFP demonstrating the relative percent of GFP positive cells (FIG. 44A), relative median GFP intensity (FIG. 44B), and relative GFP expression (FIG. 44C) post transfection with unmodified GFP or GFP 4x126TS or with 100% of uridines and cytosines substituted with pseudouridineand 5-methylcystidine when exposed to miR-126 or miR-143 mimics.
Figure 44B:
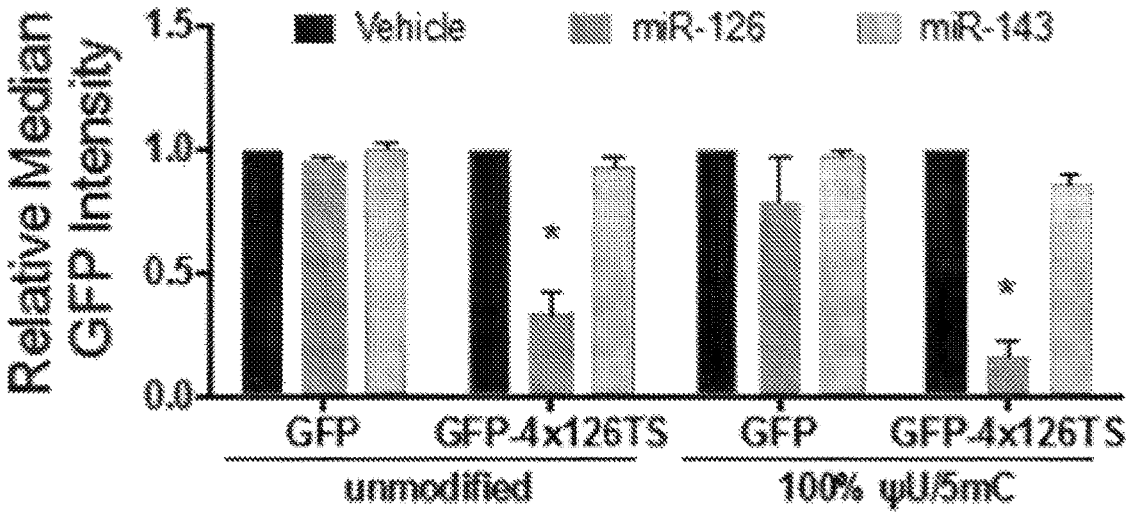
Figure 44C:
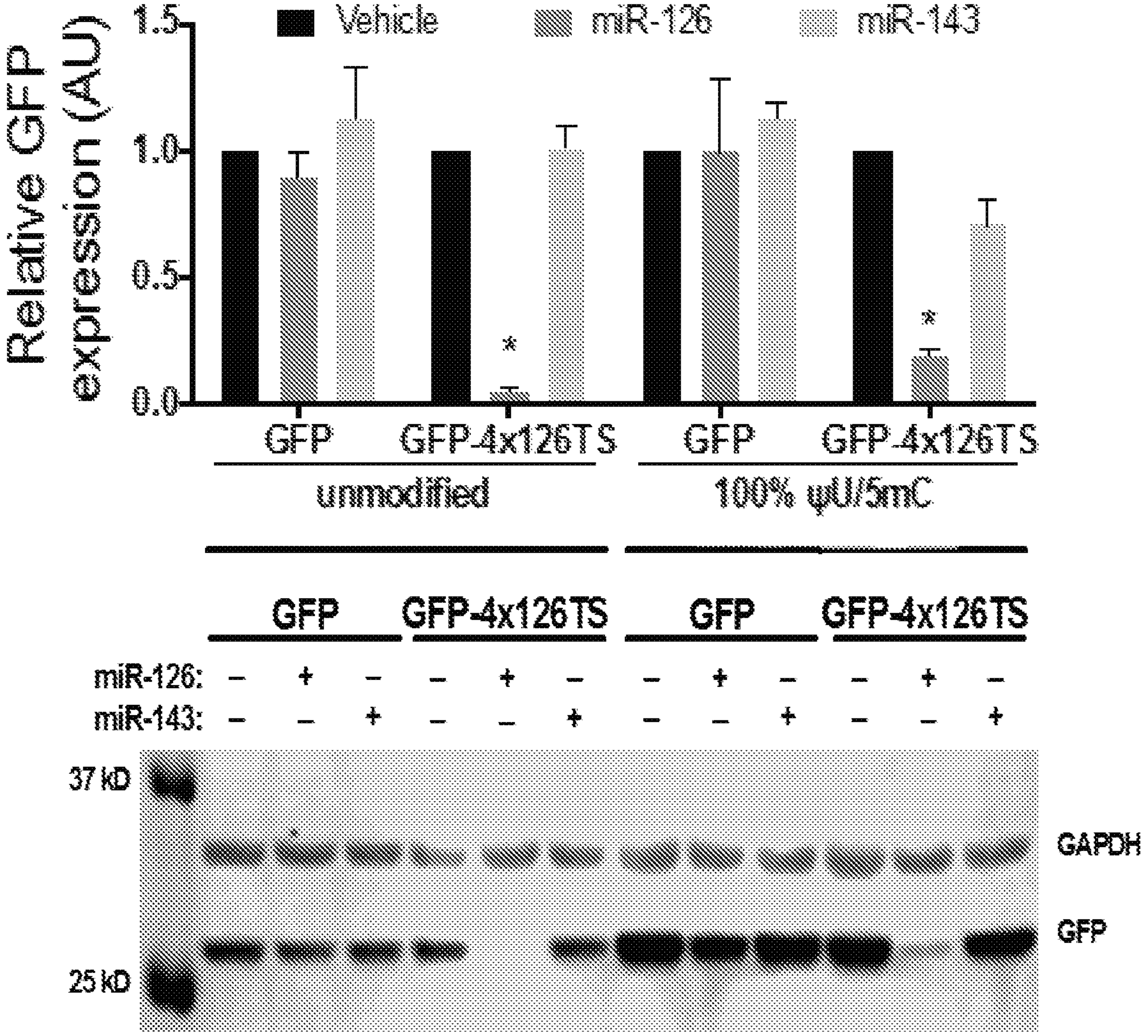

It was also tested whether 100% substitution of both uridine and cytosine with pseudouridine and 5-methylcystidine nucleotides would affect miRNA-dependent gene silencing. To that end, GFP or GFP-4x126TS mRNA were in vitro transcribed with 100% pseudouridine and 100% 5-methylcystidine and transfected into Ad-HEK293 cells that were priory (24 hr) transfected with miR-126 or miR-143 mimics. The inhibitory effect of miR-126 on the expression of the double-modified GFP-4x126TS mRNA were compared to the unmodified mRNA after 24 hr. Cells transfected with pseudouridine and 5-methylcystidine modified mRNA, miR-126 and not miR-143 reduced the percentage of GFP positive cells and inhibited GFP expression to the same extent as the unmodified mRNA (FIGS. 44A-44C). Thus, our data show that complete substitution of pseudouridine, or combination of pseudouridine and 5-methylcystidine modified mRNA, can still be targeted by microRNA-dependent silencing.

Example 10

Figure 45A:
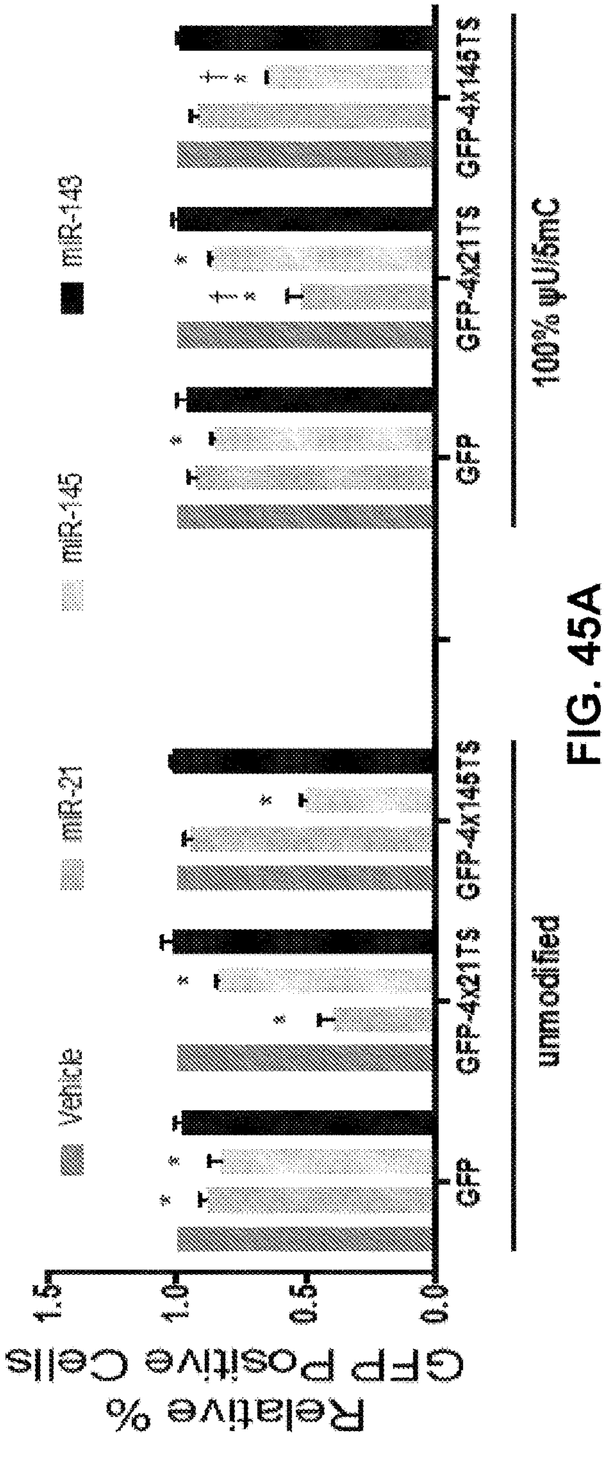
FIGS. 45A-45C show graphs and an image of an immunoblot for GFP demonstrating the relative percent of GFP positive cells (FIG. 45A), relative median GFP intensity (FIG. 45B), and relative GFP expression (FIG. 45C) post transfection with unmodified GFP, GFP 4x21TS, or GFP4x145TS or with 100% of uridines and cytosines substituted with pseudouridineand 5-methylcystidine when exposed to miR-21 or miR-145, miR143 mimics
Figure 45B:
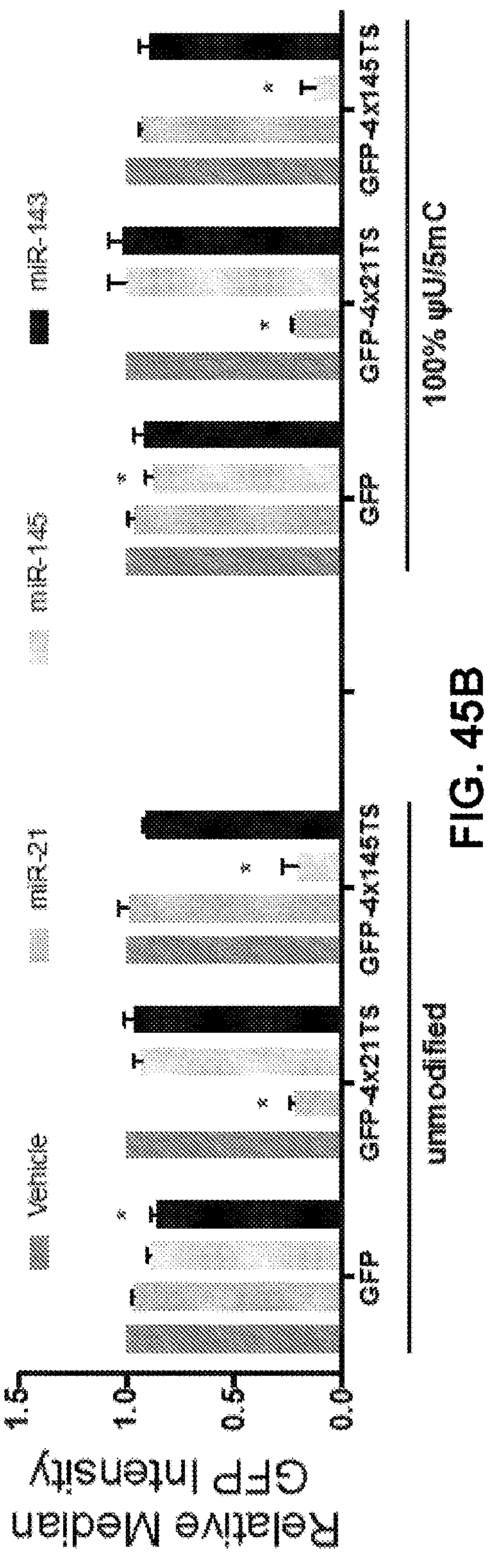
Figure 45C:
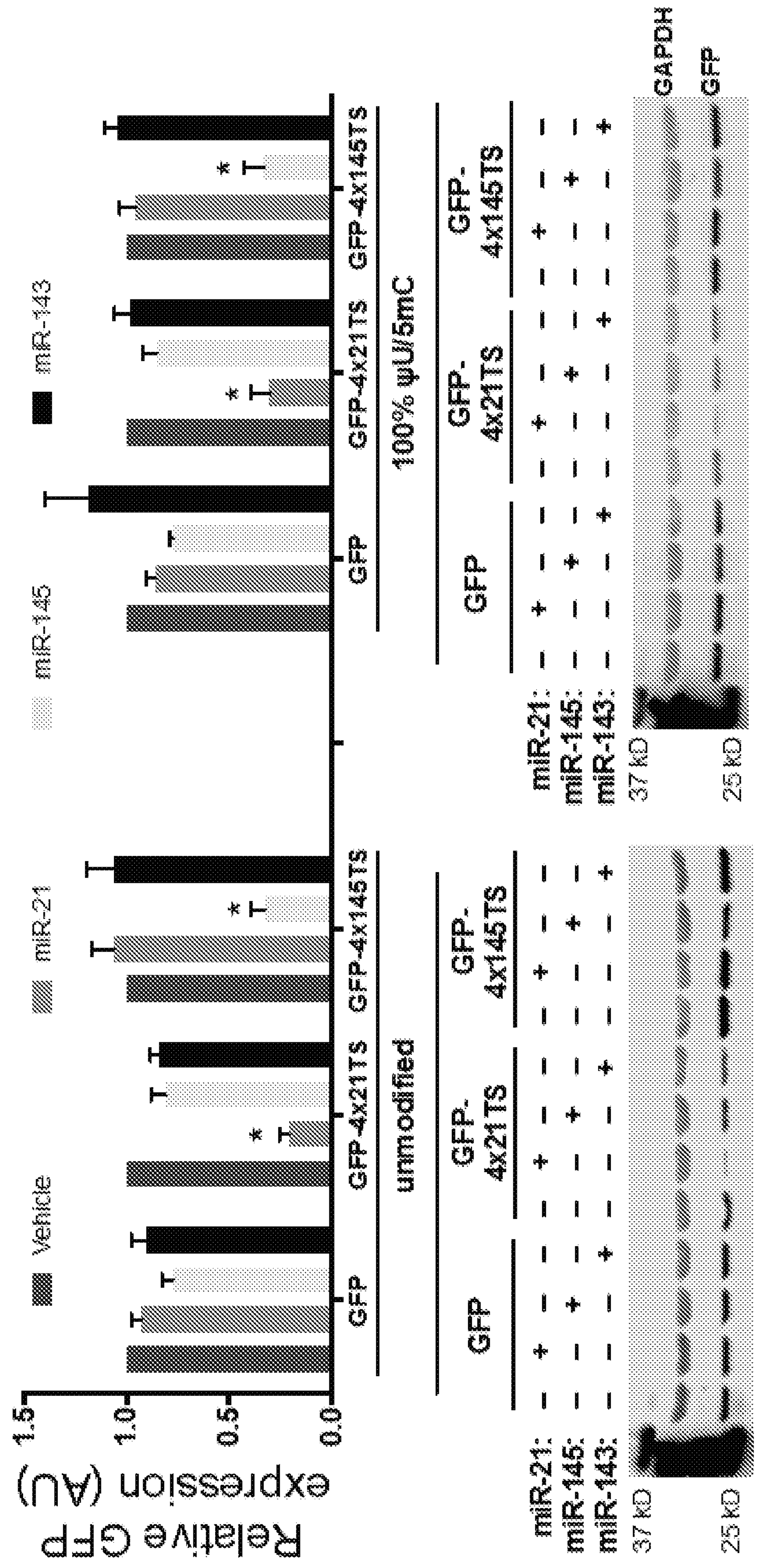

To test whether this miRNA dependent silencing of modified mRNAs is not limited to miR-126, GFP coding mRNA containing target sites for miR-21 or miR-145 was designed. Ad-HEH293 cells were transfected with miR-21, miR-145 or miR-143 mimics 24 hr prior to transfection with unmodified or pseudouridine and 5-methylcystidine modified GFP, GFP4x21TS or GFP4x145TS mRNAs to ensure for RISC assembly and the GFP expression levels were assessed after 24 hr. Cells transfected with 100% Pseudouridine and 5-methylcystidine substituted GFP4x21TS mRNA, the over-expression of miR-21 and not miR-145, miR-21 or moR-143 reduced the expression GFP to the same extent as cells transfected with unmodified GFP4x21TS mRNA (FIGS. 45A-45C). Cells transfected with 100% Pseudouridine and 5-methylcystidine substituted GFP4x154TS mRNA, showed the same reduction in GFP expression as unmodified mRNA when miR-145 mimic was added and not when miR-21, miR-126 or miR-143 mimics were added (FIGS. 45A-45C). In the control transfected cells with unmofdified or 100% substitution with Pseudouridine and 5-methylcystidine GFP mRNA (with no miRNA target sites), the over-expression of miR-21, miR-145 or miR-143 did not have an effect on GFP expression (FIGS. 45A-45C).

Example 11

Figure 46:
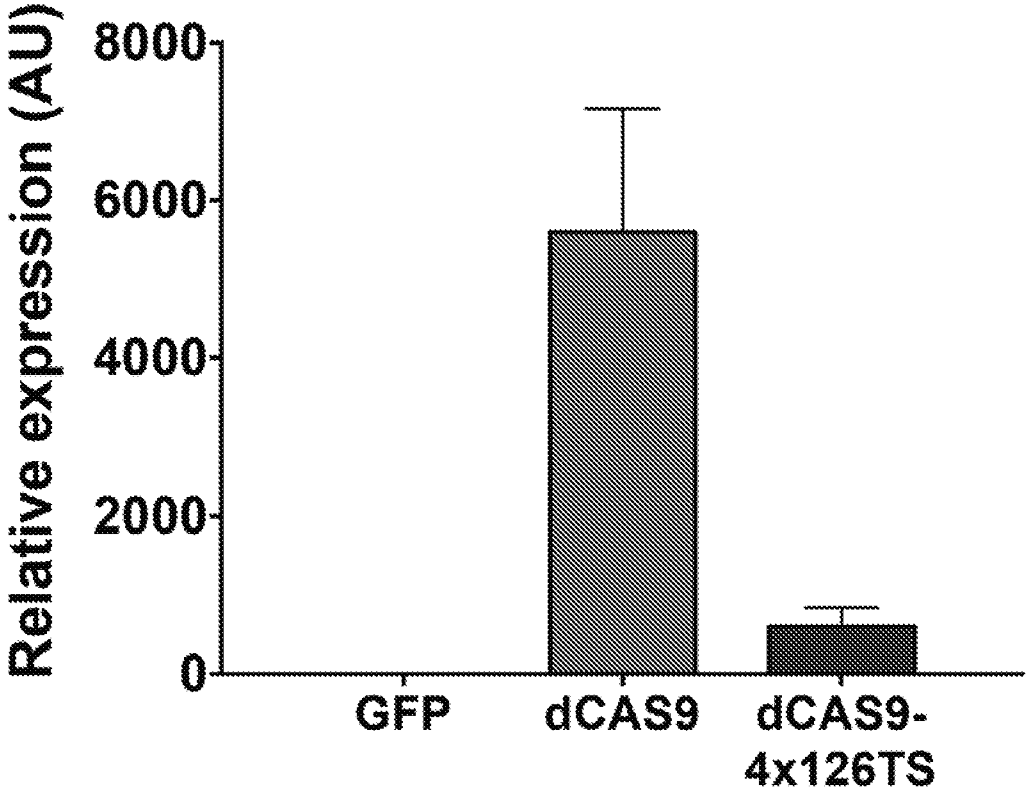
FIG. 46 shows a graph demonstrating the relative expression levels of LIN28A in cells transfected with miR-126 mimic about 24 hours prior to transfection with CRISPR-SAM components containing dCas9 or dCas9-4X126TS.

Cell-Selective Gene Activation Using CRISPR/CAS9 Synergistic Activation Mediator (SAM) System As proof of principle the modified CRISPR/dCas9 Synergistic Activation Mediator (SAM) system (Konermann et al. 2015. Nature, 517:583-588) was employed that included the sgRNA2.0, MS2-p65-HSF1 and NLS-dCas9-VP64. To activate LIN28A in a cell selective manner, we added four tandem copies of a 22-bp target sequence perfectly complementary to the mature miR-126-3p strand at dCas9 3'UTR (dCas9-4x126TS). Ad-HEK293 cells were transfected with miR-126 mimic 24 hours prior to transfection with CRISPR-SAM components containing dCas9 or dCas9-4x126TS and the expression levels of LIN28A was assessed after 72 hours after. Transient transfected adHEK293 cells transfected with CRISPR-SAM components with dCas9 activated the transcription of LIN28A by >5000 fold while adHEK293 cells transfected with CRISPR-SAM and dCas9-4x126TS showed only 600-fold in LIN28A (FIG. 46).

I claim:

1. A polyribonucleotide comprising:

at least one RNA molecule of interest (ROI), wherein the at least one ROI encodes a protein selected from the group consisting of BAX, B18R, PTEN, p16, P15, P18, P19, P21, P57, CDKN3 MS2, p65, HSF1, and p27;

a microRNA (miRNA) target sequence, wherein the miRNA target sequence is a target for miR-126, miR-122, miR-208, miR-145, or miR-143, and combinations thereof, and wherein the miRNA target sequence is operatively linked to the ROI; and a RNA molecule capable of being translated into a viral RNA replicase, wherein the RNA molecule capable of being translated into a viral RNA replicase is operatively linked to the at least one ROI, the miRNA target sequence, or both the at least one ROI and miRNA target sequence.

2. The polyribonucleotide of claim 1, wherein the viral replicase is a Venezuelan Equine Encephalitis viral replicase, a Sindbis viral replicase, or a Semliki Forest virus replicase.

3. The polyribonucleotide of claim 1, further comprising a RNA molecule capable of being translated into one or more additional nonstructural viral proteins, wherein the RNA molecule capable of being translated into one or more additional nonstructural viral proteins is operatively linked to the at least one ROI, the miRNA target sequence, or both the at least one ROI and miRNA target sequence.

4. The polyribonucleotide of claim 1, wherein the polyribonucleotide is a linear polyribonucleotide or a circular polyribonucleotide.

5. The polyribonucleotide of claim 1, wherein one or more ribonucleotides of the polyribonucleotide is modified.

6. The polyribonucleotide of claim 5, wherein the modification is a Pseudouridine, N-1-methylpseudouridineridine, 5-methoxy-Uridine, a 5-hydroxymethyl-C, a 5-methyl-C, or a combination thereof.

7. The polyribonucleotide of claim 1, wherein the miRNA-126 target has a sequence that is complementary to a sequence that is 20-100% identical to SEQ ID NO: 10, wherein the miRNA-145 target has a sequence that is complementary to a sequence that is 20-100% identical to SEQ ID NO: 11, wherein the miRNA-143 target has a sequence that is complementary to a sequence that is 20-100% identical to SEQ ID NO:12, wherein the miRNA-122 target has a sequence that is complementary to a sequence that is 20-100% identical to SEQ ID NO: 13, and wherein the miRNA-208 target has a sequence that is complementary to a sequence that is 20-100% identical to SEQ ID NO: 15.

8. The polyribonucleotide of claim 1, wherein the miRNA-126 target has a sequence that is complementary to a sequence that is 90-100% identical to a portion of SEQ ID NO: 10 and the portion is 5 or more consecutive nucleotides, wherein the miRNA-145 target has a sequence that is complementary to a sequence that is 90-100% identical to a portion of SEQ ID NO: 11 and the portion is 5 or more consecutive nucleotides, wherein the miRNA-143 target has a sequence that is complementary to a sequence that is 90-100% identical to a portion of SEQ ID NO: 12 and the portion is 5 or more consecutive nucleotides, wherein the miRNA-122 target has a sequence that is complementary to a sequence that is 90-100% identical to a portion of SEQ ID NO: 13 and the portion is 5 or more consecutive nucleotides, and wherein the miRNA-208 target has a sequence that is complementary to a sequence that is 90-100% identical to a portion of SEQ ID NO: 15 and the portion is 5 or more consecutive nucleotides.

9. A pharmaceutical formulation comprising:

at least one RNA molecule of interest (ROI), wherein the at least one ROI encodes a protein selected from the group consisting of BAX, B18R, PTEN, p16, P15, P18, P19, P21, P57, CDKN3, MS2, p65, HSF1, and p27;

a microRNA (miRNA) target sequence, wherein the miRNA target sequence is a target for miR-126, miR-122, miR-208, miR-145, or miR-143, and combinations thereof, and wherein the miRNA target sequence is operatively linked to the at least one ROI;

a RNA molecule capable of being translated into a viral RNA replicase, wherein the RNA molecule capable of being translated into a viral RNA replicase is operatively linked to the at least one ROI, the miRNA target sequence, or both the at least one ROI and miRNA target sequence; and a pharmaceutically acceptable carrier.

10. The pharmaceutical formulation of claim 9, wherein the viral replicase is a Venezuelan Equine Encephalitis viral replicase, a Sindbis viral replicase, or a Semliki Forest virus replicase.

11. The pharmaceutical formulation of claim 9, wherein the polynucleotide is present in the pharmaceutical formulation at an amount effective to treat cardiovascular disease, coronary artery disease, pulmonary hypertension, pulmonary fibrosis, liver disease, or cancer, or a symptom thereof in a subject.

12. The pharmaceutical formulation of claim 9, wherein the polynucleotide is present in the pharmaceutical formulation at an amount effective to overexpress BAX in a vascular smooth muscle cell but not overexpress BAX in a vascular endothelial cell.

13. A method comprising:

administering a polyribonucleotide to a subject, wherein the polyribonucleotide comprises:

at least one RNA molecule of interest (ROI), wherein the at least one ROI encodes a protein selected from the group consisting of BAX, B18R, PTEN, p16, P15, P18, P19, P21, P57, CDKN3, MS2, p65, HSF1, and p27;

a microRNA (miRNA) target sequence, wherein the miRNA target sequence is a target for miR-126, miR-122, miR-208, miR-145, or miR-143, and combinations thereof, and wherein the miRNA target sequence is operatively linked to the at least one ROI; and a RNA molecule capable of b eing translated into a viral RNA replicase, wherein the RNA molecule capable of being translated into a viral RNA replicase is operatively linked to the at least one ROI, the miRNA target sequence, or both the at least one ROI and miRNA target sequence.

14. The method of claim 13, wherein the viral replicase is a Venezuelan Equine Encephalitis viral replicase, a Sindbis viral replicase, or a Semliki Forest virus replicase.

15. The method of claim 13, wherein the subject has cardiovascular disease, coronary artery disease, pulmonary hypertension, pulmonary fibrosis, or liver disease, or cancer, or a symptom thereof.

* * * * *

SEQUENCE LISTING

```
<160> NUMBER OF SEQ ID NOS: 135

<210> SEQ ID NO 1
<211> LENGTH: 1725
<212> TYPE: DNA
<213> ORGANISM: Artificial Sequence
<220> FEATURE:
<223> OTHER INFORMATION: ACCESSION NC_006998 REGION: 177306..179030;
      VERSION NC_006998.1 GI:66275797; gene1..1725;Gene ID 3707576,CDS
      1..1725/gene="B18R"/locus_tag="VACWR199"
      /codon_start=1/product="ankyrin-like

<400> SEQUENCE: 1

atgagtcgtc gtctgattta tgttttaaat atcaaccgcg aatcaactca taaaatacaa      60

gagaatgaaa tatatacata ttttagtcat tgcaatatag accatacttc tacagaactt     120

gattttgtag ttaaaaacta tgatctaaac agacgacaac ctgtaactgg gtatactgca     180

ctacactgct atttgtataa taattacttt acaaacgatg tactgaagat attattaaat     240

catggagtgg atgtaacgat gaaaaccagt agcggacgta tgcctgttta tatattgctt     300

actagatgtt gcaatatttc acatgatgta gtgatagata tgatagacaa agataaaaac     360

cacttattac atagagacta ttccaaccta ttactagagt atataaaatc tcgttacatg     420

ttattaaagg aagaggatat cgatgagaac atagtatcca ctttattaga taagggaatc     480

gatcctaact ttaaacaaga cggatataca gcgttacatt attattattt gtgtctcgca     540

cacgtttata aaccaggtga gtgtagaaaa ccgataacga taaaaaaggc caagcgaatt     600

atttctttgt ttatacaaca tggagctaat ctaaacgcgt tagataattg tggtaataca     660

ccattccatt tgtatcttag tattgaaatg tgtaataata ttcatatgac taaaatgctg     720

ttgactttta atccgaattt cgaaatatgt aataatcatg gattaacgcc tatactatgt     780

tatataactt ccgactacat acaacacgat attcttgtta tgttaataca tcactatgaa     840

acaaatgttg gagaaatgcc gatagatgag cgtcgtataa tcgtattcga gtttatcaaa     900

acatattcta cacgtcctgc agattcgata acttatttga tgaataggtt taaaaatata     960

gatatttata cccgctatga aggaaagaca ttattacacg tagcatgtga atataataat    1020

acacacgtaa tagattatct tatacgtatc aacggagata taaatgcgtt aaccgacaat    1080

aacaaacacg ctacacaact cattatagat aacaaagaaa attccccata taccattaat    1140

tgtttactgt atatacttag atatattgta gataagaatg tgataagatc gttggtggat    1200

caacttccat ctctacctat cttcgatata aaatcatttg agaaattcat atcctactgt    1260

atacttttag atgacacatt ttacaataga cacgttagga atcgcgattc taaaacgtat    1320

cgatacgcat tttcaaaata catgtcgttt gataaatacg atggtataat aactaaatgt    1380

cataaagaaa caatattgct caaactatcc actgttctag acactacact atatgcagtt    1440

ttaagatgcc ataattcgaa aaagttaaga agatacctca ccgagttaaa aaaatataat    1500
```

-continued

```
aacgataagt cctttaaaat atattctaat attatgaatg agagatacct taatgtatat   1560

tataaagata tgtacgtgtc aaaggtatat gataaactat ttcctgtttt cacagataaa   1620

aattgtctac taacattact accttcagaa attatatacg aaatattata catgctgaca   1680

attaacgatc tttataatat atcgtatcca cctaccaaag tatag                   1725
```

<210> SEQ ID NO 2
<211> LENGTH: 2535
<212> TYPE: DNA
<213> ORGANISM: Artificial Sequence
<220> FEATURE:
<223> OTHER INFORMATION: Accession No.: NM_004064; NCBI Ref. Seq. NM_004064.4: Homo sapiens cyclin-dependent kinase inhibitor 1B (p27, Kip1) (CDKN1B), mRNA

<400> SEQUENCE: 2

```
ttaaggccgc gctcgccagc ctcggcgggg cggctcccgc cgccgcaacc aatggatctc     60

ctcctctgtt taaatagact cgccgtgtca atcattttct tcttcgtcag cctcccttcc    120

accgccatat tgggccacta aaaaaagggg gctcgtcttt tcggggtgtt tttctccccc    180

tcccctgtcc ccgcttgctc acggctctgc gactccgacg ccggcaaggt ttggagagcg    240

gctgggttcg cgggacccgc gggcttgcac ccgcccagac tcggacgggc tttgccaccc    300

tctccgcttg cctggtcccc tctcctctcc gccctcccgc tcgccagtcc atttgatcag    360

cggagactcg gcggccgggc cggggcttcc ccgcagcccc tgcgcgctcc tagagctcgg    420

gccgtggctc gtcggggtct gtgtcttttg gctccgaggg cagtcgctgg gcttccgaga    480

ggggttcggg ctgcgtaggg gcgctttgtt ttgttcggtt ttgttttttt gagagtgcga    540

gagaggcggt cgtgcagacc cgggagaaag atgtcaaacg tgcgagtgtc taacgggagc    600

cctagcctgg agcggatgga cgccaggcag gcggagcacc ccaagccctc ggcctgcagg    660

aacctcttcg gcccggtgga ccacgaagag ttaacccggg acttggagaa gcactgcaga    720

gacatggaag aggcgagcca gcgcaagtgg aatttcgatt ttcagaatca caaaccccta    780

gagggcaagt acgagtggca agaggtggag aagggcagct tgcccgagtt ctactacaga    840

cccccgcggc ccccaaagg tgcctgcaag gtgccggcgc aggagagcca ggatgtcagc    900

gggagccgcc cggcggcgcc tttaattggg gctccggcta actctgagga cacgcatttg    960

gtggacccaa agactgatcc gtcggacagc cagacggggt tagcggagca atgcgcagga   1020

ataaggaagc gacctgcaac cgacgattct tctactcaaa acaaaagagc caacagaaca   1080

gaagaaaatg tttcagacgg ttccccaaat gccggttctg tggagcagac gcccaagaag   1140

cctggcctca gaagacgtca aacgtaaaca gctcgaatta agaatatgtt tccttgttta   1200

tcagatacat cactgcttga tgaagcaagg aagatataca tgaaaatttt aaaaatacat   1260

atcgctgact tcatggaatg gacatcctgt ataagcactg aaaaacaaca acacaataac   1320

actaaaattt taggcactct taaatgatct gcctctaaaa gcgttggatg tagcattatg   1380

caattaggtt tttccttatt tgcttcattg tactacctgt gtatatagtt tttacctttt   1440

atgtagcaca taaactttgg ggaagggagg gcagggtggg gctgaggaac tgacgtggag   1500

cggggtatga agagcttgct ttgatttaca gcaagtagat aaatatttga cttgcatgaa   1560

gagaagcaat tttggggaag ggtttgaatt gttttcttta aagatgtaat gtccctttca   1620

gagacagctg atacttcatt taaaaaaatc acaaaaattt gaacactggc taaagataat   1680

tgctatttat ttttacaaga agtttattct catttgggag atctggtgat ctcccaagct   1740
```

-continued

```
atctaaagtt tgttagatag ctgcatgtgg ctttttttaaa aaagcaacag aaacctatcc   1800
tcactgccct ccccagtctc tcttaaagtt ggaatttacc agttaattac tcagcagaat   1860
ggtgatcact ccaggtagtt tggggcaaaa atccgaggtg cttgggagtt ttgaatgtta   1920
agaattgacc atctgctttt attaaatttg ttgacaaaat tttctcattt tcttttcact   1980
tcgggctgtg taaacacagt caaaataatt ctaaatccct cgatattttt aaagatctgt   2040
aagtaacttc acattaaaaa atgaaatatt ttttaattta aagcttactc tgtccattta   2100
tccacaggaa agtgttattt ttcaaggaag gttcatgtag agaaaagcac acttgtagga   2160
taagtgaaat ggatactaca tctttaaaca gtatttcatt gcctgtgtat ggaaaaacca   2220
tttgaagtgt acctgtgtac ataactctgt aaaaacactg aaaaattata ctaacttatt   2280
tatgttaaaa gatttttttt aatctagaca atatacaagc caaagtggca tgttttgtgc   2340
atttgtaaat gctgtgttgg gtagaatagg ttttcccctc ttttgttaaa taatatggct   2400
atgcttaaaa ggttgcatac tgagccaagt ataatttttt gtaatgtgtg aaaaagatgc   2460
caattattgt tacacattaa gtaatcaata aagaaaactt ccatagctat tcattgagtc   2520
aaaaaaaaaa aaaaa                                                      2535
```

<210> SEQ ID NO 3
<211> LENGTH: 11878
<212> TYPE: DNA
<213> ORGANISM: Artificial Sequence
<220> FEATURE:
<223> OTHER INFORMATION: . Cas9 endonuclease: KM099231

<400> SEQUENCE: 3

```
gcctcactga ttaagcattg gtaactgtca gaccaagttt actcatatat actttagatt     60
gatttaaaac ttcattttta atttaaaagg atctaggtga agatcctttt tgataatctc    120
atgaccaaaa tcccttaacg tgagttttcg ttccactgag cgtcagaccc cgtagaaaag    180
atcaaaggat cttcttgaga tccttttttt ctgcgcgtaa tctgctgctt gcaaacaaaa    240
aaaccaccgc taccagcggt ggtttgtttg ccggatcaag agctaccaac tctttttccg    300
aaggtaactg gcttcagcag agcgcagata ccaaatactg ttcttctagt gtagccgtag    360
ttaggccacc acttcaagaa ctctgtagca ccgcctacat acctcgctct gctaatcctg    420
ttaccagtgg ctgctgccag tggcgataag tcgtgtctta ccgggttgga ctcaagacga    480
tagttaccgg ataaggcgca gcggtcgggc tgaacggggg gttcgtgcac acagcccagc    540
ttggagcgaa cgacctacac cgaactgaga tacctacagc gtgagctatg agaaagcgcc    600
acgcttcccg aagggagaaa ggcggacagg tatccggtaa gcggcagggt cggaacagga    660
gagcgcacga gggagcttcc agggggaaac gcctggtatc tttatagtcc tgtcgggttt    720
cgccacctct gacttgagcg tcgatttttg tgatgctcgt caggggggcg gagcctatgg    780
aaaaacgcca gcaacgcggc ctttttacgg ttcctggcct tttgctggcc ttttgctcac    840
atgttctttc ctgcgttatc ccctgattct gtggataacc gtattaccgc ctttgagtga    900
gctgataccg ctcgccgcag ccgaacgacc gagcgcagcg agtcagtgag cgaggaagcg    960
gaagagcgcc caatacgcaa accgcctctc cccgcgcgtt ggccgattca ttaatgcagc   1020
tggcacgaca ggtttcccga ctggaaagcg ggcagtgagc gcaacgcaat taatgtgagt   1080
tagctcactc attaggcacc ccaggcttta cactttatgc ttccggctcg tatgttgtgt   1140
ggaattgtga gcggataaca atttcacaca ggaaacagct atgaccatga ttacgccaag   1200
ctatttaggt gacactatag aatactcaag cttgggggga tcctctagag tcgacctgca   1260
```

-continued

```
ggcatgctat ttgatgaatt aactacactt aaaataatac aattattatt aaattttttt   1320
ttgatttatt tattaatttt taaacttaat catttgtatt tgggaggaat tatatatatc   1380
tttataatta ttttattttt ttttattttt ttattttttt attattatta ttttttttta   1440
tttttttttt ttactgtatc aaagaaaaac ctttaaaaaa aaaattataa tttccccatc   1500
ttactatatt tttaatacat acgttttaag gaattaaatt agacaaaagc tatattatgc   1560
tttacatata attagaattt ataaacgttt ggttattaga tatttcatgt ctcagtaaag   1620
tctttcaata catatgtaaa aaaatatata tgaatacaca taagttgtta atatatttta   1680
tatgcataaa tgtataaata tatatatata tatatatata tgtatgtatg tatatgtgtg   1740
tatatgaaat tatttcaatg tttaattttt taaattttaa tttttttttt tttttttttt   1800
tttattatgt atattgatct ttattattta aatattactt ttttcgtttt ttcttctttt   1860
tattattttt tttttttttt atattttata caaatggtaa ttcaaataaa aggtataaat   1920
ttatatttaa ttttctttta tggataaata aaagaaaaat ataaatatat aaaaatataa   1980
aaatatatat atgtatattg gggtgatgat aaaatgaaag ataaatatata tatatatata   2040
tctttatttt ttttttttg tagaccccat tgtgagtaca taaatatatt atataactcg   2100
ggagcatcag tcatggaatt cttatttctt tttctttttt gcctggccgg ccttttttcgt   2160
ggccgccggc cttttgtcgc ctcccagctg agacaggtcg atccgtgtct cgtacaggcc   2220
ggtgatgctc tggtggatca gggtggcgtc cagcacctct ttggtgctgg tgtacctctt   2280
ccggtcgatg gtggtgtcaa agtacttgaa ggcggcaggg gctcccagat tggtcagggt   2340
aaacaggtgg atgatattct cggcctgctc tctgatgggc ttatcccggt gcttgttgta   2400
ggcggacagc actttgtcca gattagcgtc ggccaggatc actctcttgg agaactcgct   2460
gatctgctcg atgatctcgt ccaggtagtg cttgtgctgt tccacaaaca gctgtttctg   2520
ctcattatcc tcgggggagc ccttcagctt ctcatagtgg ctggccaggt acaggaagtt   2580
cacatatttg gagggcaggg ccagttcgtt tcccttctgc agttcgccgg cagaggccag   2640
cattctcttc cggccgtttt ccagctcgaa cagggagtac ttaggcagct tgatgatcag   2700
gtccttttc acttctttgt agcccttggc ttccagaaag tcgatgggat tcttctcgaa   2760
gctgcttctt tccatgatgg tgatccccag cagctctttc acactcttca gtttcttgga   2820
cttgcccttt tccactttgg ccaccaccag cacagaatag gccacggtgg ggctgtcgaa   2880
gccgccgtac ttcttagggt cccagtcctt ctttctggcg atcagcttat cgctgttcct   2940
cttgggcagg atagactctt tgctgaagcc gcctgtctgc acctcggtct ttttcacgat   3000
attcacttgg ggcatgctca gcactttccg cacggtggca aaatcccggc ccttatccca   3060
cacgatctcc ccggtttcgc cgtttgtctc gatcagaggc cgcttccgga tctcgccgtt   3120
ggccagggta atctcggtct tgaaaaagtt catgatgttg ctgtagaaga agtacttggc   3180
ggtagccttg ccgatttcct gctcgctctt ggcgatcatc ttccgcacgt cgtacacctt   3240
gtagtcgccg tacacgaact cgctttccag cttagggtac tttttgatca gggcggttcc   3300
cacgacggcg ttcaggtagg cgtcgtgggc gtggtggtag ttgttgatct cgcgcacttt   3360
gtaaaactgg aaatccttcc ggaaatcgga caccagcttg gacttcaggg tgatcacttt   3420
cacttcccgg atcagcttgt cattctcgtc gtacttagtg ttcatccggg agtccaggat   3480
ctgtgccacg tgctttgtga tctgccgggt ttccaccagc tgtctcttga tgaagccggc   3540
cttatccagt tcgctcaggc cgcctctctc ggccttggtc agattgtcga actttctctg   3600
```

-continued

```
ggtaatcagc ttggcgttca gcagctgccg ccagtagttc ttcatcttct tcacgacctc   3660
ttcggagggc acgttgtcgc tcttgccccg gttcttgtcg cttctggtca gcaccttgtt   3720
gtcgatggag tcgtccttca gaaagctctg aggcacgata tggtccacat cgtagtcgga   3780
cagccggttg atgtccagtt cctggtccac gtacatatcc cgcccattct gcaggtagta   3840
caggtacagc ttctcgttct gcagctgggt gttttccacg gggtgttctt tcaggatctg   3900
gctgcccagc tctttgatgc cctcttcgat ccgcttcatt ctctcgcggc tgttcttctg   3960
tcccttctgg gtggtctggt tctctctggc catttcgatc acgatgttct cgggcttgtg   4020
ccggcccatc actttcacga gctcgtccac caccttcact gtctgcagga tgcccttctt   4080
aatggcgggg ctgccggcca gattggcaat gtgctcgtgc aggctatcgc cctggccgga   4140
cacctgggct ttctggatgt cctctttaaa ggtcaggctg tcgtcgtgga tcagctgcat   4200
gaagtttctg ttggcgaagc cgtcggactt caggaaatcc aggattgtct tgccggactg   4260
cttgtcccgg atgccgttga tcagcttccg gctcagcctg ccccagccgg tgtatctccg   4320
ccgcttcagc tgcttcatca ctttgtcgtc gaacaggtgg gcataggttt tcagccgttc   4380
ctcgatcatc tctctgtcct caaacagtgt cagggtcagc acgatatctt ccagaatgtc   4440
ctcgttttcc tcattgtcca ggaagtcctt gtccttgata attttcagca gatcgtggta   4500
tgtgcccagg gaggcgttga accgatcttc cacgccggag atttccacgg agtcgaagca   4560
ctcgatttc ttgaagtagt cctctttcag ctgcttcacg gtcactttcc ggttggtctt   4620
gaacagcagg tccacgatgg cctttttctg ctcgccgctc aggaaggcgg gctttctcat   4680
tccctcggtc acgtatttca ctttggtcag ctcgttatac acggtgaagt actcgtacag   4740
caggctgtgc ttgggcagca ccttctcgtt gggcaggttc ttatcgaagt tggtcatccg   4800
ctcgatgaag ctctgggcgg aagcgccctt gtccaccact tcctcgaagt tccagggggt   4860
gatggtttcc tcgctctttc tggtcatcca ggcgaatctg ctgtttcccc tggccagagg   4920
gcccacgtag taggggatgc ggaaggtcag gatcttctcg atcttttccc ggttgtcctt   4980
caggaatggg taaaaatctt cctgccgccg cagaatggcg tgcagctctc ccaggtggat   5040
ctggtggggg atgctgccgt tgtcgaaggt ccgctgcttc cgcagcaggt cctctctgtt   5100
cagcttcacg agcagttcct cggtgccgtc catcttttcc aggatgggct tgatgaactt   5160
gtagaactct tcctggctgg ctccgccgtc aatgtagccg gcgtagccgt tcttgctctg   5220
gtcgaagaaa atctctttgt acttctcagg cagctgctgc cgcacgagag ctttcagcag   5280
ggtcaggtcc tggtggtgct cgtcgtatct cttgatcata gaggcgctca ggggggcctt   5340
ggtgatctcg gtgttcactc tcaggatgtc gctcagcagg atggcgtcgg acaggttctt   5400
ggcggccaga aacaggtcgg cgtactggtc gccgatctgg gccagcaggt tgtccaggtc   5460
gtcgtcgtag gtgtccttgc tcagctgcag tttggcatcc tcggccaggt cgaagttgct   5520
cttgaagttg gggtcaggc ccaggctcag ggcaatcagg tttccgaaca ggccattctt   5580
cttctcgccg ggcagctggg cgatcagatt ttccagccgt ctgctcttgc tcagtctggc   5640
agacaggatg gccttggcgt ccacgccgct ggcgttgatg gggttttcct cgaacagctg   5700
gttgtaggtc tgcaccagct ggatgaacag cttgtccacg tcgctgttgt cggggttcag   5760
gtcgccctcg atcaggaagt ggccccggaa cttgatcatg tgggccaggg ccagatagat   5820
cagccgcagg tcggccttgt cggtgctgtc caccagtttc tttctcaggt ggtagatggt   5880
ggggtacttc tcgtggtagg ccacctcgtc cacgatgttg ccgaagatgg ggtgccgctc   5940
gtgcttctta tcctcttcca ccaggaagga ctcttccagt ctgtggaaga agctgtcgtc   6000
```

-continued

```
caccttggcc atctcgttgc tgaagatctc ttgcagatag cagatccggt tcttccgtct   6060
ggtgtatctt cttctggcgg ttctcttcag ccgggtggcc tcggctgttt cgccgctgtc   6120
gaacagcagg gctccgatca ggttcttctt gatgctgtgc cggtcggtgt tgcccagcac   6180
cttgaatttc ttgctgggca ccttgtactc gtcggtgatc acggcccagc ccacagagtt   6240
ggtgccgatg tccaggccga tgctgtactt cttgtcggct gctgggactc cgtggatacc   6300
gaccttccgc ttcttctttg gggccatctt atcgtcatcg tctttgtaat caatatcatg   6360
atccttgtag tctccgtcgt ggtccttata gtccattttt ctcgagggat cctgatatat   6420
ttctattagg tatttattat tataaaatat aaatcttgaa tgataataaa taaaatatta   6480
gttattcctt ttctagttta aaatatacat attataaata tatatatata tatatatatt   6540
tttattgtga caagaatata taattataaa ttatattatt tatttttgta ttttttttt    6600
ttttttttt tttttctttt tttgttttat ttttcttttt ttttataaat attatttttt    6660
tcttttatca tgcacattgg aataatacat taatatatat atatatatta tattatacat   6720
atattgaata atgtttataa aaaatgcata acttatatga atataatttt ttttaaatat   6780
gacaaaaaga aaaaaaaaaa aaaccaaaaa aaattaaaat tgaaatgaaa tatataaata   6840
tattatttat atatattata cattgtttaa tactactaca tgtatatata tatattatat   6900
atatatatat atatcaattt tttcaaaaat aaattaatat aaaaagaggg gaaaaaaaaa   6960
aaaaaaaaaa aaaaaagata attaagtaag catttaaaaa tatataaatt gataatatat   7020
aaaattaatc acatataaaa gcttataaac actaggttag ctaattcgct tgtaagaggt   7080
actctcgttt atgcaaaact atttgatata gcattttaac aagtacacat atatatatgt   7140
aatatatata ctatatatat ctattgcatg tgtactaagc atgtgcatgg catccccttt   7200
ttctcgtgtt taaaacagtt tgtatgataa aatataaagg atttgaaaaa gagaaaaaaa   7260
tatatgatct catcctatat agcgccataa tttttatttg ggttgaataa aattttctac   7320
taaatttagg tgtaagtaaa ataatggaat atatataagt acaataaaaa agtgcataaa   7380
ttaaaaaatt tttataataa atattttttt taaaaaagtc aataataata ttaaatatat   7440
ataacacagg attatatatg ttcactacaa tttttatat tataatataa attcttttca    7500
attttcattt tattttacat acactttcct tttttgtcac tatattttaa tattcacata   7560
tttagtttaa atactggcta tttctttcta catttgctag taacaattgt gtagtgctta   7620
aatatataca cacacctaaa acttacaaag tatcctagga ccatggccaa gcctttgtct   7680
caagaagaat ccaccctcat tgaaagagca acggctacaa tcaacagcat ccccatctct   7740
gaagactaca gcgtcgccag cgcagctctc tctagcgacg gccgcatctt cactggtgtc   7800
aatgtatatc attttactgg gggaccttgt gcagaactcg tggtgctggg cactgctgct   7860
gctgcggcag ctggcaacct gacttgtatc gtcgcgatcg gaaatgagaa caggggcatc   7920
ttgagcccct gcggacggtg ccgacaggtg cttctcgatc tgcatcctgg gatcaaagcc   7980
atagtgaagg acagtgatgg acagccgacg gcagttggga ttcgtgaatt gctgccctct   8040
ggttatgtgt gggagggcta accgcgggta ccccattaaa tttatttaat aatagattaa   8100
aaatattata aaaataaaaa cataaacaca gaaattacaa aaaaaataca tatgaatttt   8160
ttttttgtaa tcttccttat aaatatagaa taatgaatca tataaaacat atcattattc   8220
atttatttac atttaaaatt attgtttcag tatctttaat ttattatgta tatataaaaa   8280
taacttacaa ttttattaat aaacaatata tgtttattaa ttcatgtttt gtaatttatg   8340
```

-continued

```
ggatagcgat ttttttact gtctgtattt tcttttttaa ttatgtttta attgtattta   8400
ttttattttt attattgttc tttttatagt attattttaa aacaaaatgt attttctaag   8460
aacttataat aataataata taaattttaa taaaaattat atttatcttt tacaatatga   8520
acataaagta caacattaat atatagcttt taatattttt attcctaatc atgtaaatct   8580
taaatttttc tttttaaaca tatgttaaat atttatttct cattatatat aagaacatat   8640
ttattacatc tagaggtacc gagctcgttt tcgacactgg atggcggcgt tagtatcgaa   8700
tcgacagcag tatagcgacc agcattcaca tacgattgac gcatgatatt actttctgcg   8760
cacttaactt cgcatctggg cagatgatgt cgaggcgaaa aaaaatataa atcacgctaa   8820
catttgatta aaatagaaca actacaatat aaaaaaacta tacaaatgac aagttcttga   8880
aaacaagaat ctttttattg tcagtactga ttagaaaaac tcatcgagca tcaaatgaaa   8940
ctgcaattta ttcatatcag gattatcaat accatatttt tgaaaaagcc gtttctgtaa   9000
tgaaggagaa aactcaccga ggcagttcca taggatggca agatcctggt atcggtctgc   9060
gattccgact cgtccaacat caatacaacc tattaatttc ccctcgtcaa aaataaggtt   9120
atcaagtgag aaatcaccat gagtgacgac tgaatccggt gagaatggca aaagcttatg   9180
catttctttc cagacttgtt caacaggcca gccattacgc tcgtcatcaa aatcactcgc   9240
atcaaccaaa ccgttattca ttcgtgattg cgcctgagcg agacgaaata cgcgatcgct   9300
gttaaaagga caattacaaa caggaatcga atgcaaccgg cgcaggaaca ctgccagcgc   9360
atcaacaata ttttcacctg aatcaggata ttcttctaat acctggaatg ctgttttgcc   9420
ggggatcgca gtggtgagta accatgcatc atcaggagta cggataaaat gcttgatggt   9480
cggaagaggc ataaattccg tcagccagtt tagtctgacc atctcatctg taacatcatt   9540
ggcaacgcta cctttgccat gtttcagaaa caactctggc gcatcgggct tcccatacaa   9600
tcgatagatt gtcgcacctg attgcccgac attatcgcga gcccatttat acccatataa   9660
atcagcatcc atgttggaat ttaatcgcgg cctcgaaacg tgagtctttt ccttacccat   9720
ggttgtttat gttcggatgt gatgtgagaa ctgtatccta gcaagatttt aaaaggaagt   9780
atatgaaaga agaacctcag tggcaaatcc taacctttta tatttctcta caggggcgcg   9840
gcgtggggac aattcaacgc gtctgtgagg ggagcgtttc cctgctcgca ggtctgcagc   9900
gaggagccgt aatttttgct tcgcgccgtg cggccatcaa aatgtatgga tgcaaatgat   9960
tatacatggg gatgtatggg ctaaatgtac gggcgacagt cacatcatgc ccctgagctg  10020
cgcacgtcaa gactgtcaag gagggtattc tgggcctcca tgtcgctggc ctaacattag  10080
taatgtaggt ctgactttca ctcatataag tcttatggta actaaactaa ggtcttacct  10140
ttactgatat atgtcttact ttcactaact taggtattac ttttactaac ttaggtctta  10200
aattcagtaa ctaaggtcat acttcgacta actaaggtct tacattcact gatataggtc  10260
ttatgattac taacttaggt cctaatttga ctaacataag tcctaacatt agtaatgtag  10320
gtcttaactt aactaactta ggtcttacct tcactaatat aggtcttaat attactgact  10380
taagtaatta aggtactaac ttaggtcgta aggtaactaa tatataggtc ttaaggtaac  10440
taatttaggt cttgacttaa taaatatagg tcctaacata aatagtatag gtcctaatat  10500
aagtactata ggccttaact taaccaacat aggtcctaac ataagttata taggtcttaa  10560
cgtaactaac ataagtcatt aaggtactaa gtttggtctt aatttaacaa taacatgtcg  10620
ctggcctaac attagtaatg taggtctgac tttcactcat ataagtctta tggtaactaa  10680
actaaggtct tacctttact gatatatgtc ttactttcac taacttaggt attactttta  10740
```

```
ctaacttagg tcttaaattc agtaactaag gtcatacttc gactaactaa ggtcttacat  10800

tcactgatat aggtcttatg attactaact taggtcctaa tttgactaac ataagtccta  10860

acattagtaa tgtaggtctt aacttaacta acttaggtct taccttcact aatataggtc  10920

ttaatattac tgacttaagt aattaaggta ctaacttagg tcgtaaggta actaatatat  10980

aggtcttaag gtaactaatt taggtcttga cttaataaat ataggtccta acataaatag  11040

tataggtcct aatataagta ctataggcct taacttaacc aacataggtc ctaacataag  11100

ttatataggt cttaacgtaa ctaacataag tcattaaggt actaagtttg gtcttaattt  11160

aacaataacc atgtcgctgg ccgggtggtc ttaatttaac aaatatagac catgtcgctg  11220

gccgggtgac ccggcgggga cgaggcaagc taaacagatc ctcgtgatac gcctattttt  11280

ataggttaat gtcatgataa taatggtttc ttaggacgga tcgcttgcct gtaacttaca  11340

cgcgcctcgt atcttttaat gatggaataa tttgggaatt tactctgtgt ttatttattt  11400

ttatgttttg tatttggatt ttagaaagta aataaagaag gtagaagagt tacggaatga  11460

agaaaaaaaa ataaacaaag gtttaaaaaa tttcaacaaa aagcgtactt tacatatata  11520

tttattagac aagaaaagca gattaaatag atatacattc gattaacgat aagtaaaatg  11580

taaaatcaca ggattttcgt gtgtggtctt ctacacagac aagatgaaac aattcggcat  11640

taatacctga gagcaggaag agcaagataa aaggtagtat ttgttggcga tccccctaga  11700

gtcttttaca tcttcggaaa acaaaaacta ttttttcttt aatttctttt tttactttct  11760

atttttaatt tatatattta tattaaaaaa tttaaattat aattattttt atagcacgtg  11820

atgaaaagga cccaggtggc acttttcggg gaaatctcga cctgcagcgt acgaagct    11878
```

<210> SEQ ID NO 4
<211> LENGTH: 12860
<212> TYPE: DNA
<213> ORGANISM: Artificial Sequence
<220> FEATURE:
<223> OTHER INFORMATION: Cas9n (D10A nickase version of the Cas9 enzyme generates a single-strand DNA break) Addgene # 63593

<400> SEQUENCE: 4

```
gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgttgac    240

attgattatt gactagttat taatagtaat caattacggg gtcattagtt catagcccat    300

atatggagtt ccgcgttaca taacttacgg taaatggccc gcctggctga ccgcccaacg    360

acccccgccc attgacgtca ataatgacgt atgttcccat agtaacgcca atagggactt    420

tccattgacg tcaatgggtg gagtatttac ggtaaactgc ccacttggca gtacatcaag    480

tgtatcatat gccaagtacg ccccctattg acgtcaatga cggtaaatgg cccgcctggc    540

attatgccca gtacatgacc ttatgggact ttcctacttg gcagtacatc tacgtattag    600

tcatcgctat taccatggtg atgcggtttt ggcagtacat caatgggcgt ggatagcggt    660

ttgactcacg gggatttcca agtctccacc ccattgacgt caatgggagt ttgttttggc    720

accaaaatca acgggacttt ccaaaatgtc gtaacaactc cgccccattg acgcaaatgg    780

gcggtaggcg tgtacggtgg gaggtctata taagcagcgc gttttgcctg tactgggtct    840

ctctggttag accagatctg agcctgggag ctctctggct aactagggaa cccactgctt    900
```

-continued aagcctcaat aaagcttgcc ttgagtgctt caagtagtgt gtgcccgtct gttgtgtgac 960
tctggtaact agagatccct cagacccttt tagtcagtgt ggaaaatctc tagcagtggc 1020
gcccgaacag ggacttgaaa gcgaaaggga aaccagagga gctctctcga cgcaggactc 1080
ggcttgctga agcgcgcacg gcaagaggcg aggggcggcg actggtgagt acgccaaaaa 1140
ttttgactag cggaggctag aaggagagag atgggtgcga gagcgtcagt attaagcggg 1200
ggagaattag atcgcgatgg gaaaaaattc ggttaaggcc agggggaaag aaaaaatata 1260
aattaaaaca tatagtatgg gcaagcaggg agctagaacg attcgcagtt aatcctggcc 1320
tgttagaaac atcagaaggc tgtagacaaa tactgggaca gctacaacca tcccttcaga 1380
caggatcaga agaacttaga tcattatata atacagtagc aaccctctat tgtgtgcatc 1440
aaaggataga gataaaagac accaaggaag ctttagacaa gatagaggaa gagcaaaaca 1500
aaagtaagac caccgcacag caagcggccg ctgatcttca gacctggagg aggagatatg 1560
agggacaatt ggagaagtga attatataaa tataaagtag taaaaattga accattagga 1620
gtagcaccca ccaaggcaaa gagaagagtg gtgcagagag aaaaaagagc agtgggaata 1680
ggagctttgt tccttgggtt cttgggagca gcaggaagca ctatgggcgc agcgtcaatg 1740
acgctgacgg tacaggccag acaattattg tctggtatag tgcagcagca gaacaatttg 1800
ctgagggcta ttgaggcgca acagcatctg ttgcaactca cagtctgggg catcaagcag 1860
ctccaggcaa gaatcctggc tgtggaaaga tacctaaagg atcaacagct cctggggatt 1920
tggggttgct ctggaaaact catttgcacc actgctgtgc cttggaatgc tagttggagt 1980
aataaatctc tggaacagat ttggaatcac acgacctgga tggagtggga cagagaaatt 2040
aacaattaca caagcttaat acactcctta attgaagaat cgcaaaacca gcaagaaaag 2100
aatgaacaag aattattgga attagataaa tgggcaagtt tgtggaattg gtttaacata 2160
acaaattggc tgtggtatat aaaattattc ataatgatag taggaggctt ggtaggttta 2220
agaatagttt ttgctgtact ttctatagtg aatagagtta ggcagggata ttcaccatta 2280
tcgtttcaga cccacctccc aaccccgagg ggacccgaca ggcccgaagg aatagaagaa 2340
gaaggtggag agagagacag agacagatcc attcgattag tgaacggatc ggcactgcgt 2400
gcgccaattc tgcagacaaa tggctgtatt catccacaat tttaaaagaa aaggggggat 2460
tggggggtac agtgcagggg aaagaatagt agacataata gcaacagaca tacaaactaa 2520
agaattacaa aaacaaatta caaaaattca aaattttcgg gtttattaca gggacagcag 2580
agatccagtt tggttaatta agctagctag gtcttgaaag gagtgggaat tggctccggt 2640
gcccgtcagt gggcagagcg cacatcgccc acagtccccg agaagttggg gggaggggtc 2700
ggcaattgat ccggtgccta gagaaggtgg cgcggggtaa actgggaaag tgatgtcgtg 2760
tactggctcc gcctttttcc cgagggtggg ggagaaccgt atataagtgc agtagtcgcc 2820
gtgaacgttc tttttcgcaa cgggtttgcc gccagaacac aggaccggtt ctagagcgct 2880
gccaccatgg acaagaagta cagcatcggc ctggccatcg gcaccaactc tgtgggctgg 2940
gccgtgatca ccgacgagta caaggtgccc agcaagaaat tcaaggtgct gggcaacacc 3000
gaccggcaca gcatcaagaa gaacctgatc ggagccctgc tgttcgacag cggcgaaaca 3060
gccgaggcca cccggctgaa gagaaccgcc agaagaagat acaccagacg gaagaaccgg 3120
atctgctatc tgcaagagat cttcagcaac gagatggcca aggtggacga cagcttcttc 3180
cacagactgg aagagtcctt cctggtggaa gaggataaga agcacgagcg gcaccccatc 3240

-continued

```
ttcggcaaca tcgtggacga ggtggcctac cacgagaagt accccaccat ctaccacctg   3300

agaaagaaac tggtggacag caccgacaag gccgacctgc ggctgatcta tctggccctg   3360

gcccacatga tcaagttccg gggccacttc ctgatcgagg gcgacctgaa ccccgacaac   3420

agcgacgtgg acaagctgtt catccagctg gtgcagacct acaaccagct gttcgaggaa   3480

aaccccatca acgccagcgg cgtggacgcc aaggccatcc tgtctgccag actgagcaag   3540

agcagacggc tggaaaatct gatcgcccag ctgcccggcg agaagaagaa tggcctgttc   3600

ggcaacctga ttgccctgag cctgggcctg acccccaact tcaagagcaa cttcgacctg   3660

gccgaggatg ccaaactgca gctgagcaag gacacctacg acgacgacct ggacaacctg   3720

ctggcccaga tcggcgacca gtacgccgac ctgtttctgg ccgccaagaa cctgtccgac   3780

gccatcctgc tgagcgacat cctgagagtg aacaccgaga tcaccaaggc ccccctgagc   3840

gcctctatga tcaagagata cgacgagcac caccaggacc tgaccctgct gaaagctctc   3900

gtgcggcagc agctgcctga gaagtacaaa gagattttct tcgaccagag caagaacggc   3960

tacgccggct acattgacgg cggagccagc caggaagagt tctacaagtt catcaagccc   4020

atcctggaaa agatggacgg caccgaggaa ctgctcgtga agctgaacag agaggacctg   4080

ctgcggaagc agcggacctt cgacaacggc agcatccccc accagatcca cctgggagag   4140

ctgcacgcca ttctgcggcg gcaggaagat ttttacccat tcctgaagga caaccgggaa   4200

aagatcgaga agatcctgac cttccgcatc ccctactacg tgggccctct ggccagggga   4260

aacagcagat tcgcctggat gaccagaaag agcgaggaaa ccatcacccc ctggaacttc   4320

gaggaagtgg tggacaaggg cgcttccgcc cagagcttca tcgagcggat gaccaacttc   4380

gataagaacc tgcccaacga gaaggtgctg cccaagcaca gcctgctgta cgagtacttc   4440

accgtgtata acgagctgac caaagtgaaa tacgtgaccg agggaatgag aaagcccgcc   4500

ttcctgagcg gcgagcagaa aaaggccatc gtggacctgc tgttcaagac caaccggaaa   4560

gtgaccgtga agcagctgaa agaggactac ttcaagaaaa tcgagtgctt cgactccgtg   4620

gaaatctccg gcgtggaaga tcggttcaac gcctccctgg gcacatacca cgatctgctg   4680

aaaattatca aggacaagga cttcctggac aatgaggaaa acgaggacat tctggaagat   4740

atcgtgctga ccctgacact gtttgaggac agagagatga tcgaggaacg gctgaaaacc   4800

tatgcccacc tgttcgacga caaagtgatg aagcagctga agcggcggag atacaccggc   4860

tggggcaggc tgagccggaa gctgatcaac ggcatccggg acaagcagtc cggcaagaca   4920

atcctggatt tcctgaagtc cgacggcttc gccaacagaa acttcatgca gctgatccac   4980

gacgacagcc tgacctttaa agaggacatc cagaaagccc aggtgtccgg ccagggcgat   5040

agcctgcacg agcacattgc caatctggcc ggcagccccg ccattaagaa gggcatcctg   5100

cagacagtga aggtggtgga cgagctcgtg aaagtgatgg gccggcacaa gcccgagaac   5160

atcgtgatcg aaatggccag agagaaccag accacccaga agggacagaa gaacagccgc   5220

gagagaatga agcggatcga agagggcatc aaagagctgg gcagccagat cctgaaagaa   5280

caccccgtgg aaaacaccca gctgcagaac gagaagctgt acctgtacta cctgcagaat   5340

gggcgggata tgtacgtgga ccaggaactg gacatcaacc ggctgtccga ctacgatgtg   5400

gaccatatcg tgcctcagag ctttctgaag gacgactcca tcgacaacaa ggtgctgacc   5460

agaagcgaca agaaccgggg caagagcgac aacgtgccct ccgaagaggt cgtgaagaag   5520

atgaagaact actggcggca gctgctgaac gccaagctga ttacccagag aaagttcgac   5580

aatctgacca aggccgagag aggcggcctg agcgaactgg ataaggccgg cttcatcaag   5640
```

-continued

```
agacagctgg tggaaacccg gcagatcaca aagcacgtgg cacagatcct ggactcccgg   5700
atgaacacta agtacgacga gaatgacaag ctgatccggg aagtgaaagt gatcaccctg   5760
aagtccaagc tggtgtccga tttccggaag gatttccagt tttacaaagt gcgcgagatc   5820
aacaactacc accacgccca cgacgcctac ctgaacgccg tcgtgggaac cgccctgatc   5880
aaaaagtacc ctaagctgga aagcgagttc gtgtacggcg actacaaggt gtacgacgtg   5940
cggaagatga tcgccaagag cgagcaggaa atcggcaagg ctaccgccaa gtacttcttc   6000
tacagcaaca tcatgaactt tttcaagacc gagattaccc tggccaacgg cgagatccgg   6060
aagcggcctc tgatcgagac aaacggcgaa accggggaga tcgtgtggga taagggccgg   6120
gattttgcca ccgtgcggaa agtgctgagc atgccccaag tgaatatcgt gaaaaagacc   6180
gaggtgcaga caggcggctt cagcaaagag tctatcctgc ccaagaggaa cagcgataag   6240
ctgatcgcca gaaagaagga ctgggaccct aagaagtacg gcggcttcga cagccccacc   6300
gtggcctatt ctgtgctggt ggtggccaaa gtggaaaagg gcaagtccaa gaaactgaag   6360
agtgtgaaag agctgctggg gatcaccatc atggaaagaa gcagcttcga gaagaatccc   6420
atcgactttc tggaagccaa gggctacaaa gaagtgaaaa aggacctgat catcaagctg   6480
cctaagtact ccctgttcga gctggaaaac ggccggaaga gaatgctggc ctctgccggc   6540
gaactgcaga agggaaacga actggccctg ccctccaaat atgtgaactt cctgtacctg   6600
gccagccact atgagaagct gaagggctcc cccgaggata atgagcagaa acagctgttt   6660
gtggaacagc acaagcacta cctggacgag atcatcgagc agatcagcga gttctccaag   6720
agagtgatcc tggccgacgc taatctggac aaagtgctgt ccgcctacaa caagcaccgg   6780
gataagccca tcagagagca ggccgagaat atcatccacc tgtttaccct gaccaatctg   6840
ggagcccctg ccgccttcaa gtactttgac accaccatcg accggaagag gtacaccagc   6900
accaaagagg tgctggacgc caccctgatc caccagagca tcaccggcct gtacgagaca   6960
cggatcgacc tgtctcagct gggaggcgac aagcgacctg ccgccacaaa gaaggctgga   7020
caggctaaga agaagaaaga ttacaaagac gatgacgata agggatccgg cgcaacaaac   7080
ttctctctgc tgaaacaagc cggagatgtc gaagagaatc ctggaccgat ggccaagcct   7140
ttgtctcaag aagaatccac cctcattgaa agagcaacgg ctacaatcaa cagcatcccc   7200
atctctgaag actacagcgt cgccagcgca gctctctcta gcgacggccg catcttcact   7260
ggtgtcaatg tatatcattt tactggggga ccttgtgcag aactcgtggt gctgggcact   7320
gctgctgctg cggcagctgg caacctgact tgtatcgtcg cgatcggaaa tgagaacagg   7380
ggcatcttga gcccctgcgg acggtgccga caggtgcttc tcgatctgca tcctgggatc   7440
aaagccatag tgaaggacag tgatggacag ccgacggcag ttgggattcg tgaattgctg   7500
ccctctggtt atgtgtggga gggctaagaa ttcgatatca agcttatcga taatcaacct   7560
ctggattaca aaatttgtga aagattgact ggtattctta actatgttgc tccttttacg   7620
ctatgtggat acgctgcttt aatgcctttg tatcatgcta ttgcttcccg tatggctttc   7680
attttctcct ccttgtataa atcctggttg ctgtctcttt atgaggagtt gtggcccgtt   7740
gtcaggcaac gtggcgtggt gtgcactgtg tttgctgacg caacccccac tggttggggc   7800
attgccacca cctgtcagct cctttccggg actttcgctt tccccctccc tattgccacg   7860
gcggaactca tcgccgcctg ccttgcccgc tgctggacag gggctcggct gttgggcact   7920
gacaattccg tggtgttgtc ggggaaatca tcgtcctttc cttggctgct cgcctgtgtt   7980
```

-continued

```
gccacctgga ttctgcgcgg gacgtccttc tgctacgtcc cttcggccct caatccagcg   8040
gaccttcctt cccgcggcct gctgccggct ctgcggcctc ttccgcgtct tcgccttcgc   8100
cctcagacga gtcggatctc cctttgggcc gcctccccgc atcgataccg tcgacctcga   8160
gacctagaaa aacatggagc aatcacaagt agcaatacag cagctaccaa tgctgattgt   8220
gcctggctag aagcacaaga ggaggaggag gtgggttttc cagtcacacc tcaggtacct   8280
ttaagaccaa tgacttacaa ggcagctgta gatcttagcc actttttaaa agaaaagggg   8340
ggactggaag ggctaattca ctcccaacga agacaagata tccttgatct gtggatctac   8400
cacacacaag gctacttccc tgattggcag aactacacac cagggccagg gatcagatat   8460
ccactgacct ttggatggtg ctacaagcta gtaccagttg agcaagagaa ggtagaagaa   8520
gccaatgaag gagagaacac ccgcttgtta caccctgtga gcctgcatgg gatggatgac   8580
ccggagagag aagtattaga gtggaggttt gacagccgcc tagcatttca tcacatggcc   8640
cgagagctgc atccggactg tactgggtct ctctggttag accagatctg agcctgggag   8700
ctctctggct aactagggaa cccactgctt aagcctcaat aaagcttgcc ttgagtgctt   8760
caagtagtgt gtgcccgtct gttgtgtgac tctggtaact agagatccct cagacccttt   8820
tagtcagtgt ggaaaatctc tagcagggcc cgtttaaacc cgctgatcag cctcgactgt   8880
gccttctagt tgccagccat ctgttgtttg cccctccccc gtgccttcct tgaccctgga   8940
aggtgccact cccactgtcc tttcctaata aaatgaggaa attgcatcgc attgtctgag   9000
taggtgtcat tctattctgg ggggtggggt ggggcaggac agcaaggggg aggattggga   9060
agacaatagc aggcatgctg gggatgcggt gggctctatg gcttctgagg cggaaagaac   9120
cagctggggc tctagggggt atccccacgc gccctgtagc ggcgcattaa gcgcggcggg   9180
tgtggtggtt acgcgcagcg tgaccgctac acttgccagc gccctagcgc ccgctccttt   9240
cgctttcttc ccttcctttc tcgccacgtt cgccggcttt ccccgtcaag ctctaaatcg   9300
ggggctccct ttagggttcc gatttagtgc tttacggcac ctcgacccca aaaaacttga   9360
ttagggtgat ggttcacgta gtgggccatc gccctgatag acggtttttc gccctttgac   9420
gttggagtcc acgttcttta atagtggact cttgttccaa actggaacaa cactcaaccc   9480
tatctcggtc tattcttttg atttataagg gattttgccg atttcggcct attggttaaa   9540
aaatgagctg atttaacaaa aatttaacgc gaattaattc tgtggaatgt gtgtcagtta   9600
gggtgtggaa agtccccagg ctccccagca ggcagaagta tgcaaagcat gcatctcaat   9660
tagtcagcaa ccaggtgtgg aaagtcccca ggctccccag caggcagaag tatgcaaagc   9720
atgcatctca attagtcagc aaccatagtc ccgcccctaa ctccgcccat cccgccccta   9780
actccgccca gttccgccca ttctccgccc catggctgac taattttttt tatttatgca   9840
gaggccgagg ccgcctctgc ctctgagcta ttccagaagt agtgaggagg cttttttgga   9900
ggcctaggct tttgcaaaaa gctcccggga gcttgtatat ccattttcgg atctgatcag   9960
cacgtgttga caattaatca tcggcatagt atatcggcat agtataatac gacaaggtga  10020
ggaactaaac catggccaag ttgaccagtg ccgttccggt gctcaccgcg cgcgacgtcg  10080
ccggagcggt cgagttctgg accgaccggc tcgggttctc ccgggacttc gtggaggacg  10140
acttcgccgg tgtggtccgg gacgacgtga ccctgttcat cagcgcggtc caggaccagg  10200
tggtgccgga caacaccctg gcctgggtgt gggtgcgcgg cctggacgag ctgtacgccg  10260
agtggtcgga ggtcgtgtcc acgaacttcc gggacgcctc cgggccggcc atgaccgaga  10320
tcggcgagca gccgtggggg cgggagttcg ccctgcgcga cccggccggc aactgcgtgc  10380
```

```
acttcgtggc cgaggagcag gactgacacg tgctacgaga tttcgattcc accgccgcct  10440
tctatgaaag gttgggcttc ggaatcgttt tccgggacgc cggctggatg atcctccagc  10500
gcggggatct catgctggag ttcttcgccc accccaactt gtttattgca gcttataatg  10560
gttacaaata aagcaatagc atcacaaatt tcacaaataa agcatttttt tcactgcatt  10620
ctagttgtgg tttgtccaaa ctcatcaatg tatcttatca tgtctgtata ccgtcgacct  10680
ctagctagag cttggcgtaa tcatggtcat agctgtttcc tgtgtgaaat tgttatccgc  10740
tcacaattcc acacaacata cgagccggaa gcataaagtg taaagcctgg ggtgcctaat  10800
gagtgagcta actcacatta attgcgttgc gctcactgcc cgctttccag tcgggaaacc  10860
tgtcgtgcca gctgcattaa tgaatcggcc aacgcgcggg gagaggcggt ttgcgtattg  10920
ggcgctcttc cgcttcctcg ctcactgact cgctgcgctc ggtcgttcgg ctgcggcgag  10980
cggtatcagc tcactcaaag gcggtaatac ggttatccac agaatcaggg gataacgcag  11040
gaaagaacat gtgagcaaaa ggccagcaaa aggccaggaa ccgtaaaaag gccgcgttgc  11100
tggcgttttt ccataggctc cgcccccctg acgagcatca caaaaatcga cgctcaagtc  11160
agaggtggcg aaacccgaca ggactataaa gataccaggc gtttccccct ggaagctccc  11220
tcgtgcgctc tcctgttccg accctgccgc ttaccggata cctgtccgcc tttctccctt  11280
cgggaagcgt ggcgctttct catagctcac gctgtaggta tctcagttcg gtgtaggtcg  11340
ttcgctccaa gctgggctgt gtgcacgaac cccccgttca gcccgaccgc tgcgccttat  11400
ccggtaacta tcgtcttgag tccaacccgg taagacacga cttatcgcca ctggcagcag  11460
ccactggtaa caggattagc agagcgaggt atgtaggcgg tgctacagag ttcttgaagt  11520
ggtggcctaa ctacggctac actagaagaa cagtatttgg tatctgcgct ctgctgaagc  11580
cagttacctt cggaaaaaga gttggtagct cttgatccgg caaacaaacc accgctggta  11640
gcggtggttt ttttgtttgc aagcagcaga ttacgcgcag aaaaaaagga tctcaagaag  11700
atcctttgat cttttctacg gggtctgacg ctcagtggaa cgaaaactca cgttaaggga  11760
ttttggtcat gagattatca aaaaggatct tcacctagat ccttttaaat taaaaatgaa  11820
gttttaaatc aatctaaagt atatatgagt aaacttggtc tgacagttac caatgcttaa  11880
tcagtgaggc acctatctca gcgatctgtc tatttcgttc atccatagtt gcctgactcc  11940
ccgtcgtgta gataactacg atacgggagg gcttaccatc tggccccagt gctgcaatga  12000
taccgcgaga cccacgctca ccggctccag atttatcagc aataaaccag ccagccggaa  12060
gggccgagcg cagaagtggt cctgcaactt tatccgcctc catccagtct attaattgtt  12120
gccgggaagc tagagtaagt agttcgccag ttaatagttt gcgcaacgtt gttgccattg  12180
ctacaggcat cgtggtgtca cgctcgtcgt ttggtatggc ttcattcagc tccggttccc  12240
aacgatcaag gcgagttaca tgatccccca tgttgtgcaa aaaagcggtt agctccttcg  12300
gtcctccgat cgttgtcaga agtaagttgg ccgcagtgtt atcactcatg gttatggcag  12360
cactgcataa ttctcttact gtcatgccat ccgtaagatg cttttctgtg actggtgagt  12420
actcaaccaa gtcattctga gaatagtgta tgcggcgacc gagttgctct tgcccggcgt  12480
caatacggga taataccgcg ccacatagca gaactttaaa agtgctcatc attggaaaac  12540
gttcttcggg gcgaaaactc tcaaggatct taccgctgtt gagatccagt tcgatgtaac  12600
ccactcgtgc acccaactga tcttcagcat cttttacttt caccagcgtt tctgggtgag  12660
caaaaacagg aaggcaaaat gccgcaaaaa agggaataag ggcgacacgg aaatgttgaa  12720
```

-continued

```
tactcatact cttccttttt caatattatt gaagcattta tcagggttat tgtctcatga  12780

gcggatacat atttgaatgt atttagaaaa ataaacaaat aggggttccg cgcacatttc  12840

cccgaaaagt gccacctgac                                              12860
```

<210> SEQ ID NO 5
<211> LENGTH: 10477
<212> TYPE: DNA
<213> ORGANISM: Artificial Sequence
<220> FEATURE:
<223> OTHER INFORMATION: dCas9 (A catalytically inactive Cas9 or dCas9-repressor peptide fusion can be used to knock-down gene expression by interfering with transcription of the gene). Addgene #44246

<400> SEQUENCE: 5

```
tgaaagaccc cacctgtagg tttggcaagc tagcttaagt aacgccattt tgcaaggcat     60

ggaaaataca taactgagaa tagagaagtt cagatcaagg ttaggaacag agagacagca    120

gaatatgggc caaacaggat atctgtggta agcagttcct gccccggctc agggccaaga    180

acagatggtc cccagatgcg gtcccgccct cagcagtttc tagagaacca tcagatgttt    240

ccagggtgcc ccaaggacct gaaatgaccc tgtgccttat ttgaactaac caatcagttc    300

gcttctcgct tctgttcgcg cgcttctgct ccccgagctc aataaaagag cccacaaccc    360

ctcactcggc gcgccagtcc tccgatagac tgcgtcgccc gggtacccgt attcccaata    420

aagcctcttg ctgtttgcat ccgaatcgtg gactcgctga tccttgggag ggtctcctca    480

gattgattga ctgcccacct cgggggtctt tcatttggag gttccaccga gatttggaga    540

cccctgccca gggaccaccg acccccccgc cgggaggtaa gctggccagc ggtcgtttcg    600

tgtctgtctc tgtctttgtg cgtgtttgtg ccggcatcta atgtttgcgc ctgcgtctgt    660

actagttagc taactagctc tgtatctggc ggacccgtgg tggaactgac gagttctgaa    720

cacccggccg caaccctggg agacgtccca gggactttgg gggccgtttt tgtggcccga    780

cctgaggaag ggagtcgatg tggaatccga ccccgtcagg atatgtggtt ctggtaggag    840

acgagaacct aaaacagttc ccgcctccgt ctgaattttt gctttcggtt tggaaccgaa    900

gccgcgcgtc ttgtctgctg cagcgctgca gcatcgttct gtgttgtctc tgtctgactg    960

tgtttctgta tttgtctgaa aattagggcc agactgttac cactccctta agtttgacct   1020

taggtcactg gaaagatgtc gagcggatcg ctcacaacca gtcggtagat gtcaagaaga   1080

gacgttgggt taccttctgc tctgcagaat ggccaacctt taacgtcgga tggccgcgag   1140

acggcacctt taaccgagac ctcatcaccc aggttaagat caaggtcttt tcacctggcc   1200

cgcatggaca cccagaccag gtcccctaca tcgtgacctg ggaagccttg gcttttgacc   1260

cccctccctg ggtcaagccc tttgtacacc ctaagcctcc gcctcctctt cctccatccg   1320

ccccgtctct ccccccttgaa cctcctcgtt cgaccccgcc tcgatcctcc ctttatccag   1380

ccctcactcc ttctctaggc gccggaatta gatctcgcca ccatggacaa gaagtattct   1440

atcggactgg ccatcgggac taatagcgtc gggtgggccg tgatcactga cgagtacaag   1500

gtgccctcta agaagttcaa ggtgctcggg aacaccgacc ggcattccat caagaaaaat   1560

ctgatcggag ctctcctctt tgattcaggg gagaccgctg aagcaacccg cctcaagcgg   1620

actgctagac ggcggtacac caggaggaag aaccggattt gttaccttca agagatattc   1680

tccaacgaaa tggcaaaggt cgacgacagc ttcttccata ggctggaaga atcattcctc   1740

gtggaagagg ataagaagca tgaacggcat cccatcttcg gtaatatcgt cgacgaggtg   1800

gcctatcacg agaaataccc aaccatctac catcttcgca aaaagctggt ggactcaacc   1860
```

-continued

```
gacaaggcag acctccggct tatctacctg gccctggccc acatgatcaa gttcagaggc   1920
cacttcctga tcgagggcga cctcaatcct gacaatagcg atgtggataa actgttcatc   1980
cagctggtgc agacttacaa ccagctcttt gaagagaacc ccatcaatgc aagcggagtc   2040
gatgccaagg ccattctgtc agcccggctg tcaaagagcc gcagacttga gaatcttatc   2100
gctcagctgc cgggtgaaaa gaaaaatgga ctgttcggga acctgattgc tctttcactt   2160
gggctgactc ccaatttcaa gtctaatttc gacctggcag aggatgccaa gctgcaactg   2220
tccaaggaca cctatgatga cgatctcgac aacctcctgg cccagatcgg tgaccaatac   2280
gccgaccttt tccttgctgc taagaatctt tctgacgcca tcctgctgtc tgacattctc   2340
cgcgtgaaca ctgaaatcac caaggcccct ctttcagctt caatgattaa gcggtatgat   2400
gagcaccacc aggacctgac cctgcttaag gcactcgtcc ggcagcagct tccggagaag   2460
tacaaggaaa tcttctttga ccagtcaaag aatggatacg ccggctacat cgacggaggt   2520
gcctcccaag aggaatttta taagtttatc aaacctatcc ttgagaagat ggacggcacc   2580
gaagagctcc tcgtgaaact gaatcgggag gatctgctgc ggaagcagcg cactttcgac   2640
aatgggagca ttccccacca gatccatctt ggggagcttc acgccatcct tcggcgccaa   2700
gaggacttct accccttctt taaggacaac agggagaaga ttgagaaaat tctcactttc   2760
cgcatcccct actacgtggg acccctcgcc agaggaaata gccggtttgc ttggatgacc   2820
agaaagtcag aagaaactat cactccctgg aacttcgaag aggtggtgga caagggagcc   2880
agcgctcagt cattcatcga acggatgact aacttcgata agaacctccc caatgagaag   2940
gtcctgccga aacattccct gctctacgag tactttaccg tgtacaacga gctgaccaag   3000
gtgaaatatg tcaccgaagg gatgaggaag cccgcattcc tgtcaggcga acaaaagaag   3060
gcaattgtgg accttctgtt caagaccaat agaaaggtga ccgtgaagca gctgaaggag   3120
gactatttca agaaaattga atgcttcgac tctgtggaga ttagcggggt cgaagatcgg   3180
ttcaacgcaa gcctgggtac ctaccatgat ctgcttaaga tcatcaagga caaggatttt   3240
ctggacaatg aggagaacga ggacatcctt gaggacattg tcctgactct cactctgttc   3300
gaggaccggg aaatgatcga ggagaggctt aagacctacg cccatctgtt cgacgataaa   3360
gtgatgaagc aacttaaacg gagaagatat accggatggg gacgccttag ccgcaaactc   3420
atcaacggaa tccgggacaa acagagcgga aagaccattc ttgatttcct taagagcgac   3480
ggattcgcta atcgcaactt catgcaactt atccatgatg attccctgac ctttaaggag   3540
gacatccaga aggcccaagt gtctggacaa ggtgactcac tgcacgagca tatcgcaaat   3600
ctggctggtt cacccgctat taagaagggt attctccaga ccgtgaaagt cgtggacgag   3660
ctggtcaagg tgatgggtcg ccataaacca gagaacattg tcatcgagat ggccagggaa   3720
aaccagacta cccagaaggg acagaagaac agcagggagc ggatgaaaag aattgaggaa   3780
gggattaagg agctcgggtc acagatcctt aaagagcacc cggtggaaaa cacccagctt   3840
cagaatgaga agctctatct gtactacctt caaaatggac gcgatatgta tgtggaccaa   3900
gagcttgata tcaacaggct ctcagactac gacgtggacg ccatcgtccc tcagagcttc   3960
ctcaaagacg actcaattga caataaggtg ctgactcgct cagacaagaa ccggggaaag   4020
tcagataacg tgccctcaga ggaagtcgtg aaaaagatga agaactattg gcgccagctt   4080
ctgaacgcaa agctgatcac tcagcggaag ttcgacaatc tcactaaggc tgagaggggc   4140
ggactgagcg aactggacaa agcaggattc attaaacggc aacttgtgga gactcggcag   4200
```

-continued

```
attactaaac atgtcgccca aatccttgac tcacgcatga ataccaagta cgacgaaaac   4260
gacaaactta tccgcgaggt gaaggtgatt accctgaagt ccaagctggt cagcgatttc   4320
agaaaggact ttcaattcta caaagtgcgg gagatcaata actatcatca tgctcatgac   4380
gcatatctga atgccgtggt gggaaccgcc ctgatcaaga agtacccaaa gctggaaagc   4440
gagttcgtgt acggagacta caaggtctac gacgtgcgca agatgattgc caaatctgag   4500
caggagatcg gaaaggccac cgcaaagtac ttcttctaca gcaacatcat gaatttcttc   4560
aagaccgaaa tcacccttgc aaacggtgag atccggaaga ggccgctcat cgagactaat   4620
ggggagactg gcgaaatcgt gtgggacaag ggcagagatt tcgctaccgt gcgcaaagtg   4680
ctttctatgc ctcaagtgaa catcgtgaag aaaaccgagg tgcaaaccgg aggcttttct   4740
aaggaatcaa tcctccccaa gcgcaactcc gacaagctca ttgcaaggaa gaaggattgg   4800
gaccctaaga agtacggcgg attcgattca ccaactgtgg cttattctgt cctggtcgtg   4860
gctaaggtgg aaaaaggaaa gtctaagaag ctcaagagcg tgaaggaact gctgggtatc   4920
accattatgg agcgcagctc cttcgagaag aacccaattg actttctcga agccaaaggt   4980
tacaaggaag tcaagaagga ccttatcatc aagctcccaa agtatagcct gttcgaactg   5040
gagaatgggc ggaagcggat gctcgcctcc gctggcgaac ttcagaaggg taatgagctg   5100
gctctcccct ccaagtacgt gaatttcctc taccttgcaa gccattacga gaagctgaag   5160
gggagccccg aggacaacga gcaaaagcaa ctgtttgtgg agcagcataa gcattatctg   5220
gacgagatca ttgagcagat ttccgagttt tctaaacgcg tcattctcgc tgatgccaac   5280
ctcgataaag tccttagcgc atacaataag cacagagaca aaccaattcg ggagcaggct   5340
gagaatatca tccacctgtt caccctcacc aatcttggtg cccctgccgc attcaagtac   5400
ttcgacacca ccatcgaccg gaaacgctat acctccacca aagaagtgct ggacgccacc   5460
ctcatccacc agagcatcac cggactttac gaaactcgga ttgacctctc acagctcgga   5520
ggggatgagg gagctgatcc aaaaaagaag agaaaggtag atccaaaaaa gaagagaaag   5580
gtagatccaa aaaagaagag aaaggtatag aattctaccg ggtaggggag gcgcttttcc   5640
caaggcagtc tggagcatgc gctttagcag ccccgctggg cacttggcgc tacacaagtg   5700
gcctctggcc tcgcacacat tccacatcca ccggtaggcg ccaaccggct ccgttctttg   5760
gtggcccctt cgcgccacct tctactcctc ccctagtcag gaagttcccc cccgccccgc   5820
agctcgcgtc gtgcaggacg tgacaaatgg aagtagcacg tctcactagt ctcgtgcaga   5880
tggacagcac cgctgagcaa tggaagcggg taggcctttg gggcagcggc caatagcagc   5940
tttgctcctt cgctttctgg gctcagaggc tgggaagggg tgggtccggg ggcgggctca   6000
ggggcgggct caggggcggg gcgggcgccc gaaggtcctc cggaggcccg gcattctgca   6060
cgcttcaaaa gcgcacgtct gccgcgctgt tctcctcttc ctcatctccg ggcctttcga   6120
cctgcagccc aagcttacca tgaccgagta caagcccacg gtgcgcctcg ccacccgcga   6180
cgacgtcccc agggccgtac gcaccctcgc cgccgcgttc gccgactacc ccgccacgcg   6240
ccacaccgtc gatccggacc gccacatcga gcgggtcacc gagctgcaag aactcttcct   6300
cacgcgcgtc gggctcgaca tcggcaaggt gtgggtcgcg gacgacggcg ccgcggtggc   6360
ggtctggacc acgccggaga gcgtcgaagc gggggcggtg ttcgccgaga tcggcccgcg   6420
catggccgag ttgagcggtt cccggctggc cgcgcagcaa cagatggaag gcctcctggc   6480
gccgcaccgg cccaaggagc ccgcgtggtt cctggccacc gtcggcgtct cgcccgacca   6540
ccagggcaag ggtctgggca gcgccgtcgt gctccccgga gtggaggcgg ccgagcgcgc   6600
```

cggggtgccc gccttcctgg agacctccgc gccccgcaac ctccccttct acgagcggct 6660
cggcttcacc gtcaccgccg acgtcgaggt gcccgaagga ccgcgcacct ggtgcatgac 6720
ccgcaagccc ggtgcctgac gcccgcccca cgacccgcag cgcccgaccg aaaggagcgc 6780
acgaccccat gcatcgataa aataaaagat tttatttagt ctccagaaaa agggggggaat 6840
gaaagacccc acctgtaggt ttggcaagct agcttaagta acgccatttt gcaaggcatg 6900
gaaaatacat aactgagaat agagaagttc agatcaaggt taggaacaga gagacagcag 6960
aatatgggcc aaacaggata tctgtggtaa gcagttcctg ccccggctca gggccaagaa 7020
cagatggtcc ccagatgcgg tcccgccctc agcagtttct agagaaccat cagatgtttc 7080
cagggtgccc caaggacctg aaatgaccct gtgccttatt tgaactaacc aatcagttcg 7140
cttctcgctt ctgttcgcgc gcttctgctc cccgagctca ataaaagagc ccacaacccc 7200
tcactcggcg cgccagtcct ccgatagact gcgtcgcccg ggtacccgtg tatccaataa 7260
accctcttgc agttgcatcc gacttgtggt ctcgctgttc cttgggaggg tctcctctga 7320
gtgattgact acccgtcagc gggggtcttt catgggtaac agtttcttga agttggagaa 7380
caacattctg agggtaggag tcgaatatta agtaatcctg actcaattag ccactgtttt 7440
gaatccacat actccaatac tcctgaaata gttcattatg gacagcgcag aagagctggg 7500
gagaattaat tcgtaatcat ggtcatagct gtttcctgtg tgaaattgtt atccgctcac 7560
aattccacac aacatacgag ccggaagcat aaagtgtaaa gcctggggtg cctaatgagt 7620
gagctaactc acattaattg cgttgcgctc actgcccgct ttccagtcgg gaaacctgtc 7680
gtgccagctg cattaatgaa tcggccaacg cgcggggaga ggcggtttgc gtattgggcg 7740
ctcttccgct tcctcgctca ctgactcgct gcgctcggtc gttcggctgc ggcgagcggt 7800
atcagctcac tcaaaggcgg taatacggtt atccacagaa tcaggggata acgcaggaaa 7860
gaacatgtga gcaaaaggcc agcaaaaggc caggaaccgt aaaaaggccg cgttgctggc 7920
gtttttccat aggctccgcc cccctgacga gcatcacaaa aatcgacgct caagtcagag 7980
gtggcgaaac ccgacaggac tataaagata ccaggcgttt ccccctggaa gctccctcgt 8040
gcgctctcct gttccgaccc tgccgcttac cggatacctg tccgcctttc tcccttcggg 8100
aagcgtggcg ctttctcata gctcacgctg taggtatctc agttcggtgt aggtcgttcg 8160
ctccaagctg ggctgtgtgc acgaaccccc cgttcagccc gaccgctgcg ccttatccgg 8220
taactatcgt cttgagtcca acccggtaag acacgactta tcgccactgg cagcagccac 8280
tggtaacagg attagcagag cgaggtatgt aggcggtgct acagagttct tgaagtggtg 8340
gcctaactac ggctacacta gaaggacagt atttggtatc tgcgctctgc tgaagccagt 8400
taccttcgga aaaagagttg gtagctcttg atccggcaaa caaaccaccg ctggtagcgg 8460
tggttttttt gtttgcaagc agcagattac gcgcagaaaa aaaggatctc aagaagatcc 8520
tttgatcttt tctacggggt ctgacgctca gtggaacgaa aactcacgtt aagggatttt 8580
ggtcatgaga ttatcaaaaa ggatcttcac ctagatcctt ttaaattaaa aatgaagttt 8640
taaatcaatc taaagtatat atgagtaaac ttggtctgac agttaccaat gcttaatcag 8700
tgaggcacct atctcagcga tctgtctatt tcgttcatcc atagttgcct gactccccgt 8760
cgtgtagata actacgatac gggagggctt accatctggc cccagtgctg caatgatacc 8820
gcgagaccca cgctcaccgg ctccagattt atcagcaata aaccagccag ccggaagggc 8880
cgagcgcaga agtggtcctg caactttatc cgcctccatc cagtctatta attgttgccg 8940

```
ggaagctaga gtaagtagtt cgccagttaa tagtttgcgc aacgttgttg ccattgctac   9000

aggcatcgtg gtgtcacgct cgtcgtttgg tatggcttca ttcagctccg gttcccaacg   9060

atcaaggcga gttacatgat cccccatgtt gtgcaaaaaa gcggttagct ccttcggtcc   9120

tccgatcgtt gtcagaagta agttggccgc agtgttatca ctcatggtta tggcagcact   9180

gcataattct cttactgtca tgccatccgt aagatgcttt tctgtgactg gtgagtactc   9240

aaccaagtca ttctgagaat agtgtatgcg gcgaccgagt tgctcttgcc cggcgtcaat   9300

acgggataat accgcgccac atagcagaac tttaaaagtg ctcatcattg gaaaacgttc   9360

ttcggggcga aaactctcaa ggatcttacc gctgttgaga tccagttcga tgtaacccac   9420

tcgtgcaccc aactgatctt cagcatcttt tactttcacc agcgtttctg ggtgagcaaa   9480

aacaggaagg caaaatgccg caaaaaaggg aataagggcg acacggaaat gttgaatact   9540

catactcttc ctttttcaat attattgaag catttatcag ggttattgtc tcatgagcgg   9600

atacatattt gaatgtattt agaaaaataa acaaataggg gttccgcgca catttccccg   9660

aaaagtgcca cctgacgtct aagaaaccat tattatcatg acattaacct ataaaaatag   9720

gcgtatcacg aggccctttc gtctcgcgcg tttcggtgat gacggtgaaa acctctgaca   9780

catgcagctc ccggagacgg tcacagcttg tctgtaagcg gatgccggga gcagacaagc   9840

ccgtcagggc gcgtcagcgg gtgttggcgg gtgtcggggc tggcttaact atgcggcatc   9900

agagcagatt gtactgagag tgcaccatat gcggtgtgaa ataccgcaca gatgcgtaag   9960

gagaaaatac cgcatcaggc gccattcgcc attcaggctg cgcaactgtt gggaagggcg  10020

atcggtgcgg gcctcttcgc tattacgcca gctggcgaaa gggggatgtg ctgcaaggcg  10080

attaagttgg gtaacgccag ggttttccca gtcacgacgt tgtaaaacga cggcgcaagg  10140

aatggtgcat gcaaggagat ggcgcccaac agtcccccgg ccacggggcc tgccaccata  10200

cccacgccga aacaagcgct catgagcccg aagtggcgag cccgatcttc cccatcggtg  10260

atgtcggcga tataggcgcc agcaaccgca cctgtggcgc cggtgatgcc ggccacgatg  10320

cgtccggcgt agaggcgatt agtccaattt gttaaagaca ggatatcagt ggtccaggct  10380

ctagttttga ctcaacaata tcaccagctg aagcctatag agtacgagcc atagataaaa  10440

taaaagattt tatttagtct ccagaaaaag gggggaa                           10477


<210> SEQ ID NO 6
<211> LENGTH: 14382
<212> TYPE: DNA
<213> ORGANISM: Artificial Sequence
<220> FEATURE:
<223> OTHER INFORMATION: dCAS9-VP64 activator, Addgene #61422

<400> SEQUENCE: 6

gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgttgac    240

attgattatt gactagttat taatagtaat caattacggg gtcattagtt catagcccat    300

atatggagtt ccgcgttaca taacttacgg taaatggccc gcctggctga ccgcccaacg    360

acccccgccc attgacgtca ataatgacgt atgttcccat agtaacgcca atagggactt    420

tccattgacg tcaatgggtg gagtatttac ggtaaactgc ccacttggca gtacatcaag    480

tgtatcatat gccaagtacg ccccctattg acgtcaatga cggtaaatgg cccgcctggc    540
```

```
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tgggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
```

-continued tttttcgcaa cgggtttgcc gccagaacac aggtaagtgc cgtgtgtggt tcccgcgggc 2940
ctggcctctt tacgggttat ggcccttgcg tgccttgaat tacttccact ggctgcagta 3000
cgtgattctt gatcccgagc ttcgggttgg aagtgggtgg gagagttcga ggccttgcgc 3060
ttaaggagcc ccttcgcctc gtgcttgagt tgaggcctgg cctgggcgct ggggccgccg 3120
cgtgcgaatc tggtggcacc ttcgcgcctg tctcgctgct ttcgataagt ctctagccat 3180
ttaaaatttt tgatgacctg ctgcgacgct ttttttctgg caagatagtc ttgtaaatgc 3240
gggccaagat ctgcacactg gtatttcggt ttttggggcc gcgggcggcg acggggcccg 3300
tgcgtcccag cgcacatgtt cggcgaggcg gggcctgcga gcgcggccac cgagaatcgg 3360
acgggggtag tctcaagctg gccggcctgc tctggtgcct ggcctcgcgc cgccgtgtat 3420
cgccccgccc tgggcggcaa ggctggcccg gtcggcacca gttgcgtgag cggaaagatg 3480
gccgcttccc ggccctgctg cagggagctc aaaatggagg acgcggcgct cgggagagcg 3540
ggcgggtgag tcacccacac aaaggaaaag ggcctttccg tcctcagccg tcgcttcatg 3600
tgactccacg gagtaccggg cgccgtccag gcacctcgat tagttctcga gcttttggag 3660
tacgtcgtct ttaggttggg gggaggggtt ttatgcgatg gagtttcccc acactgagtg 3720
ggtggagact gaagttaggc cagcttggca cttgatgtaa ttctccttgg aatttgccct 3780
ttttgagttt ggatcttggt tcattctcaa gcctcagaca gtggttcaaa gtttttttct 3840
tccatttcag gtgtcgtgac gtacggccac catgagcccc aagaagaaga gaaaggtgga 3900
ggccagcgac aagaagtaca gcatcggcct ggccatcggc accaactctg tgggctgggc 3960
cgtgatcacc gacgagtaca aggtgcccag caagaaattc aaggtgctgg gcaacaccga 4020
ccggcacagc atcaagaaga acctgatcgg agccctgctg ttcgacagcg gcgaaacagc 4080
cgaggccacc cggctgaaga gaaccgccag aagaagatac accagacgga agaaccggat 4140
ctgctatctg caagagatct tcagcaacga gatggccaag gtggacgaca gcttcttcca 4200
cagactggaa gagtccttcc tggtggaaga ggataagaag cacgagcggc accccatctt 4260
cggcaacatc gtggacgagg tggcctacca cgagaagtac cccaccatct accacctgag 4320
aaagaaactg gtggacagca ccgacaaggc cgacctgcgg ctgatctatc tggccctggc 4380
ccacatgatc aagttccggg gccacttcct gatcgagggc gacctgaacc ccgacaacag 4440
cgacgtggac aagctgttca tccagctggt gcagacctac aaccagctgt tcgaggaaaa 4500
ccccatcaac gccagcggcg tggacgccaa ggccatcctg tctgccagac tgagcaagag 4560
cagacggctg gaaaatctga tcgcccagct gcccggcgag aagaagaatg gcctgttcgg 4620
caacctgatt gccctgagcc tgggcctgac ccccaacttc aagagcaact tcgacctggc 4680
cgaggatgcc aaactgcagc tgagcaagga cacctacgac gacgacctgg acaacctgct 4740
ggcccagatc ggcgaccagt acgccgacct gtttctggcc gccaagaacc tgtccgacgc 4800
catcctgctg agcgacatcc tgagagtgaa caccgagatc accaaggccc ccctgagcgc 4860
ctctatgatc aagagatacg acgagcacca ccaggacctg accctgctga aagctctcgt 4920
gcggcagcag ctgcctgaga agtacaaaga gattttcttc gaccagagca agaacggcta 4980
cgccggctac attgacggcg gagccagcca ggaagagttc tacaagttca tcaagcccat 5040
cctggaaaag atggacggca ccgaggaact gctcgtgaag ctgaacagag aggacctgct 5100
gcggaagcag cggaccttcg acaacggcag catcccccac cagatccacc tgggagagct 5160
gcacgccatt ctgcggcggc aggaagattt ttacccattc ctgaaggaca accgggaaaa 5220
gatcgagaag atcctgacct tccgcatccc ctactacgtg ggccctctgg ccaggggaaa 5280
cagcagattc gcctggatga ccagaaagag cgaggaaacc atcaccccct ggaacttcga 5340
ggaagtggtg gacaagggcg cttccgccca gagcttcatc gagcggatga ccaacttcga 5400
taagaacctg cccaacgaga aggtgctgcc caagcacagc ctgctgtacg agtacttcac 5460
cgtgtataac gagctgacca aagtgaaata cgtgaccgag ggaatgagaa agcccgcctt 5520
cctgagcggc gagcagaaaa aggccatcgt ggacctgctg ttcaagacca accggaaagt 5580
gaccgtgaag cagctgaaag aggactactt caagaaaatc gagtgcttcg actccgtgga 5640
aatctccggc gtggaagatc ggttcaacgc ctccctgggc acataccacg atctgctgaa 5700
aattatcaag gacaaggact tcctggacaa tgaggaaaac gaggacattc tggaagatat 5760
cgtgctgacc ctgacactgt ttgaggacag agagatgatc gaggaacggc tgaaaaccta 5820
tgcccacctg ttcgacgaca aagtgatgaa gcagctgaag cggcggagat acaccggctg 5880
gggcaggctg agccggaagc tgatcaacgg catccgggac aagcagtccg gcaagacaat 5940
cctggatttc ctgaagtccg acggcttcgc caacagaaac ttcatgcagc tgatccacga 6000
cgacagcctg acctttaaag aggacatcca gaaagcccag gtgtccggcc agggcgatag 6060
cctgcacgag cacattgcca atctggccgg cagccccgcc attaagaagg gcatcctgca 6120
gacagtgaag gtggtggacg agctcgtgaa agtgatgggc cggcacaagc ccgagaacat 6180
cgtgatcgaa atggccagag agaaccagac cacccagaag ggacagaaga acagccgcga 6240
gagaatgaag cggatcgaag agggcatcaa agagctgggc agccagatcc tgaaagaaca 6300
ccccgtggaa aacacccagc tgcagaacga gaagctgtac ctgtactacc tgcagaatgg 6360
gcgggatatg tacgtggacc aggaactgga catcaaccgg ctgtccgact acgatgtgga 6420
cgctatcgtg cctcagagct ttctgaagga cgactccatc gacaacaagg tgctgaccag 6480
aagcgacaag aaccggggca agagcgacaa cgtgccctcc gaagaggtcg tgaagaagat 6540
gaagaactac tggcggcagc tgctgaacgc caagctgatt acccagagaa agttcgacaa 6600
tctgaccaag gccgagagag gcggcctgag cgaactggat aaggccggct tcatcaagag 6660
acagctggtg gaaacccggc agatcacaaa gcacgtggca cagatcctgg actcccggat 6720
gaacactaag tacgacgaga atgacaagct gatccgggaa gtgaaagtga tcaccctgaa 6780
gtccaagctg gtgtccgatt tccggaagga tttccagttt tacaaagtgc gcgagatcaa 6840
caactaccac cacgcccacg acgcctacct gaacgccgtc gtgggaaccg ccctgatcaa 6900
aaagtaccct aagctggaaa gcgagttcgt gtacggcgac tacaaggtgt acgacgtgcg 6960
gaagatgatc gccaagagcg agcaggaaat cggcaaggct accgccaagt acttcttcta 7020
cagcaacatc atgaactttt tcaagaccga gattaccctg gccaacggcg agatccggaa 7080
gcggcctctg atcgagacaa acggcgaaac cggggagatc gtgtgggata agggccggga 7140
ttttgccacc gtgcggaaag tgctgagcat gccccaagtg aatatcgtga aaaagaccga 7200
ggtgcagaca ggcggcttca gcaaagagtc tatcctgccc aagaggaaca gcgataagct 7260
gatcgccaga aagaaggact gggaccctaa gaagtacggc ggcttcgaca gccccaccgt 7320
ggcctattct gtgctggtgg tggccaaagt ggaaaagggc aagtccaaga aactgaagag 7380
tgtgaaagag ctgctgggga tcaccatcat ggaaagaagc agcttcgaga agaatcccat 7440
cgactttctg gaagccaagg gctacaaaga agtgaaaaag gacctgatca tcaagctgcc 7500
taagtactcc ctgttcgagc tggaaaacgg ccggaagaga atgctggcct ctgccggcga 7560
actgcagaag ggaaacgaac tggccctgcc ctccaaatat gtgaacttcc tgtacctggc 7620

-continued

```
cagccactat gagaagctga agggctcccc cgaggataat gagcagaaac agctgtttgt   7680
ggaacagcac aagcactacc tggacgagat catcgagcag atcagcgagt tctccaagag   7740
agtgatcctg gccgacgcta atctggacaa agtgctgtcc gcctacaaca agcaccggga   7800
taagcccatc agagagcagg ccgagaatat catccacctg tttaccctga ccaatctggg   7860
agcccctgcc gccttcaagt actttgacac caccatcgac cggaagaggt acaccagcac   7920
caaagaggtg ctggacgcca ccctgatcca ccagagcatc accggcctgt acgagacacg   7980
gatcgacctg tctcagctgg gaggcgacag cgctggagga ggtggaagcg gaggaggagg   8040
aagcggagga ggaggtagcg gacctaagaa aaagaggaag gtggcggccg ctggatccgg   8100
acgggctgac gcattggacg attttgatct ggatatgctg ggaagtgacg ccctcgatga   8160
ttttgacctt gacatgcttg gttcggatgc ccttgatgac tttgacctcg acatgctcgg   8220
cagtgacgcc cttgatgatt tcgacctgga catgctgatt aacgctagcg gcagtggaga   8280
gggcagagga agtctgctaa catgcggtga cgtcgaggag aatcctggcc cagtgagcaa   8340
gggcgaggag ctgttcaccg gggtggtgcc catcctggtc gagctggacg gcgacgtaaa   8400
cggccacaag ttcagcgtgt ccggcgaggg cgagggcgat gccacctacg gcaagctgac   8460
cctgaagttc atctgcacca ccggcaagct gcccgtgccc tggcccaccc tcgtgaccac   8520
cctgacctac ggcgtgcagt gcttcagccg ctaccccgac cacatgaagc agcacgactt   8580
cttcaagtcc gccatgcccg aaggctacgt ccaggagcgc accatcttct tcaaggacga   8640
cggcaactac aagacccgcg ccgaggtgaa gttcgagggc gacaccctgg tgaaccgcat   8700
cgagctgaag ggcatcgact tcaaggagga cggcaacatc ctggggcaca agctggagta   8760
caactacaac agccacaacg tctatatcat ggccgacaag cagaagaacg gcatcaaggt   8820
gaacttcaag atccgccaca acatcgagga cggcagcgtg cagctcgccg accactacca   8880
gcagaacacc cccatcggcg acggccccgt gctgctgccc gacaaccact acctgagcac   8940
ccagtccgcc ctgagcaaag accccaacga gaagcgcgat cacatggtcc tgctggagtt   9000
cgtgaccgcc gccgggatca ctctcggcat ggacgagctg tacaagtaag aattcgatat   9060
caagcttatc gataatcaac ctctggatta caaaatttgt gaaagattga ctggtattct   9120
taactatgtt gctcctttta cgctatgtgg atacgctgct ttaatgcctt tgtatcatgc   9180
tattgcttcc cgtatggctt tcattttctc ctccttgtat aaatcctggt tgctgtctct   9240
ttatgaggag ttgtggcccg ttgtcaggca acgtggcgtg gtgtgcactg tgtttgctga   9300
cgcaaccccc actggttggg gcattgccac cacctgtcag ctcctttccg ggactttcgc   9360
tttccccctc cctattgcca cggcggaact catcgccgcc tgccttgccc gctgctggac   9420
aggggctcgg ctgttgggca ctgacaattc cgtggtgttg tcggggaaat catcgtcctt   9480
tccttggctg ctcgcctgtg ttgccacctg gattctgcgc gggacgtcct tctgctacgt   9540
cccttcggcc ctcaatccag cggaccttcc ttcccgcggc ctgctgccgg ctctgcggcc   9600
tcttccgcgt cttcgccttc gccctcagac gagtcggatc tccctttggg ccgcctcccc   9660
gcatcgatac cgtcgacctc gagacctaga aaaacatgga gcaatcacaa gtagcaatac   9720
agcagctacc aatgctgatt gtgcctggct agaagcacaa gaggaggagg aggtgggttt   9780
tccagtcaca cctcaggtac ctttaagacc aatgacttac aaggcagctg tagatcttag   9840
ccacttttta aaagaaaagg ggggactgga agggctaatt cactcccaac gaagacaaga   9900
tatccttgat ctgtggatct accacacaca aggctacttc cctgattggc agaactacac   9960
accagggcca gggatcagat atccactgac ctttggatgg tgctacaagc tagtaccagt  10020
```

-continued

```
tgagcaagag aaggtagaag aagccaatga aggagagaac acccgcttgt tacaccctgt  10080
gagcctgcat gggatggatg acccggagag agaagtatta gagtggaggt ttgacagccg  10140
cctagcattt catcacatgg cccgagagct gcatccggac tgtactgggt ctctctggtt  10200
agaccagatc tgagcctggg agctctctgg ctaactaggg aacccactgc ttaagcctca  10260
ataaagcttg ccttgagtgc ttcaagtagt gtgtgcccgt ctgttgtgtg actctggtaa  10320
ctagagatcc ctcagaccct tttagtcagt gtggaaaatc tctagcaggg cccgtttaaa  10380
cccgctgatc agcctcgact gtgccttcta gttgccagcc atctgttgtt tgcccctccc  10440
ccgtgccttc cttgaccctg gaaggtgcca ctcccactgt cctttcctaa taaaatgagg  10500
aaattgcatc gcattgtctg agtaggtgtc attctattct ggggggtggg gtggggcagg  10560
acagcaaggg ggaggattgg gaagacaata gcaggcatgc tggggatgcg gtgggctcta  10620
tggcttctga ggcggaaaga accagctggg gctctagggg gtatccccac gcgccctgta  10680
gcggcgcatt aagcgcggcg ggtgtggtgg ttacgcgcag cgtgaccgct acacttgcca  10740
gcgccctagc gcccgctcct ttcgctttct tcccttcctt tctcgccacg ttcgccggct  10800
ttccccgtca agctctaaat cgggggctcc ctttagggtt ccgatttagt gctttacggc  10860
acctcgaccc caaaaaactt gattagggtg atggttcacg tagtgggcca tcgccctgat  10920
agacggtttt tcgccctttg acgttggagt ccacgttctt taatagtgga ctcttgttcc  10980
aaactggaac aacactcaac cctatctcgg tctattcttt tgatttataa gggattttgc  11040
cgatttcggc ctattggtta aaaaatgagc tgatttaaca aaaatttaac gcgaattaat  11100
tctgtggaat gtgtgtcagt tagggtgtgg aaagtcccca ggctccccag caggcagaag  11160
tatgcaaagc atgcatctca attagtcagc aaccaggtgt ggaaagtccc caggctcccc  11220
agcaggcaga agtatgcaaa gcatgcatct caattagtca gcaaccatag tcccgcccct  11280
aactccgccc atcccgcccc taactccgcc cagttccgcc cattctccgc cccatggctg  11340
actaattttt tttatttatg cagaggccga ggccgcctct gcctctgagc tattccagaa  11400
gtagtgagga ggcttttttg gaggcctagg cttttgcaaa aagctcccgg gagcttgtat  11460
atccattttc ggatctgatc agcacgtgtt gacaattaat catcggcata gtatatcggc  11520
atagtataat acgacaaggt gaggaactaa accatggcca agttgaccag tgccgttccg  11580
gtgctcaccg cgcgcgacgt cgccggagcg gtcgagttct ggaccgaccg gctcgggttc  11640
tcccgggact tcgtggagga cgacttcgcc ggtgtggtcc gggacgacgt gaccctgttc  11700
atcagcgcgg tccaggacca ggtggtgccg gacaacaccc tggcctgggt gtgggtgcgc  11760
ggcctggacg agctgtacgc cgagtggtcg gaggtcgtgt ccacgaactt ccgggacgcc  11820
tccgggccgg ccatgaccga gatcggcgag cagccgtggg ggcgggagtt cgccctgcgc  11880
gacccggccg gcaactgcgt gcacttcgtg gccgaggagc aggactgaca cgtgctacga  11940
gatttcgatt ccaccgccgc cttctatgaa aggttgggct tcggaatcgt tttccgggac  12000
gccggctgga tgatcctcca gcgcggggat ctcatgctgg agttcttcgc ccaccccaac  12060
ttgtttattg cagcttataa tggttacaaa taaagcaata gcatcacaaa tttcacaaat  12120
aaagcatttt tttcactgca ttctagttgt ggtttgtcca aactcatcaa tgtatcttat  12180
catgtctgta taccgtcgac ctctagctag agcttggcgt aatcatggtc atagctgttt  12240
cctgtgtgaa attgttatcc gctcacaatt ccacacaaca tacgagccgg aagcataaag  12300
tgtaaagcct ggggtgccta atgagtgagc taactcacat taattgcgtt gcgctcactg  12360
```

-continued

```
cccgctttcc agtcgggaaa cctgtcgtgc cagctgcatt aatgaatcgg ccaacgcgcg  12420
gggagaggcg gtttgcgtat tgggcgctct tccgcttcct cgctcactga ctcgctgcgc  12480
tcggtcgttc ggctgcggcg agcggtatca gctcactcaa aggcggtaat acggttatcc  12540
acagaatcag gggataacgc aggaaagaac atgtgagcaa aaggccagca aaaggccagg  12600
aaccgtaaaa aggccgcgtt gctggcgttt ttccataggc tccgcccccc tgacgagcat  12660
cacaaaaatc gacgctcaag tcagaggtgg cgaaacccga caggactata aagataccag  12720
gcgtttcccc ctggaagctc cctcgtgcgc tctcctgttc cgaccctgcc gcttaccgga  12780
tacctgtccg cctttctccc ttcgggaagc gtggcgcttt ctcatagctc acgctgtagg  12840
tatctcagtt cggtgtaggt cgttcgctcc aagctgggct gtgtgcacga accccccgtt  12900
cagcccgacc gctgcgcctt atccggtaac tatcgtcttg agtccaaccc ggtaagacac  12960
gacttatcgc cactggcagc agccactggt aacaggatta gcagagcgag gtatgtaggc  13020
ggtgctacag agttcttgaa gtggtggcct aactacggct acactagaag aacagtattt  13080
ggtatctgcg ctctgctgaa gccagttacc ttcggaaaaa gagttggtag ctcttgatcc  13140
ggcaaacaaa ccaccgctgg tagcggtggt ttttttgttt gcaagcagca gattacgcgc  13200
agaaaaaaag gatctcaaga agatcctttg atcttttcta cggggtctga cgctcagtgg  13260
aacgaaaact cacgttaagg gattttggtc atgagattat caaaaaggat cttcacctag  13320
atccttttaa attaaaaatg aagttttaaa tcaatctaaa gtatatatga gtaaacttgg  13380
tctgacagtt accaatgctt aatcagtgag gcacctatct cagcgatctg tctatttcgt  13440
tcatccatag ttgcctgact ccccgtcgtg tagataacta cgatacggga gggcttacca  13500
tctggcccca gtgctgcaat gataccgcga gacccacgct caccggctcc agatttatca  13560
gcaataaacc agccagccgg aagggccgag cgcagaagtg gtcctgcaac tttatccgcc  13620
tccatccagt ctattaattg ttgccgggaa gctagagtaa gtagttcgcc agttaatagt  13680
ttgcgcaacg ttgttgccat tgctacaggc atcgtggtgt cacgctcgtc gtttggtatg  13740
gcttcattca gctccggttc ccaacgatca aggcgagtta catgatcccc catgttgtgc  13800
aaaaaagcgg ttagctcctt cggtcctccg atcgttgtca gaagtaagtt ggccgcagtg  13860
ttatcactca tggttatggc agcactgcat aattctctta ctgtcatgcc atccgtaaga  13920
tgcttttctg tgactggtga gtactcaacc aagtcattct gagaatagtg tatgcggcga  13980
ccgagttgct cttgcccggc gtcaatacgg gataataccg cgccacatag cagaacttta  14040
aaagtgctca tcattggaaa acgttcttcg gggcgaaaac tctcaaggat cttaccgctg  14100
ttgagatcca gttcgatgta acccactcgt gcacccaact gatcttcagc atcttttact  14160
ttcaccagcg tttctgggtg agcaaaaaca ggaaggcaaa atgccgcaaa aaagggaata  14220
agggcgacac ggaaatgttg aatactcata ctcttccttt ttcaatatta ttgaagcatt  14280
tatcagggtt attgtctcat gagcggatac atatttgaat gtatttagaa aaataaacaa  14340
ataggggttc cgcgcacatt tccccgaaaa gtgccacctg ac                    14382
```

<210> SEQ ID NO 7
<211> LENGTH: 4952
<212> TYPE: DNA
<213> ORGANISM: Artificial Sequence
<220> FEATURE:
<223> OTHER INFORMATION: gRNA Addgene #51133

<400> SEQUENCE: 7

```
ggtaccgatt agtgaacgga tctcgacggt atcgatcacg agactagcct cgagcggccg     60
```

-continued

```
ccccccttcac cgagggccta tttcccatga ttccttcata tttgcatata cgatacaagg    120
ctgttagaga gataattgga attaatttga ctgtaaacac aaagatatta gtacaaaata    180
cgtgacgtag aaagtaataa tttcttgggt agtttgcagt tttaaaatta tgttttaaaa    240
tggactatca tatgcttacc gtaacttgaa agtatttcga tttcttggct ttatatatct    300
tgtggaaagg acgaaacacc ggtgagaccg agagagggtc tcagttttag agctagaaat    360
agcaagttaa aataaggcta gtccgttatc aacttgaaaa agtggcaccg agtcggtgct    420
tttttaaag aattctcgac ctcgagacaa atggcagtat tcatccacaa ttttaaaaga    480
aaaggggga ttgggggta cagtgcaggg gaaagaatag tagacataat agcaacagac    540
atacaaacta aagaattaca aaaacaaatt acaaaaattc aaaattttcg ggtttattac    600
agggacagca gagatccact ttggccgcgg ctcgaggggg ttggggttgc gccttttcca    660
aggcagccct gggtttgcgc agggacgcgg ctgctctggg cgtggttccg ggaaacgcag    720
cggcgccgac cctgggactc gcacattctt cacgtccgtt cgcagcgtca cccggatctt    780
cgccgctacc cttgtgggcc ccccggcgac gcttcctgct ccgcccctaa gtcgggaagg    840
ttccttgcgg ttcgcggcgt gccggacgtg acaaacggaa gccgcacgtc tcactagtac    900
cctcgcagac ggacagcgcc agggagcaat ggcagcgcgc cgaccgcgat gggctgtggc    960
caatagcggc tgctcagcag ggcgcgccga gagcagcggc cgggaagggg cggtgcggga   1020
ggcggggtgt ggggcggtag tgtgggccct gttcctgccc gcgcggtgtt ccgcattctg   1080
caagcctccg gagcgcacgt cggcagtcgg ctccctcgtt gaccgaatca ccgacctctc   1140
tccccagggg gatccaccgg agcttaccat gaccgagtac aagcccacgg tgcgcctcgc   1200
cacccgcgac gacgtcccca gggccgtacg caccctcgcc gccgcgttcg ccgactaccc   1260
cgccacgcgc cacaccgtcg atccggaccg ccacatcgag cgggtcaccg agctgcaaga   1320
actcttcctc acgcgcgtcg ggctcgacat cggcaaggtg tgggtcgcgg acgacggcgc   1380
cgcggtggcg gtctggacca cgccggagag cgtcgaagcg ggggcggtgt tcgccgagat   1440
cggcccgcgc atggccgagt tgagcggttc ccggctggcc gcgcagcaac agatggaagg   1500
cctcctggcg ccgcaccggc ccaaggagcc cgcgtggttc ctggccaccg tcggcgtctc   1560
gcccgaccac cagggcaagg gtctgggcag cgccgtcgtg ctccccggag tggaggcggc   1620
cgagcgcgcc ggggtgcccg ccttcctgga aacctccgcg ccccgcaacc tccccttcta   1680
cgagcggctc ggcttcaccg tcaccgccga cgtcgaggtg cccgaaggac cgcgcacctg   1740
gtgcatgacc cgcaagcccg gtgcctgacg cccgccccac gacccgcagc gcccgaccga   1800
aaggagcgca cgaccccatg catcggtacc tttaagacca atgacttaca aggcagctgt   1860
agatcttagc cactttctag agtcggggcg gccggccgct tcgagcagac atgataagat   1920
acattgatga gtttggacaa accacaacta gaatgcagtg aaaaaaatgc tttatttgtg   1980
aaatttgtga tgctattgct ttatttgtaa ccattataag ctgcaataaa caagttaaca   2040
acaacaattg cattcatttt atgtttcagg ttcaggggga ggtgtgggag gtttttttaaa   2100
gcaagtaaaa cctctacaaa tgtggtaaaa tcgataagga tccgtcgacc gatgcccttg   2160
agagccttca acccagtcag ctccttccgg tgggcgcggg gcatgactat cgtcgccgca   2220
cttatgactg tcttctttat catgcaactc gtaggacagg tgccggcagc gctcttccgc   2280
ttcctcgctc actgactcgc tgcgctcggt cgttcggctg cggcgagcgg tatcagctca   2340
ctcaaaggcg gtaatacggt tatccacaga atcaggggat aacgcaggaa agaacatgtg   2400
```

-continued

```
agcaaaaggc cagcaaaagg ccaggaaccg taaaaaggcc gcgttgctgg cgtttttcca   2460
taggctccgc ccccctgacg agcatcacaa aaatcgacgc tcaagtcaga ggtggcgaaa   2520
cccgacagga ctataaagat accaggcgtt tccccctgga agctccctcg tgcgctctcc   2580
tgttccgacc ctgccgctta ccggatacct gtccgccttt ctcccttcgg gaagcgtggc   2640
gctttctcaa tgctcacgct gtaggtatct cagttcggtg taggtcgttc gctccaagct   2700
gggctgtgtg cacgaacccc ccgttcagcc cgaccgctgc gccttatccg gtaactatcg   2760
tcttgagtcc aacccggtaa gacacgactt atcgccactg gcagcagcca ctggtaacag   2820
gattagcaga gcgaggtatg taggcggtgc tacagagttc ttgaagtggt ggcctaacta   2880
cggctacact agaaggacag tatttggtat ctgcgctctg ctgaagccag ttaccttcgg   2940
aaaaagagtt ggtagctctt gatccggcaa acaaaccacc gctggtagcg gtggtttttt   3000
tgtttgcaag cagcagatta cgcgcagaaa aaaaggatct caagaagatc ctttgatctt   3060
ttctacgggg tctgacgctc agtggaacga aaactcacgt taagggattt tggtcatgag   3120
attatcaaaa aggatcttca cctagatcct tttaaattaa aaatgaagtt ttaaatcaat   3180
ctaaagtata tatgagtaaa cttggtctga cagttaccaa tgcttaatca gtgaggcacc   3240
tatctcagcg atctgtctat ttcgttcatc catagttgcc tgactccccg tcgtgtagat   3300
aactacgata cgggagggct taccatctgg ccccagtgct gcaatgatac cgcgggaccc   3360
acgctcaccg gctccagatt tatcagcaat aaaccagcca gccggaaggg ccgagcgcag   3420
aagtggtcct gcaactttat ccgcctccat ccagtctatt aattgttgcc gggaagctag   3480
agtaagtagt tcgccagtta atagtttgcg caacgttgtt gccattgcta caggcatcgt   3540
ggtgtcacgc tcgtcgtttg gtatggcttc attcagctcc ggttcccaac gatcaaggcg   3600
agttacatga tcccccatgt tgtgcaaaaa agcggttagc tccttcggtc ctccgatcgt   3660
tgtcagaagt aagttggccg cagtgttatc actcatggtt atggcagcac tgcataattc   3720
tcttactgtc atgccatccg taagatgctt ttctgtgact ggtgagtact caaccaagtc   3780
attctgagaa tagtgtatgc ggcgaccgag ttgctcttgc ccggcgtcaa tacgggataa   3840
taccgcgcca catagcagaa ctttaaaagt gctcatcatt ggaaaacgtt cttcggggcg   3900
aaaactctca aggatcttac cgctgttgag atccagttcg atgtaaccca ctcgtgcacc   3960
caactgatct tcagcatctt ttactttcac cagcgtttct gggtgagcaa aaacaggaag   4020
gcaaaatgcc gcaaaaaagg gaataagggc gacacggaaa tgttgaatac tcatactctt   4080
cctttttcaa tattattgaa gcatttatca gggttattgt ctcatgagcg gatacatatt   4140
tgaatgtatt tagaaaaata aacaaatagg ggttccgcgc acatttcccc gaaaagtgcc   4200
acctgacgcg ccctgtagcg gcgcattaag cgcggcgggt gtggtggtta cgcgcagcgt   4260
gaccgctaca cttgccagcg ccctagcgcc cgctcctttc gctttcttcc cttcctttct   4320
cgccacgttc gccggctttc cccgtcaagc tctaaatcgg gggctccctt tagggttccg   4380
atttagtgct ttacggcacc tcgaccccaa aaaacttgat tagggtgatg gttcacgtag   4440
tgggccatcg ccctgataga cggtttttcg ccctttgacg ttggagtcca cgttctttaa   4500
tagtggactc ttgttccaaa ctggaacaac actcaaccct atctcggtct attcttttga   4560
tttataaggg attttgccga tttcggccta ttggttaaaa aatgagctga tttaacaaaa   4620
atttaacgcg aattttaaca aaatattaac gtttacaatt tcccattcgc cattcaggct   4680
gcgcaactgt tgggaagggc gatcggtgcg ggcctcttcg ctattacgcc agcccaagct   4740
accatgataa gtaagtaata ttaaggtacg ggaggtactt ggagcggccg caataaaata   4800
```

tctttatttt cattacatct gtgtgttggt tttttgtgtg aatcgatagt actaacatac 4860
gctctccatc aaaacaaaac gaaacaaaac aaactagcaa aataggctgt ccccagtgca 4920
agtgcaggtg ccagaacatt tctctatcga ta 4952

<210> SEQ ID NO 8
<211> LENGTH: 9996
<212> TYPE: DNA
<213> ORGANISM: Artificial Sequence
<220> FEATURE:
<223> OTHER INFORMATION: gRNA-MS2 sequence. Addgene #61427

<400> SEQUENCE: 8
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatggtg atgcggtttt ggcagtacat caatgggcgt ggatagcggt 660
ttgactcacg gggatttcca agtctccacc ccattgacgt caatgggagt ttgttttggc 720
accaaaatca acgggacttt ccaaaatgtc gtaacaactc cgccccattg acgcaaatgg 780
gcggtaggcg tgtacggtgg gaggtctata taagcagcgc gttttgcctg tactgggtct 840
ctctggttag accagatctg agcctgggag ctctctggct aactagggaa cccactgctt 900
aagcctcaat aaagcttgcc ttgagtgctt caagtagtgt gtgcccgtct gttgtgtgac 960
tctggtaact agagatccct cagacccttt tagtcagtgt ggaaaatctc tagcagtggc 1020
gcccgaacag ggacttgaaa gcgaaaggga aaccagagga gctctctcga cgcaggactc 1080
ggcttgctga agcgcgcacg gcaagaggcg aggggcggcg actggtgagt acgccaaaaa 1140
ttttgactag cggaggctag aaggagagag atgggtgcga gagcgtcagt attaagcggg 1200
ggagaattag atcgcgatgg gaaaaaattc ggttaaggcc agggggaaag aaaaaatata 1260
aattaaaaca tatagtatgg gcaagcaggg agctagaacg attcgcagtt aatcctggcc 1320
tgttagaaac atcagaaggc tgtagacaaa tactgggaca gctacaacca tcccttcaga 1380
caggatcaga agaacttaga tcattatata atacagtagc aaccctctat tgtgtgcatc 1440
aaaggataga gataaaagac accaaggaag ctttagacaa gatagaggaa gagcaaaaca 1500
aaagtaagac caccgcacag caagcggccg ctgatcttca gacctggagg aggagatatg 1560
agggacaatt ggagaagtga attatataaa tataaagtag taaaaattga accattagga 1620
gtagcaccca ccaaggcaaa gagaagagtg gtgcagagag aaaaaagagc agtgggaata 1680
ggagctttgt tccttgggtt cttgggagca gcaggaagca ctatgggcgc agcgtcaatg 1740
acgctgacgg tacaggccag acaattattg tctggtatag tgcagcagca gaacaatttg 1800
ctgagggcta ttgaggcgca acagcatctg ttgcaactca cagtctgggg catcaagcag 1860

-continued

```
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta gctagcgagg gcctatttcc catgattcct tcatatttgc   2640
atatacgata caaggctgtt agagagataa ttggaattaa tttgactgta aacacaaaga   2700
tattagtaca aaatacgtga cgtagaaagt aataatttct tgggtagttt gcagttttaa   2760
aattatgttt taaaatggac tatcatatgc ttaccgtaac ttgaaagtat ttcgatttct   2820
tggctttata tatcttgtgg aaaggacgaa acaccggaga cgggataccg tctctgtttt   2880
agagctaggc caacatgagg atcacccatg tctgcagggc ctagcaagtt aaaataaggc   2940
tagtccgtta tcaacttggc caacatgagg atcacccatg tctgcagggc caagtggcac   3000
cgagtcggtg cttttttttgg atcctgcaaa gatggataaa gttttaaaca gagaggaatc   3060
tttgcagcta atggaccttc taggtcttga aaggagtggg aattggctcc ggtgcccgtc   3120
agtgggcaga gcgcacatcg cccacagtcc ccgagaagtt ggggggaggg gtcggcaatt   3180
gatccggtgc ctagagaagg tggcgcgggg taaactggga aagtgatgtc gtgtactggc   3240
tccgcctttt tcccgagggt gggggagaac cgtatataag tgcagtagtc gccgtgaacg   3300
ttctttttcg caacgggttt gccgccagaa cacaggtaag tgccgtgtgt ggttcccgcg   3360
ggcctggcct ctttacgggt tatggccctt gcgtgccttg aattacttcc actggctgca   3420
gtacgtgatt cttgatcccg agcttcgggt tggaagtggg tgggagagtt cgaggccttg   3480
cgcttaagga gccccttcgc ctcgtgcttg agttgaggcc tggcctgggc gctggggccg   3540
ccgcgtgcga atctggtggc accttcgcgc ctgtctcgct gctttcgata agtctctagc   3600
catttaaaat ttttgatgac ctgctgcgac gcttttttttc tggcaagata gtcttgtaaa   3660
tgcgggccaa gatctgcaca ctggtatttc ggtttttggg gccgcgggcg gcgacggggc   3720
ccgtgcgtcc cagcgcacat gttcggcgag gcggggcctg cgagcgcggc caccgagaat   3780
cggacggggg tagtctcaag ctggccggcc tgctctggtg cctggcctcg cgccgccgtg   3840
tatcgccccg ccctgggcgg caaggctggc ccggtcggca ccagttgcgt gagcggaaag   3900
atggccgctt cccggccctg ctgcagggag ctcaaaatgg aggacgcggc gctcgggaga   3960
gcgggcgggt gagtcaccca cacaaaggaa aagggccttt ccgtcctcag ccgtcgcttc   4020
atgtgactcc acggagtacc gggcgccgtc caggcacctc gattagttct cgagcttttg   4080
gagtacgtcg tctttaggtt ggggggaggg gttttatgcg atggagtttc cccacactga   4140
gtgggtggag actgaagtta ggccagcttg gcacttgatg taattctcct tggaatttgc   4200
ccttttttgag tttggatctt ggttcattct caagcctcag acagtggttc aaagtttttt   4260
```

-continued tcttccattt caggtgtcgt gatgtacaat ggccaagttg accagtgccg ttccggtgct 4320
caccgcgcgc gacgtcgccg gagcggtcga gttctggacc gaccggctcg ggttctcccg 4380
ggacttcgtg gaggacgact tcgccggtgt ggtccgggac gacgtgaccc tgttcatcag 4440
cgcggtccag gaccaggtgg tgccggacaa caccctggcc tgggtgtggg tgcgcggcct 4500
ggacgagctg tacgccgagt ggtcggaggt cgtgtccacg aacttccggg acgcctccgg 4560
gccggccatg accgagatcg gcgagcagcc gtgggggcgg gagttcgccc tgcgcgaccc 4620
ggccggcaac tgcgtgcact tcgtggccga ggagcaggac tgagaattcg atatcaagct 4680
tatcggtaat caacctctgg attacaaaat ttgtgaaaga ttgactggta ttcttaacta 4740
tgttgctcct tttacgctat gtggatacgc tgctttaatg cctttgtatc atgctattgc 4800
ttcccgtatg gctttcattt tctcctcctt gtataaatcc tggttgctgt ctctttatga 4860
ggagttgtgg cccgttgtca ggcaacgtgg cgtggtgtgc actgtgtttg ctgacgcaac 4920
ccccactggt tggggcattg ccaccacctg tcagctcctt tccgggactt tcgctttccc 4980
cctccctatt gccacggcgg aactcatcgc cgcctgcctt gcccgctgct ggacaggggc 5040
tcggctgttg ggcactgaca attccgtggt gttgtcgggg aaatcatcgt cctttccttg 5100
gctgctcgcc tgtgttgcca cctggattct gcgcgggacg tccttctgct acgtcccttc 5160
ggccctcaat ccagcggacc ttccttcccg cggcctgctg ccggctctgc ggcctcttcc 5220
gcgtcttcgc cttcgccctc agacgagtcg gatctccctt tgggccgcct ccccgcatcg 5280
ataccgtcga cctcgagacc tagaaaaaca tggagcaatc acaagtagca atacagcagc 5340
taccaatgct gattgtgcct ggctagaagc acaagaggag gaggaggtgg gttttccagt 5400
cacacctcag gtacctttaa gaccaatgac ttacaaggca gctgtagatc ttagccactt 5460
tttaaaagaa aaggggggac tggaagggct aattcactcc caacgaagac aagatatcct 5520
tgatctgtgg atctaccaca cacaaggcta cttccctgat tggcagaact acacaccagg 5580
gccagggatc agatatccac tgacctttgg atggtgctac aagctagtac cagttgagca 5640
agagaaggta gaagaagcca atgaaggaga gaacacccgc ttgttacacc ctgtgagcct 5700
gcatgggatg gatgacccgg agagagaagt attagagtgg aggtttgaca gccgcctagc 5760
atttcatcac atggcccgag agctgcatcc ggactgtact gggtctctct ggttagacca 5820
gatctgagcc tgggagctct ctggctaact agggaaccca ctgcttaagc ctcaataaag 5880
cttgccttga gtgcttcaag tagtgtgtgc ccgtctgttg tgtgactctg gtaactagag 5940
atccctcaga cccttttagt cagtgtggaa aatctctagc agggcccgtt taaacccgct 6000
gatcagcctc gactgtgcct tctagttgcc agccatctgt tgtttgcccc tcccccgtgc 6060
cttccttgac cctggaaggt gccactccca ctgtcctttc ctaataaaat gaggaaattg 6120
catcgcattg tctgagtagg tgtcattcta ttctgggggg tggggtgggg caggacagca 6180
agggggagga ttgggaagac aatagcaggc atgctgggga tgcggtgggc tctatggctt 6240
ctgaggcgga aagaaccagc tggggctcta gggggtatcc ccacgcgccc tgtagcggcg 6300
cattaagcgc ggcgggtgtg gtggttacgc gcagcgtgac cgctacactt gccagcgccc 6360
tagcgcccgc tcctttcgct ttcttccctt cctttctcgc cacgttcgcc ggctttcccc 6420
gtcaagctct aaatcggggg ctccctttag ggttccgatt tagtgcttta cggcacctcg 6480
accccaaaaa acttgattag ggtgatggtt cacgtagtgg gccatcgccc tgatagacgg 6540
tttttcgccc tttgacgttg gagtccacgt tctttaatag tggactcttg ttccaaactg 6600

-continued

```
gaacaacact caaccctatc tcggtctatt cttttgattt ataagggatt ttgccgattt   6660
cggcctattg gttaaaaaat gagctgattt aacaaaaatt taacgcgaat taattctgtg   6720
gaatgtgtgt cagttagggt gtggaaagtc cccaggctcc ccagcaggca gaagtatgca   6780
aagcatgcat ctcaattagt cagcaaccag gtgtggaaag tccccaggct ccccagcagg   6840
cagaagtatg caaagcatgc atctcaatta gtcagcaacc atagtcccgc ccctaactcc   6900
gcccatcccg cccctaactc cgcccagttc cgcccattct ccgccccatg gctgactaat   6960
ttttttattt tatgcagagg ccgaggccgc ctctgcctct gagctattcc agaagtagtg   7020
aggaggcttt tttggaggcc taggcttttg caaaaagctc ccgggagctt gtatatccat   7080
tttcggatct gatcagcacg tgttgacaat taatcatcgg catagtatat cggcatagta   7140
taatacgaca aggtgaggaa ctaaaccatg gccaagttga ccagtgccgt tccggtgctc   7200
accgcgcgcg acgtcgccgg agcggtcgag ttctggaccg accggctcgg gttctcccgg   7260
gacttcgtgg aggacgactt cgccggtgtg gtccgggacg acgtgaccct gttcatcagc   7320
gcggtccagg accaggtggt gccggacaac accctggcct gggtgtgggt gcgcggcctg   7380
gacgagctgt acgccgagtg gtcggaggtc gtgtccacga acttccggga cgcctccggg   7440
ccggccatga ccgagatcgg cgagcagccg tgggggcggg agttcgccct gcgcgacccg   7500
gccggcaact gcgtgcactt cgtggccgag gagcaggact gacacgtgct acgagatttc   7560
gattccaccg ccgccttcta tgaaaggttg ggcttcggaa tcgttttccg ggacgccggc   7620
tggatgatcc tccagcgcgg ggatctcatg ctggagttct tcgcccaccc caacttgttt   7680
attgcagctt ataatggtta caaataaagc aatagcatca caaatttcac aaataaagca   7740
tttttttcac tgcattctag ttgtggtttg tccaaactca tcaatgtatc ttatcatgtc   7800
tgtataccgt cgacctctag ctagagcttg gcgtaatcat ggtcatagct gtttcctgtg   7860
tgaaattgtt atccgctcac aattccacac aacatacgag ccggaagcat aaagtgtaaa   7920
gcctggggtg cctaatgagt gagctaactc acattaattg cgttgcgctc actgcccgct   7980
ttccagtcgg gaaacctgtc gtgccagctg cattaatgaa tcggccaacg cgcggggaga   8040
ggcggtttgc gtattgggcg ctcttccgct tcctcgctca ctgactcgct gcgctcggtc   8100
gttcggctgc ggcgagcggt atcagctcac tcaaaggcgg taatacggtt atccacagaa   8160
tcaggggata acgcaggaaa gaacatgtga gcaaaaggcc agcaaaaggc caggaaccgt   8220
aaaaaggccg cgttgctggc gtttttccat aggctccgcc cccctgacga gcatcacaaa   8280
aatcgacgct caagtcagag gtggcgaaac ccgacaggac tataaagata ccaggcgttt   8340
ccccctggaa gctccctcgt gcgctctcct gttccgaccc tgccgcttac cggatacctg   8400
tccgcctttc tcccttcggg aagcgtggcg ctttctcata gctcacgctg taggtatctc   8460
agttcggtgt aggtcgttcg ctccaagctg ggctgtgtgc acgaaccccc cgttcagccc   8520
gaccgctgcg ccttatccgg taactatcgt cttgagtcca acccggtaag acacgactta   8580
tcgccactgg cagcagccac tggtaacagg attagcagag cgaggtatgt aggcggtgct   8640
acagagttct tgaagtggtg gcctaactac ggctacacta gaagaacagt atttggtatc   8700
tgcgctctgc tgaagccagt taccttcgga aaaagagttg gtagctcttg atccggcaaa   8760
caaaccaccg ctggtagcgg tggttttttt gtttgcaagc agcagattac gcgcagaaaa   8820
aaaggatctc aagaagatcc tttgatcttt tctacggggt ctgacgctca gtggaacgaa   8880
aactcacgtt aagggatttt ggtcatgaga ttatcaaaaa ggatcttcac ctagatcctt   8940
ttaaattaaa aatgaagttt taaatcaatc taaagtatat atgagtaaac ttggtctgac   9000
```

agttaccaat gcttaatcag tgaggcacct atctcagcga tctgtctatt tcgttcatcc 9060
atagttgcct gactccccgt cgtgtagata actacgatac gggagggctt accatctggc 9120
cccagtgctg caatgatacc gcgagaccca cgctcaccgg ctccagattt atcagcaata 9180
aaccagccag ccggaagggc cgagcgcaga agtggtcctg caactttatc cgcctccatc 9240
cagtctatta attgttgccg ggaagctaga gtaagtagtt cgccagttaa tagtttgcgc 9300
aacgttgttg ccattgctac aggcatcgtg gtgtcacgct cgtcgtttgg tatggcttca 9360
ttcagctccg gttcccaacg atcaaggcga gttacatgat cccccatgtt gtgcaaaaaa 9420
gcggttagct ccttcggtcc tccgatcgtt gtcagaagta agttggccgc agtgttatca 9480
ctcatggtta tggcagcact gcataattct cttactgtca tgccatccgt aagatgcttt 9540
tctgtgactg gtgagtactc aaccaagtca ttctgagaat agtgtatgcg gcgaccgagt 9600
tgctcttgcc cggcgtcaat acgggataat accgcgccac atagcagaac tttaaaagtg 9660
ctcatcattg gaaaacgttc ttcggggcga aaactctcaa ggatcttacc gctgttgaga 9720
tccagttcga tgtaacccac tcgtgcaccc aactgatctt cagcatcttt tactttcacc 9780
agcgtttctg ggtgagcaaa aacaggaagg caaaatgccg caaaaaaggg aataagggcg 9840
acacggaaat gttgaatact catactcttc ctttttcaat attattgaag catttatcag 9900
ggttattgtc tcatgagcgg atacatattt gaatgtattt agaaaaataa acaaataggg 9960
gttccgcgca catttccccg aaaagtgcca cctgac 9996

<210> SEQ ID NO 9
<211> LENGTH: 11409
<212> TYPE: DNA
<213> ORGANISM: Artificial Sequence
<220> FEATURE:
<223> OTHER INFORMATION: MS2-P65-HS1_GFP sequence. Addgene #61427

<400> SEQUENCE: 9
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatggtg atgcggtttt ggcagtacat caatgggcgt ggatagcggt 660
ttgactcacg gggatttcca agtctccacc ccattgacgt caatgggagt ttgttttggc 720
accaaaatca acgggacttt ccaaaatgtc gtaacaactc cgccccattg acgcaaatgg 780
gcggtaggcg tgtacggtgg gaggtctata taagcagcgc gttttgcctg tactgggtct 840
ctctggttag accagatctg agcctgggag ctctctggct aactagggaa cccactgctt 900
aagcctcaat aaagcttgcc ttgagtgctt caagtagtgt gtgcccgtct gttgtgtgac 960
tctggtaact agagatccct cagacccttt tagtcagtgt ggaaaatctc tagcagtggc 1020

-continued

```
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
tttttcgcaa cgggtttgcc gccagaacac aggtaagtgc cgtgtgtggt tcccgcgggc   2940
ctggcctctt tacgggttat ggcccttgcg tgccttgaat tacttccact ggctgcagta   3000
cgtgattctt gatcccgagc ttcgggttgg aagtgggtgg gagagttcga ggccttgcgc   3060
ttaaggagcc ccttcgcctc gtgcttgagt tgaggcctgg cctgggcgct ggggccgccg   3120
cgtgcgaatc tggtggcacc ttcgcgcctg tctcgctgct ttcgataagt ctctagccat   3180
ttaaaatttt tgatgacctg ctgcgacgct ttttttctgg caagatagtc ttgtaaatgc   3240
gggccaagat ctgcacactg gtatttcggt ttttggggcc gcgggcggcg acggggcccg   3300
tgcgtcccag cgcacatgtt cggcgaggcg gggcctgcga gcgcggccac cgagaatcgg   3360
acgggggtag tctcaagctg gccggcctgc tctggtgcct ggcctcgcgc cgccgtgtat   3420
```

-continued cgccccgccc tgggcggcaa ggctggcccg gtcggcacca gttgcgtgag cggaaagatg 3480
gccgcttccc ggccctgctg cagggagctc aaaatggagg acgcggcgct cgggagagcg 3540
ggcgggtgag tcacccacac aaaggaaaag ggcctttccg tcctcagccg tcgcttcatg 3600
tgactccacg gagtaccggg cgccgtccag gcacctcgat tagttctcga gcttttggag 3660
tacgtcgtct ttaggttggg gggaggggtt ttatgcgatg gagtttcccc acactgagtg 3720
ggtggagact gaagttaggc cagcttggca cttgatgtaa ttctccttgg aatttgccct 3780
ttttgagttt ggatcttggt tcattctcaa gcctcagaca gtggttcaaa gtttttttct 3840
tccatttcag gtgtcgtgac gtacggccac catggcttca aactttactc agttcgtgct 3900
cgtggacaat ggtgggacag ggatgtgac agtggctcct tctaatttcg ctaatggggt 3960
ggcagagtgg atcagctcca actcacggag ccaggcctac aaggtgacat gcagcgtcag 4020
gcagtctagt gcccagaaga gaaagtatac catcaaggtg gaggtcccca aagtggctac 4080
ccagacagtg ggcggagtcg aactgcctgt cgccgcttgg aggtcctacc tgaacatgga 4140
gctcactatc ccaattttcg ctaccaattc tgactgtgaa ctcatcgtga aggcaatgca 4200
ggggctcctc aaagacggta atcctatccc ttccgccatc gccgctaact caggtatcta 4260
cagcgctgga ggaggtggaa gcggaggagg aggaagcgga ggaggaggta gcggacctaa 4320
gaaaaagagg aaggtggcgg ccgctggatc cccttcaggg cagatcagca accaggccct 4380
ggctctggcc cctagctccg ctccagtgct ggcccagact atggtgccct ctagtgctat 4440
ggtgcctctg gcccagccac ctgctccagc ccctgtgctg accccaggac caccccagtc 4500
actgagcgct ccagtgccca agtctacaca ggccggcgag gggactctga gtgaagctct 4560
gctgcacctg cagttcgacg ctgatgagga cctgggagct ctgctgggga acagcaccga 4620
tcccggagtg ttcacagatc tggcctccgt ggacaactct gagtttcagc agctgctgaa 4680
tcagggcgtg tccatgtctc atagtacagc cgaaccaatg ctgatggagt accccgaagc 4740
cattacccgg ctggtgaccg gcagccagcg gccccccgac cccgctccaa ctcccctggg 4800
aaccagcggc ctgcctaatg ggctgtccgg agatgaagac ttctcaagca tcgctgatat 4860
ggactttagt gccctgctgt cacagatttc ctctagtggg cagggaggag gtggaagcgg 4920
cttcagcgtg gacaccagtg ccctgctgga cctgttcagc ccctcggtga ccgtgcccga 4980
catgagcctg cctgaccttg acagcagcct ggccagtatc caagagctcc tgtctcccca 5040
ggagcccccc aggcctcccg aggcagagaa cagcagcccg gattcaggga agcagctggt 5100
gcactacaca gcgcagccgc tgttcctgct ggaccccggc tccgtggaca ccgggagcaa 5160
cgacctgccg gtgctgtttg agctgggaga gggctcctac ttctccgaag gggacggctt 5220
cgccgaggac cccaccatct ccctgctgac aggctcggag cctcccaaag ccaaggaccc 5280
cactgtctcc gctagcggca gtggagaggg cagaggaagt ctgctaacat gcggtgacgt 5340
cgaggagaat cctggcccag tgagcaaggg cgaggagctg ttcaccgggg tggtgcccat 5400
cctggtcgag ctggacggcg acgtaaacgg ccacaagttc agcgtgtccg gcgagggcga 5460
gggcgatgcc acctacggca agctgaccct gaagttcatc tgcaccaccg gcaagctgcc 5520
cgtgccctgg cccaccctcg tgaccaccct gacctacggc gtgcagtgct tcagccgcta 5580
ccccgaccac atgaagcagc acgacttctt caagtccgcc atgcccgaag gctacgtcca 5640
ggagcgcacc atcttcttca aggacgacgg caactacaag acccgcgccg aggtgaagtt 5700
cgagggcgac accctggtga accgcatcga gctgaagggc atcgacttca aggaggacgg 5760

-continued

```
caacatcctg gggcacaagc tggagtacaa ctacaacagc cacaacgtct atatcatggc   5820
cgacaagcag aagaacggca tcaaggtgaa cttcaagatc cgccacaaca tcgaggacgg   5880
cagcgtgcag ctcgccgacc actaccagca gaacaccccc atcggcgacg gccccgtgct   5940
gctgcccgac aaccactacc tgagcaccca gtccgccctg agcaaagacc ccaacgagaa   6000
gcgcgatcac atggtcctgc tggagttcgt gaccgccgcc gggatcactc tcggcatgga   6060
cgagctgtac aagtaagaat tcgatatcaa gcttatcgat aatcaacctc tggattacaa   6120
aatttgtgaa agattgactg gtattcttaa ctatgttgct ccttttacgc tatgtggata   6180
cgctgcttta atgcctttgt atcatgctat tgcttcccgt atggctttca ttttctcctc   6240
cttgtataaa tcctggttgc tgtctcttta tgaggagttg tggcccgttg tcaggcaacg   6300
tggcgtggtg tgcactgtgt ttgctgacgc aacccccact ggttggggca ttgccaccac   6360
ctgtcagctc ctttccggga ctttcgcttt ccccctccct attgccacgg cggaactcat   6420
cgccgcctgc cttgcccgct gctggacagg ggctcggctg ttgggcactg acaattccgt   6480
ggtgttgtcg gggaaatcat cgtcctttcc ttggctgctc gcctgtgttg ccacctggat   6540
tctgcgcggg acgtccttct gctacgtccc ttcggccctc aatccagcgg accttccttc   6600
ccgcggcctg ctgccggctc tgcggcctct tccgcgtctt cgccttcgcc ctcagacgag   6660
tcggatctcc ctttgggccg cctccccgca tcgataccgt cgacctcgag acctagaaaa   6720
acatggagca atcacaagta gcaatacagc agctaccaat gctgattgtg cctggctaga   6780
agcacaagag gaggaggagg tgggttttcc agtcacacct caggtacctt taagaccaat   6840
gacttacaag gcagctgtag atcttagcca ctttttaaaa gaaaaggggg gactggaagg   6900
gctaattcac tcccaacgaa gacaagatat ccttgatctg tggatctacc acacacaagg   6960
ctacttccct gattggcaga actacacacc agggccaggg atcagatatc cactgacctt   7020
tggatggtgc tacaagctag taccagttga gcaagagaag gtagaagaag ccaatgaagg   7080
agagaacacc cgcttgttac accctgtgag cctgcatggg atggatgacc cggagagaga   7140
agtattagag tggaggtttg acagccgcct agcatttcat cacatggccc gagagctgca   7200
tccggactgt actgggtctc tctggttaga ccagatctga gcctgggagc tctctggcta   7260
actagggaac ccactgctta agcctcaata aagcttgcct tgagtgcttc aagtagtgtg   7320
tgcccgtctg ttgtgtgact ctggtaacta gagatccctc agaccctttt agtcagtgtg   7380
gaaaatctct agcagggccc gtttaaaccc gctgatcagc ctcgactgtg ccttctagtt   7440
gccagccatc tgttgtttgc ccctcccccg tgccttcctt gaccctggaa ggtgccactc   7500
ccactgtcct ttcctaataa aatgaggaaa ttgcatcgca ttgtctgagt aggtgtcatt   7560
ctattctggg gggtggggtg gggcaggaca gcaaggggga ggattgggaa gacaatagca   7620
ggcatgctgg ggatgcggtg ggctctatgg cttctgaggc ggaaagaacc agctggggct   7680
ctagggggta tccccacgcg ccctgtagcg gcgcattaag cgcggcgggt gtggtggtta   7740
cgcgcagcgt gaccgctaca cttgccagcg ccctagcgcc cgctcctttc gctttcttcc   7800
cttcctttct cgccacgttc gccggctttc cccgtcaagc tctaaatcgg gggctccctt   7860
tagggttccg atttagtgct ttacggcacc tcgaccccaa aaaacttgat tagggtgatg   7920
gttcacgtag tgggccatcg ccctgataga cggtttttcg ccctttgacg ttggagtcca   7980
cgttctttaa tagtggactc ttgttccaaa ctggaacaac actcaaccct atctcggtct   8040
attcttttga tttataaggg atttgccga tttcggccta ttggttaaaa aatgagctga   8100
tttaacaaaa atttaacgcg aattaattct gtggaatgtg tgtcagttag ggtgtggaaa   8160
```

-continued

```
gtccccaggc tccccagcag gcagaagtat gcaaagcatg catctcaatt agtcagcaac   8220
caggtgtgga aagtccccag gctccccagc aggcagaagt atgcaaagca tgcatctcaa   8280
ttagtcagca accatagtcc cgcccctaac tccgcccatc ccgcccctaa ctccgcccag   8340
ttccgcccat tctccgcccc atggctgact aatttttttt atttatgcag aggccgaggc   8400
cgcctctgcc tctgagctat tccagaagta gtgaggaggc ttttttggag gcctaggctt   8460
ttgcaaaaag ctcccgggag cttgtatatc cattttcgga tctgatcagc acgtgttgac   8520
aattaatcat cggcatagta tatcggcata gtataatacg acaaggtgag gaactaaacc   8580
atggccaagt tgaccagtgc cgttccggtg ctcaccgcgc gcgacgtcgc cggagcggtc   8640
gagttctgga ccgaccggct cgggttctcc cgggacttcg tggaggacga cttcgccggt   8700
gtggtccggg acgacgtgac cctgttcatc agcgcggtcc aggaccaggt ggtgccggac   8760
aacaccctgg cctgggtgtg ggtgcgcggc ctggacgagc tgtacgccga gtggtcggag   8820
gtcgtgtcca cgaacttccg ggacgcctcc gggccggcca tgaccgagat cggcgagcag   8880
ccgtgggggc gggagttcgc cctgcgcgac ccggccggca actgcgtgca cttcgtggcc   8940
gaggagcagg actgacacgt gctacgagat ttcgattcca ccgccgcctt ctatgaaagg   9000
ttgggcttcg gaatcgtttt ccgggacgcc ggctggatga tcctccagcg cggggatctc   9060
atgctggagt tcttcgccca ccccaacttg tttattgcag cttataatgg ttacaaataa   9120
agcaatagca tcacaaattt cacaaataaa gcattttttt cactgcattc tagttgtggt   9180
ttgtccaaac tcatcaatgt atcttatcat gtctgtatac cgtcgacctc tagctagagc   9240
ttggcgtaat catggtcata gctgtttcct gtgtgaaatt gttatccgct cacaattcca   9300
cacaacatac gagccggaag cataaagtgt aaagcctggg gtgcctaatg agtgagctaa   9360
ctcacattaa ttgcgttgcg ctcactgccc gctttccagt cgggaaacct gtcgtgccag   9420
ctgcattaat gaatcggcca acgcgcgggg agaggcggtt tgcgtattgg gcgctcttcc   9480
gcttcctcgc tcactgactc gctgcgctcg gtcgttcggc tgcggcgagc ggtatcagct   9540
cactcaaagg cggtaatacg gttatccaca gaatcagggg ataacgcagg aaagaacatg   9600
tgagcaaaag gccagcaaaa ggccaggaac cgtaaaaagg ccgcgttgct ggcgtttttc   9660
cataggctcc gcccccctga cgagcatcac aaaaatcgac gctcaagtca gaggtggcga   9720
aacccgacag gactataaag ataccaggcg tttccccctg gaagctccct cgtgcgctct   9780
cctgttccga ccctgccgct taccggatac ctgtccgcct ttctcccttc gggaagcgtg   9840
gcgctttctc atagctcacg ctgtaggtat ctcagttcgg tgtaggtcgt tcgctccaag   9900
ctgggctgtg tgcacgaacc ccccgttcag cccgaccgct gcgccttatc cggtaactat   9960
cgtcttgagt ccaacccggt aagacacgac ttatcgccac tggcagcagc cactggtaac  10020
aggattagca gagcgaggta tgtaggcggt gctacagagt tcttgaagtg gtggcctaac  10080
tacggctaca ctagaagaac agtatttggt atctgcgctc tgctgaagcc agttaccttc  10140
ggaaaaagag ttggtagctc ttgatccggc aaacaaacca ccgctggtag cggtggtttt  10200
tttgtttgca agcagcagat tacgcgcaga aaaaaaggat ctcaagaaga tcctttgatc  10260
ttttctacgg ggtctgacgc tcagtggaac gaaaactcac gttaagggat tttggtcatg  10320
agattatcaa aaaggatctt cacctagatc cttttaaatt aaaaatgaag ttttaaatca  10380
atctaaagta tatatgagta aacttggtct gacagttacc aatgcttaat cagtgaggca  10440
cctatctcag cgatctgtct atttcgttca tccatagttg cctgactccc cgtcgtgtag  10500
```

ataactacga tacgggaggg cttaccatct ggccccagtg ctgcaatgat accgcgagac 10560
ccacgctcac cggctccaga tttatcagca ataaaccagc cagccggaag ggccgagcgc 10620
agaagtggtc ctgcaacttt atccgcctcc atccagtcta ttaattgttg ccgggaagct 10680
agagtaagta gttcgccagt taatagtttg cgcaacgttg ttgccattgc tacaggcatc 10740
gtggtgtcac gctcgtcgtt tggtatggct tcattcagct ccggttccca acgatcaagg 10800
cgagttacat gatcccccat gttgtgcaaa aaagcggtta gctccttcgg tcctccgatc 10860
gttgtcagaa gtaagttggc cgcagtgtta tcactcatgg ttatggcagc actgcataat 10920
tctcttactg tcatgccatc cgtaagatgc ttttctgtga ctggtgagta ctcaaccaag 10980
tcattctgag aatagtgtat gcggcgaccg agttgctctt gcccggcgtc aatacgggat 11040
aataccgcgc cacatagcag aactttaaaa gtgctcatca ttggaaaacg ttcttcgggg 11100
cgaaaactct caaggatctt accgctgttg agatccagtt cgatgtaacc cactcgtgca 11160
cccaactgat cttcagcatc ttttactttc accagcgttt ctgggtgagc aaaaacagga 11220
aggcaaaatg ccgcaaaaaa gggaataagg gcgacacgga aatgttgaat actcatactc 11280
ttcctttttc aatattattg aagcatttat cagggttatt gtctcatgag cggatacata 11340
tttgaatgta tttagaaaaa taaacaaata ggggttccgc gcacatttcc ccgaaaagtg 11400
ccacctgac 11409

<210> SEQ ID NO 10
<211> LENGTH: 85
<212> TYPE: RNA
<213> ORGANISM: Artificial Sequence
<220> FEATURE:
<223> OTHER INFORMATION: miRBase Accession No.: MI0000471: human miR126 (stem-loop)

<400> SEQUENCE: 10
cgcuggcgac gggacauuau uacuuuuggu acgcgcugug acacuucaaa cucguaccgu 60
gaguaauaau gcgccgucca cggca 85

<210> SEQ ID NO 11
<211> LENGTH: 88
<212> TYPE: RNA
<213> ORGANISM: Artificial Sequence
<220> FEATURE:
<223> OTHER INFORMATION: miRBase Accession No.: MI0000461: human miR145 (stem-loop)

<400> SEQUENCE: 11
caccuugucc ucacggucca guuuucccag gaaucccuua gaugcuaaga uggggauucc 60
uggaaauacu guucuugagg ucaugguu 88

<210> SEQ ID NO 12
<211> LENGTH: 106
<212> TYPE: RNA
<213> ORGANISM: Artificial Sequence
<220> FEATURE:
<223> OTHER INFORMATION: miRBase Accession No.: MI0000459: human miR143 (stem-loop)

<400> SEQUENCE: 12
gcgcagcgcc cugucuccca gccugaggug cagugcugca ucucugguca guugggaguc 60
ugagaugaag cacuguagcu caggaagaga gaaguuguuc ugcagc 106

<210> SEQ ID NO 13

<211> LENGTH: 85
<212> TYPE: RNA
<213> ORGANISM: Artificial Sequence
<220> FEATURE:
<223> OTHER INFORMATION: miRBase Accession No.: MI0000442 Human miR-122
(stem-loop)

<400> SEQUENCE: 13
ccuuagcaga gcuguggagu gugacaaugg uguuugugucc uaaacuauca aacgccauua 60
ucacacuaaa uagcuacugc uaggc 85

<210> SEQ ID NO 14
<211> LENGTH: 73
<212> TYPE: RNA
<213> ORGANISM: Artificial Sequence
<220> FEATURE:
<223> OTHER INFORMATION: miRBase Accession No.: MI0017383 Human miR-3591
(stem-loop)

<400> SEQUENCE: 14
caguagcuau uuagugugau aauggcguuu gauaguuuag acacaaacac cauugucaca 60
cuccacagcu cug 73

<210> SEQ ID NO 15
<211> LENGTH: 71
<212> TYPE: RNA
<213> ORGANISM: Artificial Sequence
<220> FEATURE:
<223> OTHER INFORMATION: miRBase Accession No.: MI0000251 Human miR-208a
(stem-loop)

<400> SEQUENCE: 15
ugacgggcga gcuuuuggcc cggguuauac cugaugcuca cguauaagac gagcaaaaag 60
cuuguugguc a 71

<210> SEQ ID NO 16
<211> LENGTH: 77
<212> TYPE: RNA
<213> ORGANISM: Artificial Sequence
<220> FEATURE:
<223> OTHER INFORMATION: miRBase Accession No.: MI0005570 Human miR-208b
(stem-loop)

<400> SEQUENCE: 16
ccucucaggg aagcuuuuug cucgaauuau guuucugauc cgaauauaag acgaacaaaa 60
gguuugucug agggcag 77

<210> SEQ ID NO 17
<211> LENGTH: 88
<212> TYPE: RNA
<213> ORGANISM: Artificial Sequence
<220> FEATURE:
<223> OTHER INFORMATION: miRBase Accession No.: MI0000450Human miR-133a-
1 (stem-loop)

<400> SEQUENCE: 17
acaaugcuuu gcuagagcug guaaaaugga accaaaucgc cucuucaaug gauuuggucc 60
ccuucaacca gcuguagcua ugcauuga 88

<210> SEQ ID NO 18
<211> LENGTH: 102
<212> TYPE: RNA
<213> ORGANISM: Artificial Sequence
<220> FEATURE:

<223> OTHER INFORMATION: miRBase Accession No.: MI0000451 Human miR-
133a-2 (stem-loop)

<400> SEQUENCE: 18
gggagccaaa ugcuuugcua gagcugguaa aauggaacca aaucgacugu ccaauggauu 60
ugguccccuu caaccagcug uagcugugca uugauggcgc cg 102

<210> SEQ ID NO 19
<211> LENGTH: 119
<212> TYPE: RNA
<213> ORGANISM: Artificial Sequence
<220> FEATURE:
<223> OTHER INFORMATION: miRBase Accession No.: MI0000822 Human miR-133b
(stem-loop)

<400> SEQUENCE: 19
ccucagaaga aagaugcccc cugcucuggc uggucaaacg gaaccaaguc cgucuuccug 60
agagguuugg uccccuucaa ccagcuacag cagggcuggc aaugcccagu ccuuggaga 119

<210> SEQ ID NO 20
<211> LENGTH: 69
<212> TYPE: RNA
<213> ORGANISM: Artificial Sequence
<220> FEATURE:
<223> OTHER INFORMATION: miRBase Accession No.: MI0000738 Human miR-302a
(stem-loop)

<400> SEQUENCE: 20
ccaccacuua aacguggaug uacuugcuuu gaaacuaaag aaguaagugc uuccauguuu 60
uggugaugg 69

<210> SEQ ID NO 21
<211> LENGTH: 73
<212> TYPE: RNA
<213> ORGANISM: Artificial Sequence
<220> FEATURE:
<223> OTHER INFORMATION: miRBase Accession No.: MI0000772 Human miR-302b
(stem-loop)

<400> SEQUENCE: 21
gcucccuuca acuuuaacau ggaagugcuu ucugugacuu uaaaaguaag ugcuuccaug 60
uuuuaguagg agu 73

<210> SEQ ID NO 22
<211> LENGTH: 68
<212> TYPE: RNA
<213> ORGANISM: Artificial Sequence
<220> FEATURE:
<223> OTHER INFORMATION: miRBase Accession No.: MI0000773 Human miR-302c
(stem-loop)

<400> SEQUENCE: 22
ccuuugcuuu aacaugggggg uaccugcugu gugaaacaaa aguaagugcu uccauguuuc 60
aguggagg 68

<210> SEQ ID NO 23
<211> LENGTH: 68
<212> TYPE: RNA
<213> ORGANISM: Artificial Sequence
<220> FEATURE:
<223> OTHER INFORMATION: . miRBase Accession No.: MI0000774 Human miR-
302d (stem-loop)

<400> SEQUENCE: 23
ccucuacuuu aacauggagg cacuugcugu gacaugacaa aaauaagugc uuccauguuu 60
gagugugg 68

<210> SEQ ID NO 24
<211> LENGTH: 51
<212> TYPE: RNA
<213> ORGANISM: Artificial Sequence
<220> FEATURE:
<223> OTHER INFORMATION: miRBase Accession No.: MI0006418 Human miR-302f (stem-loop)

<400> SEQUENCE: 24
ucuguguaaa ccuggcaauu uucacuuaau ugcuuccaug uuuauaaaag a 51

<210> SEQ ID NO 25
<211> LENGTH: 71
<212> TYPE: RNA
<213> ORGANISM: Artificial Sequence
<220> FEATURE:
<223> OTHER INFORMATION: miRBase Accession No.: MI0006418 Human miR-1-1 (stem-loop)

<400> SEQUENCE: 25
ugggaaacau acuucuuuau augcccauau ggaccugcua agcuauggaa uguaaagaag 60
uauguaucuc a 71

<210> SEQ ID NO 26
<211> LENGTH: 85
<212> TYPE: RNA
<213> ORGANISM: Artificial Sequence
<220> FEATURE:
<223> OTHER INFORMATION: miRBase Accession No.: MI0000437 Human miR-1-2 (stem-loop)

<400> SEQUENCE: 26
accuacucag aguacauacu ucuuuaugua cccauaugaa cauacaaugc uauggaaugu 60
aaagaaguau guauuuuugg uaggc 85

<210> SEQ ID NO 27
<211> LENGTH: 86
<212> TYPE: RNA
<213> ORGANISM: Artificial Sequence
<220> FEATURE:
<223> OTHER INFORMATION: miRBase Accession No.: MI0000490 Human miR-206 (stem-loop)

<400> SEQUENCE: 27
ugcuucccga ggccacaugc uucuuuauau ccccauaugg auuacuuugc uauggaaugu 60
aaggaagugu gugguuucgg caagug 86

<210> SEQ ID NO 28
<211> LENGTH: 73
<212> TYPE: RNA
<213> ORGANISM: Artificial Sequence
<220> FEATURE:
<223> OTHER INFORMATION: miRBase Accession No.: MI0000474 Human miR-134 (stem-loop)

<400> SEQUENCE: 28
cagggugugu gacugguuga ccagaggggc augcacugug uucacccugu gggccaccua 60
gucaccaacc cuc 73

<210> SEQ ID NO 29
<211> LENGTH: 88
<212> TYPE: RNA
<213> ORGANISM: Artificial Sequence
<220> FEATURE:
<223> OTHER INFORMATION: miRBase Accession No.: MI0000487 Human miR-193a (stem-loop)

<400> SEQUENCE: 29
cgaggauggg agcugagggc ugggucuuug cgggcgagau gagggugucg gaucaacugg 60
ccuacaaagu cccaguucuc ggcccccg 88

<210> SEQ ID NO 30
<211> LENGTH: 83
<212> TYPE: RNA
<213> ORGANISM: Artificial Sequence
<220> FEATURE:
<223> OTHER INFORMATION: miRBase Accession No.: MI0003137 Human miR-193b (stem-loop)

<400> SEQUENCE: 30
guggucucag aaucggggguu uugagggcga gaugaguuua uguuuuaucc aacuggcccu 60
caaagucccg cuuuuggggu cau 83

<210> SEQ ID NO 31
<211> LENGTH: 82
<212> TYPE: RNA
<213> ORGANISM: Artificial Sequence
<220> FEATURE:
<223> OTHER INFORMATION: miRBase Accession No.: MI0000447 Human miR-128-1 (stem-loop)

<400> SEQUENCE: 31
ugagcuguug gauucggggc cguagcacug ucugagaggu uuacauuucu cacagugaac 60
cggucucuuu uucagcugcu uc 82

<210> SEQ ID NO 32
<211> LENGTH: 84
<212> TYPE: RNA
<213> ORGANISM: Artificial Sequence
<220> FEATURE:
<223> OTHER INFORMATION: miRBase Accession No.: MI0000727 Human miR-128-2 (stem-loop)

<400> SEQUENCE: 32
ugugcagugg gaagggggc cgauacacug uacgagagug aguagcaggu cucacaguga 60
accggucucu uucccuacug uguc 84

<210> SEQ ID NO 33
<211> LENGTH: 81
<212> TYPE: RNA
<213> ORGANISM: Artificial Sequence
<220> FEATURE:
<223> OTHER INFORMATION: miRBase Accession No.: MI0000097 Human miR-95 (stem-loop)

<400> SEQUENCE: 33
aacacagugg gcacucaaua aaugucuguu gaauugaaau gcguuacauu caacggguau 60
uuauugagca cccacucugu g 81

<210> SEQ ID NO 34
<211> LENGTH: 84
<212> TYPE: RNA
<213> ORGANISM: Artificial Sequence
<220> FEATURE:
<223> OTHER INFORMATION: miRBase Accession No.: MI0000082 Human miR-25
(stem-loop)

<400> SEQUENCE: 34
ggccaguguu gagaggcgga gacuugggca auugcuggac gcugcccugg gcauugcacu 60
ugucucgguc ugacagugcc ggcc 84

<210> SEQ ID NO 35
<211> LENGTH: 78
<212> TYPE: RNA
<213> ORGANISM: Artificial Sequence
<220> FEATURE:
<223> OTHER INFORMATION: miRBase Accession No.: MI0000093 Human miR-92a-
1 (stem-loop)

<400> SEQUENCE: 35
cuuucuacac agguugggau cgguugcaau gcuguguuuc uguaugguau ugcacuuguc 60
ccggccuguu gaguuugg 78

<210> SEQ ID NO 36
<211> LENGTH: 75
<212> TYPE: RNA
<213> ORGANISM: Artificial Sequence
<220> FEATURE:
<223> OTHER INFORMATION: miRBase Accession No.: MI0000094 Human miR-92a-
2 (stem-loop)

<400> SEQUENCE: 36
ucaucccugg guggggauuu guugcauuac uuguguucua uauaaaguau ugcacuuguc 60
ccggccugug gaaga 75

<210> SEQ ID NO 37
<211> LENGTH: 96
<212> TYPE: RNA
<213> ORGANISM: Artificial Sequence
<220> FEATURE:
<223> OTHER INFORMATION: miRBase Accession No.: MI0003560 Human miR-92b
(stem-loop)

<400> SEQUENCE: 37
cgggccccgg gcgggcggga gggacgggac gcggugcagu guuguuuuuu cccccgccaa 60
uauugcacuc gucccggccu ccggcccccc cggccc 96

<210> SEQ ID NO 38
<211> LENGTH: 95
<212> TYPE: RNA
<213> ORGANISM: Artificial Sequence
<220> FEATURE:
<223> OTHER INFORMATION: miRBase Accession No.: MI0000457 Human miR-141
(stem-loop)

<400> SEQUENCE: 38
cggccggccc ugggguccauc uuccaguaca guguuggaug gucuaauugu gaagcuccua 60
acacugucug guaaagaugg cucccgggug gguuc 95

<210> SEQ ID NO 39
<211> LENGTH: 90
<212> TYPE: RNA
<213> ORGANISM: Artificial Sequence
<220> FEATURE:
<223> OTHER INFORMATION: miRBase Accession No.: MI0000737 Human miR-200a
(stem-loop)

<400> SEQUENCE: 39
ccgggccccu gugagcaucu uaccggacag ugcuggauuu cccagcuuga cucuaacacu 60
gucugguaac gauguucaaa ggugacccgc 90

<210> SEQ ID NO 40
<211> LENGTH: 95
<212> TYPE: RNA
<213> ORGANISM: Artificial Sequence
<220> FEATURE:
<223> OTHER INFORMATION: miRBase Accession No.: MI0000342 Human miR-200b (stem-loop)

<400> SEQUENCE: 40
ccagcucggg cagccguggc caucuuacug ggcagcauug gauggaguca ggucucuaau 60
acugccuggu aaugaugacg gcggagcccu gcacg 95

<210> SEQ ID NO 41
<211> LENGTH: 68
<212> TYPE: RNA
<213> ORGANISM: Artificial Sequence
<220> FEATURE:
<223> OTHER INFORMATION: miRBase Accession No.: MI0000650 Human miR-200c (stem-loop)

<400> SEQUENCE: 41
cccucgucuu acccagcagu guuugggugc gguugggagu cucuaauacu gccggguaau 60
gauggagg 68

<210> SEQ ID NO 42
<211> LENGTH: 70
<212> TYPE: RNA
<213> ORGANISM: Artificial Sequence
<220> FEATURE:
<223> OTHER INFORMATION: miRBase Accession No.: MI0000238 Human miR-196a-1 (stem-loop)

<400> SEQUENCE: 42
gugaauuagg uaguuucaug uuguugggcc uggguuucug aacacaacaa cauuaaacca 60
cccgauucac 70

<210> SEQ ID NO 43
<211> LENGTH: 110
<212> TYPE: RNA
<213> ORGANISM: Artificial Sequence
<220> FEATURE:
<223> OTHER INFORMATION: miRBase Accession No.: MI0000279 Human miR-196a-2(stem-loop)

<400> SEQUENCE: 43
ugcucgcuca gcugaucugu ggcuuaggua guuucauguu guugggauug aguuuugaac 60
ucggcaacaa gaaacugccu gaguuacauc agucgguuuu cgucgagggc 110

<210> SEQ ID NO 44
<211> LENGTH: 84
<212> TYPE: RNA
<213> ORGANISM: Artificial Sequence
<220> FEATURE:
<223> OTHER INFORMATION: miRBase Accession No.: MI0001150 Human miR-196b (stem-loop)

<400> SEQUENCE: 44
acuggucggu gauuuaggua guuuccuguu guugggaucc accuuucucu cgacagcacg 60
acacugccuu cauuacuuca guug 84

<210> SEQ ID NO 45
<211> LENGTH: 110
<212> TYPE: RNA
<213> ORGANISM: Artificial Sequence
<220> FEATURE:
<223> OTHER INFORMATION: miRBase Accession No.: MI0000266 Human miR-10a
(stem-loop)

<400> SEQUENCE: 45
gaucugucug ucuucuguau auacccugua gauccgaauu uguguaagga auuuuguggu 60
cacaaauucg uaucuagggg aauauguagu ugacauaaac acuccgcucu 110

<210> SEQ ID NO 46
<211> LENGTH: 110
<212> TYPE: RNA
<213> ORGANISM: Artificial Sequence
<220> FEATURE:
<223> OTHER INFORMATION: miRBase Accession No.: MI0000267 Human miR-10b
(stem-loop)

<400> SEQUENCE: 46
ccagagguug uaacguuguc uauauauacc cuguagaacc gaauuugugu gguauccgua 60
uagucacaga uucgauucua ggggaauaua uggucgaugc aaaaacuuca 110

<210> SEQ ID NO 47
<211> LENGTH: 81
<212> TYPE: RNA
<213> ORGANISM: Artificial Sequence
<220> FEATURE:
<223> OTHER INFORMATION: miRBase Accession No.: MI0000101 Human miR-99a
(stem-loop)

<400> SEQUENCE: 47
cccauuggca uaaacccgua gauccgaucu uguggugaag uggaccgcac aagcucgcuu 60
cuaugggucu gugucagugu g 81

<210> SEQ ID NO 48
<211> LENGTH: 70
<212> TYPE: RNA
<213> ORGANISM: Artificial Sequence
<220> FEATURE:
<223> OTHER INFORMATION: miRBase Accession No.: MI0000746 Human miR-99b
(stem-loop)

<400> SEQUENCE: 48
ggcacccacc cguagaaccg accuugcggg gccuucgccg cacacaagcu cgugucugug 60
gguccguguc 70

<210> SEQ ID NO 49
<211> LENGTH: 80
<212> TYPE: RNA
<213> ORGANISM: Artificial Sequence
<220> FEATURE:
<223> OTHER INFORMATION: miRBase Accession No.: MI0000102 Human miR-100
(stem-loop)

<400> SEQUENCE: 49
ccuguugcca caaacccgua gauccgaacu ugugguauua guccgcacaa gcuuguaucu 60
auagguaugu gucuguuagg 80

<210> SEQ ID NO 50

<211> LENGTH: 86
<212> TYPE: RNA
<213> ORGANISM: Artificial Sequence
<220> FEATURE:
<223> OTHER INFORMATION: miRBase Accession No.: MI0000469Human miR-125a (stem-loop)

<400> SEQUENCE: 50
ugccagucuc uaggucccug agacccuuua accugugagg acauccaggg ucacagguga    60
gguucuuggg agccuggcgu cuggcc                                        86

<210> SEQ ID NO 51
<211> LENGTH: 88
<212> TYPE: RNA
<213> ORGANISM: Artificial Sequence
<220> FEATURE:
<223> OTHER INFORMATION: miRBase Accession No.: MI0000446 Human miR-125b-1 (stem-loop)

<400> SEQUENCE: 51
ugcgcuccuc ucagucccug agacccuaac uugugauguu uaccguuuaa auccacgggu    60
uaggcucuug ggagcugcga gucgugcu                                      88

<210> SEQ ID NO 52
<211> LENGTH: 89
<212> TYPE: RNA
<213> ORGANISM: Artificial Sequence
<220> FEATURE:
<223> OTHER INFORMATION: miRBase Accession No.: MI0000470 Human miR-125b-2 (stem-loop)

<400> SEQUENCE: 52
accagacuuu uccuaguccc ugagacccua acuugugagg uauuuuagua acaucacaag    60
ucaggcucuu gggaccuagg cggaggggga                                    89

<210> SEQ ID NO 53
<211> LENGTH: 99
<212> TYPE: RNA
<213> ORGANISM: Artificial Sequence
<220> FEATURE:
<223> OTHER INFORMATION: miRBase Accession No.: MI0000477 Human miR-146a (stem-loop)

<400> SEQUENCE: 53
ccgaugugua uccucagcuu ugagaacuga auuccauggg uugugucagu gucagaccuc    60
ugaaauucag uucuucagcu gggauaucuc ugucaucgu                          99

<210> SEQ ID NO 54
<211> LENGTH: 73
<212> TYPE: RNA
<213> ORGANISM: Artificial Sequence
<220> FEATURE:
<223> OTHER INFORMATION: miRBase Accession No.: MI0003129 Human miR-146b (stem-loop)

<400> SEQUENCE: 54
ccuggcacug agaacugaau uccauaggcu gugagcucua gcaaugcccu guggacucag    60
uucuggugcc cgg                                                      73

<210> SEQ ID NO 55
<211> LENGTH: 71
<212> TYPE: RNA
<213> ORGANISM: Artificial Sequence
<220> FEATURE:

<223> OTHER INFORMATION: miRBase Accession No.: MI0000088 Human miR-30a
(stem-loop)

<400> SEQUENCE: 55
gcgacuguaa acauccucga cuggaagcug ugaagccaca gaugggcuuu cagucggaug 60
uuugcagcug c 71

<210> SEQ ID NO 56
<211> LENGTH: 88
<212> TYPE: RNA
<213> ORGANISM: Artificial Sequence
<220> FEATURE:
<223> OTHER INFORMATION: miRBase Accession No.: MI0000441 Human miR-30b
(stem-loop)

<400> SEQUENCE: 56
accaaguuuc aguucaugua aacauccuac acucagcugu aauacaugga uuggcuggga 60
gguggauguu uacuucagcu gacuugga 88

<210> SEQ ID NO 57
<211> LENGTH: 89
<212> TYPE: RNA
<213> ORGANISM: Artificial Sequence
<220> FEATURE:
<223> OTHER INFORMATION: miRBase Accession No.: MI0000736 Human miR-30c-
1 (stem-loop)

<400> SEQUENCE: 57
accaugcugu agugugugua aacauccuac acucucagcu gugagcucaa gguggcuggg 60
agaggguugu uuacuccuuc ugccaugga 89

<210> SEQ ID NO 58
<211> LENGTH: 72
<212> TYPE: RNA
<213> ORGANISM: Artificial Sequence
<220> FEATURE:
<223> OTHER INFORMATION: miRBase Accession No.: MI0000254 Human miR-30c-
2 (stem-loop)

<400> SEQUENCE: 58
agauacugua aacauccuac acucucagcu guggaaagua agaaagcugg gagaaggcug 60
uuuacucuuu cu 72

<210> SEQ ID NO 59
<211> LENGTH: 70
<212> TYPE: RNA
<213> ORGANISM: Artificial Sequence
<220> FEATURE:
<223> OTHER INFORMATION: miRBase Accession No.: MI0000255 Human miR-30d
(stem-loop)

<400> SEQUENCE: 59 guguuguaa acauccccga cuggaagcug uaagacacag cuaagcuuuc agucagaugu 60
uugcugcuac 70

<210> SEQ ID NO 60
<211> LENGTH: 92
<212> TYPE: RNA
<213> ORGANISM: Artificial Sequence
<220> FEATURE:
<223> OTHER INFORMATION: miRBase Accession No.: MI0000749 Human miR-30e
(stem-loop)

<400> SEQUENCE: 60
gggcagucuu ugcuacugua aacauccuug acuggaagcu guaagguguu cagaggagcu 60
uucagucgga uguuuacagc ggcaggcugc ca 92

<210> SEQ ID NO 61
<211> LENGTH: 76
<212> TYPE: RNA
<213> ORGANISM: Artificial Sequence
<220> FEATURE:
<223> OTHER INFORMATION: miRBase Accession No.: MI0002467 Human miR-483 (stem-loop)

<400> SEQUENCE: 61 gaggggaag acgggaggaa agaagggagu gguuccauca cgccuccuca cuccucuccu 60
cccgucuucu ccucuc 76

<210> SEQ ID NO 62
<211> LENGTH: 110
<212> TYPE: RNA
<213> ORGANISM: Artificial Sequence
<220> FEATURE:
<223> OTHER INFORMATION: miRBase Accession No.: MI0000234 Human miR-192 (stem-loop)

<400> SEQUENCE: 62
gccgagaccg agugcacagg gcucugaccu augaauugac agccagugcu cucgucuccc 60
cucuggcugc caauuccaua ggucacaggu auguucgccu caaugccagc 110

<210> SEQ ID NO 63
<211> LENGTH: 110
<212> TYPE: RNA
<213> ORGANISM: Artificial Sequence
<220> FEATURE:
<223> OTHER INFORMATION: miRBase Accession No.: MI0000291 Human miR-215 (stem-loop)

<400> SEQUENCE: 63
aucauucaga aaugguauac aggaaaauga ccuaugaauu gacagacaau auagcugagu 60
uugucuguca uuucuuuagg ccaauauucu guaugacugu gcuacuucaa 110

<210> SEQ ID NO 64
<211> LENGTH: 71
<212> TYPE: RNA
<213> ORGANISM: Artificial Sequence
<220> FEATURE:
<223> OTHER INFORMATION: miRBase Accession No.: MI0000242 Human miR-199a-1 (stem-loop)

<400> SEQUENCE: 64
gccaacccag uguucagacu accuguucag gaggcucuca auguguacag uagucugcac 60
auugguuagg c 71

<210> SEQ ID NO 65
<211> LENGTH: 110
<212> TYPE: RNA
<213> ORGANISM: Artificial Sequence
<220> FEATURE:
<223> OTHER INFORMATION: miRBase Accession No.: MI0000281 Human miR-199a-2 (stem-loop)

<400> SEQUENCE: 65
aggaagcuuc uggagauccu gcuccgucgc cccaguguuc agacuaccug uucaggacaa 60
ugccguugua caguagucug cacauugguu agacugggca agggagagca 110

<210> SEQ ID NO 66
<211> LENGTH: 110
<212> TYPE: RNA
<213> ORGANISM: Artificial Sequence
<220> FEATURE:
<223> OTHER INFORMATION: miRBase Accession No.: MI0000282 Human miR-199b
(stem-loop)

<400> SEQUENCE: 66
ccagaggaca ccuccacucc gucuacccag uguuuagacu aucuguucag gacucccaaa 60
uuguacagua gucugcacau ugguuaggcu gggcuggguu agacccucgg 110

<210> SEQ ID NO 67
<211> LENGTH: 110
<212> TYPE: RNA
<213> ORGANISM: Artificial Sequence
<220> FEATURE:
<223> OTHER INFORMATION: miRBase Accession No.: MI0000290 Human miR-214
(stem-loop)

<400> SEQUENCE: 67
ggccuggcug gacagaguug ucaugugucu gccugucuac acuugcugug cagaacaucc 60
gcucaccugu acagcaggca cagacaggca gucacaugac aacccagccu 110

<210> SEQ ID NO 68
<211> LENGTH: 81
<212> TYPE: RNA
<213> ORGANISM: Artificial Sequence
<220> FEATURE:
<223> OTHER INFORMATION: miRBase Accession No.: MI0014136 Human miR-3120
(stem-loop)

<400> SEQUENCE: 68
gucaugugac ugccugucug ugccugcugu acaggugagc ggauguucug cacagcaagu 60
guagacaggc agacacauga c 81

<210> SEQ ID NO 69
<211> LENGTH: 110
<212> TYPE: RNA
<213> ORGANISM: Artificial Sequence
<220> FEATURE:
<223> OTHER INFORMATION: miRBase Accession No.: MI0000266 Human miR-10a
(stem-loop)

<400> SEQUENCE: 69
gaucugucug ucuucuguau auacccugua gauccgaauu uguguaagga auuuuguggu 60
cacaaauucg uaucuagggg aauauguagu ugacauaaac acuccgcucu 110

<210> SEQ ID NO 70
<211> LENGTH: 110
<212> TYPE: RNA
<213> ORGANISM: Artificial Sequence
<220> FEATURE:
<223> OTHER INFORMATION: miRBase Accession No.: MI0000267 Human miR-10b
(stem-loop)

<400> SEQUENCE: 70
ccagagguug uaacguuguc uauauauacc cuguagaacc gaauuugugu gguauccgua 60
uagucacaga uucgauucua ggggaauaua uggucgaugc aaaaacuuca 110

<210> SEQ ID NO 71
<211> LENGTH: 81

```
<212> TYPE: RNA
<213> ORGANISM: Artificial Sequence
<220> FEATURE:
<223> OTHER INFORMATION: miRBase Accession No.: MI0000101 Human miR-99a
      (stem-loop)

<400> SEQUENCE: 71

cccauuggca uaaacccgua gauccgaucu uguggugaag uggaccgcac aagcucgcuu     60

cuaugggucu gugucagugu g                                               81


<210> SEQ ID NO 72
<211> LENGTH: 70
<212> TYPE: RNA
<213> ORGANISM: Artificial Sequence
<220> FEATURE:
<223> OTHER INFORMATION: miRBase Accession No.: MI0000746 Human miR-99b
      (stem-loop)

<400> SEQUENCE: 72

ggcacccacc cguagaaccg accuugcggg gccuucgccg cacacaagcu cgugucugug     60

gguccguguc                                                            70


<210> SEQ ID NO 73
<211> LENGTH: 80
<212> TYPE: RNA
<213> ORGANISM: Artificial Sequence
<220> FEATURE:
<223> OTHER INFORMATION: miRBase Accession No.: MI0000102 Human miR-100
      (stem-loop)

<400> SEQUENCE: 73

ccuguugcca caaacccgua gauccgaacu ugugguauua guccgcacaa gcuuguaucu     60

auagguaugu gucuguuagg                                                 80


<210> SEQ ID NO 74
<211> LENGTH: 86
<212> TYPE: RNA
<213> ORGANISM: Artificial Sequence
<220> FEATURE:
<223> OTHER INFORMATION: miRBase Accession No.: MI0000469 Human miR-125a
      (stem-loop)

<400> SEQUENCE: 74

ugccagucuc uagguccug agacccuuua accugugagg acauccaggg ucacagguga     60

gguucuuggg agccuggcgu cuggcc                                          86


<210> SEQ ID NO 75
<211> LENGTH: 88
<212> TYPE: RNA
<213> ORGANISM: Artificial Sequence
<220> FEATURE:
<223> OTHER INFORMATION: miRBase Accession No.: MI0000446 Human miR-
      125b-1(stem-loop)

<400> SEQUENCE: 75

ugcgcuccuc ucagucccug agacccuaac uugugauguu uaccguuuaa auccacgggu     60

uaggcucuug ggagcugcga gucgugcu                                        88


<210> SEQ ID NO 76
<211> LENGTH: 89
<212> TYPE: RNA
<213> ORGANISM: Artificial Sequence
<220> FEATURE:
<223> OTHER INFORMATION: miRBase Accession No.: MI0000470 Human miR-
```

125b-2 (stem-loop)

<400> SEQUENCE: 76
accagacuuu uccuaguccc ugagacccua acuugugagg uauuuuagua acaucacaag 60
ucaggcucuu gggaccuagg cggagggga 89

<210> SEQ ID NO 77
<211> LENGTH: 110
<212> TYPE: RNA
<213> ORGANISM: Artificial Sequence
<220> FEATURE:
<223> OTHER INFORMATION: 78

<400> SEQUENCE: 77
uuggauguug gccuaguucu guguggaaga cuagugauuu uguuguuuuu agauaacuaa 60
aucgacaaca aaucacaguc ugccauaugg cacaggccau gccucuacag 110

<210> SEQ ID NO 78
<211> LENGTH: 110
<212> TYPE: RNA
<213> ORGANISM: Artificial Sequence
<220> FEATURE:
<223> OTHER INFORMATION: miRBase Accession No.: MI0000264 Human miR-7-2 (stem-loop)

<400> SEQUENCE: 78
cuggauacag aguggaccgg cuggccccau cuggaagacu agugauuuug uuguugucuu 60
acugcgcuca acaacaaauc ccagucuacc uaauggugcc agccaucgca 110

<210> SEQ ID NO 79
<211> LENGTH: 110
<212> TYPE: RNA
<213> ORGANISM: Artificial Sequence
<220> FEATURE:
<223> OTHER INFORMATION: miRBase Accession No.: MI0000265 Human miR-7-3 (stem-loop)

<400> SEQUENCE: 79
agauuagagu ggcugugguc uagugcugug uggaagacua gugauuuugu uguucugaug 60
uacuacgaca acaagucaca gccggccuca uagcgcagac ucccuucgac 110

<210> SEQ ID NO 80
<211> LENGTH: 71
<212> TYPE: RNA
<213> ORGANISM: Artificial Sequence
<220> FEATURE:
<223> OTHER INFORMATION: miRBase Accession No.: MI0000089 Human miR-31 (stem-loop)

<400> SEQUENCE: 80
ggagaggagg caagaugcug gcauagcugu ugaacuggga accugcuaug ccaacauauu 60
gccaucuuuc c 71

<210> SEQ ID NO 81
<211> LENGTH: 72
<212> TYPE: RNA
<213> ORGANISM: Artificial Sequence
<220> FEATURE:
<223> OTHER INFORMATION: miRBase Accession No.: MI0000252 Human miR-129-1 (stem-loop)

<400> SEQUENCE: 81
ggaucuuuuu gcggucuggg cuugcuguuc cucucaacag uagucaggaa gcccuuaccc 60

-continued caaaaaguau cu 72

<210> SEQ ID NO 82
<211> LENGTH: 90
<212> TYPE: RNA
<213> ORGANISM: Artificial Sequence
<220> FEATURE:
<223> OTHER INFORMATION: miRBase Accession No.: MI0000473 Human miR-129-2 (stem-loop)

<400> SEQUENCE: 82
ugcccuucgc gaaucuuuuu gcggucuggg cuugcuguac auaacucaau agccggaagc 60
ccuuacccca aaaagcauuu gcggagggcg 90

<210> SEQ ID NO 83
<211> LENGTH: 110
<212> TYPE: RNA
<213> ORGANISM: Artificial Sequence
<220> FEATURE:
<223> OTHER INFORMATION: miRBase Accession No.: MI0000294 Human miR-218-1 (stem-loop)

<400> SEQUENCE: 83
gugauaaugu agcgagauuu ucuguugugc uugaucuaac caugugguug cgagguauga 60
guaaaacaug guuccgucaa gcaccaugga acgucacgca gcuuucuaca 110

<210> SEQ ID NO 84
<211> LENGTH: 110
<212> TYPE: RNA
<213> ORGANISM: Artificial Sequence
<220> FEATURE:
<223> OTHER INFORMATION: miRBase Accession No.: MI0000295 Human miR-218-2 (stem-loop)

<400> SEQUENCE: 84
gaccagucgc ugcggggcuu uccuuugugc uugaucuaac cauguggugg aacgauggaa 60
acggaacaug guucugucaa gcaccgcgga aagcaccgug cucuccugca 110

<210> SEQ ID NO 85
<211> LENGTH: 89
<212> TYPE: RNA
<213> ORGANISM: Artificial Sequence
<220> FEATURE:
<223> OTHER INFORMATION: miRBase Accession No.: MI0000466 Human miR-9-1 (stem-loop)

<400> SEQUENCE: 85
cgggguuggu uguuaucuuu gguuaucuag cuguaugagu gguguggagu cuucauaaag 60
cuagauaacc gaaaguaaaa auaacccca 89

<210> SEQ ID NO 86
<211> LENGTH: 87
<212> TYPE: RNA
<213> ORGANISM: Artificial Sequence
<220> FEATURE:
<223> OTHER INFORMATION: miRBase Accession No.: MI0000467 Human miR-9-2 (stem-loop)

<400> SEQUENCE: 86
ggaagcgagu uguuaucuuu gguuaucuag cuguaugagu guauuggucu ucauaaagcu 60
agauaaccga aaguaaaaac uccuuca 87

<210> SEQ ID NO 87
<211> LENGTH: 90
<212> TYPE: RNA
<213> ORGANISM: Artificial Sequence
<220> FEATURE:
<223> OTHER INFORMATION: miRBase Accession No.: MI0000468 Human miR-9-3 (stem-loop)

<400> SEQUENCE: 87

```
ggaggcccgu uucucucuuu gguuaucuag cuguaugagu gccacagagc cgucauaaag      60

cuagauaacc gaaaguagaa augauucuca                                       90
```

<210> SEQ ID NO 88
<211> LENGTH: 82
<212> TYPE: RNA
<213> ORGANISM: Artificial Sequence
<220> FEATURE:
<223> OTHER INFORMATION: miRBase Accession No.: MI0000447 Human miR-128-1 (stem-loop)

<400> SEQUENCE: 88

```
ugagcuguug gauucggggc cguagcacug ucugagaggu uuacauuucu cacagugaac      60

cggucucuuu uucagcugcu uc                                               82
```

<210> SEQ ID NO 89
<211> LENGTH: 84
<212> TYPE: RNA
<213> ORGANISM: Artificial Sequence
<220> FEATURE:
<223> OTHER INFORMATION: miRBase Accession No.: MI0000727 Human miR-128-2 (stem-loop)

<400> SEQUENCE: 89

```
ugugcagugg aaggggggc cgauacacug uacgagagug aguagcaggu cucacaguga       60

accggucucu uucccuacug uguc                                             84
```

<210> SEQ ID NO 90
<211> LENGTH: 86
<212> TYPE: RNA
<213> ORGANISM: Artificial Sequence
<220> FEATURE:
<223> OTHER INFORMATION: miRBase Accession No.: MI0000483 Human miR-186 (stem-loop)

<400> SEQUENCE: 90

```
ugcuuguaac uuccaaaga auucuccuuu ugggcuuucu gguuuuauuu uaagcccaaa       60

ggugaauuuu uugggaaguu ugagcu                                           86
```

<210> SEQ ID NO 91
<211> LENGTH: 110
<212> TYPE: RNA
<213> ORGANISM: Artificial Sequence
<220> FEATURE:
<223> OTHER INFORMATION: miRBase Accession No.: MI0000272 Human miR-182 (stem-loop)

<400> SEQUENCE: 91

```
gagcugcuug ccuccccccg uuuuuggcaa ugguagaacu cacacuggug agguaacagg      60

auccgguggu ucuagacuug ccaacuaugg ggcgaggacu cagccggcac                110
```

<210> SEQ ID NO 92
<211> LENGTH: 110
<212> TYPE: RNA
<213> ORGANISM: Artificial Sequence
<220> FEATURE:
<223> OTHER INFORMATION: miRBase Accession No.: MI0000285 Human miR-205
(stem-loop)

<400> SEQUENCE: 92
aaagauccuc agacaaucca ugugcuucuc uuguccuuca uuccaccgga gucugucuca 60
uacccaacca gauuucagug gagugaaguu caggaggcau ggagcugaca 110

<210> SEQ ID NO 93
<211> LENGTH: 85
<212> TYPE: RNA
<213> ORGANISM: Artificial Sequence
<220> FEATURE:
<223> OTHER INFORMATION: miRBase Accession No.: MI0003167 Human miR-
516b-2 (stem-loop)

<400> SEQUENCE: 93
ucucaugaug ugaccaucug gagguaagaa gcacuuugug uuuugugaaa gaaagugcuu 60
ccuuucagag gguuacucuu ugaga 85

<210> SEQ ID NO 94
<211> LENGTH: 84
<212> TYPE: RNA
<213> ORGANISM: Artificial Sequence
<220> FEATURE:
<223> OTHER INFORMATION: miRBase Accession No.: MI0003145 Human miR-519e
(stem-loop)

<400> SEQUENCE: 94
ucucaugcag ucauucucca aaagggagca cuuucuguuu gaaagaaaac aaagugccuc 60
cuuuuagagu guuacuguuu gaga 84

<210> SEQ ID NO 95
<211> LENGTH: 85
<212> TYPE: RNA
<213> ORGANISM: Artificial Sequence
<220> FEATURE:
<223> OTHER INFORMATION: miRBase Accession No.: MI0003178 Human miR-
519a-1 (stem-loop)

<400> SEQUENCE: 95
cucaggcugu gacacucuag agggaagcgc uuucuguugu cugaaagaaa ggaaagugca 60
uccuuuuaga guguuacugu uugag 85

<210> SEQ ID NO 96
<211> LENGTH: 124
<212> TYPE: RNA
<213> ORGANISM: Artificial Sequence
<220> FEATURE:
<223> OTHER INFORMATION: miRBase Accession No.: MI0003193Human miR-506
(stem-loop)

<400> SEQUENCE: 96
gccaccacca ucagccauac uauguguagu gccuuauuca ggaagguguu acuuaauaga 60
uuaauauuug uaaggcaccc uucugaguag aguaaugugc aacauggaca acauuugugg 120
uggc 124

<210> SEQ ID NO 97
<211> LENGTH: 115
<212> TYPE: RNA
<213> ORGANISM: Artificial Sequence
<220> FEATURE:
<223> OTHER INFORMATION: miRBase Accession No.: MI0003195 Human miR-508

(stem-loop)

<400> SEQUENCE: 97
ccaccuucag cugaguguag ugcccuacuc cagagggcgu cacucaugua aacuaaaaca 60
ugauuguagc cuuuuggagu agaguaauac acaucacgua acgcauauuu ggugg 115

<210> SEQ ID NO 98
<211> LENGTH: 94
<212> TYPE: RNA
<213> ORGANISM: Artificial Sequence
<220> FEATURE:
<223> OTHER INFORMATION: miRBase Accession No.: MI0003196 Human miR-509-1 (stem-loop)

<400> SEQUENCE: 98
caugcugugu gugguacccu acugcagaca guggcaauca uguauaauua aaaaugauug 60
guacgucugu ggguagagua cugcaugaca caug 94

<210> SEQ ID NO 99
<211> LENGTH: 91
<212> TYPE: RNA
<213> ORGANISM: Artificial Sequence
<220> FEATURE:
<223> OTHER INFORMATION: miRBase Accession No.: MI0005530 Human miR-509-2 (stem-loop)

<400> SEQUENCE: 99
caugcugugu gugguacccu acugcagaca guggcaauca uguauaauua aaaaugauug 60
guacgucugu ggguagagua cugcaugaca c 91

<210> SEQ ID NO 100
<211> LENGTH: 75
<212> TYPE: RNA
<213> ORGANISM: Artificial Sequence
<220> FEATURE:
<223> OTHER INFORMATION: miRBase Accession No.: MI0005717 Human miR-509-3 (stem-loop)

<400> SEQUENCE: 100
gugguacccu acugcagacg uggcaaucau guauaauuaa aaaugauugg uacgucugug 60
gguagaguac ugcau 75

<210> SEQ ID NO 101
<211> LENGTH: 74
<212> TYPE: RNA
<213> ORGANISM: Artificial Sequence
<220> FEATURE:
<223> OTHER INFORMATION: miRBase Accession No.: MI0003197 Human miR-510 (stem-loop)

<400> SEQUENCE: 101
gugguguccu acucaggaga guggcaauca cauguaauua ggugugauug aaaccucuaa 60
gaguggagua acac 74

<210> SEQ ID NO 102
<211> LENGTH: 84
<212> TYPE: RNA
<213> ORGANISM: Artificial Sequence
<220> FEATURE:
<223> OTHER INFORMATION: miRBase Accession No.: MI0006649 Human miR-513c (stem-loop)

<400> SEQUENCE: 102

-continued

```
gcguacagug ccuuucucaa ggaggugucg uuuaugugaa cuaaaauaua aauuucaccu     60

uucugagaag aguaauguac agca                                            84


<210> SEQ ID NO 103
<211> LENGTH: 98
<212> TYPE: RNA
<213> ORGANISM: Artificial Sequence
<220> FEATURE:
<223> OTHER INFORMATION: miRBase Accession No.: MI0003198 Human miR-
      514a-1 (stem-loop)

<400> SEQUENCE: 103

aacauguugu cugugguacc cuacucugga gagugacaau cauguauaau uaaauuugau     60

ugacacuucu gugaguagag uaacgcauga cacguacg                             98


<210> SEQ ID NO 104
<211> LENGTH: 88
<212> TYPE: RNA
<213> ORGANISM: Artificial Sequence
<220> FEATURE:
<223> OTHER INFORMATION: miRBase Accession No.: MI0003199 Human miR-
      514a-2 (stem-loop)

<400> SEQUENCE: 104

guugucugug guacccuacu cuggagagug acaaucaugu auaacuaaau uugauugaca     60

cuucugugag uagaguaacg caugacac                                        88


<210> SEQ ID NO 105
<211> LENGTH: 88
<212> TYPE: RNA
<213> ORGANISM: Artificial Sequence
<220> FEATURE:
<223> OTHER INFORMATION: miRBase Accession No.: MI0003200 Human miR-
      514a-3 (stem-loop)

<400> SEQUENCE: 105

guugucugug guacccuacu cuggagagug acaaucaugu auaacuaaau uugauugaca     60

cuucugugag uagaguaacg caugacac                                        88


<210> SEQ ID NO 106
<211> LENGTH: 80
<212> TYPE: RNA
<213> ORGANISM: Artificial Sequence
<220> FEATURE:
<223> OTHER INFORMATION: miRBase Accession No.: MI0014251 Human miR-514b
      (stem-loop)

<400> SEQUENCE: 106

caugugguac ucuucucaag agggaggcaa ucauguguaa uuagauauga uugacaccuc     60

ugugagugga guaacacaug                                                 80


<210> SEQ ID NO 107
<211> LENGTH: 83
<212> TYPE: RNA
<213> ORGANISM: Artificial Sequence
<220> FEATURE:
<223> OTHER INFORMATION: miRBase Accession No.: MI0000069 Human miR-15a
      (stem-loop)

<400> SEQUENCE: 107

ccuuggagua aaguagcagc acauaauggu uuguggauuu ugaaaaggug caggccauau     60

ugugcugccu caaaaauaca agg                                             83
```

<210> SEQ ID NO 108
<211> LENGTH: 98
<212> TYPE: RNA
<213> ORGANISM: Artificial Sequence
<220> FEATURE:
<223> OTHER INFORMATION: miRBase Accession No.: MI0000438Human miR-15b
(stem-loop)

<400> SEQUENCE: 108
uugaggccuu aaaguacugu agcagcacau caugguuuac augcuacagu caagaugcga 60
aucauuauuu gcugcucuag aaauuuaagg aaauucau 98

<210> SEQ ID NO 109
<211> LENGTH: 89
<212> TYPE: RNA
<213> ORGANISM: Artificial Sequence
<220> FEATURE:
<223> OTHER INFORMATION: miRBase Accession No.: MI0000070 Human miR-16-1
(stem-loop)

<400> SEQUENCE: 109
gucagcagug ccuuagcagc acguaaauau uggcguuaag auucuaaaau uaucuccagu 60
auuaacugug cugcugaagu aagguugac 89

<210> SEQ ID NO 110
<211> LENGTH: 81
<212> TYPE: RNA
<213> ORGANISM: Artificial Sequence
<220> FEATURE:
<223> OTHER INFORMATION: miRBase Accession No.: MI0000115 Human miR-16-2
(stem-loop)

<400> SEQUENCE: 110
guuccacucu agcagcacgu aaauauuggc guagugaaau auauauuaaa caccaauauu 60
acugugcugc uuuaguguga c 81

<210> SEQ ID NO 111
<211> LENGTH: 87
<212> TYPE: RNA
<213> ORGANISM: Artificial Sequence
<220> FEATURE:
<223> OTHER INFORMATION: miRBase Accession No.: MI0000489 Human miR-195
(stem-loop)

<400> SEQUENCE: 111
agcuucccug gcucuagcag cacagaaaua uuggcacagg gaagcgaguc ugccaauauu 60
ggcugugcug cuccaggcag gguggug 87

<210> SEQ ID NO 112
<211> LENGTH: 119
<212> TYPE: RNA
<213> ORGANISM: Artificial Sequence
<220> FEATURE:
<223> OTHER INFORMATION: miRBase Accession No.: MI0000100 Human miR-98
(stem-loop)

<400> SEQUENCE: 112
aggauucugc ucaugccagg gugagguagu aaguuguauu guuguggggu agggauauua 60
ggccccaauu agaagauaac uauacaacuu acuacuuucc cuggugugug gcauauuca 119

<210> SEQ ID NO 113
<211> LENGTH: 80
<212> TYPE: RNA

<213> ORGANISM: Artificial Sequence
<220> FEATURE:
<223> OTHER INFORMATION: miRBase Accession No.: MI0000060 Human let-7a-1
(stem-loop)

<400> SEQUENCE: 113
ugggaugagg uaguagguug uauaguuuua gggucacacc caccacuggg agauaacuau 60
acaaucuacu gucuuuccua 80

<210> SEQ ID NO 114
<211> LENGTH: 72
<212> TYPE: RNA
<213> ORGANISM: Artificial Sequence
<220> FEATURE:
<223> OTHER INFORMATION: miRBase Accession No.: MI0000061 Human let-7a-2
(stem-loop)

<400> SEQUENCE: 114
agguugaggu aguagguugu auaguuuaga auuacaucaa gggagauaac uguacagccu 60
ccuagcuuuc cu 72

<210> SEQ ID NO 115
<211> LENGTH: 74
<212> TYPE: RNA
<213> ORGANISM: Artificial Sequence
<220> FEATURE:
<223> OTHER INFORMATION: miRBase Accession No.: MI0000062 Human let-7a-3
(stem-loop)

<400> SEQUENCE: 115
gggugaggua guagguugua uaguuugggg cucugcccug cuaugggaua acuauacaau 60
cuacugucuu uccu 74

<210> SEQ ID NO 116
<211> LENGTH: 83
<212> TYPE: RNA
<213> ORGANISM: Artificial Sequence
<220> FEATURE:
<223> OTHER INFORMATION: miRBase Accession No.: MI0000063 Human let-7b
(stem-loop)

<400> SEQUENCE: 116
cggggugagg uaguagguug ugugguuuca gggcagugau guugccccuc ggaagauaac 60
uauacaaccu acugccuucc cug 83

<210> SEQ ID NO 117
<211> LENGTH: 84
<212> TYPE: RNA
<213> ORGANISM: Artificial Sequence
<220> FEATURE:
<223> OTHER INFORMATION: miRBase Accession No.: MI0000064 Human let-7c
(stem-loop)

<400> SEQUENCE: 117
gcauccgggu ugagguagua gguuguaugg uuuagaguua cacccuggga guuaacugua 60
caaccuucua gcuuuccuug gagc 84

<210> SEQ ID NO 118
<211> LENGTH: 87
<212> TYPE: RNA
<213> ORGANISM: Artificial Sequence
<220> FEATURE:
<223> OTHER INFORMATION: miRBase Accession No.: MI0000065 Human let-7d
(stem-loop)

<400> SEQUENCE: 118
ccuaggaaga gguaguaggu ugcauaguuu uagggcaggg auuuugccca caaggaggua 60
acuauacgac cugcugccuu ucuuagg 87

<210> SEQ ID NO 119
<211> LENGTH: 79
<212> TYPE: RNA
<213> ORGANISM: Artificial Sequence
<220> FEATURE:
<223> OTHER INFORMATION: miRBase Accession No.: MI0000066 Human let-7e (stem-loop)

<400> SEQUENCE: 119
cccgggcuga gguaggaggu uguauaguug aggaggacac ccaaggagau cacuauacgg 60
ccuccuagcu uuccccagg 79

<210> SEQ ID NO 120
<211> LENGTH: 87
<212> TYPE: RNA
<213> ORGANISM: Artificial Sequence
<220> FEATURE:
<223> OTHER INFORMATION: miRBase Accession No.: MI0000067 Human let-7f-1 (stem-loop)

<400> SEQUENCE: 120
ucagagugag guaguagauu guauaguugu gggguaguga uuuuacccug uucaggagau 60
aacuauacaa ucuauugccu ucccuga 87

<210> SEQ ID NO 121
<211> LENGTH: 83
<212> TYPE: RNA
<213> ORGANISM: Artificial Sequence
<220> FEATURE:
<223> OTHER INFORMATION: miRBase Accession No.: MI0000068 Human let-7f-2 (stem-loop)

<400> SEQUENCE: 121
ugugggauga gguaguagau uguauaguuu uagggucaua ccccaucuug gagauaacua 60
uacagucuac ugucuuuccc acg 83

<210> SEQ ID NO 122
<211> LENGTH: 84
<212> TYPE: RNA
<213> ORGANISM: Artificial Sequence
<220> FEATURE:
<223> OTHER INFORMATION: miRBase Accession No.: MI0000433 Human let-7g (stem-loop)

<400> SEQUENCE: 122
aggcugaggu aguaguuugu acaguuugag ggucuaugau accacccggu acaggagaua 60
acuguacagg ccacugccuu gcca 84

<210> SEQ ID NO 123
<211> LENGTH: 84
<212> TYPE: RNA
<213> ORGANISM: Artificial Sequence
<220> FEATURE:
<223> OTHER INFORMATION: miRBase Accession No.: MI0000434 Human let-7i (stem-loop)

<400> SEQUENCE: 123
cuggcugagg uaguaguuug ugcuguuggu cggguuguga cauugcccgc uguggagaua 60
acugcgcaag cuacugccuu gcua 84

<210> SEQ ID NO 124
<211> LENGTH: 110
<212> TYPE: RNA
<213> ORGANISM: Artificial Sequence
<220> FEATURE:
<223> OTHER INFORMATION: miRBase Accession No.: MI0000289 Human miR-181a-1 (stem-loop)

<400> SEQUENCE: 124
ugaguuuuga gguugcuuca gugaacauuc aacgcugucg gugaguuugg aauuaaaauc 60
aaaaccaucg accguugauu guacccuaug gcuaaccauc aucuacucca 110

<210> SEQ ID NO 125
<211> LENGTH: 110
<212> TYPE: RNA
<213> ORGANISM: Artificial Sequence
<220> FEATURE:
<223> OTHER INFORMATION: miRBase Accession No.: MI0000269 Human miR-181a-2 (stem-loop)

<400> SEQUENCE: 125
agaagggcua ucaggccagc cuucagagga cuccaaggaa cauucaacgc ugucggugag 60
uuugggauuu gaaaaaacca cugaccguug acuguaccuu gggguccuua 110

<210> SEQ ID NO 126
<211> LENGTH: 110
<212> TYPE: RNA
<213> ORGANISM: Artificial Sequence
<220> FEATURE:
<223> OTHER INFORMATION: miRBase Accession No.: MI0000270 Human miR-181b-1 (stem-loop)

<400> SEQUENCE: 126
ccugugcaga gauuauuuuu uaaaagguca caaucaacau ucauugcugu cgguggguug 60
aacugugugg acaagcucac ugaacaauga augcaacugu ggccccgcuu 110

<210> SEQ ID NO 127
<211> LENGTH: 89
<212> TYPE: RNA
<213> ORGANISM: Artificial Sequence
<220> FEATURE:
<223> OTHER INFORMATION: miRBase Accession No.: MI0000683 Human miR-181b-2 (stem-loop)

<400> SEQUENCE: 127
cugauggcug cacucaacau ucauugcugu cgguggguuu gagucugaau caacucacug 60
aucaaugaau gcaaacugcg gaccaaaca 89

<210> SEQ ID NO 128
<211> LENGTH: 110
<212> TYPE: RNA
<213> ORGANISM: Artificial Sequence
<220> FEATURE:
<223> OTHER INFORMATION: miRBase Accession No.: MI0000271 Human miR-181c (stem-loop)

<400> SEQUENCE: 128
cggaaaauuu gccaaggguu uggggaaca uucaaccugu cggugaguuu gggcagcuca 60
ggcaaaccau cgaccguuga guggacccug aggccuggaa uugccauccu 110

-continued

<210> SEQ ID NO 129
<211> LENGTH: 137
<212> TYPE: RNA
<213> ORGANISM: Artificial Sequence
<220> FEATURE:
<223> OTHER INFORMATION: miRBase Accession No.: MI0003139 Human miR-181d
(stem-loop)

<400> SEQUENCE: 129
guccccuccc cuaggccaca gccgagguca caaucaacau ucauuguugu cgguggguug 60
ugaggacuga ggccagaccc accgggggau gaaugucacu guggcugggc cagacacggc 120
uuaaggggaa uggggac 137

<210> SEQ ID NO 130
<211> LENGTH: 110
<212> TYPE: RNA
<213> ORGANISM: Artificial Sequence
<220> FEATURE:
<223> OTHER INFORMATION: miRBase Accession No.: MI0000284 Human miR-204
(stem-loop)

<400> SEQUENCE: 130
ggcuacaguc uuucuucaug ugacucgugg acuucccuuu gucauccuau gccugagaau 60
auaugaagga ggcugggaag gcaaagggac guucaauugu caucacuggc 110

<210> SEQ ID NO 131
<211> LENGTH: 110
<212> TYPE: RNA
<213> ORGANISM: Artificial Sequence
<220> FEATURE:
<223> OTHER INFORMATION: miRBase Accession No.: MI0000287 Human miR-211
(stem-loop)

<400> SEQUENCE: 131
ucaccuggcc augugacuug ugggcuuccc uuugucaucc uucgccuagg gcucugagca 60
gggcagggac agcaaagggg ugcucaguug ucacuuccca cagcacggag 110

<210> SEQ ID NO 132
<211> LENGTH: 85
<212> TYPE: RNA
<213> ORGANISM: Artificial Sequence
<220> FEATURE:
<223> OTHER INFORMATION: miRBase Accession No.: MI0000078 Human miR-22
(stem-loop)

<400> SEQUENCE: 132
ggcugagccg caguaguucu ucaguggcaa gcuuuauguc cugacccagc uaaagcugcc 60
aguugaagaa cuguugcccu cugcc 85

<210> SEQ ID NO 133
<211> LENGTH: 110
<212> TYPE: RNA
<213> ORGANISM: Artificial Sequence
<220> FEATURE:
<223> OTHER INFORMATION: miRBase Accession No.: MI0000268 Human miR-34a
(stem-loop)

<400> SEQUENCE: 133
ggccagcugu gaguguuucu uuggcagugu cuuagcuggu uguugugagc aauaguaagg 60
aagcaaucag caaguauacu gcccuagaag ugcugcacgu uguggggccc 110

<210> SEQ ID NO 134
<211> LENGTH: 84

-continued

```
<212> TYPE: RNA
<213> ORGANISM: Artificial Sequence
<220> FEATURE:
<223> OTHER INFORMATION: miRBase Accession No.: MI0000742 Human miR-34b
      (stem-loop)

<400> SEQUENCE: 134

gugcucgguu uguaggcagu gucauuagcu gauuguacug uggugguuac aaucacuaac     60

uccacugcca ucaaaacaag gcac                                           84


<210> SEQ ID NO 135
<211> LENGTH: 77
<212> TYPE: RNA
<213> ORGANISM: Artificial Sequence
<220> FEATURE:
<223> OTHER INFORMATION: miRBase Accession No.: MI0000743 Human miR-34c
      (stem-loop)

<400> SEQUENCE: 135

agucuaguua cuaggcagug uaguuagcug auugcuaaua guaccaauca cuaaccacac     60

ggccagguaa aaagauu                                                   77
```